(12) United States Patent
Altae-Tran et al.

(10) Patent No.: US 12,065,510 B2
(45) Date of Patent: Aug. 20, 2024

(54) TARGET RECOGNITION MOTIFS AND USES THEREOF

(71) Applicants: THE BROAD INSTITUTE, INC., Cambridge, MA (US); MASSACHUSETTS INSTITUTE OF TECHNOLOGY, Cambridge, MA (US)

(72) Inventors: Han Altae-Tran, Cambridge, MA (US); Linyi Gao, Cambridge, MA (US); Feng Zhang, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

(21) Appl. No.: 16/937,286

(22) Filed: Jul. 23, 2020

(65) Prior Publication Data
US 2021/0024655 A1 Jan. 28, 2021

Related U.S. Application Data

(60) Provisional application No. 62/877,358, filed on Jul. 23, 2019.

(51) Int. Cl.
*C07K 19/00* (2006.01)
*C07K 14/47* (2006.01)
*C07K 14/705* (2006.01)

(52) U.S. Cl.
CPC .............. *C07K 19/00* (2013.01); *C07K 14/47* (2013.01); *C07K 14/705* (2013.01); *C07K 2319/02* (2013.01)

(58) Field of Classification Search
CPC ...... C07K 19/00; C07K 14/47; C07K 14/705; C07K 2319/02; C07K 14/00; C07K 2319/036
See application file for complete search history.

(56) References Cited

PUBLICATIONS

Duchard et al, 2015 Acc#CAL42282. Alignment with SID70.*
Rao et al, pH shift assembly of adenoviral serotype 5 capsid protein nanosystems for enhanced delivery of nanoparticles, proteins and nucleic acids. Journal of Controlled Release 172 (2013) 341-350.*
Castillo et al., Bacteriophage Resistance Mechanisms in the Fish Pathogen Flavobacterium psychrophilum: Linking Genomic Mutations to Changes in Bacterial Virulence Factors. Appl. Environ Microbiol., 2015, vol. 81(3): 1157-1167. (Year: 2015).*
Duchaud et al., Complete genome sequence of the fish pathogen Flavobacterium psychrophilum. Nat. Biotechnol., 2007, vol. 25: 763-769. (Year: 2007).*
Dumetz et al., Analysis of the Flavobacterium psychrophilum outer-membrane subproteome and identification of new antigenic targets for vaccine by immunomics. Microbiol., 2008, vol. 154: 1793-1801. (Year: 2008).*
Adamala, et al., "Programmable RNA-Binding Protein Composed of Repeats of a Single Modular Unit", Proceedings of the National Academy of Sciences, vol. 113, No. 19, Apr. 26, 2016, E2579-E2588.
Albert, et al., "Molecular Mimicry and Autoimmunity", The New England Journal of Medicine, vol. 341, Dec. 30, 1999, 2068-2074.
Bonazzi, et al., "Listeria Monocytogenes Internalin and E-Cadherin: from Structure to Pathogenesis", Cellular Microbiology, vol. 11, No. 5, 2009, 693-702.
Cao, et al., "Structure of the Nonameric Bacterial Amyloid Secretion Channel", Proceedings of the National Academy of Sciences of the United States of America, vol. 111, No. 50, Dec. 16, 2014, E5439-E5444.
Castillo, et al., "Comparative Genome Analysis Provides Insights into the Pathogenicity of Flavobacterium psychrophilum", Plos One, vol. 11, No. 4, Apr. 12, 2016, 18 pages.
Christie, et al., "Structural and Dynamic Properties of Bacterial Type IV Secretion Systems", Molecular Membrane Biology, vol. 22, No. 0, 2005, 15 pages.
Doxey, et al., "Prediction of Molecular Mimicry Candidates in Human Pathogenic Bacteria", Virulence, vol. 4, No. 6, Aug. 15, 2013, 453-466.
Grant, et al., "Subterfuge and Manipulation: Type III Effector Proteins of Phytopathogenic Bacteria", Annual Review of Microbiology, vol. 60, 2006, 44 pages.
Groschel, et al., "ESX Secretion Systems: Mycobacterial Evolution to Counter Host Immunity", Nature Reviews Microbiology, vol. 14, 2016, 15 pages.
Iyer, et al., "Evolution of the Deaminase Fold and Multiple Origins of Eukaryotic Editing and Mutagenic Nucleic Acid Deaminases from Bacterial Toxin Systems", Nucleic Acids Research, vol. 39, No. 22, Sep. 3, 2011, 9473-9497.
Kobe, et al., "The Leucine-rich Repeat as a Protein Recognition Motif", Current Opinion in Structural Biology, vol. 11, No. 6, Dec. 2001, 725-732.
Lasica, et al., "The Type IX Secretion System (T9SS): Highlights and Recent Insights into Its Structure and Function". Frontiers in Cellular and Infection Microbiology, vol. 7, No. 215, May 2017, 19 pages.
Ng, et al., "Human Leucine-rich Repeat Proteins: A Genome-wide Bioinformatic Categorization and Functional Analysis in Innate Immunity", Proceedings of the National Academy of Sciences of the United States of America, vol. 108, Supplement 1, Mar. 15, 2011, 4631-4638.
Ng, et al., "Leucine-rich Repeat (LRR) Proteins: Integrators of Pattern Recognition and Signaling in Immunity", Autophagy, vol. 7, No. 9, Sep. 2011, 1082-1084.
Palmer, et al., "The Twin-arginine Translocation (Tat) Protein Export Pathway", Nature Reviews Microbiology , vol. 10, No. 7, Jul. 2012, 483-496.

(Continued)

*Primary Examiner* — Ganapathirama Raghu
(74) *Attorney, Agent, or Firm* — F. Brent Nix, Esq.; Johnson, Marcou, Isaacs & Nix, LLC

(57) ABSTRACT

Novel programmable targeting sequences and applications thereof. The targeting sequences can be engineered for binding to proteins, polypeptides, and other macromolecules.

20 Claims, 19 Drawing Sheets
Specification includes a Sequence Listing.

(56) References Cited

PUBLICATIONS

Parmeggiani, et al., "A General Computational Approach for Repeat Protein Design", Journal of Molecular Biology, vol. 427, No. 2, Jan. 30, 2015, 22 pages.

Raby, et al., "Targeting the TLR Co-Receptor CD14 with TLR2-Derived Peptides Modulates Immune Responses to Pathogens", Science Transnational Medicine, vol. 5, Issue 185, May 15, 2013, 13 pages.

Ramisch, et al., "Computational Design of a Leucine-rich Repeat Protein with a Predefined Geometry", Proceedings of the National Academy of Sciences of the United States of America, vol. 111, No. 50, Dec. 16, 2014, 17875-17880.

Tseng, et al., "Protein Secretion Systems in Bacterial-host Associations, and their Description in the Gene Ontology", BMC Microbiology, vol. 9, Supplement 01, 2009, 9 pages.

Xu, et al., "A Unique Mycobacterium ESX-1 Protein Co-secretes with CFP-10/ESAT-6 and is Necessary for Inhibiting Phagosome Maturation", Molecular Microbiology, vol. 66, No. 3, 2007, 787-800.

Zenevich, et al., "Distinct Regions of NLRP1B Are Required To Respond to Anthrax Lethal Toxin and Metabolic Inhibition", Infection and Immunity, vol. 82, No. 9, Sep. 2014, 3697-3703.

Zhang, et al., "A Novel Immunity System for Bacterial Nucleic Acid Degrading Toxins and its Recruitment in Various Eukaryotic and DNA Viral Systems", Nucleic Acids Research, vol. 39, No. 11, Feb. 8, 2011, 4532-4552.

Zhang, et al., "LMOh7858_0369, A Gene Encoding a Putative Leucine-rich Repeat-Containing Protein, is Required for Virulence of Listeria Monocytogenes", FEMS Microbiology Letters, vol. 363, No. 9, 2016, 8 pages.

Zhang, et al., "Polymorphic Toxin Systems: Comprehensive Characterization of Trafficking Modes, Processing, Mechanisms of Action, Immunity and Ecology using Comparative Genomics", Biology Direct, vol. 7, No. 18, 2012, 76 pages.

Zhu, et al., "Leureptin: A Soluble, Extracellular Leucine-rich Repeat Protein from Manduca Sexta that Binds Lipopolysaccharide", Insect Biochemistry and Molecular Biology, vol. 40, Issue 10, Oct. 2010, 713-722.

\* cited by examiner

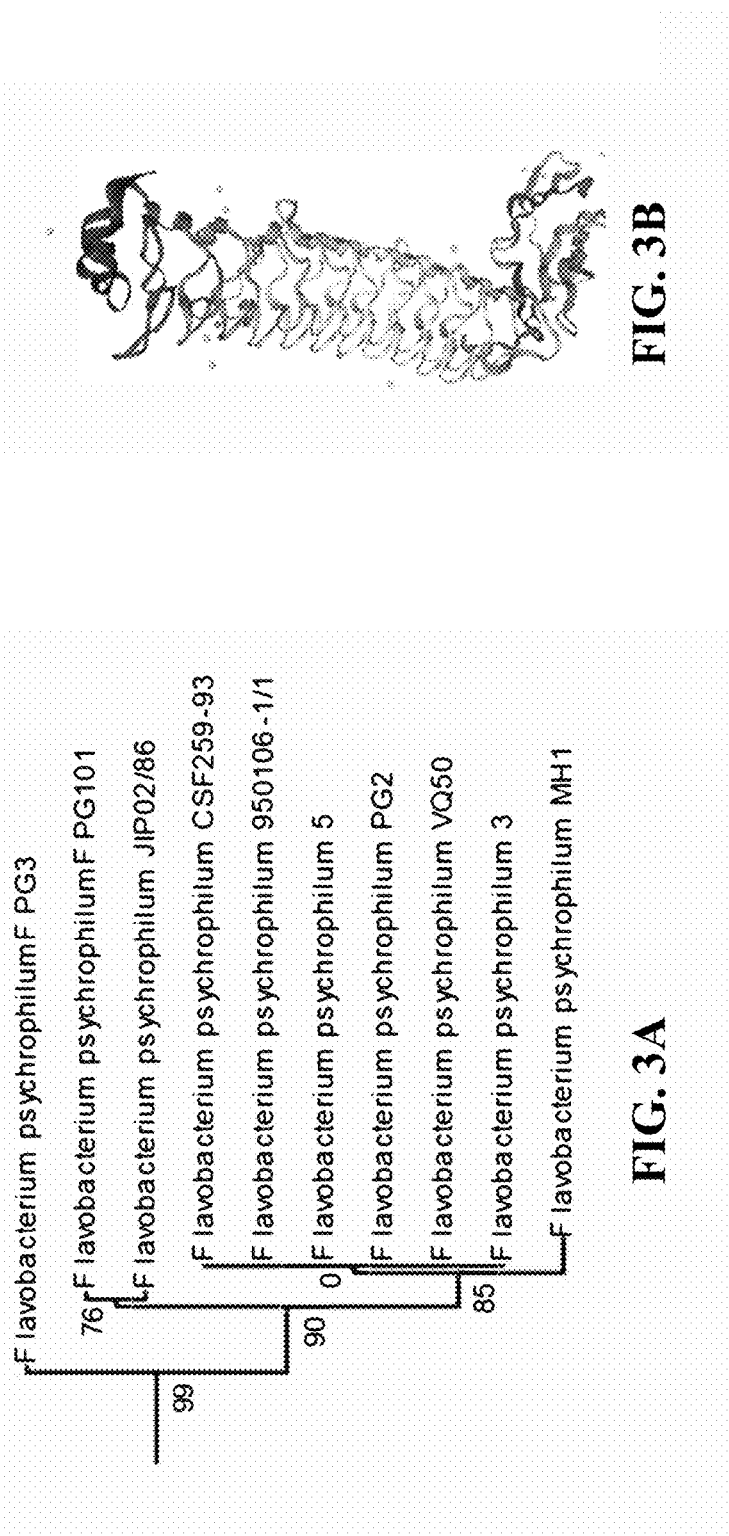
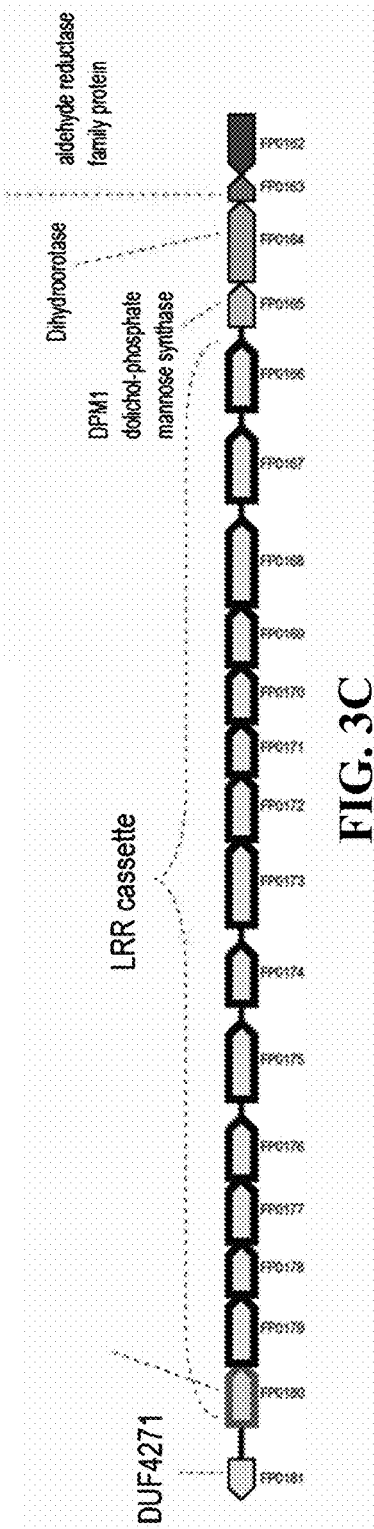
FIG. 3A
FIG. 3B
FIG. 3C

FIG. 5B

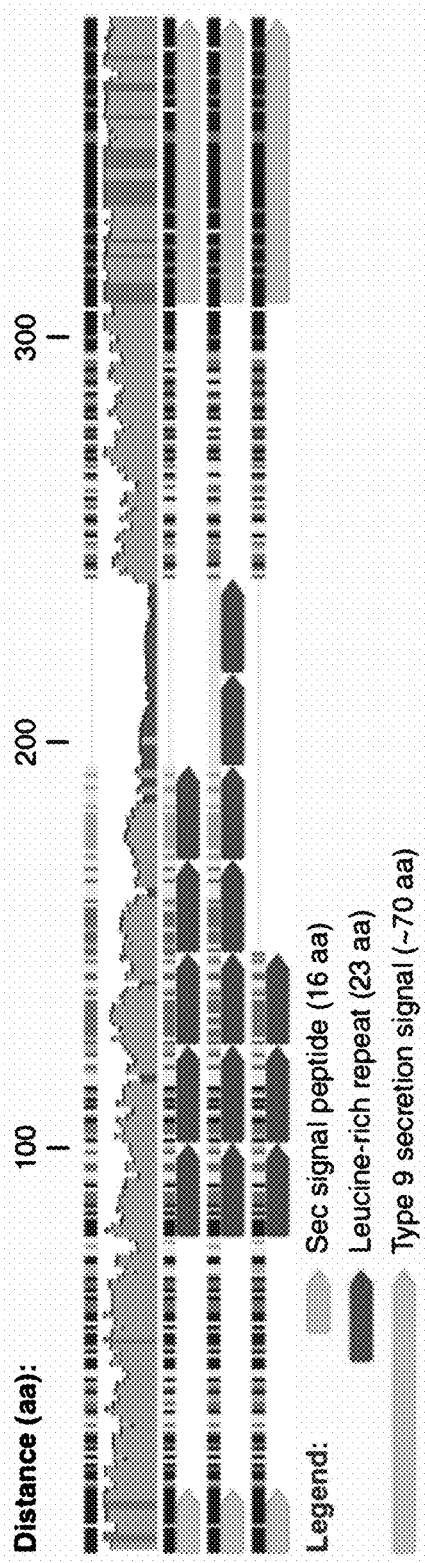
FIG. 7A
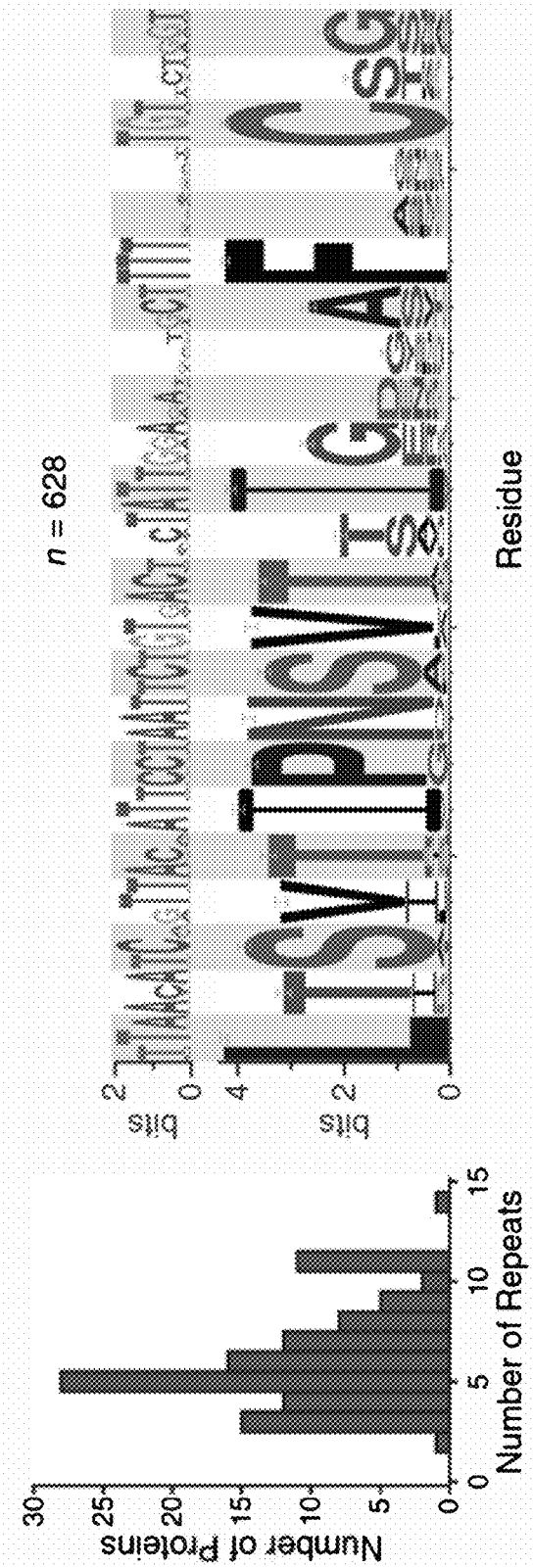
FIG. 7B
FIG. 7C

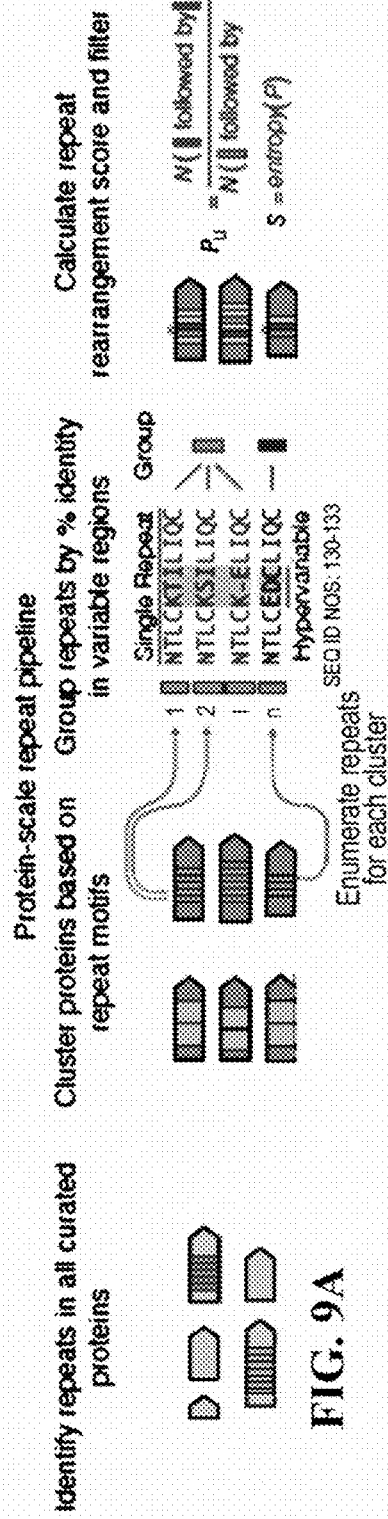
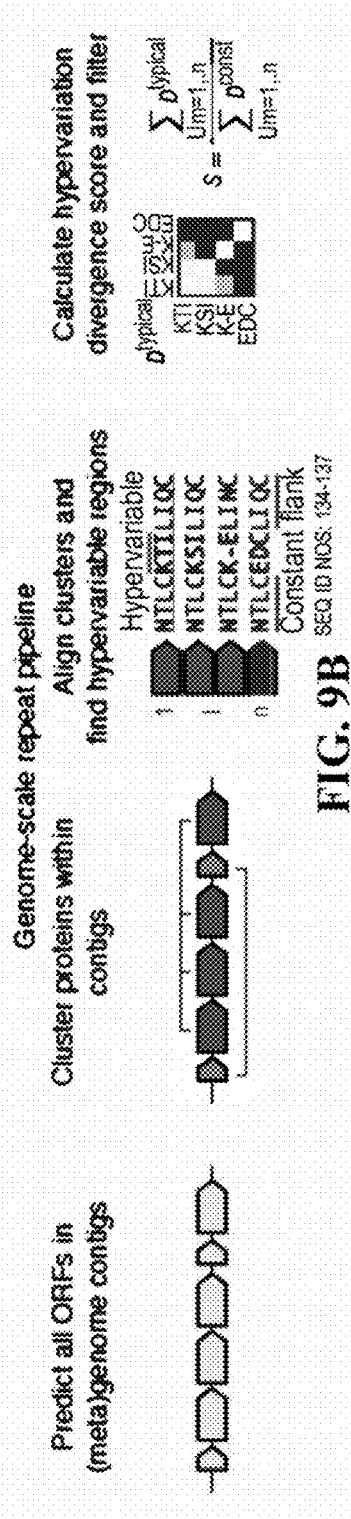
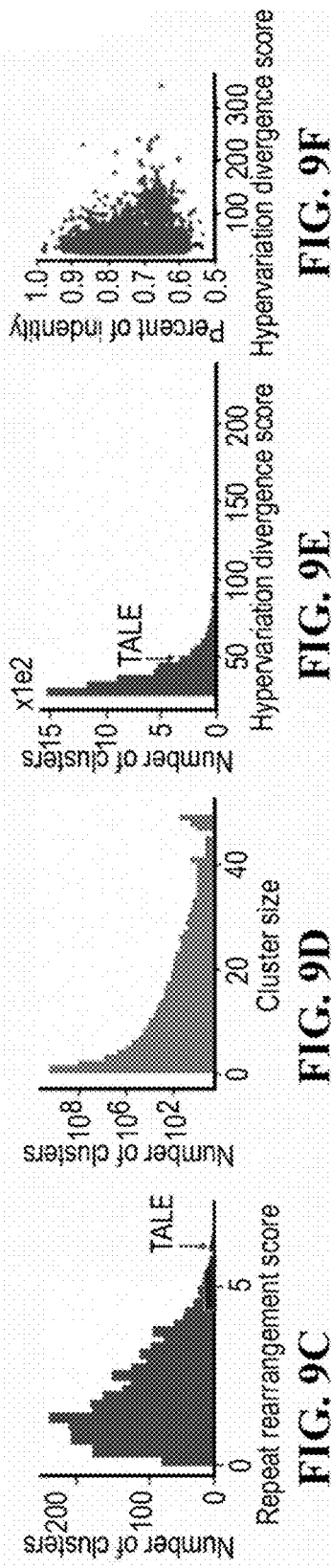
FIG. 9A, FIG. 9B, FIG. 9C, FIG. 9D, FIG. 9E, FIG. 9F

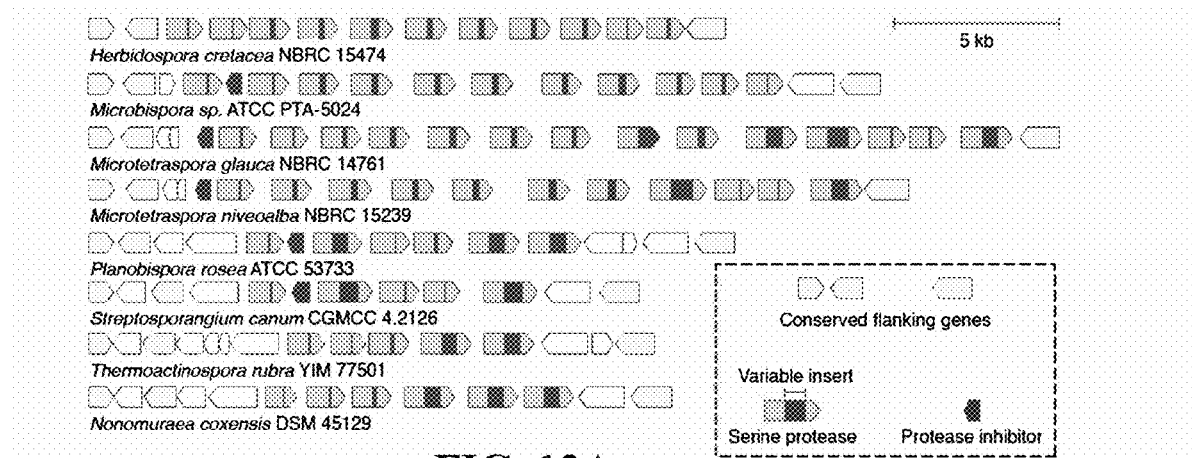
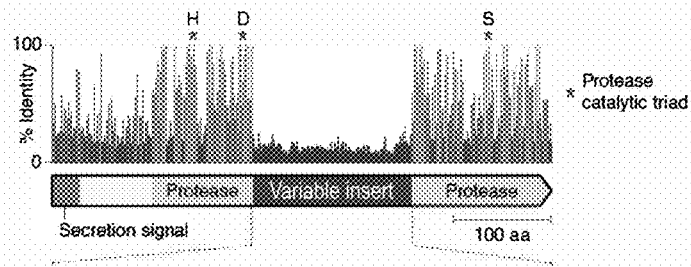
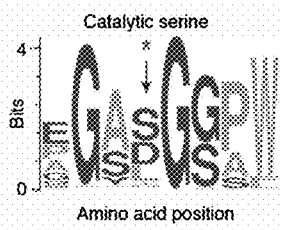
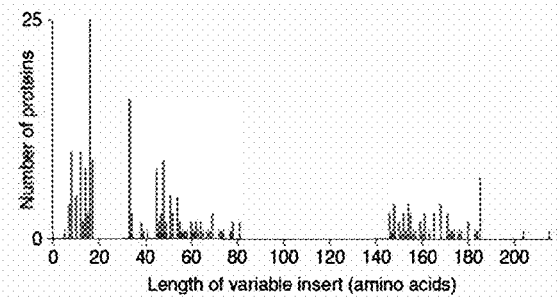
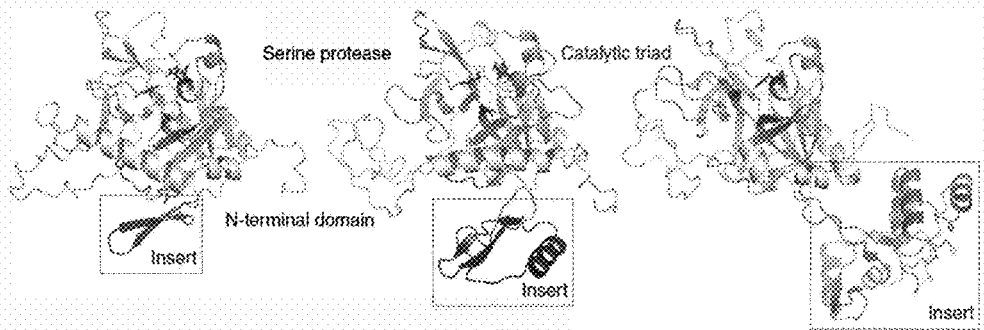
FIG. 13A
FIG. 13B
FIG. 13C
FIG. 13D
FIG. 13E
FIG. 13F

SEQUENCE LISTING

```
<160> NUMBER OF SEQ ID NOS: 141

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = any amino acid

<400> SEQUENCE: 1

Leu Xaa Xaa Leu Xaa Leu Xaa Xaa Asn Xaa Leu
1               5                   10

<210> SEQ ID NO 2
<211> LENGTH: 16
<212> TYPE: PRT
<213> ORGANISM: Herbidospora cretacea

<400> SEQUENCE: 2

Lys Ala Ser Trp Glu Lys Val Asp Gly Lys Tyr Lys Leu Val Lys Thr
1               5                   10                  15
```

-continued

```
<210> SEQ ID NO 3
<211> LENGTH: 8
<212> TYPE: PRT
<213> ORGANISM: Herbidospora cretacea

<400> SEQUENCE: 3

Thr Trp Lys Gly Ala Gln Arg Val
1               5

<210> SEQ ID NO 4
<211> LENGTH: 30
<212> TYPE: PRT
<213> ORGANISM: Herbidospora cretacea

<400> SEQUENCE: 4

Lys Ala Pro His Asp Gly Gly Pro Leu Asp Gly Asp Trp Lys Gln Val
1               5                   10                  15

Ser Lys Ser Glu Trp Asp Lys Tyr Arg Ser Tyr Gly Thr Tyr
            20                  25                  30

<210> SEQ ID NO 5
<211> LENGTH: 30
<212> TYPE: PRT
<213> ORGANISM: Herbidospora cretacea

<400> SEQUENCE: 5

Lys Ala Pro Ser Ser Gly Leu Pro Ala Lys Gly Ser Glu Phe Ala Arg
1               5                   10                  15

Trp Met Arg Thr Glu Asn Thr Lys Glu Val Thr Lys Ala Glu
            20                  25                  30

<210> SEQ ID NO 6
<211> LENGTH: 30
<212> TYPE: PRT
<213> ORGANISM: Herbidospora cretacea

<400> SEQUENCE: 6

Lys Ala Pro His Asp Gly Pro Ala Phe Gly Gly Pro Thr Pro Lys Thr
1               5                   10                  15

Pro Lys Trp Tyr Asp Thr Ser Gly Gly Thr Gly Trp Asn Asp
            20                  25                  30

<210> SEQ ID NO 7
<211> LENGTH: 30
<212> TYPE: PRT
<213> ORGANISM: Herbidospora cretacea

<400> SEQUENCE: 7

Thr Leu Asn Gly Pro Asp Gln Ser Ala Pro Val Ser Lys Val Glu Val
1               5                   10                  15

Thr Glu Ala Glu Tyr Lys Thr Tyr Trp Glu Asn Ser Asn Arg
            20                  25                  30

<210> SEQ ID NO 8
<211> LENGTH: 30
<212> TYPE: PRT
<213> ORGANISM: Herbidospora cretacea

<400> SEQUENCE: 8

Lys Leu Pro His Gly Gly Leu Lys Asp Val Thr Pro Glu Asn Ile Gly
1               5                   10                  15
```

```
Ser Trp Val Glu Val Ser Pro Glu Leu Ala Lys Gln Tyr Glu
            20                  25                  30

<210> SEQ ID NO 9
<211> LENGTH: 30
<212> TYPE: PRT
<213> ORGANISM: Herbidospora cretacea

<400> SEQUENCE: 9

Gln Leu Gly Thr Ala Ala Pro Val Glu Ile Thr Gln Ala Glu Tyr Asp
1               5                   10                  15

Thr Tyr Gln Lys Asn Gly Gly Gly Phe Thr Thr Arg Arg Lys
            20                  25                  30

<210> SEQ ID NO 10
<211> LENGTH: 30
<212> TYPE: PRT
<213> ORGANISM: Herbidospora cretacea

<400> SEQUENCE: 10

Ala Leu Gly Gln Gly Ala Pro Ala Glu Ile Thr Glu Ala Glu Tyr Asn
1               5                   10                  15

Thr Tyr Gln Lys Asn Gly Gly Gly Phe Leu Thr Arg Lys Lys
            20                  25                  30

<210> SEQ ID NO 11
<211> LENGTH: 8
<212> TYPE: PRT
<213> ORGANISM: Herbidospora cretacea

<400> SEQUENCE: 11

Thr Pro Ala Asp Gly Lys Trp Lys
1               5

<210> SEQ ID NO 12
<211> LENGTH: 30
<212> TYPE: PRT
<213> ORGANISM: Herbidospora cretacea

<400> SEQUENCE: 12

Lys Phe Glu Ala Thr Lys Ser Val Ser Glu Lys Thr Tyr Lys Gly His
1               5                   10                  15

Gly Gly Glu Arg Trp Arg Asp Lys Gly Lys Trp Trp Ile Leu
            20                  25                  30

<210> SEQ ID NO 13
<211> LENGTH: 21
<212> TYPE: PRT
<213> ORGANISM: Photorhabdus thracensis

<400> SEQUENCE: 13

Gly Val Ala Pro Phe Asp Asn Asn Gly Lys Ser Ile Arg Ser Gly Ser
1               5                   10                  15

Asn Val Asp Asn Lys
            20

<210> SEQ ID NO 14
<211> LENGTH: 21
<212> TYPE: PRT
<213> ORGANISM: Photorhabdus thracensis

<400> SEQUENCE: 14

Gly Lys Ser Thr Thr Glu Asn Lys Asn Ser Ser Phe Asn Pro Gln Ser
```

```
1               5                  10                  15

Lys Val Asp Thr Lys
            20

<210> SEQ ID NO 15
<211> LENGTH: 21
<212> TYPE: PRT
<213> ORGANISM: Photorhabdus thracensis

<400> SEQUENCE: 15

Gly Val Ala Pro Ser Glu Asn Ile Gly Asn Ser Thr Glu Lys Arg Ser
1               5                  10                  15

Arg Val Asp Asn Lys
            20

<210> SEQ ID NO 16
<211> LENGTH: 21
<212> TYPE: PRT
<213> ORGANISM: Photorhabdus thracensis

<400> SEQUENCE: 16

Gly Ser Lys Pro Pro Lys Asn Asn Asp Asp Ser Ser Lys Gln Lys Ser
1               5                  10                  15

Lys Met Asp Asn Lys
            20

<210> SEQ ID NO 17
<211> LENGTH: 21
<212> TYPE: PRT
<213> ORGANISM: Photorhabdus thracensis

<400> SEQUENCE: 17

Gly Thr Lys Pro Thr Lys Asp Arg Gly Ser Phe Val Gly Asn Ile Thr
1               5                  10                  15

Asn Ser Thr Thr Lys
            20

<210> SEQ ID NO 18
<211> LENGTH: 21
<212> TYPE: PRT
<213> ORGANISM: Photorhabdus thracensis

<400> SEQUENCE: 18

Gly Lys Gly Ile Thr Lys Asn Asn Asp Asp Ser Ile Lys Gln Asn Ser
1               5                  10                  15

Lys Leu Gly Asp Lys
            20

<210> SEQ ID NO 19
<211> LENGTH: 21
<212> TYPE: PRT
<213> ORGANISM: Photorhabdus thracensis

<400> SEQUENCE: 19

Gly Thr Ala Pro Ser Lys Asn Glu Glu Ala Val Phe Asn His Lys Ser
1               5                  10                  15

Lys Thr Asp Thr Lys
            20

<210> SEQ ID NO 20
<211> LENGTH: 21
<212> TYPE: PRT
```

<213> ORGANISM: Photorhabdus thracensis

<400> SEQUENCE: 20

Gly Ile Ser Pro Pro Glu Asn Asn Asp Glu Ser Ser Lys Gln Lys Ser
1               5                   10                  15

Lys Met Asp Ala Lys
            20

<210> SEQ ID NO 21
<211> LENGTH: 33
<212> TYPE: DNA
<213> ORGANISM: Artificial Sequence
<220> FEATURE:
<223> OTHER INFORMATION: Synthetic

<400> SEQUENCE: 21
gtttactttc taatcattca aataaacgtt tca                                   33

<210> SEQ ID NO 22
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Leu = Leu, Ile, Val, or Phe
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Leu = Leu, Ile, Val, or Phe
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Leu = Leu, Ile, Val, or Phe
<220> FEATURE:
<221> NAME/KEY: MISC_FEATURE
<222> LOCATION: (7)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Cys = is Cys, Ser, or Asn
<220> FEATURE:
<221> NAME/KEY: MISC_FEATURE
<222> LOCATION: (10)..(11)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Leu = Leu, Ile, Val, or Phe

<400> SEQUENCE: 22

Leu Xaa Xaa Leu Xaa Leu Xaa Xaa Cys Xaa Xaa Leu
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Ser = Ser or Thr
<220> FEATURE:
<221> NAME/KEY: MISC_FEATURE
<222> LOCATION: (4)..(4)
<223> OTHER INFORMATION: Xaa = a polar amino acid

<400> SEQUENCE: 23

Ser Arg Arg Xaa Phe Leu Lys
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic grouping of hydrophobic amino acids

<400> SEQUENCE: 24

Phe Trp Tyr His Lys Met Ile Leu Val Ala Gly Cys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic grouping of polar amino acids

<400> SEQUENCE: 25

Trp Tyr His Lys Arg Glu Asp Cys Ser Thr Asn Gln
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic grouping of small amino acids

<400> SEQUENCE: 26

Val Cys Ala Gly Ser Pro Thr Asn Asp
1               5

<210> SEQ ID NO 27
<211> LENGTH: 7
<212> TYPE: PRT
<213> ORGANISM: Simian virus 40

<400> SEQUENCE: 27

Pro Lys Lys Lys Arg Lys Val
1               5

<210> SEQ ID NO 28
<211> LENGTH: 16
<212> TYPE: PRT
<213> ORGANISM: Simian virus 40

<400> SEQUENCE: 28

Lys Arg Pro Ala Ala Thr Lys Lys Ala Gly Gln Ala Lys Lys Lys Lys
1               5                   10                  15

<210> SEQ ID NO 29
<211> LENGTH: 9
<212> TYPE: PRT
<213> ORGANISM: Homo sapiens
```

```
<400> SEQUENCE: 29

Pro Ala Ala Lys Arg Val Lys Leu Asp
1               5

<210> SEQ ID NO 30
<211> LENGTH: 11
<212> TYPE: PRT
<213> ORGANISM: Homo sapiens

<400> SEQUENCE: 30

Arg Gln Arg Arg Asn Glu Leu Lys Arg Ser Pro
1               5                   10

<210> SEQ ID NO 31
<211> LENGTH: 38
<212> TYPE: PRT
<213> ORGANISM: Homo sapiens

<400> SEQUENCE: 31

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 32
<211> LENGTH: 42
<212> TYPE: PRT
<213> ORGANISM: Homo sapiens

<400> SEQUENCE: 32

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 33
<211> LENGTH: 8
<212> TYPE: PRT
<213> ORGANISM: Homo sapiens

<400> SEQUENCE: 33

Val Ser Arg Lys Arg Pro Arg Pro
1               5

<210> SEQ ID NO 34
<211> LENGTH: 8
<212> TYPE: PRT
<213> ORGANISM: Homo sapiens

<400> SEQUENCE: 34

Pro Pro Lys Lys Ala Arg Glu Asp
1               5

<210> SEQ ID NO 35
<211> LENGTH: 8
<212> TYPE: PRT
<213> ORGANISM: Homo sapiens
```

```
<400> SEQUENCE: 35

Pro Gln Pro Lys Lys Pro Leu
1               5

<210> SEQ ID NO 36
<211> LENGTH: 12
<212> TYPE: PRT
<213> ORGANISM: Mus sp.

<400> SEQUENCE: 36

Ser Ala Leu Ile Lys Lys Lys Lys Lys Met Ala Pro
1               5                   10

<210> SEQ ID NO 37
<211> LENGTH: 5
<212> TYPE: PRT
<213> ORGANISM: Influenza virus

<400> SEQUENCE: 37

Asp Arg Leu Arg Arg
1               5

<210> SEQ ID NO 38
<211> LENGTH: 7
<212> TYPE: PRT
<213> ORGANISM: Influenza virus

<400> SEQUENCE: 38

Pro Lys Gln Lys Lys Arg Lys
1               5

<210> SEQ ID NO 39
<211> LENGTH: 10
<212> TYPE: PRT
<213> ORGANISM: Hepatitis D virus

<400> SEQUENCE: 39

Arg Lys Leu Lys Lys Ile Lys Lys Leu
1               5                   10

<210> SEQ ID NO 40
<211> LENGTH: 10
<212> TYPE: PRT
<213> ORGANISM: Mus sp.

<400> SEQUENCE: 40

Arg Glu Lys Lys Lys Phe Leu Lys Arg Arg
1               5                   10

<210> SEQ ID NO 41
<211> LENGTH: 20
<212> TYPE: PRT
<213> ORGANISM: Homo sapiens

<400> SEQUENCE: 41

Lys Arg Lys Gly Asp Glu Val Asp Gly Val Asp Glu Val Ala Lys Lys
1               5                   10                  15

Lys Ser Lys Lys
            20

<210> SEQ ID NO 42
<211> LENGTH: 17
<212> TYPE: PRT
<213> ORGANISM: Homo sapiens
```

-continued

<400> SEQUENCE: 42

Arg Lys Cys Leu Gln Ala Gly Met Asn Leu Glu Ala Arg Lys Thr Lys
1               5                   10                  15

Lys

<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43

Leu Tyr Pro Glu Arg Leu Arg Arg Ile Leu Thr
1               5                   10

<210> SEQ ID NO 44
<211> LENGTH: 33
<212> TYPE: PRT
<213> ORGANISM: Artificial Sequene
<220> FEATURE:
<223> OTHER INFORMATION: Synthetic

<400> SEQUENCE: 44

Cys Thr Gly Thr Ala Cys Cys Thr Gly Ala Gly Cys Gly Gly Cys
1               5                   10                  15

Thr Gly Cys Gly Gly Cys Gly Gly Ala Thr Cys Cys Thr Gly Ala Cys
            20                  25                  30

Cys

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Gly Gly Gly Gly Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic

<400> SEQUENCE: 46

Gly Gly Gly Gly Ser Gly Gly Gly Gly Ser
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

Gly Gly Gly Gly Ser Gly Gly Gly Gly Ser Gly Gly Gly Gly Ser
1               5                   10                  15

```
<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Glu Asn Leu Tyr Phe Gln Gly
1               5

<210> SEQ ID NO 49
<211> LENGTH: 299
<212> TYPE: PRT
<213> ORGANISM: Artificial Sequence
<220> FEATURE:
<223> OTHER INFORMATION: Synthetic

<400> SEQUENCE: 49

Met Arg Lys Leu Leu Phe Ile Ile Leu Ile Pro Phe Leu Gly Ile Ala
1               5                   10                  15

Gln Asp Phe Thr Ala Asn Arg Ile Lys Tyr Thr Val Thr Ser Ser Thr
            20                  25                  30

Ala Pro Phe Thr Val Lys Val Ala Arg Asn Ala Asn Phe Thr Gly Ala
        35                  40                  45

Ala Glu Ile Pro Glu Thr Val Val Tyr Asn Ser Glu Asn Tyr Ala Val
50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
            100                 105                 110

Ile Gly Asn Ser Ala Phe Ile Gly Ser Ser Leu Thr Ser Leu Thr Ile
        115                 120                 125

Gly Asn Ser Val Ala Ser Ile Gly Ser Phe Ala Phe Phe Gly Cys Phe
    130                 135                 140

Gly Leu Thr Ser Leu Thr Ile Pro Ser Ser Val Thr Ser Ile Ala Asn
145                 150                 155                 160

Gln Ala Phe Ser Glu Cys Thr Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala Val Thr Ser Ile Gly Asp Tyr Thr
        195                 200                 205

Phe Ser Asn Cys Thr Ser Leu Thr Thr Val Asn Ser Tyr Ala Thr Ile
    210                 215                 220

Pro Leu Val Ile Asn Glu Asn Ala Phe His Asn Leu Asp Lys Ser Ile
225                 230                 235                 240

Cys Ala Leu Asn Val Pro Ala Gly Thr Glu Ala Ala Tyr Gln Ala Ala
                245                 250                 255

Ala Val Trp Lys Asp Phe Ser Pro Ile Ser Gly Ser Leu Leu Ser Asn
            260                 265                 270

Leu Ser Ser Phe Ala Lys Gly Asn Tyr Phe Val Glu Val Met Thr Asn
        275                 280                 285

Gln Gly Lys Ala Thr Lys Thr Ile Ile Ile Gln
    290                 295
```

<210> SEQ ID NO 50
<211> LENGTH: 351
<212> TYPE: PRT
<213> ORGANISM: Artificial Sequence
<220> FEATURE:
<223> OTHER INFORMATION: Synthetic

<400> SEQUENCE: 50

```
Met Arg Lys Leu Leu Phe Ile Ile Leu Ile Pro Phe Leu Gly Ile Ala
1               5                   10                  15

Gln Asp Phe Thr Ala Asn Gly Ile Asn Tyr Thr Val Thr Ser Ser Thr
                20                  25                  30

Ala Pro Phe Thr Ala Ser Val Ala Ser Asn Thr Arg Phe Ser Gly Asp
            35                  40                  45

Ala Val Ile Pro Glu Thr Val Val Tyr Asn Ser Glu Asn Tyr Ala Val
        50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
                100                 105                 110

Ile Gly Asn Ser Ala Phe Ile Gly Ser Ser Leu Thr Ser Leu Thr Ile
            115                 120                 125

Gly Asn Ser Val Ala Ser Ile Gly Ser Phe Ala Phe Phe Gly Cys Phe
        130                 135                 140

Gly Leu Thr Ser Leu Thr Ile Pro Ser Ser Val Thr Ser Ile Ala Asn
145                 150                 155                 160

Gln Ala Phe Ser Glu Cys Thr Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala Val Thr Ser Ile Gly Asp Tyr Thr
        195                 200                 205

Phe Ser Asn Cys Thr Ser Leu Thr Thr Val Asn Ser Tyr Ala Thr Ile
    210                 215                 220

Pro Leu Val Ile Asn Glu Asn Ala Phe His Asn Leu Asp Lys Ser Ile
225                 230                 235                 240

Cys Ala Leu Asn Val Pro Ala Gly Thr Glu Ala Ala Tyr Gln Ala Ala
                245                 250                 255

Ala Val Trp Lys Asp Phe Ser Pro Ile Ser Gly Ser Leu Leu Ser Asn
            260                 265                 270

His Ser Phe Ala Ile Glu Ser Asn Leu Lys Ile Tyr Pro Asn Pro Val
        275                 280                 285

Ser Glu Ile Leu Asn Ile Ala Leu Gln Glu Asn Leu Gln Leu Gln Lys
    290                 295                 300

Val Asn Phe Tyr Asn Thr Leu Gly Gln Leu Ile Lys Thr Thr Asn His
305                 310                 315                 320

Ser Glu Ile Asn Ile Ser Ser Phe Ala Lys Gly Ile Tyr Phe Val Glu
                325                 330                 335

Val Met Thr Asn Gln Gly Lys Ala Thr Lys Thr Ile Ile Val Gln
            340                 345                 350
```

<210> SEQ ID NO 51
<211> LENGTH: 351

<212> TYPE: PRT
<213> ORGANISM: Artificial Sequence
<220> FEATURE:
<223> OTHER INFORMATION: Synthetic

<400> SEQUENCE: 51

Met Arg Lys Leu Leu Phe Ile Ile Leu Ile Pro Phe Leu Gly Ile Ala
1               5                   10                  15

Gln Asp Phe Thr Ala Asn Gly Ile Asn Tyr Thr Val Thr Ser Ser Thr
            20                  25                  30

Ala Pro Phe Thr Ala Ser Val Ala Ser Asn Thr Arg Phe Ser Gly Asp
        35                  40                  45

Ala Val Ile Pro Glu Thr Val Val Tyr Asn Ser Glu Asn Tyr Ala Val
    50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
            100                 105                 110

Ile Gly Asn Ser Ala Phe Ile Gly Ser Ser Leu Thr Ser Leu Thr Ile
        115                 120                 125

Gly Asn Ser Val Ala Ser Ile Gly Ser Phe Ala Phe Phe Gly Cys Phe
    130                 135                 140

Gly Leu Thr Ser Leu Thr Ile Pro Ser Ser Val Thr Ser Ile Ala Asn
145                 150                 155                 160

Gln Ala Phe Ser Glu Cys Thr Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala Val Thr Ser Ile Gly Asp Tyr Thr
        195                 200                 205

Phe Ser Asn Cys Thr Ser Leu Thr Thr Val Asn Ser Tyr Ala Thr Ile
    210                 215                 220

Pro Leu Val Ile Asn Glu Asn Ala Phe His Asn Leu Asp Lys Ser Ile
225                 230                 235                 240

Cys Ala Leu Asn Val Pro Ala Gly Thr Glu Ala Ala Tyr Gln Ala Ala
                245                 250                 255

Ala Val Trp Lys Asp Phe Ser Pro Ile Ser Gly Ser Leu Leu Ser Asn
            260                 265                 270

His Ser Phe Ala Ile Glu Ser Asn Leu Lys Ile Tyr Pro Asn Pro Val
        275                 280                 285

Ser Glu Ile Leu Asn Ile Ala Leu Gln Glu Asn Leu Gln Leu Gln Lys
    290                 295                 300

Val Asn Phe Tyr Asn Thr Leu Gly Gln Leu Ile Lys Thr Thr Asn His
305                 310                 315                 320

Ser Glu Ile Asn Ile Ser Ser Phe Ala Lys Gly Ile Tyr Phe Val Glu
                325                 330                 335

Val Met Thr Asn Gln Gly Lys Ala Thr Lys Thr Ile Ile Val Gln
            340                 345                 350

<210> SEQ ID NO 52
<211> LENGTH: 351
<212> TYPE: PRT
<213> ORGANISM: Artificial Sequence
<220> FEATURE:

<223> OTHER INFORMATION: Synthetic

<400> SEQUENCE: 52

```
Met Arg Lys Leu Leu Phe Ile Ile Leu Met Pro Phe Leu Gly Ile Ala
1               5                   10                  15

Gln Asp Phe Thr Glu Asn Gly Ile Asn Tyr Thr Ile Thr Ser Ser Thr
            20                  25                  30

Ala Pro Phe Thr Ala Ser Val Ala Ser Asn Thr Arg Phe Ser Gly Asp
        35                  40                  45

Ala Val Ile Pro Glu Thr Val Val Tyr Asn Ser Glu Asn Tyr Ala Val
    50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Ile Ser
            100                 105                 110

Ile Gly Asn Ser Ala Phe Ile Gly Ser Ser Leu Thr Ser Leu Thr Ile
        115                 120                 125

Gly Asn Ser Val Ala Ser Ile Gly Ser Leu Ala Phe Phe Gly Cys Phe
    130                 135                 140

Gly Leu Thr Ser Leu Thr Ile Pro Ser Ser Val Thr Ser Ile Ala Asn
145                 150                 155                 160

Gln Ala Phe Ser Met Cys Ser Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala Val Thr Ser Ile Gly Asp Tyr Thr
        195                 200                 205

Phe Met Asn Cys Thr Ser Leu Thr Thr Val Asn Ser Tyr Ala Thr Ile
    210                 215                 220

Pro Leu Val Ile Asn Glu Asn Ala Phe His Asn Leu Asp Lys Ser Ile
225                 230                 235                 240

Cys Ala Leu Asn Val Pro Ala Gly Thr Glu Ala Ala Tyr Gln Ala Ala
                245                 250                 255

Ala Val Trp Lys Asp Phe Ser Pro Ile Ser Gly Ser Leu Leu Ser Asn
            260                 265                 270

His Ser Phe Ala Ile Glu Ser Asn Leu Lys Ile Tyr Pro Asn Pro Val
        275                 280                 285

Ser Glu Ile Leu Asn Ile Ala Leu Gln Glu Asn Leu Gln Leu Gln Lys
    290                 295                 300

Val Asn Phe Tyr Asn Thr Leu Gly Gln Leu Ile Lys Thr Thr Asn His
305                 310                 315                 320

Ser Glu Ile Asn Ile Ser Ser Phe Ala Lys Gly Ile Tyr Phe Val Glu
                325                 330                 335

Val Met Thr Asn Gln Gly Lys Ala Thr Lys Thr Ile Ile Val Gln
            340                 345                 350
```

<210> SEQ ID NO 53
<211> LENGTH: 351
<212> TYPE: PRT
<213> ORGANISM: Artificial Sequence
<220> FEATURE:
<223> OTHER INFORMATION: Synthetic

<400> SEQUENCE: 53

Met Arg Lys Leu Leu Phe Ile Ile Leu Ile Pro Phe Leu Gly Ile Ala
1               5                   10                  15

Gln Asp Phe Thr Glu Asn Gly Ile Asn Tyr Thr Ile Thr Ser Ser Thr
                20                  25                  30

Ala Pro Phe Thr Ala Ser Val Ala Ser Asn Thr Arg Phe Ser Gly Asp
            35                  40                  45

Ala Val Ile Pro Glu Thr Val Val Tyr Asn Ser Glu Asn Tyr Ala Val
        50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
            100                 105                 110

Ile Gly Asn Ser Ala Phe Ile Gly Ser Ser Leu Thr Ser Leu Thr Ile
        115                 120                 125

Gly Asn Ser Val Ala Ser Ile Gly Ser Phe Ala Phe Phe Gly Cys Phe
130                 135                 140

Gly Leu Thr Ser Leu Thr Ile Pro Ser Ser Val Thr Ser Ile Ala Asn
145                 150                 155                 160

Gln Ala Phe Ser Met Cys Ser Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala Val Thr Ser Ile Gly Asp Tyr Thr
        195                 200                 205

Phe Ser Asn Cys Thr Ser Leu Thr Thr Val Asn Ser Tyr Ala Thr Ile
210                 215                 220

Pro Leu Val Ile Asn Glu Asn Ala Phe His Asn Leu Asp Lys Ser Ile
225                 230                 235                 240

Cys Ala Leu Asn Val Pro Ala Gly Thr Glu Ala Ala Tyr Gln Ala Ala
                245                 250                 255

Ala Val Trp Lys Asp Phe Ser Pro Ile Ser Gly Ser Leu Leu Ser Asn
            260                 265                 270

His Ser Phe Ala Ile Glu Ser Asn Leu Lys Ile Tyr Pro Asn Pro Val
        275                 280                 285

Ser Glu Ile Leu Asn Ile Ala Leu Gln Glu Asn Leu Gln Leu Gln Lys
290                 295                 300

Val Asn Phe Tyr Asn Thr Leu Gly Gln Leu Ile Lys Thr Thr Asn His
305                 310                 315                 320

Ser Glu Ile Asn Ile Ser Ser Phe Ala Lys Gly Ile Tyr Phe Val Glu
                325                 330                 335

Val Met Thr Asn Gln Gly Lys Ala Thr Lys Thr Ile Ile Val Gln
            340                 345                 350

<210> SEQ ID NO 54
<211> LENGTH: 329
<212> TYPE: PRT
<213> ORGANISM: Artificial Sequence
<220> FEATURE:
<223> OTHER INFORMATION: Synthetic

<400> SEQUENCE: 54

Met Arg Lys Leu Leu Phe Val Ile Leu Met Pro Phe Leu Gly Ile Ala
1               5                   10                  15

```
Gln Asn Phe Thr Ala Asn Gly Ile Asn Tyr Thr Val Thr Ser Ser Val
            20                  25                  30

Ala Pro Phe Thr Val Ser Val Ser Asp Asn Thr Arg Phe Ser Gly Val
        35                  40                  45

Ala Val Ile Pro Glu Thr Val Ala Tyr Asn Ser Glu Asn Tyr Ala Val
    50                  55                  60

Thr Ala Ile Thr Ala Ser Ala Phe Lys Ser Cys Ser Gly Leu Thr Ser
65                  70                  75                  80

Val Thr Ile Gly Asn Phe Ile Thr Ser Ile Glu Arg Asp Ala Phe Arg
                85                  90                  95

Asp Ser Thr Asn Leu Thr Thr Val Thr Ile Gly Asn Ser Val Asn Ser
            100                 105                 110

Ile Glu Arg Phe Ala Phe Asn Asn Cys Ser Arg Leu Thr Ser Ile Thr
        115                 120                 125

Ile Pro Asp Ser Val Thr Ala Ile Arg Asn Ser Ala Phe Ala Ser Cys
    130                 135                 140

Thr Gly Leu Thr Ser Val Thr Phe Pro Asn Ser Val Ser Phe Ile Asp
145                 150                 155                 160

Ala Phe Ala Phe Ser Arg Cys Thr Asn Leu Thr Ser Val Thr Ile Pro
                165                 170                 175

Asn Ser Val Thr His Ile Gly Gly Tyr Ala Phe Asn Asn Cys Ser Ser
            180                 185                 190

Leu Thr Thr Val Asn Cys Tyr Ile Thr Thr Pro Leu Ala Ile Asn Val
        195                 200                 205

Thr Thr Phe Arg Lys Val Asn Lys Ser Thr Cys Ala Leu Asn Val Pro
    210                 215                 220

Ala Gly Thr Glu Ala Ala Tyr Gln Ala Ala Val Trp Lys Asp Phe
225                 230                 235                 240

Ser Pro Ile Ser Gly Ser Leu Leu Ser Asn His Ser Phe Ala Ile Glu
                245                 250                 255

Ser Ala Leu Lys Ile Tyr Pro Asn Pro Val Ser Glu Ile Leu Asn Ile
            260                 265                 270

Ala Leu Gln Glu Asp Leu Gln Leu Glu Lys Val Asn Phe Tyr Asn Thr
        275                 280                 285

Leu Gly Gln Leu Ile Lys Thr Thr Asn His Ser Gly Ile Asn Val Ser
    290                 295                 300

Ser Phe Ala Lys Gly Asn Tyr Phe Val Glu Ile Met Thr Asn Gln Gly
305                 310                 315                 320

Lys Val Thr Lys Thr Ile Ile Val Gln
                325

<210> SEQ ID NO 55
<211> LENGTH: 329
<212> TYPE: PRT
<213> ORGANISM: Artificial Sequence
<220> FEATURE:
<223> OTHER INFORMATION: Synthetic

<400> SEQUENCE: 55

Met Arg Lys Leu Leu Phe Val Ile Leu Met Pro Phe Leu Gly Ile Ala
1               5                   10                  15

Gln Asn Phe Thr Ala Asn Gly Ile Asn Tyr Thr Val Thr Ser Ser Val
            20                  25                  30

Ala Pro Phe Thr Val Ser Val Ser Asp Asn Thr Arg Phe Ser Gly Val
        35                  40                  45
```

```
Ala Val Ile Pro Glu Thr Val Ala Tyr Asn Ser Glu Asn Tyr Ala Val
     50                  55                  60

Thr Ala Ile Thr Ala Ser Ala Phe Lys Ser Cys Ser Gly Leu Thr Ser
 65                  70                  75                  80

Val Thr Ile Gly Asn Phe Ile Thr Ser Ile Glu Arg Asp Ala Phe Arg
                 85                  90                  95

Asp Ser Thr Asn Leu Thr Thr Val Thr Ile Gly Asn Ser Val Asn Ser
                100                 105                 110

Ile Glu Arg Phe Ala Phe Asn Asn Cys Ser Arg Leu Thr Ser Ile Thr
            115                 120                 125

Ile Pro Asp Ser Val Thr Ala Ile Arg Asn Ser Ala Phe Ala Ser Cys
        130                 135                 140

Thr Gly Leu Thr Ser Val Thr Phe Pro Asn Ser Val Ser Phe Ile Asp
145                 150                 155                 160

Ala Phe Ala Phe Ser Arg Cys Thr Asn Leu Thr Ser Val Thr Ile Pro
                165                 170                 175

Asn Ser Val Thr His Ile Gly Gly Tyr Ala Phe Asn Asn Cys Ser Ser
            180                 185                 190

Leu Thr Thr Val Asn Cys Tyr Ile Thr Thr Pro Leu Ala Ile Asn Val
        195                 200                 205

Thr Thr Phe Arg Lys Val Asn Lys Ser Thr Cys Ala Leu Asn Val Pro
    210                 215                 220

Ala Gly Thr Glu Ala Ala Tyr Gln Ala Ala Val Trp Lys Asp Phe
225                 230                 235                 240

Ser Pro Ile Ser Gly Ser Leu Leu Ser Asn His Ser Phe Ala Ile Glu
                245                 250                 255

Ser Ala Leu Lys Ile Tyr Pro Asn Pro Val Ser Glu Ile Leu Asn Ile
            260                 265                 270

Ala Leu Gln Glu Asp Leu Gln Leu Glu Lys Val Asn Phe Tyr Asn Thr
        275                 280                 285

Leu Gly Gln Leu Ile Lys Thr Thr Asn His Ser Gly Ile Asn Val Ser
    290                 295                 300

Ser Phe Ala Lys Gly Asn Tyr Phe Val Glu Ile Met Thr Asn Gln Gly
305                 310                 315                 320

Lys Val Thr Lys Thr Ile Ile Val Gln
                325

<210> SEQ ID NO 56
<211> LENGTH: 328
<212> TYPE: PRT
<213> ORGANISM: Artificial Sequence
<220> FEATURE:
<223> OTHER INFORMATION: Synthetic

<400> SEQUENCE: 56

Met Arg Lys Leu Leu Phe Ile Ile Leu Met Pro Phe Leu Gly Ile Ala
  1               5                  10                  15

Gln Asn Phe Thr Ala Asn Gly Ile Asn Tyr Thr Val Thr Ser Ser Thr
                 20                  25                  30

Val Pro Leu Thr Val Ser Val Ala Asn Asn Thr Arg Phe Thr Gly Val
             35                  40                  45

Ala Glu Ile Pro Glu Ile Val Val Tyr Asn Ser Glu Asn Tyr Ala Val
         50                  55                  60

Thr Ala Ile Arg Val Asn Ala Phe Asn Gly Ser Arg Leu Thr Ser Ile
 65                  70                  75                  80
```

```
Thr Ile Pro Asn Ser Val Thr Ala Ile Gly Lys Phe Ala Phe Tyr Asn
                85                  90                  95

Cys Thr Arg Leu Ile Ser Ile Ser Ile Pro Asn Ser Val Thr Ser Ile
            100                 105                 110

Glu Glu Gly Thr Phe Ser Phe Cys Thr Gly Leu Ile Ser Ile Thr Ile
            115                 120                 125

Pro Asn Ser Val Thr Val Ile Gly Lys Lys Ala Phe Ser Glu Cys Leu
        130                 135                 140

Gly Leu Thr Ser Val Thr Phe Pro Asn Ala Leu Ala Thr Ile Gly Ser
145                 150                 155                 160

Tyr Cys Phe Tyr Phe Cys Thr Ser Leu Thr Ser Val Thr Ile Pro Asn
                165                 170                 175

Ser Val Thr Asp Ile Gly Val Gly Ala Phe Tyr Asp Cys Thr Ser Leu
            180                 185                 190

Ser Thr Val Asn Cys Gln Ile Thr Thr Pro Leu Val Ile Asn Val Thr
            195                 200                 205

Thr Phe Arg Lys Val Asn Lys Ser Thr Cys Ala Leu Asn Val Pro Ala
        210                 215                 220

Gly Thr Glu Ala Ala Tyr Gln Ala Ala Val Trp Lys Asp Phe Ser
225                 230                 235                 240

Leu Ile Tyr Gly Ser Leu Leu Ser Asn His Ser Phe Ala Ile Glu Ser
                245                 250                 255

Asn Leu Lys Ile Tyr Pro Asn Pro Val Ser Glu Ile Leu Asn Ile Ala
            260                 265                 270

Leu Gln Glu Asp Leu Gln Leu Glu Lys Val Asn Phe Tyr Asn Thr Leu
        275                 280                 285

Gly Gln Leu Ile Lys Thr Thr Asn His Ser Gly Ile Asn Val Ser Ser
290                 295                 300

Phe Thr Lys Gly Asn Tyr Phe Val Glu Ile Met Thr Asn Gln Gly Lys
305                 310                 315                 320

Val Thr Lys Thr Ile Ile Val Gln
                325

<210> SEQ ID NO 57
<211> LENGTH: 328
<212> TYPE: PRT
<213> ORGANISM: Artificial Sequence
<220> FEATURE:
<223> OTHER INFORMATION: Synthetic

<400> SEQUENCE: 57

Met Arg Lys Leu Leu Phe Ile Ile Leu Met Pro Phe Leu Gly Ile Ala
1               5                   10                  15

Gln Asn Phe Thr Ala Asn Gly Ile Asn Tyr Thr Val Thr Ser Ser Thr
            20                  25                  30

Val Pro Leu Thr Val Ser Val Ala Asn Asn Thr Arg Phe Thr Gly Val
        35                  40                  45

Ala Glu Ile Pro Glu Ile Val Val Tyr Asn Ser Glu Asn Tyr Ala Val
    50                  55                  60

Thr Ala Ile Arg Val Asn Ala Phe Asn Gly Ser Arg Leu Thr Ser Ile
65                  70                  75                  80

Thr Ile Pro Asn Ser Val Thr Ala Ile Gly Lys Phe Ala Phe Tyr Asn
                85                  90                  95

Cys Thr Arg Leu Ile Ser Ile Ser Ile Pro Asn Ser Val Thr Ser Ile
            100                 105                 110
```

```
Glu Glu Gly Thr Phe Ser Phe Cys Thr Gly Leu Ile Ser Ile Thr Ile
            115                 120                 125

Pro Asn Ser Val Thr Val Ile Gly Lys Lys Ala Phe Ser Glu Cys Leu
        130                 135                 140

Gly Leu Thr Ser Val Thr Phe Pro Asn Ala Leu Ala Thr Ile Gly Ser
145                 150                 155                 160

Tyr Cys Phe Tyr Phe Cys Thr Ser Leu Thr Ser Val Thr Ile Pro Asn
                165                 170                 175

Ser Val Thr Asp Ile Gly Val Gly Ala Phe Tyr Asp Cys Thr Ser Leu
            180                 185                 190

Ser Thr Val Asn Cys Gln Ile Thr Thr Pro Leu Val Ile Asn Val Thr
        195                 200                 205

Thr Phe Arg Lys Val Asn Lys Ser Thr Cys Ala Leu Asn Val Pro Ala
        210                 215                 220

Gly Thr Glu Ala Ala Tyr Gln Ala Ala Val Trp Lys Asp Phe Ser
225                 230                 235                 240

Leu Ile Tyr Gly Ser Leu Leu Ser Asn His Ser Phe Ala Ile Glu Ser
                245                 250                 255

Asn Leu Lys Ile Tyr Pro Asn Pro Val Ser Glu Ile Leu Asn Ile Ala
            260                 265                 270

Leu Gln Glu Asp Leu Gln Leu Glu Lys Val Asn Phe Tyr Asn Thr Leu
        275                 280                 285

Gly Gln Leu Ile Lys Thr Thr Asn His Ser Glu Ile Asn Val Ser Ser
        290                 295                 300

Phe Thr Lys Gly Asn Tyr Phe Val Glu Ile Met Thr Asn Gln Gly Lys
305                 310                 315                 320

Val Thr Lys Thr Ile Ile Val Gln
                325

<210> SEQ ID NO 58
<211> LENGTH: 328
<212> TYPE: PRT
<213> ORGANISM: Artificial Sequence
<220> FEATURE:
<223> OTHER INFORMATION: Synthetic

<400> SEQUENCE: 58

Met Arg Lys Leu Leu Phe Ile Ile Leu Met Pro Phe Leu Gly Ile Ala
1               5                   10                  15

Gln Asn Phe Thr Ala Asn Gly Ile Asn Tyr Thr Val Thr Ser Ser Thr
            20                  25                  30

Val Pro Leu Thr Val Ser Val Ala Asn Asn Thr Arg Phe Thr Gly Val
        35                  40                  45

Ala Glu Ile Pro Glu Ile Val Val Tyr Asn Ser Glu Asn Tyr Ala Val
    50                  55                  60

Thr Ala Ile Arg Val Asn Ala Phe Asn Gly Ser Arg Leu Thr Ser Ile
65                  70                  75                  80

Thr Ile Pro Asn Ser Val Thr Ala Ile Gly Lys Phe Ala Phe Tyr Asn
                85                  90                  95

Cys Thr Arg Leu Ile Ser Ile Ser Ile Pro Asn Ser Val Thr Ser Ile
            100                 105                 110

Glu Glu Gly Thr Phe Ser Phe Cys Thr Gly Leu Ile Ser Ile Thr Ile
        115                 120                 125

Pro Asn Ser Val Thr Val Ile Gly Lys Lys Ala Phe Ser Glu Cys Leu
        130                 135                 140
```

```
Gly Leu Thr Ser Val Thr Phe Pro Asn Ala Leu Ala Thr Ile Gly Ser
145                 150                 155                 160

His Cys Phe Tyr Phe Cys Thr Ser Leu Thr Ser Val Thr Ile Pro Asn
                165                 170                 175

Ser Val Thr Asp Ile Gly Val Gly Ala Phe Tyr Asp Cys Thr Ser Leu
            180                 185                 190

Ser Thr Val Asn Cys Gln Ile Thr Thr Pro Leu Val Ile Asn Ala Thr
        195                 200                 205

Ala Phe Arg Lys Val Asn Lys Ser Thr Cys Arg Leu Asn Val Pro Ala
    210                 215                 220

Gly Thr Glu Ala Ala Tyr Gln Ala Ala Val Trp Lys Asp Phe Ser
225                 230                 235                 240

Leu Ile Tyr Gly Ser Leu Leu Ser Asn His Ser Phe Ala Ile Glu Ser
                245                 250                 255

Asn Leu Lys Ile Tyr Pro Asn Pro Val Ser Glu Ile Leu Asn Ile Ala
            260                 265                 270

Leu Gln Glu Asp Leu Gln Leu Glu Lys Val Asn Phe Tyr Asn Thr Leu
        275                 280                 285

Gly Gln Leu Ile Lys Thr Thr Asn His Ser Glu Ile Asn Val Ser Ser
290                 295                 300

Phe Thr Lys Gly Asn Tyr Phe Val Glu Ile Met Thr Asn Gln Gly Lys
305                 310                 315                 320

Val Thr Lys Thr Ile Ile Val Gln
            325

<210> SEQ ID NO 59
<211> LENGTH: 282
<212> TYPE: PRT
<213> ORGANISM: Artificial Sequence
<220> FEATURE:
<223> OTHER INFORMATION: Synthetic

<400> SEQUENCE: 59

Met Arg Lys Leu Leu Phe Ile Ile Leu Ile Pro Phe Leu Gly Ile Ala
1               5                   10                  15

Gln Asp Phe Thr Ala Asn Gly Ile Lys Tyr Thr Val Thr Ser Ser Arg
                20                  25                  30

Thr Pro Phe Thr Val Lys Val Ala Arg Asn Ala Gly Phe Thr Gly Val
            35                  40                  45

Ala Glu Ile Pro Glu Thr Val Ala Tyr Asn Ser Lys Asn Tyr Ala Val
    50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
                85                  90                  95

Cys Thr Asp Leu Thr Ser Val Thr Ile Pro Asn Ala Val Ala Thr Ile
            100                 105                 110

Gly Glu Asn Cys Phe Tyr Ser Cys Lys Lys Leu Arg Ser Leu Thr Ile
        115                 120                 125

Pro Asn Ser Leu Thr Val Ile Gly Asn Gly Ala Phe Ser Glu Cys Thr
    130                 135                 140

Gly Leu Arg Thr Val Asn Cys Gln Ile Thr Ile Pro Phe Ala Ile Asn
145                 150                 155                 160

Thr Asn Thr Phe Tyr Asn Leu Asn Arg Ser Ile Cys Ala Leu Asn Val
                165                 170                 175
```

```
Pro Pro Gly Thr Glu Ala Ala Tyr Lys Ala Ala Ala Val Trp Lys Asp
            180                 185                 190

Phe Ser Pro Ile Ser Gly Gly Phe Leu Ser Ser Asn Ser Phe Ala Ile
        195                 200                 205

Glu Ser Asn Leu Lys Ile Tyr Pro Asn Pro Val Ser Glu Ile Leu Asn
    210                 215                 220

Ile Ala Leu Gln Glu Asp Ile Gln Leu Glu Lys Val Asn Phe Tyr Asn
225                 230                 235                 240

Thr Leu Gly Gln Leu Ile Lys Thr Thr Asn His Ser Glu Ile Asn Val
            245                 250                 255

Ser Ser Phe Ala Lys Gly Asn Tyr Phe Val Glu Ile Met Thr Asn Gln
            260                 265                 270

Gly Lys Val Thr Lys Thr Ile Ile Ile Gln
            275                 280

<210> SEQ ID NO 60
<211> LENGTH: 282
<212> TYPE: PRT
<213> ORGANISM: Artificial Sequence
<220> FEATURE:
<223> OTHER INFORMATION: Synthetic

<400> SEQUENCE: 60

Met Arg Lys Leu Leu Phe Ile Ile Leu Ile Pro Phe Leu Gly Ile Ala
1               5                   10                  15

Gln Asp Phe Thr Ala Asn Gly Ile Lys Tyr Thr Val Thr Ser Ser Arg
            20                  25                  30

Thr Pro Phe Thr Val Lys Val Ala Arg Asn Ala Gly Phe Thr Gly Val
        35                  40                  45

Ala Glu Ile Pro Glu Thr Val Ala Tyr Asn Ser Lys Asn Tyr Ala Val
    50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
            85                  90                  95

Cys Thr Asp Leu Thr Ser Val Thr Ile Pro Asn Ala Val Ala Thr Ile
            100                 105                 110

Gly Lys His Cys Phe Tyr Ser Cys Lys Lys Leu Arg Ser Leu Thr Ile
            115                 120                 125

Pro Asn Ser Leu Thr Val Ile Gly Asn Gly Ala Phe Ser Glu Cys Thr
    130                 135                 140

Gly Leu Arg Thr Val Asn Cys Gln Ile Thr Ile Pro Phe Ala Ile Asn
145                 150                 155                 160

Thr Asn Thr Phe Tyr Asn Leu Asn Arg Ser Ile Cys Ala Leu Asn Val
            165                 170                 175

Pro Pro Gly Thr Glu Ala Ala Tyr Lys Ala Ala Ala Val Trp Lys Asp
            180                 185                 190

Phe Ser Pro Ile Ser Gly Gly Phe Leu Ser Ser Asn Ser Phe Ala Ile
        195                 200                 205

Glu Ser Asn Leu Lys Ile Tyr Pro Asn Pro Ala Ser Glu Ile Leu Asn
    210                 215                 220

Ile Ala Leu Gln Glu Gly Leu Gln Leu Glu Lys Val Asn Phe Tyr Asn
225                 230                 235                 240

Thr Leu Gly Gln Leu Ile Lys Thr Thr Asn His Ser Glu Ile Asn Val
            245                 250                 255
```

```
Ser Ser Phe Ala Lys Gly Asn Tyr Phe Val Glu Val Met Thr Asn Gln
        260                 265                 270

Gly Lys Val Thr Lys Ser Val Ile Ile Gln
        275                 280

<210> SEQ ID NO 61
<211> LENGTH: 282
<212> TYPE: PRT
<213> ORGANISM: Artificial Sequence
<220> FEATURE:
<223> OTHER INFORMATION: Synthetic

<400> SEQUENCE: 61

Met Arg Lys Leu Leu Phe Ile Ile Leu Ile Pro Phe Leu Gly Ile Ala
1               5                   10                  15

Gln Asp Phe Thr Ala Asn Gly Ile Lys Tyr Thr Val Thr Ser Ser Arg
            20                  25                  30

Thr Pro Phe Thr Val Lys Val Ala Arg Asn Ala Gly Phe Thr Gly Val
        35                  40                  45

Ala Glu Ile Pro Glu Thr Val Ala Tyr Asn Ser Lys Asn Tyr Ala Val
    50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
                85                  90                  95

Cys Thr Asp Leu Thr Ser Val Thr Ile Pro Asn Ala Val Ala Thr Ile
            100                 105                 110

Gly Glu Asn Cys Phe Tyr Ser Cys Lys Lys Leu Arg Ser Leu Thr Ile
        115                 120                 125

Pro Asn Ser Leu Thr Val Ile Gly Asn Gly Ala Phe Ser Glu Cys Thr
    130                 135                 140

Gly Leu Arg Thr Val Asn Cys Gln Ile Thr Ile Pro Phe Ala Ile Asn
145                 150                 155                 160

Thr Asn Thr Phe Tyr Asn Leu Asn Arg Ser Ile Cys Ala Leu Asn Val
                165                 170                 175

Pro Pro Gly Thr Glu Ala Ala Tyr Lys Ala Ala Ala Val Trp Lys Asp
            180                 185                 190

Phe Ser Pro Ile Ser Gly Gly Phe Leu Ser Ser Asn Ser Phe Ala Ile
        195                 200                 205

Glu Ser Asn Leu Lys Ile Tyr Pro Asn Pro Val Ser Glu Ile Leu Asn
    210                 215                 220

Ile Ala Leu Gln Glu Gly Leu Gln Leu Glu Lys Val Asn Phe Tyr Asn
225                 230                 235                 240

Thr Leu Gly Gln Leu Ile Lys Thr Thr Asn His Ser Glu Ile Asn Val
                245                 250                 255

Ser Ser Phe Ala Lys Gly Asn Tyr Phe Val Glu Ile Met Thr Asn Gln
            260                 265                 270

Gly Lys Ala Thr Lys Ser Val Ile Ile Gln
        275                 280

<210> SEQ ID NO 62
<211> LENGTH: 282
<212> TYPE: PRT
<213> ORGANISM: Artificial Sequence
<220> FEATURE:
<223> OTHER INFORMATION: Synthetic
```

-continued

```
<400> SEQUENCE: 62

Met Arg Lys Leu Leu Phe Ile Ile Leu Ile Pro Phe Leu Gly Ile Ala
1               5                   10                  15

Gln Asp Phe Thr Ala Asn Gly Ile Lys Tyr Thr Val Thr Ser Ser Arg
            20                  25                  30

Thr Pro Phe Thr Val Lys Val Ala Arg Asn Ala Gly Phe Thr Gly Val
        35                  40                  45

Ala Glu Ile Pro Glu Thr Val Ala Tyr Asn Ser Lys Asn Tyr Ala Val
50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
                85                  90                  95

Cys Thr Asp Leu Thr Ser Val Thr Ile Pro Asn Ala Val Ala Thr Ile
            100                 105                 110

Gly Glu Asn Cys Phe Tyr Ser Cys Lys Lys Leu Arg Ser Leu Thr Ile
        115                 120                 125

Pro Asn Ser Leu Thr Val Ile Gly Asn Gly Ala Phe Ser Glu Cys Thr
130                 135                 140

Gly Leu Arg Thr Val Asn Cys Gln Ile Thr Ile Pro Phe Ala Ile Asn
145                 150                 155                 160

Thr Asn Thr Phe Tyr Asn Leu Asn Arg Ser Ile Cys Ala Leu Asn Val
                165                 170                 175

Pro Pro Gly Thr Glu Ala Ala Tyr Lys Ala Ala Val Trp Lys Asp
            180                 185                 190

Phe Ser Pro Ile Ser Gly Gly Phe Leu Ser Ser Asn Ser Phe Ala Ile
        195                 200                 205

Glu Ser Asn Leu Lys Ile Tyr Pro Asn Pro Val Ser Glu Ile Leu Asn
210                 215                 220

Ile Ala Leu Gln Glu Gly Leu Gln Leu Glu Lys Val Asn Phe Tyr Asn
225                 230                 235                 240

Thr Leu Gly Gln Leu Ile Lys Thr Thr Asn His Ser Glu Ile Asn Val
            245                 250                 255

Ser Ser Phe Ala Lys Gly Asn Tyr Phe Val Glu Ile Met Thr Asn Gln
        260                 265                 270

Gly Lys Ala Thr Lys Ser Val Ile Ile Gln
            275                 280

<210> SEQ ID NO 63
<211> LENGTH: 236
<212> TYPE: PRT
<213> ORGANISM: Artificial Sequence
<220> FEATURE:
<223> OTHER INFORMATION: Synthetic

<400> SEQUENCE: 63

Met Lys Lys Leu Leu Phe Val Ile Leu Ile Pro Phe Leu Gly Ile Ala
1               5                   10                  15

Gln Asp Phe Thr Ala Asn Gly Ile Lys Tyr Thr Val Thr Ser Ser Thr
            20                  25                  30

Ala Pro Phe Thr Val Lys Val Ala Arg Asn Ala Gly Phe Thr Gly Val
        35                  40                  45

Ala Glu Ile Pro Glu Thr Val Ala Tyr Asn Ser Lys Asn Tyr Ala Val
50                  55                  60

Thr Ala Ile Ser Glu Asn Ala Phe Arg Leu Ser Asp Leu Thr Ala Ile
```

```
65                  70                  75                  80
Thr Ile Pro Asn Ser Val Thr Val Ile Glu Glu Gly Ala Phe Gly Tyr
                85                  90                  95
Cys Thr Asp Leu Thr Ser Val Thr Ile Pro Asn Ala Val Ala Thr Ile
            100                 105                 110
Gly Glu Asn Cys Phe Tyr Ser Cys Lys Lys Leu Arg Ser Leu Thr Ile
            115                 120                 125
Pro Asn Ser Leu Thr Val Ile Gly Asn Gly Ala Phe Ser Glu Cys Thr
        130                 135                 140
Gly Leu Arg Thr Val Asn Cys Gln Ile Thr Ile Pro Phe Ala Ile Asn
145                 150                 155                 160
Thr Asn Thr Phe Tyr Asn Leu Asn Arg Ser Ile Cys Ala Leu Asn Val
                165                 170                 175
Pro Pro Gly Thr Glu Ala Ala Tyr Lys Ala Ala Ala Val Trp Lys Asp
            180                 185                 190
Phe Ser Pro Ile Ser Gly Gly Phe Leu Ser Ser Asn Ser Phe Ala Ile
            195                 200                 205
Asn Val Ser Ser Phe Ala Lys Gly Asn Tyr Phe Val Glu Ile Met Thr
        210                 215                 220
Asn Gln Gly Lys Ala Thr Lys Ser Val Ile Ile Gln
225                 230                 235

<210> SEQ ID NO 64
<211> LENGTH: 282
<212> TYPE: PRT
<213> ORGANISM: Artificial Sequence
<220> FEATURE:
<223> OTHER INFORMATION: Synthetic

<400> SEQUENCE: 64

Met Lys Lys Leu Leu Phe Phe Ile Leu Ile Pro Phe Leu Gly Ile Ala
1               5                   10                  15
Gln Asp Phe Thr Ala Asn Gly Ile Lys Tyr Thr Val Thr Ser Ser Arg
            20                  25                  30
Thr Pro Phe Thr Val Lys Val Ala Arg Asn Ala Gly Phe Thr Gly Val
        35                  40                  45
Ala Glu Ile Pro Glu Thr Val Ala Tyr Asn Ser Lys Asn Tyr Ala Val
    50                  55                  60
Thr Ala Ile Ser Glu Asn Ala Phe Arg Leu Ser Asp Leu Thr Ala Ile
65                  70                  75                  80
Thr Ile Pro Asn Ser Val Thr Val Ile Glu Glu Gly Ala Phe Gly Tyr
                85                  90                  95
Cys Thr Asp Leu Thr Ser Val Thr Ile Pro Asn Ala Val Ala Thr Ile
            100                 105                 110
Gly Glu Asn Cys Phe Tyr Ser Cys Lys Lys Leu Arg Ser Leu Thr Ile
            115                 120                 125
Pro Asn Ser Leu Thr Val Ile Gly Asn Gly Ala Phe Ser Glu Cys Thr
        130                 135                 140
Gly Leu Arg Thr Val Asn Cys Gln Ile Thr Ile Pro Phe Ala Ile Asn
145                 150                 155                 160
Thr Asn Thr Phe Tyr Asn Leu Asn Arg Ser Ile Cys Ala Leu Asn Val
                165                 170                 175
Pro Pro Gly Thr Glu Ala Ala Tyr Lys Ala Ala Ala Val Trp Lys Asp
            180                 185                 190
Phe Ser Pro Ile Ser Gly Gly Phe Leu Ser Ser Asn Ser Phe Ala Ile
```

```
            195                 200                 205
Glu Ser Asn Leu Lys Ile Tyr Pro Asn Pro Val Ser Glu Ile Leu Asn
        210                 215                 220

Ile Ala Leu Gln Glu Gly Leu Gln Leu Glu Lys Val Asn Phe Tyr Asn
225                 230                 235                 240

Thr Leu Gly Gln Leu Ile Lys Thr Thr Asn His Ser Glu Ile Asn Val
            245                 250                 255

Ser Ser Phe Ala Lys Gly Asn Tyr Phe Val Glu Ile Met Thr Asn Gln
        260                 265                 270

Gly Lys Ala Thr Lys Ser Val Ile Ile Gln
            275                 280

<210> SEQ ID NO 65
<211> LENGTH: 398
<212> TYPE: PRT
<213> ORGANISM: Artificial Sequence
<220> FEATURE:
<223> OTHER INFORMATION: Synthetic

<400> SEQUENCE: 65

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Ile Thr Ser Ser Thr
            20                  25                  30

Ala Pro Phe Thr Val Lys Val Ala Arg Asn Ala Asn Phe Thr Gly Ala
        35                  40                  45

Ala Glu Ile Pro Glu Thr Val Ala Tyr Asn Ser Glu Asn Tyr Ala Val
50                  55                  60

Thr Ala Ile Gly Glu Ser Ala Phe Glu His Cys Asn Asn Leu Thr Ser
65                  70                  75                  80

Val Thr Ile Pro Asn Ser Ala Thr Ser Ile Gly Arg Tyr Ala Phe Val
                85                  90                  95

Gly Cys Ser Gly Leu Ile Ser Val Thr Ile Pro Asn Ser Val Thr Thr
            100                 105                 110

Ile Gly Asp Glu Ala Phe Ala Asp Cys Ser Gly Leu Thr Ser Val Thr
        115                 120                 125

Ile Pro Asn Ser Val Thr Asp Ile Glu Asn Ser Ala Phe Phe Ser Cys
130                 135                 140

Ser Gly Leu Thr Ser Val Thr Ile Pro Asn Ser Val Thr Thr Ile Gly
145                 150                 155                 160

Asp Gly Ser Phe Ala Glu Cys Ser Gly Leu Thr Ser Val Thr Ile Pro
                165                 170                 175

Asn Ser Val Thr Thr Ile Gly Glu Gly Ser Phe Ala Gly Cys Ser Gly
            180                 185                 190

Leu Ile Ser Ile Thr Ile Pro Asn Ser Val Thr Thr Ile Arg Arg Gly
        195                 200                 205

Val Phe Ser Ala Cys Ser Gly Leu Ile Ser Val Thr Ile Pro Asn Ser
210                 215                 220

Val Thr Asp Ile Glu Asn Gly Ala Phe Phe Ser Cys Ser Gly Leu Thr
225                 230                 235                 240

Ser Val Thr Ile Pro Asn Ser Val Thr Ala Ile Gly Lys Asp Ala Phe
                245                 250                 255

Ala Gly Cys Arg Ser Leu Lys Thr Val Asn Cys His Ile Thr Ser Pro
            260                 265                 270

Leu Val Ile Asn Ala Asn Val Phe Gly Asn Ile Thr Gln Ser Asn Cys
```

```
            275                 280                 285
Ala Leu Asn Val Pro Thr Gly Thr Gln Val Ala Tyr Gln Ala Ala
    290                 295                 300

Val Trp Arg Asn Phe Ser Pro Ile Ser Gly Gly Leu Leu Ser Asn His
305                 310                 315                 320

Ser Phe Ala Ile Glu Ser Ala Leu Lys Ile Tyr Pro Asn Pro Val Ser
                325                 330                 335

Glu Ile Leu Asn Ile Ala Leu Gln Glu Gly Leu Gln Leu Gln Lys Val
                340                 345                 350

Asn Phe Tyr Asn Thr Leu Gly Gln Leu Ile Lys Thr Thr Asn His Ser
                355                 360                 365

Glu Ile Asn Val Ser Ser Phe Ala Lys Gly Asn Tyr Phe Val Glu Val
                370                 375                 380

Ile Thr Asn Gln Gly Lys Ala Thr Lys Thr Ile Ile Gln
385                 390                 395
```

<210> SEQ ID NO 66
<211> LENGTH: 398
<212> TYPE: PRT
<213> ORGANISM: Artificial Sequence
<220> FEATURE:
<223> OTHER INFORMATION: Synthetic

<400> SEQUENCE: 66

```
Met Lys Lys Leu Leu Phe Phe Ile Leu Ile Pro Phe Leu Gly Ile Ala
1               5                   10                  15

Gln Asp Phe Thr Ala Asn His Ile Arg Tyr Thr Ile Thr Ser Ser Glu
                20                  25                  30

Ala Pro Phe Thr Ala Lys Val Ala Arg Asn Pro Asp Phe Ser Gly Val
                35                  40                  45

Ala Val Ile Pro Glu Thr Val Ala Tyr Asn Ser Lys Asn Tyr Ile Val
        50                  55                  60

Thr Ala Ile Gly Glu Ser Ala Phe Glu His Cys Asn Asn Leu Thr Ser
65                  70                  75                  80

Val Thr Ile Pro Asn Ser Ala Thr Ser Ile Gly Arg Tyr Ala Phe Val
                85                  90                  95

Gly Cys Ser Gly Leu Ile Ser Val Thr Ile Pro Asn Ser Val Thr Thr
            100                 105                 110

Ile Gly Asp Glu Ala Phe Ala Asp Cys Ser Gly Leu Thr Ser Val Thr
        115                 120                 125

Ile Pro Asn Ser Val Thr Thr Ile Gly Asp Gly Ser Phe Phe Ser Cys
    130                 135                 140

Ser Gly Leu Thr Ser Val Thr Ile Pro Asn Ser Val Thr Thr Ile Gly
145                 150                 155                 160

Lys Asp Ala Phe Ala Asp Cys Ser Gly Leu Thr Ser Val Thr Ile Pro
                165                 170                 175

Asn Ser Val Thr Thr Ile Gly Glu Gly Ser Phe Ala Gly Cys Ser Gly
                180                 185                 190

Leu Ile Ser Ile Thr Ile Pro Asn Ser Val Thr Val Ile Arg Arg Gly
            195                 200                 205

Ile Phe Ala Gly Cys Ser Gly Leu Ile Ser Val Thr Ile Pro Asn Ser
        210                 215                 220

Val Thr Asp Ile Glu Asn Gly Ala Phe Phe Ser Cys Ser Gly Leu Thr
225                 230                 235                 240

Ser Val Thr Ile Pro Asn Ser Val Thr Ala Ile Gly Lys Asp Ala Phe
```

```
            245                 250                 255
Ala Gly Cys Arg Ser Leu Lys Thr Val Asn Cys His Ile Thr Ser Pro
                260                 265                 270

Leu Val Ile Asn Ala Asn Val Phe Gly Asn Ile Thr Gln Ser Asn Cys
            275                 280                 285

Ala Leu Asn Val Pro Thr Gly Thr Gln Val Ala Tyr Gln Ala Ala Ala
        290                 295                 300

Val Trp Arg Asn Phe Ser Pro Ile Ser Gly Gly Leu Leu Ser Asn His
305                 310                 315                 320

Ser Phe Ala Ile Glu Ser Ala Leu Lys Ile Tyr Pro Asn Pro Val Ser
                325                 330                 335

Glu Ile Leu Asn Ile Ala Leu Gln Glu Gly Leu Gln Leu Glu Lys Val
            340                 345                 350

Asn Phe Tyr Asn Thr Leu Gly Gln Leu Ile Lys Thr Thr Asn His Ser
        355                 360                 365

Glu Ile Asn Val Ser Ser Phe Ala Lys Gly Asn Tyr Phe Val Glu Val
    370                 375                 380

Met Thr Asn Gln Gly Lys Ala Thr Lys Thr Ile Ile Val Gln
385                 390                 395

<210> SEQ ID NO 67
<211> LENGTH: 398
<212> TYPE: PRT
<213> ORGANISM: Artificial Sequence
<220> FEATURE:
<223> OTHER INFORMATION: Synthetic

<400> SEQUENCE: 67

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Ile Thr Ser Ser Thr
            20                  25                  30

Ala Pro Phe Thr Val Lys Val Ala Arg Asn Ala Asn Phe Thr Gly Ala
        35                  40                  45

Ala Glu Ile Pro Glu Thr Val Ala Tyr Asn Ser Glu Asn Tyr Ala Val
    50                  55                  60

Thr Ala Ile Gly Glu Asp Ala Phe Glu Tyr Cys Asn Asn Leu Thr Ser
65                  70                  75                  80

Val Thr Ile Pro Asn Ser Ala Thr Ser Ile Gly Arg Tyr Ala Phe Val
                85                  90                  95

Gly Cys Ser Gly Leu Ile Ser Val Thr Ile Pro Asn Ser Val Thr Thr
            100                 105                 110

Ile Gly Asp Glu Ala Phe Ala Asp Cys Ser Gly Leu Thr Ser Val Thr
        115                 120                 125

Ile Pro Asn Ser Val Thr Thr Ile Gly Asp Gly Ser Phe Phe Ser Cys
    130                 135                 140

Ser Gly Leu Thr Ser Val Thr Ile Pro Asn Ser Val Thr Thr Ile Gly
145                 150                 155                 160

Lys Asp Ala Phe Ala Asp Cys Ser Gly Leu Thr Ser Val Thr Ile Pro
                165                 170                 175

Asn Ser Val Thr Thr Ile Gly Glu Gly Ser Phe Ala Gly Cys Ser Gly
            180                 185                 190

Leu Ile Ser Ile Thr Ile Pro Asn Ser Val Thr Thr Ile Arg Arg Gly
        195                 200                 205

Val Phe Ser Ala Cys Ser Gly Leu Ile Ser Val Thr Ile Pro Asn Ser
```

```
            210                 215                 220
Val Thr Asp Ile Glu Asn Gly Ala Phe Phe Ser Cys Ser Gly Leu Thr
225                 230                 235                 240

Ser Val Thr Ile Pro Asn Ser Val Thr Ala Ile Gly Lys Asp Ala Phe
                245                 250                 255

Ala Gly Cys Arg Ser Leu Lys Thr Val Asn Cys His Ile Thr Ser Pro
            260                 265                 270

Leu Val Ile Asn Ala Asn Val Phe Gly Asn Ile Thr Gln Ser Asn Cys
                275                 280                 285

Ala Leu Asn Val Pro Thr Gly Thr Gln Val Ala Tyr Gln Ala Ala Ala
            290                 295                 300

Val Trp Arg Asn Phe Ser Pro Ile Ser Gly Gly Leu Leu Ser Asn His
305                 310                 315                 320

Ser Phe Ala Ile Glu Ser Ala Leu Lys Ile Tyr Pro Asn Pro Val Ser
                325                 330                 335

Glu Ile Leu Asn Ile Ala Leu Gln Glu Gly Leu Gln Leu Glu Lys Val
            340                 345                 350

Asn Phe Tyr Asn Thr Leu Gly Gln Leu Ile Lys Thr Thr Asn His Ser
                355                 360                 365

Glu Ile Asn Val Ser Ser Phe Ala Lys Gly Asn Tyr Phe Val Glu Val
            370                 375                 380

Met Thr Asn Gln Gly Lys Ala Thr Lys Thr Ile Ile Val Gln
385                 390                 395

<210> SEQ ID NO 68
<211> LENGTH: 398
<212> TYPE: PRT
<213> ORGANISM: Artificial Sequence
<220> FEATURE:
<223> OTHER INFORMATION: Synthetic

<400> SEQUENCE: 68

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Ile Thr Ser Ser Thr
                20                  25                  30

Ala Pro Phe Thr Val Lys Val Ala Arg Asn Ala Asn Phe Thr Gly Ala
            35                  40                  45

Ala Glu Ile Pro Glu Thr Val Ala Tyr Asn Ser Glu Asn Tyr Ala Val
        50                  55                  60

Thr Ala Ile Gly Glu Ser Ala Phe Glu Tyr Cys Asn Asn Leu Thr Ser
65                  70                  75                  80

Val Thr Ile Pro Asn Ser Ala Thr Ser Ile Gly Arg Tyr Ala Phe Val
                85                  90                  95

Gly Cys Ser Gly Leu Ile Ser Val Thr Ile Pro Asn Ser Val Thr Thr
            100                 105                 110

Ile Gly Asp Glu Ala Phe Ala Asp Cys Ser Gly Leu Thr Ser Val Thr
        115                 120                 125

Ile Pro Asn Ser Val Thr Asp Ile Glu Asn Ser Ala Phe Phe Ser Cys
    130                 135                 140

Ser Gly Leu Thr Ser Val Thr Ile Pro Asn Ser Val Thr Ile Gly
145                 150                 155                 160

Asp Gly Ser Phe Ala Glu Cys Ser Gly Leu Thr Ser Val Thr Ile Pro
                165                 170                 175

Asn Ser Val Thr Thr Ile Gly Glu Gly Ser Phe Ala Gly Cys Ser Gly
```

```
                180                 185                 190
Leu Ile Ser Ile Thr Ile Pro Asn Ser Val Thr Thr Ile Arg Arg Gly
            195                 200                 205

Val Phe Ser Ala Cys Ser Gly Leu Ile Ser Val Thr Ile Pro Asn Ser
        210                 215                 220

Val Thr Asp Ile Glu Asn Gly Ala Phe Phe Ser Cys Ser Gly Leu Thr
225                 230                 235                 240

Ser Val Thr Ile Pro Asn Ser Val Thr Ala Ile Gly Glu Asp Ala Phe
                245                 250                 255

Ala Gly Cys Arg Ser Leu Lys Thr Val Asn Cys His Ile Thr Ser Pro
            260                 265                 270

Leu Val Ile Asn Ala Asn Val Phe Gly Asn Ile Thr Gln Ser Asn Cys
        275                 280                 285

Ala Leu Asn Val Pro Thr Gly Thr Gln Val Ala Tyr Gln Ala Ala Ala
        290                 295                 300

Val Trp Arg Asn Phe Ser Pro Ile Ser Gly Gly Leu Leu Ser Asn His
305                 310                 315                 320

Ser Phe Ala Ile Glu Ser Ala Leu Lys Ile Tyr Pro Asn Pro Val Ser
                325                 330                 335

Glu Ile Leu Asn Ile Ala Leu Gln Glu Gly Leu Gln Leu Gln Lys Val
            340                 345                 350

Asn Phe Tyr Asn Thr Leu Gly Gln Leu Ile Lys Thr Thr Asn His Ser
        355                 360                 365

Glu Ile Asn Val Ser Ser Phe Ala Lys Gly Asn Tyr Phe Val Glu Val
        370                 375                 380

Ile Thr Asn Gln Gly Lys Ala Thr Lys Thr Ile Ile Gln
385                 390                 395

<210> SEQ ID NO 69
<211> LENGTH: 391
<212> TYPE: PRT
<213> ORGANISM: Artificial Sequence
<220> FEATURE:
<223> OTHER INFORMATION: Synthetic

<400> SEQUENCE: 69

Ile Leu Ile Pro Phe Leu Gly Ile Ala Gln Asp Phe Thr Ala Asn Arg
1               5                   10                  15

Ile Asn Tyr Thr Ile Thr Ser Ser Thr Ala Pro Phe Thr Val Lys Val
            20                  25                  30

Ala Arg Asn Ala Asn Phe Thr Gly Ala Ala Glu Ile Pro Glu Thr Val
        35                  40                  45

Ala Tyr Asn Ser Glu Asn Tyr Ile Val Thr Ala Ile Gly Glu Ser Ala
    50                  55                  60

Phe Ile His Cys Asn Asn Leu Thr Ser Val Thr Ile Pro Asn Ser Ala
65              70                  75                  80

Thr Ser Ile Gly Arg Tyr Ala Phe Val Gly Cys Ser Gly Leu Ile Ser
            85                  90                  95

Val Thr Ile Pro Asn Ser Val Thr Thr Ile Gly Asp Glu Ala Phe Ala
        100                 105                 110

Asp Cys Ser Gly Leu Thr Ser Val Thr Ile Pro Asn Ser Val Thr Asp
    115                 120                 125

Ile Glu Asn Ser Ala Phe Phe Ser Cys Ser Gly Leu Thr Ser Val Thr
130                 135                 140

Ile Pro Asn Ser Val Thr Ala Ile Gly Lys Asp Ala Phe Ala Glu Cys
```

```
              145                 150                 155                 160
Ser Gly Leu Thr Ser Val Thr Ile Pro Asn Ser Val Thr Thr Ile Gly
                165                 170                 175

Glu Gly Ser Phe Ala Gly Cys Ser Gly Leu Ile Ser Ile Thr Ile Pro
                180                 185                 190

Asn Ser Val Thr Thr Ile Gly Glu Gly Ser Phe Ala Gly Cys Ser Gly
                195                 200                 205

Leu Ile Ser Val Thr Ile Pro Asn Ser Val Thr Asp Ile Glu Asn Gly
            210                 215                 220

Ala Phe Phe Ser Cys Ser Gly Leu Thr Ser Val Thr Ile Pro Asn Ser
225                 230                 235                 240

Val Thr Ala Ile Gly Lys Asp Ala Phe Ala Gly Cys Arg Ser Leu Lys
                245                 250                 255

Thr Val Asn Cys His Ile Thr Ser Pro Leu Val Ile Asn Ala Asn Val
                260                 265                 270

Phe Gly Asn Ile Thr Gln Ser Asn Cys Ala Leu Asn Val Pro Thr Gly
            275                 280                 285

Thr Gln Ala Val Tyr Gln Ala Ala Val Trp Arg Asn Phe Ser Pro
            290                 295                 300

Ile Ser Gly Gly Leu Leu Ser Asn His Ser Phe Ala Ile Glu Ser Ala
305                 310                 315                 320

Leu Lys Ile Tyr Pro Asn Pro Val Ser Glu Ile Leu Asn Ile Ala Leu
                325                 330                 335

Gln Glu Gly Leu Gln Leu Glu Lys Val Asn Phe Tyr Asn Thr Leu Gly
            340                 345                 350

Gln Leu Ile Lys Thr Thr Asn His Leu Glu Thr Asn Val Ser Ser Phe
            355                 360                 365

Ala Lys Gly Asn Tyr Phe Val Glu Val Met Thr Asn Gln Gly Lys Ala
            370                 375                 380

Thr Lys Thr Ile Ile Ile Gln
385                 390

<210> SEQ ID NO 70
<211> LENGTH: 375
<212> TYPE: PRT
<213> ORGANISM: Artificial Sequence
<220> FEATURE:
<223> OTHER INFORMATION: Synthetic

<400> SEQUENCE: 70

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Val Thr Ser Ser Thr
                20                  25                  30

Ala Pro Phe Thr Val Ser Val Ala Arg Asn Pro Tyr Phe Ser Gly Val
            35                  40                  45

Ala Glu Ile Pro Glu Thr Val Val Tyr Asn Ser Lys Asn Tyr Ala Val
        50                  55                  60

Thr Tyr Ile Lys Glu Ile Ala Phe Gln Glu Cys Asn Thr Leu Thr Ser
65                  70                  75                  80

Val Ser Ile Pro Asn Ser Val Thr Ile Gly Asn Ser Ala Phe Glu
                85                  90                  95

Arg Cys Ser Ser Leu Ile Ser Val Thr Ile Pro Asn Ser Val Thr Ala
                100                 105                 110

Ile Gly Lys Gly Ala Phe Phe Ser Cys Ser Gly Leu Thr Ser Val Thr
```

```
              115                 120                 125
Ile Pro Asn Ser Val Thr Thr Ile Gly Asp Glu Ala Phe Ala Asp Cys
    130                 135                 140

Ser Gly Leu Thr Ser Val Thr Ile Pro Asn Ser Val Thr Thr Ile Gly
145                 150                 155                 160

Asp Gly Ser Phe Ala Glu Cys Ser Gly Leu Thr Ser Val Thr Ile Pro
                165                 170                 175

Asn Ser Val Thr Thr Ile Gly Asp Gly Ser Phe Ala Arg Cys Ser Gly
            180                 185                 190

Leu Thr Ser Val Thr Ile Pro Asn Ser Val Ile Thr Ile Asn Arg Gly
        195                 200                 205

Ala Phe Val Ser Cys Ser Gly Leu Thr Ser Val Thr Ile Pro Asn Ser
    210                 215                 220

Val Thr Thr Ile Gly Glu Glu Ala Phe Ala Gly Cys Ser Ser Leu Arg
225                 230                 235                 240

Thr Val Asn Cys His Ile Thr Ser Pro Leu Val Ile Asn Ala Asn Val
                245                 250                 255

Phe Gly Asn Val Thr Gln Ser Asn Cys Ala Leu Asn Val Pro Thr Gly
                260                 265                 270

Thr Gln Ala Val Tyr Gln Ala Ala Val Trp Arg Asn Phe Ser Pro
            275                 280                 285

Ile Ser Gly Asn Leu Leu Ser Asn His Ser Phe Ala Ile Glu Ser Ala
    290                 295                 300

Leu Lys Ile Tyr Pro Asn Pro Val Ser Glu Ile Leu Asn Ile Ala Leu
305                 310                 315                 320

Gln Glu Gly Leu Gln Leu Glu Lys Val Asn Phe Tyr Asn Thr Leu Gly
                325                 330                 335

Gln Leu Ile Lys Thr Thr Asn His Ser Glu Ile Asn Val Ser Ser Phe
            340                 345                 350

Ala Lys Gly Asn Tyr Phe Val Glu Ile Ile Thr Asn Gln Gly Lys Ala
        355                 360                 365

Thr Lys Thr Ile Ile Ile Gln
    370                 375

<210> SEQ ID NO 71
<211> LENGTH: 375
<212> TYPE: PRT
<213> ORGANISM: Artificial Sequence
<220> FEATURE:
<223> OTHER INFORMATION: Synthetic

<400> SEQUENCE: 71

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Val Thr Ser Ser Thr
            20                  25                  30

Ala Pro Phe Thr Val Ser Val Ala Arg Asn Pro Asn Phe Ser Gly Val
        35                  40                  45

Ala Glu Ile Pro Glu Thr Val Val Tyr Asn Ser Lys Asn Tyr Ala Val
    50                  55                  60

Thr Tyr Ile Lys Glu Ile Ala Phe Gln Glu Cys Asn Thr Leu Thr Ser
65                  70                  75                  80

Val Ser Ile Pro Asn Ser Val Thr Thr Ile Gly Asn Ser Ala Phe Glu
                85                  90                  95

Arg Cys Ser Ser Leu Ile Ser Val Thr Ile Pro Asn Ser Val Thr Ala
```

```
            100                 105                 110
Ile Gly Asn Gly Ala Phe Phe Ser Cys Ser Gly Leu Thr Ser Val Thr
            115                 120                 125
Ile Pro Asn Ser Val Thr Thr Ile Gly Asp Glu Ala Phe Ala Asp Cys
        130                 135                 140
Ser Gly Leu Thr Ser Val Thr Ile Pro Asn Ser Val Thr Thr Ile Gly
145                 150                 155                 160
Asp Gly Ser Phe Ala Glu Cys Ser Gly Leu Thr Ser Val Thr Ile Pro
                165                 170                 175
Asn Ser Val Thr Thr Ile Gly Asp Gly Ser Phe Ala Arg Cys Ser Gly
            180                 185                 190
Leu Thr Ser Val Thr Ile Pro Asn Ser Val Ile Thr Ile Asn Arg Gly
        195                 200                 205
Ala Phe Val Ser Cys Ser Gly Leu Thr Ser Val Thr Ile Pro Asn Ser
    210                 215                 220
Val Thr Thr Ile Gly Glu Asn Ala Phe Ala Gly Cys Ser Ser Leu Arg
225                 230                 235                 240
Thr Val Asn Cys His Ile Thr Ser Pro Leu Val Ile Asn Ala Asn Val
                245                 250                 255
Phe Gly Asn Val Thr Gln Ser Asn Cys Ala Leu Asn Val Pro Thr Gly
            260                 265                 270
Thr Gln Ala Val Tyr Gln Ala Ala Val Trp Arg Asn Phe Ser Pro
        275                 280                 285
Ile Ser Gly Asn Leu Leu Ser Asn His Ser Phe Ala Ile Glu Ser Ala
    290                 295                 300
Leu Lys Ile Tyr Pro Asn Pro Val Ser Glu Ile Leu Asn Ile Ala Leu
305                 310                 315                 320
Gln Glu Gly Leu Gln Leu Glu Lys Val Asn Phe Tyr Asn Thr Leu Gly
                325                 330                 335
Gln Leu Ile Lys Thr Thr Asn His Ser Glu Ile Asn Val Ser Ser Phe
            340                 345                 350
Ala Lys Gly Asn Tyr Phe Val Glu Ile Ile Thr Asn Gln Gly Lys Ala
        355                 360                 365
Thr Lys Thr Ile Ile Gln
    370                 375
```

<210> SEQ ID NO 72
<211> LENGTH: 398
<212> TYPE: PRT
<213> ORGANISM: Artificial Sequence
<220> FEATURE:
<223> OTHER INFORMATION: Synthetic

<400> SEQUENCE: 72

```
Met Lys Lys Leu Leu Phe Leu Ile Leu Ile Pro Phe Leu Gly Ile Ala
1               5                   10                  15
Gln Asp Phe Thr Ala Asn Arg Ile Asn Tyr Thr Ile Thr Ser Ser Thr
            20                  25                  30
Ala Pro Phe Thr Val Lys Val Ala Arg Asn Ala Asn Phe Thr Gly Ala
        35                  40                  45
Ala Glu Ile Pro Glu Thr Val Ala Tyr Asn Ser Glu Asn Tyr Ala Val
    50                  55                  60
Thr Ala Ile Gly Glu Ser Ala Phe Glu His Cys Asn Asn Leu Thr Ser
65                  70                  75                  80
Val Thr Ile Pro Asn Ser Ala Thr Ser Ile Gly Arg Tyr Ala Phe Val
```

```
                         85                  90                  95
Gly Cys Ser Gly Leu Ile Ser Val Thr Ile Pro Asn Ser Val Thr Thr
               100                 105                 110

Ile Gly Asp Glu Ala Phe Ala Asp Cys Ser Gly Leu Thr Ser Val Thr
               115                 120                 125

Ile Pro Asn Ser Val Thr Asp Ile Glu Asn Ser Ala Phe Phe Ser Cys
           130                 135                 140

Ser Gly Leu Thr Ser Val Thr Ile Pro Asn Ser Val Thr Thr Ile Gly
145                 150                 155                 160

Asp Gly Ser Phe Ala Glu Cys Ser Gly Leu Thr Ser Val Thr Ile Pro
                   165                 170                 175

Asn Ser Val Thr Thr Ile Gly Glu Gly Ser Phe Ala Asp Cys Ser Gly
               180                 185                 190

Leu Thr Ser Val Thr Ile Pro Asn Ser Val Thr Ile Gly Arg Gly
       195                 200                 205

Val Phe Ser Ala Cys Ser Gly Leu Ile Ser Val Thr Ile Pro Asn Ser
210                 215                 220

Val Thr Ala Ile Gly Gly Ala Phe Phe Ser Cys Ser Gly Leu Thr
225                 230                 235                 240

Ser Val Thr Ile Pro Asn Ser Val Thr Ala Ile Gly Asn Asp Ala Phe
                   245                 250                 255

Glu Lys Cys Arg Ser Leu Thr Lys Val Asn Cys Tyr Ile Thr Met Pro
               260                 265                 270

Leu Ile Ile Asn Ala Asn Val Phe Arg Asn Ile Thr Gln Ser Asn Cys
           275                 280                 285

Ala Leu Asn Val Pro Thr Gly Thr Gln Ala Val Tyr Gln Ala Ala Ala
       290                 295                 300

Val Trp Arg Asn Phe Ser Pro Ile Ser Gly Asn Leu Leu Ser Asn His
305                 310                 315                 320

Ser Phe Ala Ile Glu Ser Thr Leu Lys Ile Tyr Pro Asn Pro Val Ser
                   325                 330                 335

Glu Ile Leu Asn Ile Ala Leu Gln Glu Gly Leu Gln Leu Gln Lys Val
               340                 345                 350

Asn Phe Tyr Asn Thr Leu Gly Gln Leu Ile Lys Thr Thr Asn His Ser
           355                 360                 365

Glu Ile Asn Val Ser Ser Phe Ala Lys Gly Asn Tyr Phe Val Glu Val
       370                 375                 380

Ile Thr Asn Gln Gly Lys Ala Thr Lys Thr Ile Ile Gln
385                 390                 395

<210> SEQ ID NO 73
<211> LENGTH: 398
<212> TYPE: PRT
<213> ORGANISM: Artificial Sequence
<220> FEATURE:
<223> OTHER INFORMATION: Synthetic

<400> SEQUENCE: 73

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Ile Ser Ser Thr
               20                  25                  30

Ala Pro Phe Thr Val Lys Val Ala Arg Asn Ala Asn Phe Thr Gly Ala
           35                  40                  45

Ala Glu Ile Pro Glu Thr Val Ala Tyr Asn Ser Glu Asn Tyr Ala Val
```

```
            50                  55                  60
Thr Ala Ile Gly Glu Ser Ala Phe Glu His Cys Asn Asn Leu Thr Ser
 65                      70                  75                  80

Val Thr Ile Pro Asn Ser Ala Thr Ser Ile Gly Arg Tyr Ala Phe Val
                     85                  90                  95

Gly Cys Ser Gly Leu Ile Ser Val Thr Ile Pro Asn Ser Val Thr Thr
                100                 105                 110

Ile Gly Asp Glu Ala Phe Ala Asp Cys Ser Gly Leu Thr Ser Val Thr
            115                 120                 125

Ile Pro Asn Ser Val Thr Asp Ile Glu Asn Ser Ala Phe Phe Ser Cys
130                 135                 140

Ser Gly Leu Thr Ser Val Thr Ile Pro Asn Ser Val Thr Thr Ile Gly
145                 150                 155                 160

Asp Gly Ser Phe Ala Glu Cys Ser Gly Leu Thr Ser Val Thr Ile Pro
                165                 170                 175

Asn Ser Val Thr Thr Ile Gly Glu Gly Ser Phe Ala Gly Cys Ser Gly
                180                 185                 190

Leu Thr Ser Val Thr Ile Pro Asn Ser Val Thr Ser Ile Gly Arg Gly
            195                 200                 205

Ala Phe Ala Ala Cys Ser Gly Leu Thr Ser Val Thr Ile Pro Asn Ser
210                 215                 220

Val Thr Ala Ile Gly Gly Gly Ala Phe Phe Ser Cys Ser Asp Leu Thr
225                 230                 235                 240

Ser Val Thr Ile Pro Asn Ser Val Thr Ala Ile Gly Asn Tyr Ala Phe
                245                 250                 255

Glu Lys Cys Arg Ser Leu Thr Thr Val Asn Cys Tyr Ile Thr Met Pro
                260                 265                 270

Leu Val Ile Asn Ala Asn Val Phe Gly Asn Val Thr Gln Ser Asn Cys
            275                 280                 285

Ala Leu Asn Val Pro Thr Gly Thr Gln Ala Val Tyr Gln Ala Ala
290                 295                 300

Val Trp Arg Asn Phe Ser Pro Ile Ser Gly Asn Leu Leu Ser Asn His
305                 310                 315                 320

Ser Phe Ala Ile Glu Ser Ala Leu Lys Ile Tyr Pro Asn Pro Val Ser
                325                 330                 335

Glu Ile Leu Asn Ile Ala Leu Gln Glu Gly Leu Gln Leu Gln Lys Val
                340                 345                 350

Asn Phe Tyr Asn Thr Leu Gly Gln Leu Ile Lys Thr Thr Asn His Ser
            355                 360                 365

Glu Ile Asn Val Ser Ser Phe Ala Lys Gly Asn Tyr Phe Val Glu Val
370                 375                 380

Ile Thr Asn Gln Gly Lys Ala Thr Lys Thr Ile Ile Gln
385                 390                 395
```

<210> SEQ ID NO 74
<211> LENGTH: 398
<212> TYPE: PRT
<213> ORGANISM: Artificial Sequence
<220> FEATURE:
<223> OTHER INFORMATION: Synthetic

<400> SEQUENCE: 74

```
Met Lys Lys Leu Leu Phe Leu Ile Leu Ile Pro Phe Leu Gly Ile Ala
 1               5                  10                  15

Gln Asp Phe Thr Ala Asn Arg Ile Asn Tyr Thr Ile Thr Ser Ser Thr
```

```
                    20                  25                  30
Ala Pro Phe Thr Val Lys Val Ala Arg Asn Ala Asn Phe Thr Gly Ala
                35                  40                  45
Ala Glu Ile Pro Glu Thr Val Ala Tyr Asn Ser Glu Asn Tyr Ala Val
        50                  55                  60
Thr Ala Ile Gly Glu Ser Ala Phe Glu His Cys Asn Asn Leu Thr Ser
65                  70                  75                  80
Val Thr Ile Pro Asn Ser Ala Thr Ser Ile Gly Arg Tyr Ala Phe Val
                85                  90                  95
Gly Cys Ser Gly Leu Ile Ser Val Thr Ile Pro Asn Ser Val Thr Thr
                100                 105                 110
Ile Gly Asp Glu Ala Phe Ala Asp Cys Ser Gly Leu Thr Ser Val Thr
                115                 120                 125
Ile Pro Asn Ser Val Thr Asp Ile Glu Asn Ser Ala Phe Phe Ser Cys
                130                 135                 140
Ser Gly Leu Thr Ser Val Thr Ile Pro Asn Ser Val Thr Thr Ile Gly
145                 150                 155                 160
Asp Gly Ser Phe Ala Glu Cys Ser Gly Leu Thr Ser Val Thr Ile Pro
                165                 170                 175
Asn Ser Val Thr Thr Ile Gly Glu Gly Ser Phe Ala Gly Cys Ser Gly
                180                 185                 190
Leu Ile Ser Ile Thr Ile Pro Asn Ser Val Thr Thr Ile Arg Arg Gly
                195                 200                 205
Val Phe Ser Ala Cys Ser Gly Leu Ile Ser Val Thr Ile Pro Asn Ser
                210                 215                 220
Val Thr Asp Ile Glu Asn Gly Ala Phe Phe Ser Cys Ser Gly Leu Thr
225                 230                 235                 240
Ser Val Thr Ile Pro Asn Ser Val Thr Ala Ile Gly Lys Asp Ala Phe
                245                 250                 255
Ala Gly Cys Arg Ser Leu Lys Thr Val Asn Cys His Ile Thr Ser Pro
                260                 265                 270
Leu Val Ile Asn Ala Asn Val Phe Gly Asn Ile Thr Gln Ser Asn Cys
                275                 280                 285
Ala Leu Asn Val Pro Thr Gly Thr Gln Val Ala Tyr Gln Ala Ala Ala
                290                 295                 300
Val Trp Arg Asn Phe Ser Pro Ile Ser Gly Gly Leu Leu Ser Asn His
305                 310                 315                 320
Ser Phe Ala Ile Glu Ser Ala Leu Lys Ile Tyr Pro Asn Pro Val Ser
                325                 330                 335
Glu Ile Leu Asn Ile Ala Leu Gln Glu Gly Leu Gln Leu Gln Lys Val
                340                 345                 350
Asn Phe Tyr Asn Thr Leu Gly Gln Leu Ile Lys Thr Thr Asn His Ser
                355                 360                 365
Glu Ile Asn Val Ser Ser Phe Ala Lys Gly Asn Tyr Phe Val Glu Val
                370                 375                 380
Ile Thr Asn Gln Gly Lys Ala Thr Lys Thr Ile Ile Gln
385                 390                 395

<210> SEQ ID NO 75
<211> LENGTH: 421
<212> TYPE: PRT
<213> ORGANISM: Artificial Sequence
<220> FEATURE:
<223> OTHER INFORMATION: Synthetic
```

<400> SEQUENCE: 75

```
Met Lys Lys Leu Leu Phe Leu Ile Leu Ile Pro Phe Leu Gly Ile Ala
1               5                   10                  15

Gln Thr Phe Thr Ala Asn Arg Ile Asn Tyr Thr Ile Thr Ser Ser Thr
            20                  25                  30

Ala Pro Phe Thr Val Lys Val Ala Arg Asn Ala Asn Phe Thr Gly Ala
        35                  40                  45

Ala Glu Ile Pro Glu Thr Val Ala Tyr Asn Ser Glu Asn Tyr Ala Val
    50                  55                  60

Thr Ala Ile Gly Glu Ser Ala Phe Glu His Cys Asn Asn Leu Thr Ser
65                  70                  75                  80

Val Thr Ile Pro Asn Ser Val Thr Ile Gly Asn Tyr Thr Phe Ser
                85                  90                  95

Asp Cys Pro Asp Leu Thr Ser Val Thr Ile Pro Asn Ser Val Thr Ser
                100                 105                 110

Ile Gly Asp Glu Ala Phe Ser Gly Cys Thr Gly Leu Ile Ser Val Thr
            115                 120                 125

Ile Pro Asn Ser Val Thr Ser Ile Gly Asp Glu Ala Phe Phe Asn Cys
        130                 135                 140

Ser Gly Leu Thr Ser Val Thr Ile Pro Asn Ser Val Thr Thr Ile Gly
145                 150                 155                 160

Glu Gly Ser Phe Ala Gly Cys Ser Gly Leu Ile Ser Ile Thr Ile Pro
                165                 170                 175

Asn Ser Val Thr Thr Ile Arg Gly Gly Val Phe Ser Ala Cys Ser Gly
            180                 185                 190

Leu Ile Ser Val Thr Ile Pro Asn Ser Val Thr Asp Ile Glu Asn Gly
        195                 200                 205

Ala Phe Phe Ser Cys Ser Gly Leu Thr Ser Val Thr Ile Pro Asn Ser
    210                 215                 220

Val Ile Thr Ile Asn Arg Gly Ala Phe Phe Ser Cys Ser Gly Leu Thr
225                 230                 235                 240

Ser Val Thr Ile Pro Asn Ser Val Thr Ile Arg Glu Asn Ala Phe
                245                 250                 255

Ala Asp Cys Ser Gly Leu Thr Ser Val Thr Ile Pro Asn Ser Val Thr
            260                 265                 270

Ala Ile Gly Glu Asn Ala Phe Ala Gly Cys Ser Ser Leu Arg Thr Val
        275                 280                 285

Asn Cys His Ile Thr Ser Pro Leu Val Ile Asn Ala Asn Val Phe Gly
    290                 295                 300

Asn Val Thr Gln Ser Asn Cys Ala Leu Asn Val Pro Thr Gly Thr Gln
305                 310                 315                 320

Ala Val Tyr Gln Ala Ala Val Trp Arg Asn Phe Ser Pro Ile Ser
                325                 330                 335

Gly Asn Leu Leu Ser Asn His Ser Phe Ala Ile Glu Ser Ala Leu Lys
            340                 345                 350

Ile Tyr Pro Asn Pro Ala Ser Glu Ile Leu Asn Ile Ala Leu Gln Glu
        355                 360                 365

Gly Leu Gln Leu Glu Lys Val Asn Phe Tyr Asn Thr Leu Gly Gln Leu
    370                 375                 380

Ile Lys Thr Thr Asn His Ser Glu Ile Asn Val Ser Ser Phe Ala Lys
385                 390                 395                 400

Gly Asn Tyr Phe Val Glu Val Met Thr Asn Gln Gly Lys Ala Thr Lys
                405                 410                 415
```

Thr Ile Ile Ile Gln
            420

<210> SEQ ID NO 76
<211> LENGTH: 398
<212> TYPE: PRT
<213> ORGANISM: Artificial Sequence
<220> FEATURE:
<223> OTHER INFORMATION: Synthetic

<400> SEQUENCE: 76

Met Lys Lys Leu Leu Phe Leu Ile Leu Ile Pro Phe Leu Gly Ile Ala
1               5                   10                  15

Gln Asp Phe Thr Ala Asn Arg Ile Asn Tyr Thr Ile Thr Ser Ser Thr
            20                  25                  30

Ala Pro Phe Thr Val Lys Val Ala Arg Asn Ala Asn Phe Thr Gly Ala
        35                  40                  45

Ala Glu Ile Pro Glu Thr Val Ala Tyr Asn Ser Glu Asn Tyr Ala Val
50                  55                  60

Thr Ala Ile Gly Glu Ser Ala Phe Glu His Cys Asn Asn Leu Thr Ser
65                  70                  75                  80

Val Thr Ile Pro Asn Ser Ala Thr Ser Ile Gly Arg Tyr Ala Phe Val
                85                  90                  95

Gly Cys Ser Gly Leu Ile Ser Val Thr Ile Pro Asn Ser Val Thr Thr
            100                 105                 110

Ile Gly Asp Glu Ala Phe Ala Asp Cys Ser Gly Leu Thr Ser Val Thr
        115                 120                 125

Ile Pro Asn Ser Val Thr Asp Ile Glu Asn Ser Ala Phe Phe Ser Cys
130                 135                 140

Ser Gly Leu Thr Ser Val Thr Ile Pro Asn Ser Val Thr Thr Ile Gly
145                 150                 155                 160

Asp Glu Ala Phe Ala Asp Cys Ser Gly Leu Thr Ser Val Thr Ile Pro
                165                 170                 175

Asn Ser Val Thr Thr Ile Gly Asp Gly Ser Phe Ala Glu Cys Ser Gly
            180                 185                 190

Leu Thr Ser Val Thr Ile Pro Asn Ser Val Thr Thr Ile Gly Asp Gly
        195                 200                 205

Ser Phe Ala Arg Cys Ser Gly Leu Thr Ser Val Thr Ile Pro Asn Ser
210                 215                 220

Val Ile Thr Ile Asn Arg Gly Ala Phe Ala Leu Cys Ser Gly Leu Thr
225                 230                 235                 240

Ser Val Thr Ile Pro Asn Ser Val Thr Thr Ile Arg Glu Asn Ala Phe
                245                 250                 255

Ala Gly Cys Ser Ser Leu Arg Thr Val Asn Cys His Ile Thr Ser Pro
            260                 265                 270

Leu Val Ile Asn Ala Asn Val Phe Gly Asn Val Thr Gln Ser Asn Cys
        275                 280                 285

Ala Leu Asn Val Pro Thr Gly Thr Gln Ala Val Tyr Gln Ala Ala Ala
290                 295                 300

Val Trp Arg Asn Phe Ser Pro Ile Ser Gly Asn Leu Leu Ser Asn His
305                 310                 315                 320

Ser Phe Ala Ile Glu Ser Ala Leu Lys Ile Tyr Pro Asn Pro Ala Ser
                325                 330                 335

Glu Ile Leu Asn Ile Ala Leu Gln Glu Gly Leu Gln Leu Glu Lys Val
            340                 345                 350

```
Asn Phe Tyr Asn Thr Leu Gly Gln Leu Ile Lys Thr Thr Asn His Ser
        355                 360                 365

Glu Ile Asn Val Ser Ser Phe Ala Lys Gly Asn Tyr Phe Val Glu Ile
    370                 375                 380

Ile Thr Asn Gln Gly Lys Ala Thr Lys Thr Ile Ile Ile Gln
385                 390                 395

<210> SEQ ID NO 77
<211> LENGTH: 445
<212> TYPE: PRT
<213> ORGANISM: Artificial Sequence
<220> FEATURE:
<223> OTHER INFORMATION: Synthetic

<400> SEQUENCE: 77

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Glu Asn Ala Phe Ala
                85                  90                  95

Leu Cys Ser Asn Leu Thr Ser Ile Thr Ile Pro Asn Asn Thr Val Thr
            100                 105                 110

Ser Ile Gly Gly Thr Ala Phe Glu Arg Cys Ser Gly Leu Thr Ser Val
        115                 120                 125

Thr Ile Pro Asn Ser Val Thr Thr Ile Gly Glu Gly Ser Phe Ala Gly
    130                 135                 140

Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Phe Ser Cys Ser
            180                 185                 190

Gly Leu Thr Ser Val Thr Ile Pro Asn Ser Val Thr Thr Ile Gly Asp
        195                 200                 205

Gly Ser Phe Ala Arg Cys Ser Gly Leu Thr Ser Val Thr Ile Pro Asn
    210                 215                 220

Ser Val Thr Thr Ile Gly Asp Glu Ala Phe Ala Asp Cys Ser Gly Leu
225                 230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ala Asp Cys Ser Gly Leu Thr Ser
        275                 280                 285

Val Thr Ile Pro Asn Ser Val Thr Ala Ile Gly Glu Asn Ala Phe Ala
    290                 295                 300

Gly Cys Ser Ser Leu Arg Thr Val Asn Cys His Ile Thr Ser Pro Leu
305                 310                 315                 320
```

```
Val Ile Asn Ala Asn Val Phe Gly Asn Val Thr Gln Ser Asn Cys Ala
            325                 330                 335

Leu Asn Val Pro Thr Gly Thr Gln Ala Val Tyr Gln Ala Ala Ala Val
            340                 345                 350

Trp Arg Asn Phe Ser Pro Ile Ser Gly Ser Leu Leu Ser Asn His Ser
            355                 360                 365

Phe Ala Ile Glu Ser Ala Leu Lys Ile Tyr Pro Asn Pro Val Ser Glu
            370                 375                 380

Ile Leu Asn Ile Ala Leu Gln Glu Gly Leu Gln Leu Glu Lys Val Asn
385                 390                 395                 400

Phe Tyr Asn Thr Leu Gly Gln Leu Ile Lys Thr Thr Asn His Ser Glu
                405                 410                 415

Ile Asn Val Ser Ser Phe Ala Lys Gly Asn Tyr Phe Val Glu Val Ile
                420                 425                 430

Thr Asn Gln Gly Lys Ala Thr Lys Thr Ile Ile Gln
                435                 440                 445
```

<210> SEQ ID NO 78
<211> LENGTH: 445
<212> TYPE: PRT
<213> ORGANISM: Artificial Sequence
<220> FEATURE:
<223> OTHER INFORMATION: Synthetic

<400> SEQUENCE: 78

```
Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
            35                  40                  45

Ala Val Ile Pro Glu Ile Val Thr Tyr Asn Ser Glu Asn Tyr Ile Val
        50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Glu Asn Ala Phe Ala
                85                  90                  95

Leu Cys Ser Asn Leu Thr Ser Ile Thr Ile Pro Asn Asn Thr Val Thr
            100                 105                 110

Ser Ile Gly Gly Thr Ala Phe Glu Arg Cys Ser Gly Leu Thr Ser Val
            115                 120                 125

Thr Ile Pro Asn Ser Val Thr Thr Ile Gly Glu Gly Ser Phe Ala Gly
        130                 135                 140

Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Phe Ser Cys Ser
            180                 185                 190

Gly Leu Thr Ser Val Thr Ile Pro Asn Ser Val Thr Thr Ile Gly Asp
            195                 200                 205

Gly Ser Phe Ala Arg Cys Ser Gly Leu Thr Ser Val Thr Ile Pro Asn
        210                 215                 220

Ser Val Thr Thr Ile Gly Asp Glu Ala Phe Ala Asp Cys Ser Gly Leu
225                 230                 235                 240
```

```
Thr Ser Val Thr Ile Pro Asn Ser Val Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Glu Asn Ala Phe Ala Asp Cys Ser Gly Leu Thr Ser
            275                 280                 285

Val Thr Ile Pro Asn Ser Val Thr Ala Ile Gly Glu Asn Ala Phe Ala
        290                 295                 300

Gly Cys Ser Ser Leu Arg Thr Val Asn Cys His Ile Thr Ser Pro Leu
305                 310                 315                 320

Val Ile Asn Ala Asn Val Phe Gly Asn Val Thr Gln Ser Asn Cys Ala
                325                 330                 335

Leu Asn Val Pro Thr Gly Lys Gln Val Ala Tyr Gln Ala Ala Ala Val
            340                 345                 350

Trp Arg Asn Phe Ser Pro Ile Ser Gly Ser Leu Leu Ser Asn His Ser
            355                 360                 365

Phe Ala Ile Glu Ser Ala Leu Lys Ile Tyr Pro Asn Pro Val Ser Glu
        370                 375                 380

Ile Leu Asn Ile Thr Leu Gln Glu Gly Leu Gln Leu Glu Lys Val Asn
385                 390                 395                 400

Phe Tyr Asn Thr Leu Gly Gln Leu Ile Lys Thr Thr Asn His Ser Glu
                405                 410                 415

Ile Asn Val Ser Ser Phe Ala Lys Gly Asn Tyr Phe Val Glu Val Met
            420                 425                 430

Thr Asn Gln Gly Lys Ala Thr Lys Thr Ile Ile Gln
            435                 440                 445

<210> SEQ ID NO 79
<211> LENGTH: 468
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (209)..(209)
<223> OTHER INFORMATION: Xaa can be any naturally occurring amino acid

<400> SEQUENCE: 79

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Lys Asn Ala Phe Ala
                85                  90                  95

Leu Cys Ser Asn Leu Thr Ser Ile Thr Ile Pro Asn Asn Thr Val Thr
            100                 105                 110

Ser Ile Gly Asp Ala Ala Phe Glu Arg Cys Ser Gly Leu Thr Ser Val
        115                 120                 125

Thr Ile Pro Asn Ser Val Thr Thr Ile Gly Lys Gly Ser Phe Ala Gly
```

```
                130             135             140
Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Phe Ser Cys Ser
            180                 185                 190

Gly Leu Thr Ser Val Thr Ile Pro Asn Ser Val Thr Thr Ile Gly Asp
        195                 200                 205

Xaa Ser Phe Ala Arg Cys Ser Gly Leu Thr Ser Val Thr Ile Pro Asn
    210                 215                 220

Ser Val Thr Thr Ile Gly Asp Glu Ala Phe Ala Asp Cys Ser Gly Leu
225                 230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ala Asp Cys Ser Gly Leu Thr Ser
        275                 280                 285

Val Thr Ile Pro Asn Ser Val Thr Ile Gly Asp Gly Ser Phe Ala
    290                 295                 300

Arg Cys Ser Gly Leu Thr Ser Val Thr Ile Pro Asn Ser Val Thr Ser
305                 310                 315                 320

Ile Gly Asp Tyr Ala Phe Asn Ser Cys Pro Ser Leu Thr Thr Ile Asn
                325                 330                 335

Cys Tyr Thr Thr Thr Pro Leu Val Ile Asn Pro Asn Val Phe Gly Asp
            340                 345                 350

Thr Asn Gln Ser Ala Cys Thr Leu Asn Val Pro Ala Gly Thr Glu Ala
        355                 360                 365

Val Tyr Gln Ala Thr Glu Ile Trp Gln Asp Phe Ser Pro Ile Thr Gly
    370                 375                 380

Gly Phe Leu Ser Ser Asn Ser Phe Ala Ile Glu Ser Asn Leu Lys Ile
385                 390                 395                 400

Tyr Pro Asn Pro Val Ser Glu Ile Leu Asn Ile Ala Leu Gln Glu Gly
                405                 410                 415

Leu Gln Leu Gln Lys Val Asn Phe Tyr Asn Thr Leu Gly Gln Leu Ile
            420                 425                 430

Lys Thr Thr Asn His Leu Glu Thr Asn Val Ser Ser Phe Ala Lys Gly
        435                 440                 445

Asn Tyr Phe Val Glu Val Ile Thr Asn Gln Gly Lys Ala Thr Lys Thr
    450                 455                 460

Ile Ile Ile Gln
465

<210> SEQ ID NO 80
<211> LENGTH: 468
<212> TYPE: PRT
<213> ORGANISM: Artificial Sequence
<220> FEATURE:
<223> OTHER INFORMATION: Synthetic

<400> SEQUENCE: 80

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
```

```
                    20                  25                  30
Ala Pro Phe Thr Ala Lys Val Ala Arg Asn Pro Asp Phe Ser Gly Val
                35                  40                  45
Ala Val Ile Pro Glu Ile Val Thr Tyr Asn Ser Glu Asn Tyr Ile Val
            50                  55                  60
Thr Ala Ile Gly Glu Ser Ala Phe Phe Ser Cys Gln Gly Leu Thr Ser
65                  70                  75                  80
Val Asn Val Gly Asn Phe Val Arg Ser Ile Gly Lys Asn Ala Phe Ala
                85                  90                  95
Leu Cys Ser Asn Leu Thr Ser Ile Thr Ile Pro Asn Asn Thr Val Thr
                100                 105                 110
Ser Ile Gly Asp Ala Ala Phe Glu Arg Cys Ser Gly Leu Thr Ser Val
            115                 120                 125
Thr Ile Pro Asn Ser Val Thr Thr Ile Gly Lys Gly Ser Phe Ala Gly
            130                 135                 140
Cys Ser Gly Leu Ile Ser Ile Thr Ile Pro Asn Ser Val Thr Thr Ile
145                 150                 155                 160
Arg Arg Gly Val Phe Ser Ala Cys Ser Gly Leu Ile Ser Val Thr Ile
                165                 170                 175
Pro Asn Ser Val Thr Asp Ile Glu Asn Gly Ala Phe Phe Ser Cys Ser
                180                 185                 190
Gly Leu Thr Ser Val Thr Ile Pro Asn Ser Val Thr Thr Ile Gly Asp
            195                 200                 205
Glu Ser Phe Ala Arg Cys Ser Gly Leu Thr Ser Val Thr Ile Pro Asn
            210                 215                 220
Ser Val Thr Thr Ile Gly Asp Glu Ala Phe Ala Asp Cys Ser Gly Leu
225                 230                 235                 240
Thr Ser Val Thr Ile Pro Asn Ser Val Thr Thr Ile Gly Asp Gly Ser
                245                 250                 255
Phe Ala Glu Cys Ser Gly Leu Thr Ser Val Thr Ile Pro Asn Ser Val
                260                 265                 270
Thr Thr Ile Gly Asp Glu Ala Phe Ala Asp Cys Ser Gly Leu Thr Ser
            275                 280                 285
Val Thr Ile Pro Asn Ser Val Thr Thr Ile Gly Asp Gly Ser Phe Ala
            290                 295                 300
Arg Cys Ser Gly Leu Thr Ser Val Thr Ile Pro Asn Ser Val Thr Ser
305                 310                 315                 320
Ile Gly Asp Tyr Ala Phe Asn Ser Cys Pro Ser Leu Thr Thr Ile Asn
                325                 330                 335
Cys Tyr Thr Thr Thr Pro Leu Val Ile Asn Pro Asn Val Phe Gly Asp
                340                 345                 350
Thr Asn Gln Ser Ala Cys Thr Leu Asn Val Pro Ala Gly Thr Glu Ala
            355                 360                 365
Val Tyr Gln Ala Thr Glu Ile Trp Gln Asp Phe Ser Pro Ile Thr Gly
            370                 375                 380
Gly Phe Leu Ser Ser Asn Ser Phe Ala Ile Glu Ser Asn Leu Lys Ile
385                 390                 395                 400
Tyr Pro Asn Pro Val Ser Glu Ile Leu Asn Ile Ala Leu Gln Glu Gly
                405                 410                 415
Leu Gln Leu Gln Lys Val Asn Phe Tyr Asn Thr Leu Gly Gln Leu Ile
                420                 425                 430
Lys Thr Thr Asn His Leu Glu Thr Asn Val Ser Ser Phe Ala Lys Gly
            435                 440                 445
```

```
Asn Tyr Phe Val Glu Val Ile Thr Asn Gln Gly Lys Ala Thr Lys Thr
            450                 455                 460

Ile Ile Ile Gln
465

<210> SEQ ID NO 81
<211> LENGTH: 468
<212> TYPE: PRT
<213> ORGANISM: Artificial Sequence
<220> FEATURE:
<223> OTHER INFORMATION: Synthetic

<400> SEQUENCE: 81

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Glu Asn Ala Phe Ala
                85                  90                  95

Leu Cys Ser Asn Leu Thr Ser Ile Thr Ile Pro Asn Asn Thr Val Thr
            100                 105                 110

Ser Ile Gly Asp Ala Ala Phe Gly Arg Cys Ser Gly Leu Thr Ser Val
        115                 120                 125

Thr Ile Pro Asn Ser Val Thr Thr Ile Gly Glu Gly Ser Phe Ala Gly
    130                 135                 140

Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Phe Ser Cys Ser
            180                 185                 190

Gly Leu Thr Ser Val Thr Ile Pro Asn Ser Val Thr Thr Ile Gly Asp
        195                 200                 205

Gly Ser Phe Ala Arg Cys Ser Gly Leu Thr Ser Val Thr Ile Pro Asn
    210                 215                 220

Ser Val Thr Thr Ile Gly Asp Glu Ala Phe Ala Asp Cys Ser Gly Leu
225                 230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ala Asp Cys Ser Gly Leu Thr Ser
        275                 280                 285

Val Thr Ile Pro Asn Ser Val Thr Thr Ile Gly Asp Gly Ser Phe Ala
    290                 295                 300

Arg Cys Ser Gly Leu Thr Ser Val Thr Ile Pro Asn Ser Val Thr Ser
305                 310                 315                 320

Ile Gly Asp Tyr Ala Phe Asn Ser Cys Pro Ser Leu Thr Ile Thr Asn
                325                 330                 335
```

-continued

```
Cys Tyr Thr Thr Thr Pro Leu Val Ile Asn Pro Asn Val Phe Gly Asp
                340                 345                 350

Thr Asn Gln Ser Ala Cys Thr Leu Asn Val Pro Ala Gly Thr Glu Ala
            355                 360                 365

Val Tyr Gln Ala Thr Glu Ile Trp Gln Asp Phe Ser Pro Ile Thr Gly
        370                 375                 380

Gly Phe Leu Ser Ser Asn Ser Phe Ala Ile Glu Ser Asn Leu Lys Ile
385                 390                 395                 400

Tyr Pro Asn Pro Val Ser Glu Ile Leu Asn Ile Ala Leu Gln Glu Gly
                405                 410                 415

Leu Gln Leu Gln Lys Val Asn Phe Tyr Asn Thr Leu Gly Gln Leu Ile
            420                 425                 430

Lys Thr Thr Asn His Leu Glu Thr Asn Val Ser Ser Phe Ala Lys Gly
        435                 440                 445

Asn Tyr Phe Val Glu Val Ile Thr Asn Gln Gly Lys Ala Thr Lys Thr
    450                 455                 460

Ile Ile Ile Gln
465

<210> SEQ ID NO 82
<211> LENGTH: 468
<212> TYPE: PRT
<213> ORGANISM: Artificial Sequence
<220> FEATURE:
<223> OTHER INFORMATION: Synthetic

<400> SEQUENCE: 82

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Glu Asn Ala Phe Ala
                85                  90                  95

Leu Cys Ser Asn Leu Thr Ser Ile Thr Ile Pro Asn Asn Thr Val Thr
            100                 105                 110

Ser Ile Gly Asp Ala Ala Phe Asp Arg Cys Ser Gly Leu Thr Ser Val
        115                 120                 125

Thr Ile Pro Asn Ser Val Thr Thr Ile Gly Glu Gly Ser Phe Ala Gly
    130                 135                 140

Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Phe Ser Cys Ser
            180                 185                 190

Gly Leu Thr Ser Val Thr Ile Pro Asn Ser Val Thr Thr Ile Gly Ile
        195                 200                 205

Gly Ser Phe Ala Arg Cys Ser Gly Leu Thr Ser Val Thr Ile Pro Asn
    210                 215                 220
```

```
Ser Val Thr Thr Ile Gly Asp Glu Ala Phe Ala Asp Cys Ser Gly Leu
225                 230                 235                 240

Thr Ser Val Thr Ile Pro Asn Ser Val Thr Thr Ile Gly Asp Gly Ser
            245                 250                 255

Phe Ala Glu Cys Ser Gly Leu Thr Ser Val Thr Ile Pro Asn Ser Val
        260                 265                 270

Thr Thr Ile Gly Asp Glu Ala Phe Ala Asp Cys Ser Gly Leu Thr Ser
    275                 280                 285

Val Thr Ile Pro Asn Ser Val Thr Ile Gly Asp Gly Ser Phe Ala
290                 295                 300

Arg Cys Ser Gly Leu Thr Ser Val Thr Ile Pro Asn Ser Val Thr Ser
305                 310                 315                 320

Ile Gly Asp Tyr Ala Phe Asn Ser Cys Pro Ser Leu Thr Thr Ile Asn
                325                 330                 335

Cys Tyr Thr Thr Thr Pro Leu Val Ile Asn Pro Asn Val Phe Gly Asp
                340                 345                 350

Thr Asn Gln Ser Ala Cys Thr Leu Asn Val Pro Ala Gly Thr Glu Ala
            355                 360                 365

Val Tyr Gln Ala Thr Glu Ile Trp Gln Asp Phe Ser Pro Ile Thr Gly
370                 375                 380

Gly Phe Leu Ser Ser Asn Ser Phe Ala Ile Glu Ser Asn Leu Lys Ile
385                 390                 395                 400

Tyr Pro Asn Pro Val Ser Glu Ile Leu Asn Ile Ala Leu Gln Glu Gly
                405                 410                 415

Leu Gln Leu Gln Lys Val Asn Phe Tyr Asn Thr Leu Gly Gln Leu Ile
            420                 425                 430

Lys Thr Thr Asn His Leu Glu Thr Asn Val Ser Ser Phe Ala Lys Gly
                435                 440                 445

Asn Tyr Phe Val Glu Val Ile Thr Asn Gln Gly Lys Ala Thr Lys Thr
    450                 455                 460

Ile Ile Ile Gln
465

<210> SEQ ID NO 83
<211> LENGTH: 468
<212> TYPE: PRT
<213> ORGANISM: Artificial Sequence
<220> FEATURE:
<223> OTHER INFORMATION: Synthetic

<400> SEQUENCE: 83

Met Arg Lys Leu Leu Phe Val Ile Leu Ile Pro Phe Leu Gly Ile Ala
1               5                   10                  15

Gln Asp Phe Thr Ala Asn Gly Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Thr Cys Gln Gly Leu Thr Ser
65                  70                  75                  80

Val Asn Val Gly Asn Phe Val Arg Ser Ile Glu Lys Asp Ala Phe Ala
                85                  90                  95

Leu Cys Ser Asn Leu Thr Ser Ile Thr Ile Pro Asn Asn Thr Val Thr
            100                 105                 110
```

Ser Ile Gly Asp Ala Ala Phe Glu Arg Cys Ser Arg Leu Thr Ser Val
            115                 120                 125

Thr Ile Pro Asn Ser Val Thr Thr Ile Gly Lys Gly Ser Phe Thr Gly
        130                 135                 140

Cys Ser Gly Leu Ile Ser Val Thr Ile Pro Asn Ser Val Thr Ser Ile
145                 150                 155                 160

Arg Arg Asp Ala Phe Thr Ala Cys Ser Ser Leu Ile Ser Val Thr Ile
                165                 170                 175

Pro Asn Ser Val Thr Thr Ile Gly Asn Gly Ala Phe Phe Ser Cys Ser
            180                 185                 190

Gly Leu Thr Ser Val Thr Ile Pro Asn Ser Val Thr Thr Ile Gly Asp
        195                 200                 205

Gly Ser Phe Ala Ser Cys Ser Gly Leu Thr Ser Val Thr Ile Pro Asn
    210                 215                 220

Ser Val Thr Thr Ile Gly Asp Gly Ala Phe Ala Asp Cys Ser Gly Leu
225                 230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ala Asp Cys Ser Gly Leu Thr Ser
        275                 280                 285

Val Thr Ile Pro Asn Ser Val Thr Ile Gly Asn Trp Ser Phe Glu
    290                 295                 300

Arg Cys Ser Gly Leu Thr Ser Val Thr Ile Pro Asn Ser Val Thr Ser
305                 310                 315                 320

Ile Gly Asp Tyr Ala Phe Asn Leu Cys Pro Ser Leu Thr Thr Ile Asn
                325                 330                 335

Cys His Thr Thr Thr Pro Leu Val Ile Asn Pro Asn Val Phe Gly Asp
            340                 345                 350

Thr Asn Gln Ser Ala Cys Thr Leu Asn Val Pro Ala Gly Thr Glu Ala
        355                 360                 365

Val Tyr Gln Ala Thr Glu Ile Trp Gln Asp Phe Ser Pro Ile Thr Gly
    370                 375                 380

Gly Phe Leu Ser Ser Asn Ser Phe Ala Ile Lys Ser Asn Leu Lys Ile
385                 390                 395                 400

Tyr Pro Asn Pro Val Ser Glu Ile Leu Asn Ile Ala Leu Gln Glu Gly
                405                 410                 415

Leu Gln Leu Glu Lys Val Asn Phe Tyr Asn Thr Leu Gly Gln Leu Ile
            420                 425                 430

Lys Thr Thr Asn His Leu Glu Thr Asn Val Ser Ser Phe Ala Lys Gly
        435                 440                 445

Asn Tyr Phe Val Glu Val Ile Thr Asn Gln Gly Lys Ala Thr Lys Thr
    450                 455                 460

Ile Ile Ile Gln
465

<210> SEQ ID NO 84
<211> LENGTH: 468
<212> TYPE: PRT
<213> ORGANISM: Artificial Sequence
<220> FEATURE:
<223> OTHER INFORMATION: Synthetic

<400> SEQUENCE: 84

```
Met Arg Lys Leu Leu Phe Val Ile Leu Ile Pro Phe Leu Gly Ile Ala
1               5                   10                  15

Gln Asp Phe Thr Ala Asn Gly Ile Arg Tyr Thr Ile Thr Ser Ser Glu
                20                  25                  30

Ala Pro Phe Thr Ala Lys Val Ala Arg Asn Pro Asp Phe Ser Gly Val
                35                  40                  45

Ala Val Ile Pro Glu Ile Val Thr Tyr Asn Ser Glu Asn Tyr Ile Val
50                      55                  60

Thr Ala Ile Gly Glu Ser Ala Phe Phe Thr Cys Gln Gly Leu Thr Ser
65                      70                  75                  80

Val Asn Val Gly Asn Phe Val Arg Ser Ile Glu Lys Asp Ala Phe Ala
                85                  90                  95

Leu Cys Ser Asn Leu Thr Ser Ile Thr Ile Pro Asn Asn Thr Val Thr
                100                 105                 110

Ser Ile Gly Asp Ala Ala Phe Glu Arg Cys Ser Arg Leu Thr Ser Val
                115                 120                 125

Thr Ile Pro Asn Ser Val Thr Thr Ile Gly Lys Gly Ser Phe Thr Gly
130                     135                 140

Cys Ser Gly Leu Ile Ser Val Thr Ile Pro Asn Ser Val Thr Ser Ile
145                     150                 155                 160

Arg Arg Asp Ala Phe Thr Leu Cys Ser Ser Leu Ile Ser Val Thr Ile
                165                 170                 175

Pro Asn Ser Val Thr Thr Ile Gly Asn Gly Ala Phe Phe Ser Cys Ser
                180                 185                 190

Gly Leu Thr Ser Val Thr Ile Pro Asn Ser Val Thr Thr Ile Gly Asn
                195                 200                 205

Gly Ser Phe Ala Ser Cys Ser Gly Leu Thr Ser Val Thr Ile Pro Asn
                210                 215                 220

Ser Val Thr Thr Ile Gly Asp Glu Ala Phe Ala Asp Cys Ser Gly Leu
225                     230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
                260                 265                 270

Thr Thr Ile Gly Asp Glu Ala Phe Ala Asp Cys Ser Gly Leu Thr Ser
                275                 280                 285

Val Thr Ile Pro Asn Ser Val Thr Thr Ile Gly Asp Gly Ser Phe Ala
                290                 295                 300

Gly Cys Ser Gly Leu Thr Ser Val Thr Ile Pro Asn Ser Val Thr Ser
305                     310                 315                 320

Ile Gly Asp Tyr Ala Phe Asn Leu Cys Pro Ser Leu Thr Thr Ile Asn
                325                 330                 335

Cys His Thr Thr Thr Pro Leu Val Ile Asn Pro Asn Val Phe Gly Asp
                340                 345                 350

Thr Asn Gln Ser Ala Cys Thr Leu Asn Val Pro Ala Gly Thr Glu Ala
                355                 360                 365

Val Tyr Gln Ala Thr Glu Ile Trp Gln Asp Phe Ser Pro Ile Thr Gly
                370                 375                 380

Gly Phe Leu Ser Ser Asn Ser Phe Ala Ile Lys Ser Asn Leu Lys Ile
385                     390                 395                 400

Tyr Pro Asn Pro Val Ser Glu Ile Leu Asn Ile Ala Leu Gln Glu Gly
                405                 410                 415
```

```
Leu Gln Leu Glu Lys Val Asn Phe Tyr Asn Thr Leu Gly Gln Leu Ile
            420                 425                 430

Lys Thr Thr Asn His Leu Glu Thr Asn Val Ser Ser Phe Ala Lys Gly
        435                 440                 445

Asn Tyr Phe Val Glu Val Ile Thr Asn Gln Gly Lys Ala Thr Lys Thr
    450                 455                 460

Ile Ile Ile Gln
465

<210> SEQ ID NO 85
<211> LENGTH: 468
<212> TYPE: PRT
<213> ORGANISM: Artificial Sequence
<220> FEATURE:
<223> OTHER INFORMATION: Synthetic

<400> SEQUENCE: 85

Met Arg Lys Leu Leu Phe Val Ile Leu Ile Pro Phe Leu Gly Ile Ala
1               5                   10                  15

Gln Asp Phe Thr Ala Asn Gly Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Thr Cys Gln Gly Leu Thr Ser
65                  70                  75                  80

Val Asn Val Gly Asn Phe Val Arg Ser Ile Glu Lys Asp Ala Phe Ala
                85                  90                  95

Leu Cys Ser Asn Leu Thr Ser Ile Thr Ile Pro Asn Asn Thr Val Thr
            100                 105                 110

Ser Ile Gly Asp Ala Ala Phe Glu Arg Cys Ser Arg Leu Thr Ser Val
        115                 120                 125

Thr Ile Pro Asn Ser Val Thr Thr Ile Gly Lys Gly Ser Phe Thr Gly
    130                 135                 140

Cys Ser Gly Leu Ile Ser Val Thr Ile Pro Asn Ser Val Thr Ser Ile
145                 150                 155                 160

Arg Arg Asp Ala Phe Thr Leu Cys Ser Ser Leu Ile Ser Val Thr Ile
                165                 170                 175

Pro Asn Ser Val Thr Ala Ile Gly Asn Gly Ala Phe Ser Cys Ser
            180                 185                 190

Gly Leu Thr Ser Val Thr Ile Pro Asn Ser Val Thr Thr Ile Gly Asn
        195                 200                 205

Gly Ser Phe Ala Ser Cys Ser Gly Leu Thr Ser Val Thr Ile Pro Asn
    210                 215                 220

Ser Val Thr Thr Ile Gly Asp Glu Ala Phe Ala Asp Cys Ser Gly Leu
225                 230                 235                 240

Thr Ser Val Thr Ile Pro Asn Ser Val Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ser Asp Cys Ser Gly Leu Thr Ser
        275                 280                 285

Val Thr Ile Pro Asn Ser Val Thr Thr Ile Gly Asp Gly Ser Phe Glu
    290                 295                 300
```

-continued

```
Gly Cys Ser Gly Leu Thr Ser Val Thr Ile Pro Asn Ser Val Thr Ser
305                 310                 315                 320

Ile Gly Asp Tyr Ala Phe Asn Leu Cys Pro Ser Leu Thr Thr Ile Asn
            325                 330                 335

Cys His Thr Thr Thr Pro Leu Val Ile Asn Pro Asn Val Phe Gly Asp
            340                 345                 350

Thr Asn Gln Ser Ala Cys Thr Leu Asn Val Pro Ala Gly Thr Glu Ala
        355                 360                 365

Val Tyr Gln Ala Thr Glu Ile Trp Gln Asp Phe Ser Pro Ile Thr Gly
    370                 375                 380

Gly Phe Leu Ser Ser Asn Ser Phe Ala Ile Lys Ser Asn Leu Lys Ile
385                 390                 395                 400

Tyr Pro Asn Pro Val Ser Glu Ile Leu Asn Ile Ala Leu Gln Glu Gly
            405                 410                 415

Leu Gln Leu Glu Lys Val Asn Phe Tyr Asn Thr Leu Gly Gln Leu Ile
        420                 425                 430

Lys Thr Thr Asn His Leu Glu Thr Asn Val Ser Ser Phe Ala Lys Gly
    435                 440                 445

Asn Tyr Phe Val Glu Val Ile Thr Asn Gln Gly Lys Ala Thr Lys Thr
450                 455                 460

Ile Ile Ile Gln
465

<210> SEQ ID NO 86
<211> LENGTH: 468
<212> TYPE: PRT
<213> ORGANISM: Artificial Sequence
<220> FEATURE:
<223> OTHER INFORMATION: Synthetic

<400> SEQUENCE: 86

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Ile Val Thr Tyr Asn Ser Glu Asn Tyr Ile Val
    50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Glu Asn Ala Phe Ala
                85                  90                  95

Leu Cys Ser Asn Leu Thr Ser Ile Thr Ile Pro Asn Asn Thr Val Thr
            100                 105                 110

Ser Ile Gly Asp Ala Ala Phe Glu Arg Cys Ser Gly Leu Thr Ser Val
        115                 120                 125

Thr Ile Pro Asn Ser Val Thr Thr Ile Gly Glu Gly Ser Phe Ala Gly
    130                 135                 140

Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Ser Cys Ser
            180                 185                 190
```

Gly Leu Thr Ser Val Thr Ile Pro Asn Ser Val Thr Thr Ile Gly Asp
            195                 200                 205

Gly Ser Phe Ala Arg Cys Ser Gly Leu Thr Ser Val Thr Ile Pro Asn
        210                 215                 220

Ser Val Thr Thr Ile Gly Asp Glu Ala Phe Ala Asp Cys Ser Gly Leu
225                 230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ala Asp Cys Ser Gly Leu Thr Ser
        275                 280                 285

Val Thr Ile Pro Asn Ser Val Thr Thr Ile Gly Asp Gly Ser Phe Ala
290                 295                 300

Arg Cys Ser Gly Leu Thr Ser Val Thr Ile Pro Asn Ser Val Thr Ser
305                 310                 315                 320

Ile Gly Asp Tyr Ala Phe Asn Ser Cys Pro Ser Leu Thr Thr Ile Asn
                325                 330                 335

Cys Tyr Thr Thr Thr Pro Leu Val Ile Asn Pro Asn Val Phe Gly Asp
            340                 345                 350

Thr Asn Gln Ser Ala Cys Thr Leu Asn Val Pro Ala Gly Thr Glu Ala
        355                 360                 365

Val Tyr Gln Ala Thr Glu Ile Trp Gln Asp Phe Ser Pro Ile Thr Gly
370                 375                 380

Gly Phe Leu Ser Ser Asn Ser Phe Ala Ile Glu Ser Asn Leu Lys Ile
385                 390                 395                 400

Tyr Pro Asn Pro Val Ser Glu Ile Leu Asn Ile Ala Leu Gln Glu Gly
                405                 410                 415

Leu Gln Leu Gln Lys Val Asn Phe Tyr Asn Thr Leu Gly Gln Leu Ile
            420                 425                 430

Lys Thr Thr Asn His Leu Glu Thr Asn Val Ser Ser Phe Ala Lys Gly
        435                 440                 445

Asn Tyr Phe Val Glu Val Ile Thr Asn Gln Gly Lys Ala Thr Lys Thr
450                 455                 460

Ile Ile Ile Gln
465

<210> SEQ ID NO 87
<211> LENGTH: 468
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature

```
<222> LOCATION: (305)..(305)
<223> OTHER INFORMATION: Xaa can be any naturally occurring amino acid

<400> SEQUENCE: 87

Met Lys Lys Leu Leu Phe Val Ile Leu Ile Pro Phe Leu Gly Ile Ala
1               5                   10                  15

Gln Asp Phe Thr Ala Asn His Ile Arg Tyr Thr Ile Thr Ser Ser Glu
            20                  25                  30

Ala Pro Phe Thr Ala Lys Val Ala Arg Asn Pro Asp Phe Ser Gly Val
        35                  40                  45

Ala Val Ile Pro Glu Thr Val Ala Tyr Asn Ser Xaa Asn Tyr Ile Val
    50                  55                  60

Thr Ala Ile Gly Glu Ser Ala Phe Phe Ser Cys Gln Gly Leu Thr Ser
65                  70                  75                  80

Val Asn Val Gly Asn Phe Val Arg Ser Ile Gly Xaa Asn Ala Phe Ala
                85                  90                  95

Leu Cys Ser Asn Leu Thr Ser Ile Thr Ile Pro Asn Asn Thr Val Thr
            100                 105                 110

Ser Ile Gly Asp Ala Ala Phe Xaa Arg Cys Ser Gly Leu Thr Ser Val
        115                 120                 125

Thr Ile Pro Asn Ser Val Thr Thr Ile Gly Glu Gly Ser Phe Ala Gly
    130                 135                 140

Cys Ser Gly Leu Ile Ser Ile Thr Ile Pro Asn Ser Val Thr Thr Ile
145                 150                 155                 160

Arg Arg Gly Val Phe Ser Ala Cys Ser Gly Leu Ile Ser Val Thr Ile
                165                 170                 175

Pro Asn Ser Val Thr Asp Ile Glu Asn Gly Ala Phe Phe Ser Cys Ser
            180                 185                 190

Gly Leu Thr Ser Val Thr Ile Pro Asn Ser Val Thr Thr Ile Gly Asp
        195                 200                 205

Xaa Ser Phe Ala Arg Cys Ser Gly Leu Thr Ser Val Thr Ile Pro Asn
    210                 215                 220

Ser Val Thr Thr Ile Gly Asp Glu Ala Phe Ala Asp Cys Ser Gly Leu
225                 230                 235                 240

Thr Ser Val Thr Ile Pro Asn Ser Val Thr Thr Ile Gly Asp Gly Ser
                245                 250                 255

Phe Ala Glu Cys Ser Gly Leu Thr Ser Val Thr Ile Pro Asn Ser Val
            260                 265                 270

Thr Thr Ile Gly Asp Glu Ala Phe Ala Asp Cys Ser Gly Leu Thr Ser
        275                 280                 285

Val Thr Ile Pro Asn Ser Val Thr Thr Ile Gly Asp Gly Ser Phe Ala
    290                 295                 300

Xaa Cys Ser Gly Leu Thr Ser Val Thr Ile Pro Asn Ser Val Thr Ser
305                 310                 315                 320

Ile Gly Asp Tyr Ala Phe Asn Ser Cys Pro Ser Leu Thr Thr Ile Asn
                325                 330                 335

Cys Tyr Thr Thr Thr Pro Leu Val Ile Asn Pro Asn Val Phe Gly Asp
            340                 345                 350

Thr Asn Gln Ser Ala Cys Thr Leu Asn Val Pro Ala Gly Thr Glu Ala
        355                 360                 365

Val Tyr Gln Ala Thr Glu Ile Trp Gln Asp Phe Ser Pro Ile Thr Gly
    370                 375                 380

Gly Phe Leu Ser Ser Asn Ser Phe Ala Ile Glu Ser Asn Leu Lys Ile
385                 390                 395                 400
```

```
Tyr Pro Asn Pro Val Ser Glu Ile Leu Asn Ile Ala Leu Gln Glu Gly
            405                 410                 415

Leu Gln Leu Gln Lys Val Asn Phe Tyr Asn Thr Leu Gly Gln Leu Ile
        420                 425                 430

Lys Thr Thr Asn His Leu Glu Thr Asn Val Ser Ser Phe Ala Lys Gly
        435                 440                 445

Asn Tyr Phe Val Glu Val Ile Thr Asn Gln Gly Lys Ala Thr Lys Thr
        450                 455                 460

Ile Ile Ile Gln
465

<210> SEQ ID NO 88
<211> LENGTH: 101
<212> TYPE: PRT
<213> ORGANISM: Artificial Sequence
<220> FEATURE:
<223> OTHER INFORMATION: Synthetic

<400> SEQUENCE: 88

Ser Thr Gln Thr Leu Lys Leu Ile Glu Thr His Leu Lys Thr Ile Pro
1               5                   10                  15

Ser Leu Ala Phe Ser Ser Leu Pro Asn Ile Ser Arg Ile Tyr Leu Ser
            20                  25                  30

Ile Asp Ala Thr Leu Gln Arg Leu Glu Pro His Ser Phe Tyr Asn Leu
        35                  40                  45

Ser Lys Met Thr His Ile Glu Ile Arg Asn Thr Arg Ser Leu Thr Tyr
    50                  55                  60

Ile Asp Pro Asp Ala Leu Thr Glu Leu Pro Leu Leu Lys Phe Leu Gly
65                  70                  75                  80

Ile Phe Asn Thr Gly Leu Arg Ile Phe Pro Asp Leu Thr Lys Ile Tyr
                85                  90                  95

Ser Thr Asp Ile Phe
            100

<210> SEQ ID NO 89
<211> LENGTH: 4
<212> TYPE: PRT
<213> ORGANISM: Artificial Sequence
<220> FEATURE:
<223> OTHER INFORMATION: Synthetic peptide

<400> SEQUENCE: 89

Lys Asp Glu Leu
1

<210> SEQ ID NO 90
<211> LENGTH: 4
<212> TYPE: PRT
<213> ORGANISM: Artificial Sequence
<220> FEATURE:
<223> OTHER INFORMATION: Synthetic grouping of aromatic amino acids

<400> SEQUENCE: 90

Phe Trp Tyr His
1

<210> SEQ ID NO 91
<211> LENGTH: 5
<212> TYPE: PRT
<213> ORGANISM: Artificial Sequence
<220> FEATURE:
```

```
<223> OTHER INFORMATION: Synthetic grouping of charged amino acids

<400> SEQUENCE: 91

His Lys Arg Glu Asp
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic peptide

<400> SEQUENCE: 92

Ala Pro Arg Pro Gly
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic octapeptide

<400> SEQUENCE: 93

Gly Pro Leu Gly Ile Ala Gly Gln
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic peptide

<400> SEQUENCE: 94

Arg Gly Asp Tyr Cys
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide

<400> SEQUENCE: 95

Ala Ser Ser His Asn
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic peptide

<400> SEQUENCE: 96

Lys Cys Cys Tyr Ser Leu
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 97

Tyr Glu Val Gly His Arg Cys
1               5

<210> SEQ ID NO 98
<211> LENGTH: 200
<212> TYPE: PRT
<213> ORGANISM: Flavobacterium psychrophilum

<400> SEQUENCE: 98

Met Arg Lys Leu Leu Phe Ile Ile Leu Ile Pro Phe Leu Gly Ile Ala
1               5                   10                  15

Gln Asp Phe Thr Ala Asn Arg Ile Lys Tyr Thr Val Thr Ser Ser Thr
                20                  25                  30

Ala Pro Phe Thr Val Lys Val Ala Arg Asn Ala Asn Phe Thr Gly Ala
            35                  40                  45

Ala Glu Ile Pro Glu Thr Val Val Tyr Asn Ser Glu Asn Tyr Ala Val
50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
            100                 105                 110

Ile Gly Asn Ser Ala Phe Ile Gly Ser Ser Leu Thr Ser Leu Thr Ile
        115                 120                 125

Gly Asn Ser Val Ala Ser Ile Gly Ser Phe Ala Phe Phe Gly Cys Phe
    130                 135                 140

Gly Leu Thr Ser Leu Thr Ile Pro Ser Ser Val Thr Ser Ile Ala Asn
145                 150                 155                 160

Gln Ala Phe Ser Glu Cys Thr Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala
        195                 200

<210> SEQ ID NO 99
<211> LENGTH: 200
<212> TYPE: PRT
<213> ORGANISM: Flavobacterium psychrophilum

<400> SEQUENCE: 99

Met Arg Lys Leu Leu Phe Ile Ile Leu Ile Pro Phe Leu Gly Ile Ala
1               5                   10                  15

Gln Asp Phe Thr Ala Asn Gly Ile Asn Tyr Thr Val Thr Ser Ser Thr
                20                  25                  30

Ala Pro Phe Thr Ala Ser Val Ala Ser Asn Thr Arg Phe Ser Gly Asp
            35                  40                  45

Ala Val Ile Pro Glu Thr Val Val Tyr Asn Ser Glu Asn Tyr Ala Val
50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

```
Asn Cys Val Ala Leu Thr Ser Val Thr Ile Gly Asn Ser Val Val Ser
            100                 105                 110

Ile Gly Asn Ser Ala Phe Ile Gly Ser Ser Leu Thr Ser Leu Thr Ile
            115                 120                 125

Gly Asn Ser Val Ala Ser Ile Gly Ser Phe Ala Phe Phe Gly Cys Phe
130                 135                 140

Gly Leu Thr Ser Leu Thr Ile Pro Ser Ser Val Thr Ser Ile Ala Asn
145                 150                 155                 160

Gln Ala Phe Ser Glu Cys Thr Gly Leu Thr Ser Val Thr Ile Pro Asn
            165                 170                 175

Phe Val Thr Ser Ile Gly Asp Gly Ala Phe Ser Met Cys Ser Gly Leu
            180                 185                 190

Ile Ser Val Thr Ile Pro Asn Ala
            195                 200

<210> SEQ ID NO 100
<211> LENGTH: 200
<212> TYPE: PRT
<213> ORGANISM: Flavobacterium psychrophilum

<400> SEQUENCE: 100

Met Arg Lys Leu Leu Phe Ile Ile Leu Ile Pro Phe Leu Gly Ile Ala
1               5                   10                  15

Gln Asp Phe Thr Ala Asn Gly Ile Asn Tyr Thr Val Thr Ser Ser Thr
            20                  25                  30

Ala Pro Phe Thr Ala Ser Val Ala Ser Asn Thr Arg Phe Ser Gly Asp
            35                  40                  45

Ala Val Ile Pro Glu Thr Val Val Tyr Asn Ser Glu Asn Tyr Ala Val
        50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
            100                 105                 110

Ile Gly Asn Ser Ala Phe Ile Gly Ser Ser Leu Thr Ser Leu Thr Ile
            115                 120                 125

Gly Asn Ser Val Ala Ser Ile Gly Ser Phe Ala Phe Phe Gly Cys Phe
130                 135                 140

Gly Leu Thr Ser Leu Thr Ile Pro Ser Ser Val Thr Ser Ile Ala Asn
145                 150                 155                 160

Gln Ala Phe Ser Glu Cys Thr Gly Leu Thr Ser Val Thr Ile Pro Asn
            165                 170                 175

Phe Val Thr Ser Ile Gly Asp Gly Ala Phe Ser Met Cys Ser Gly Leu
            180                 185                 190

Ile Ser Val Thr Ile Pro Asn Ala
            195                 200

<210> SEQ ID NO 101
<211> LENGTH: 200
<212> TYPE: PRT
<213> ORGANISM: Flavobacterium psychrophilum

<400> SEQUENCE: 101

Met Arg Lys Leu Leu Phe Ile Ile Leu Met Pro Phe Leu Gly Ile Ala
1               5                   10                  15
```

Gln Asp Phe Thr Glu Asn Gly Ile Asn Tyr Thr Thr Thr Ser Ser Thr
            20                  25                  30

Ala Pro Phe Thr Ala Ser Val Ala Ser Asn Thr Arg Phe Ser Gly Asp
        35                  40                  45

Ala Val Ile Pro Glu Thr Val Val Tyr Asn Ser Glu Asn Tyr Ala Val
    50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Ile Ser
                100                 105                 110

Ile Gly Asn Ser Ala Phe Ile Gly Ser Ser Leu Thr Ser Leu Thr Ile
            115                 120                 125

Gly Asn Ser Val Ala Ser Ile Gly Ser Leu Ala Phe Phe Gly Cys Phe
        130                 135                 140

Gly Leu Thr Ser Leu Thr Ile Pro Ser Ser Val Thr Ser Ile Ala Asn
145                 150                 155                 160

Gln Ala Phe Ser Glu Cys Ser Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

Ile Ser Val Thr Ile Pro Asn Ala
        195                 200

<210> SEQ ID NO 102
<211> LENGTH: 200
<212> TYPE: PRT
<213> ORGANISM: Flavobacterium psychrophilum

<400> SEQUENCE: 102

Met Arg Lys Leu Leu Phe Ile Ile Leu Ile Pro Phe Leu Gly Ile Ala
1               5                   10                  15

Gln Asp Phe Thr Glu Asn Gly Ile Asn Tyr Thr Thr Thr Ser Ser Thr
            20                  25                  30

Ala Pro Phe Thr Ala Ser Val Ala Ser Asn Thr Arg Phe Ser Gly Asp
        35                  40                  45

Ala Val Ile Pro Glu Thr Val Val Tyr Asn Ser Glu Asn Tyr Ala Val
    50                  55                  60

Thr Ala Ile Ala Asp Glu Ala Phe Lys Gly Asn Tyr Asn Leu Thr Ser
65                  70                  75                  80

Val Ser Ile Gly Asp Ala Val Thr Ser Val Gly Glu Ser Ala Phe Asn
                85                  90                  95

Asn Cys Val Ala Leu Thr Ser Val Thr Ile Gly Asn Ser Val Val Ser
                100                 105                 110

Ile Gly Asn Ser Ala Phe Ile Gly Ser Ser Leu Thr Ser Leu Thr Ile
            115                 120                 125

Gly Asn Ser Val Ala Ser Ile Gly Ser Phe Ala Phe Phe Gly Cys Phe
        130                 135                 140

Gly Leu Thr Ser Leu Thr Ile Pro Ser Ser Val Thr Ser Ile Ala Asn
145                 150                 155                 160

Gln Ala Phe Ser Met Cys Ser Gly Leu Thr Ser Val Thr Ile Pro Asn
                165                 170                 175

Phe Val Thr Ser Ile Gly Asp Gly Ala Phe Ser Met Cys Ser Gly Leu
            180                 185                 190

```
Ile Ser Val Thr Ile Pro Asn Ala
        195                 200

<210> SEQ ID NO 103
<211> LENGTH: 178
<212> TYPE: PRT
<213> ORGANISM: Flavobacterium psychrophilum

<400> SEQUENCE: 103

Met Arg Lys Leu Leu Phe Val Ile Leu Met Pro Phe Leu Gly Ile Ala
1               5                   10                  15

Gln Asn Phe Ile Ala Asn Gly Ile Asn Tyr Thr Thr Thr Ser Ser Val
            20                  25                  30

Ala Pro Phe Thr Val Ser Val Ser Asn Thr Arg Phe Ser Cys Val
        35                  40                  45

Ala Val Ile Pro Glu Thr Val Ala Tyr Asn Ser Glu Asn Tyr Ala Val
    50                  55                  60

Thr Ala Ile Thr Ala Ser Ala Phe Lys Ser Cys Ser Gly Leu Thr Ser
65                  70                  75                  80

Val Thr Ile Gly Asn Phe Ile Thr Ser Val Glu Arg Asp Ala Phe Arg
                85                  90                  95

Asp Ser Thr Asn Leu Thr Thr Val Thr Ile Gly Asn Ser Val Asn Ser
            100                 105                 110

Ile Glu Arg Phe Ala Phe Asn Asn Cys Ser Arg Leu Thr Ser Ile Thr
        115                 120                 125

Ile Pro Asp Ser Val Thr Ala Ile Arg Asn Ser Ala Phe Ala Ser Cys
    130                 135                 140

Thr Gly Leu Thr Ser Val Thr Phe Pro Asn Ser Val Ser Phe Ile Asp
145                 150                 155                 160

Ala Phe Ala Phe Ser Arg Cys Thr Asn Leu Thr Ser Val Thr Ile Pro
                165                 170                 175

Asn Ser

<210> SEQ ID NO 104
<211> LENGTH: 177
<212> TYPE: PRT
<213> ORGANISM: Flavobacterium psychrophilum

<400> SEQUENCE: 104

Met Arg Lys Leu Leu Phe Ile Ile Leu Met Pro Phe Leu Gly Ile Ala
1               5                   10                  15

Gln Asn Phe Thr Ala Asn Gly Ile Asn Tyr Thr Val Thr Ser Ser Thr
            20                  25                  30

Val Pro Leu Thr Val Ser Val Ala Asn Asn Thr Arg Phe Ile Cys Val
        35                  40                  45

Ala Glu Ile Pro Glu Ile Val Val Tyr Asn Ser Glu Asn Tyr Ala Val
    50                  55                  60

Thr Ala Ile Arg Gly Asn Ala Phe Asn Gly Ser Pro Leu Thr Ser Val
65                  70                  75                  80

Thr Ile Pro Asn Ser Val Thr Ala Ile Gly Lys Phe Ala Phe Tyr Ser
                85                  90                  95

Cys Glu Arg Leu Ile Ser Ile Ser Ile Pro Asn Ser Val Thr Ser Ile
            100                 105                 110

Glu Glu Gly Thr Phe Ser Phe Cys Thr Gly Leu Ile Ser Ile Thr Ile
        115                 120                 125
```

```
Pro Asn Ser Val Thr Val Ile Gly Lys Lys Ala Phe Ser Glu Cys Leu
        130                 135                 140

Gly Leu Thr Ser Val Thr Phe Pro Asn Ala Leu Thr Thr Ile Gly Ser
145                 150                 155                 160

His Cys Phe Tyr Phe Cys Thr Ser Leu Thr Ser Val Thr Ile Pro Asn
                165                 170                 175

Ser

<210> SEQ ID NO 105
<211> LENGTH: 177
<212> TYPE: PRT
<213> ORGANISM: Flavobacterium psychrophilum

<400> SEQUENCE: 105

Met Arg Lys Leu Leu Phe Ile Ile Leu Met Pro Phe Leu Gly Ile Ala
1               5                   10                  15

Gln Asn Phe Thr Ala Asn Gly Ile Asn Tyr Thr Val Thr Ser Ser Thr
                20                  25                  30

Val Pro Leu Thr Val Ser Val Ala Asn Asn Thr Arg Phe Ile Cys Val
            35                  40                  45

Ala Glu Ile Pro Glu Ile Val Val Tyr Asn Ser Glu Asn Tyr Ala Val
        50                  55                  60

Thr Ala Ile Arg Val Asn Ala Phe Asn Gly Ser Arg Leu Thr Ser Ile
65                  70                  75                  80

Thr Ile Pro Asn Ser Val Thr Ala Ile Gly Lys Phe Ala Phe Tyr Asn
                85                  90                  95

Cys Thr Arg Leu Ile Ser Ile Ser Ile Pro Asn Ser Val Thr Ser Ile
                100                 105                 110

Glu Glu Gly Thr Phe Ser Phe Cys Thr Gly Leu Ile Ser Ile Thr Ile
            115                 120                 125

Pro Asn Ser Val Thr Val Ile Gly Lys Lys Ala Phe Ser Glu Cys Leu
        130                 135                 140

Gly Leu Thr Ser Val Thr Phe Pro Asn Ala Leu Ala Thr Ile Gly Ser
145                 150                 155                 160

Tyr Cys Phe Tyr Phe Cys Thr Ser Leu Thr Ser Val Thr Ile Pro Asn
                165                 170                 175

Ser

<210> SEQ ID NO 106
<211> LENGTH: 177
<212> TYPE: PRT
<213> ORGANISM: Flavobacterium psychrophilum

<400> SEQUENCE: 106

Met Arg Lys Leu Leu Phe Ile Ile Leu Met Pro Phe Leu Gly Ile Ala
1               5                   10                  15

Gln Asn Phe Thr Ala Asn Gly Ile Asn Tyr Thr Val Thr Ser Ser Thr
                20                  25                  30

Val Pro Leu Thr Val Ser Val Ala Asn Asn Thr Arg Phe Ile Gly Val
            35                  40                  45

Ala Glu Ile Pro Glu Ile Val Val Tyr Asn Ser Glu Asn Tyr Ala Val
        50                  55                  60

Thr Ala Ile Arg Val Asn Ala Phe Asn Gly Ser Arg Leu Thr Ser Ile
65                  70                  75                  80

Thr Ile Pro Asn Ser Val Thr Ala Ile Gly Lys Phe Ala Phe Tyr Asn
                85                  90                  95
```

```
Cys Thr Arg Leu Ile Ser Ile Ser Ile Pro Asn Ser Val Thr Ser Ile
                100                 105                 110

Glu Glu Gly Thr Phe Ser Phe Cys Thr Gly Leu Ile Ser Ile Thr Ile
            115                 120                 125

Pro Asn Ser Val Thr Val Ile Gly Lys Lys Ala Phe Ser Glu Cys Leu
        130                 135                 140

Gly Leu Thr Ser Val Thr Phe Pro Asn Ala Leu Ala Thr Ile Gly Ser
145                 150                 155                 160

Tyr Cys Phe Tyr Phe Cys Thr Ser Leu Thr Ser Val Thr Ile Pro Asn
                165                 170                 175

Ser

<210> SEQ ID NO 107
<211> LENGTH: 177
<212> TYPE: PRT
<213> ORGANISM: Flavobacterium psychrophilum

<400> SEQUENCE: 107

Met Arg Lys Leu Leu Phe Ile Ile Leu Met Pro Phe Leu Gly Ile Ala
1               5                   10                  15

Gln Asn Phe Thr Ala Asn Gly Ile Asn Tyr Thr Val Thr Ser Ser Thr
            20                  25                  30

Val Pro Leu Thr Val Ser Val Ala Asn Asn Thr Arg Phe Ile Gly Val
        35                  40                  45

Ala Glu Ile Pro Glu Ile Val Val Tyr Asn Ser Glu Asn Tyr Ala Val
    50                  55                  60

Thr Ala Ile Arg Val Asn Ala Phe Asn Gly Ser Arg Leu Thr Ser Ile
65                  70                  75                  80

Thr Ile Pro Asn Ser Val Thr Ala Ile Gly Lys Phe Ala Phe Tyr Asn
                85                  90                  95

Cys Thr Arg Leu Ile Ser Ile Ser Ile Pro Asn Ser Val Thr Ser Ile
                100                 105                 110

Glu Glu Gly Thr Phe Ser Phe Cys Thr Gly Leu Ile Ser Ile Thr Ile
            115                 120                 125

Pro Asn Ser Val Thr Val Ile Gly Lys Lys Ala Phe Ser Glu Cys Leu
        130                 135                 140

Gly Leu Thr Ser Val Thr Phe Pro Asn Ala Leu Ala Thr Ile Gly Ser
145                 150                 155                 160

His Cys Phe Tyr Phe Cys Thr Ser Leu Thr Ser Val Thr Ile Pro Asn
                165                 170                 175

Ser

<210> SEQ ID NO 108
<211> LENGTH: 131
<212> TYPE: PRT
<213> ORGANISM: Flavobacterium psychrophilum

<400> SEQUENCE: 108

Met Arg Lys Leu Leu Phe Ile Ile Leu Ile Pro Phe Leu Gly Ile Ala
1               5                   10                  15

Gln Asp Phe Thr Ala Asn Gly Ile Lys Tyr Thr Val Ser Ser Ser Arg
            20                  25                  30

Thr Pro Phe Thr Val Lys Val Ala Arg Asn Ala Gly Phe Ile Gly Val
        35                  40                  45

Ala Glu Ile Pro Glu Ile Val Ala Tyr Asn Ser Glu Asn Tyr Ala Val
```

```
                    50                  55                  60
Thr Ala Ile Ser Glu Asn Ala Phe Arg Leu Ser Asp Leu Thr Ala Ile
 65                  70                  75                  80

Thr Ile Pro Asn Ser Val Thr Val Ile Glu Glu Gly Ala Phe Gly Tyr
                     85                  90                  95

Cys Thr Asp Leu Thr Ser Val Thr Ile Pro Asn Ala Val Ala Thr Ile
                100                 105                 110

Gly Glu Asn Cys Phe Tyr Ser Cys Lys Lys Leu Arg Ser Leu Thr Ile
                115                 120                 125

Pro Asn Ser
    130

<210> SEQ ID NO 109
<211> LENGTH: 131
<212> TYPE: PRT
<213> ORGANISM: Flavobacterium psychrophilum

<400> SEQUENCE: 109

Met Arg Lys Leu Leu Phe Ile Ile Leu Ile Pro Phe Leu Gly Ile Ala
 1                5                  10                  15

Gln Asp Phe Thr Ala Asn Gly Ile Lys Tyr Thr Val Thr Ser Ser Arg
                 20                  25                  30

Thr Pro Phe Thr Val Lys Val Ala Arg Asn Ala Gly Phe Ile Gly Val
             35                  40                  45

Ala Glu Ile Pro Glu Ile Val Ala Tyr Asn Ser Lys Asn Tyr Ala Val
         50                  55                  60

Thr Ala Ile Ser Glu Asn Ala Phe Arg Leu Ser Asp Leu Thr Ala Ile
 65                  70                  75                  80

Thr Ile Pro Asn Ser Val Thr Val Ile Glu Glu Gly Ala Phe Gly Tyr
                     85                  90                  95

Cys Thr Asp Leu Thr Ser Val Thr Ile Pro Asn Ala Val Ala Thr Ile
                100                 105                 110

Gly Glu Asn Cys Phe Tyr Ser Cys Lys Lys Leu Arg Ser Leu Thr Ile
                115                 120                 125

Pro Asn Ser
    130

<210> SEQ ID NO 110
<211> LENGTH: 131
<212> TYPE: PRT
<213> ORGANISM: Flavobacterium psychrophilum

<400> SEQUENCE: 110

Met Arg Lys Leu Leu Phe Ile Ile Leu Ile Pro Phe Leu Gly Ile Ala
 1                5                  10                  15

Gln Asp Phe Thr Ala Asn Gly Ile Lys Tyr Thr Val Thr Ser Ser Arg
                 20                  25                  30

Thr Pro Phe Thr Val Lys Val Ala Arg Asn Ala Gly Phe Ile Gly Val
             35                  40                  45

Ala Glu Ile Pro Glu Ile Val Ala Tyr Asn Ser Lys Asn Tyr Ala Val
         50                  55                  60

Thr Ala Ile Ser Glu Asn Ala Phe Arg Leu Ser Asp Leu Thr Ala Ile
 65                  70                  75                  80

Thr Ile Pro Asn Ser Val Thr Val Ile Glu Glu Gly Ala Phe Gly Tyr
                     85                  90                  95

Cys Thr Asp Leu Thr Ser Val Thr Ile Pro Asn Ala Val Ala Thr Ile
```

```
                100                 105                 110
Gly Glu Asn Cys Phe Tyr Ser Cys Lys Lys Leu Arg Ser Leu Thr Ile
            115                 120                 125

Pro Asn Ser
    130
```

<210> SEQ ID NO 111
<211> LENGTH: 131
<212> TYPE: PRT
<213> ORGANISM: Flavobacterium psychrophilum

<400> SEQUENCE: 111

```
Met Arg Lys Leu Leu Phe Ile Ile Leu Ile Pro Phe Leu Gly Ile Ala
1               5                   10                  15

Gln Asp Phe Thr Ala Asn Gly Ile Lys Tyr Thr Val Thr Ser Ser Arg
            20                  25                  30

Thr Pro Phe Thr Val Lys Val Ala Arg Asn Ala Gly Phe Ile Gly Val
        35                  40                  45

Ala Glu Ile Pro Glu Ile Val Ala Tyr Asn Ser Lys Asn Tyr Ala Val
    50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
                85                  90                  95

Cys Thr Asp Leu Thr Ser Val Thr Ile Pro Asn Ala Val Ala Thr Ile
            100                 105                 110

Gly Glu Asn Cys Phe Tyr Ser Cys Lys Lys Leu Arg Ser Leu Thr Ile
            115                 120                 125

Pro Asn Ser
    130
```

<210> SEQ ID NO 112
<211> LENGTH: 131
<212> TYPE: PRT
<213> ORGANISM: Flavobacterium psychrophilum

<400> SEQUENCE: 112

```
Met Lys Lys Leu Leu Phe Val Ile Leu Ile Pro Phe Leu Gly Ile Ala
1               5                   10                  15

Gln Asp Phe Thr Ala Asn Gly Ile Lys Tyr Thr Val Thr Ser Ser Thr
            20                  25                  30

Ala Pro Phe Thr Val Lys Val Ala Arg Asn Ala Gly Phe Ile Gly Val
        35                  40                  45

Ala Glu Ile Pro Glu Ile Val Ala Tyr Asn Ser Lys Asn Tyr Ala Val
    50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
                85                  90                  95

Cys Thr Asp Leu Thr Ser Val Thr Ile Pro Asn Ala Val Ala Thr Ile
            100                 105                 110

Gly Glu Asn Cys Phe Tyr Ser Cys Lys Lys Leu Arg Ser Leu Thr Ile
            115                 120                 125

Pro Asn Ser
    130
```

```
<210> SEQ ID NO 113
<211> LENGTH: 131
<212> TYPE: PRT
<213> ORGANISM: Flavobacterium psychrophilum

<400> SEQUENCE: 113

Met Arg Lys Leu Leu Phe Phe Ile Leu Ile Pro Phe Leu Gly Ile Ala
1               5                   10                  15

Gln Asp Phe Thr Ala Asn Gly Ile Lys Tyr Thr Val Thr Ser Ser Arg
            20                  25                  30

Thr Pro Phe Thr Val Lys Val Ala Arg Asn Ala Gly Phe Ile Gly Val
        35                  40                  45

Ala Glu Ile Pro Glu Thr Val Ala Tyr Asn Ser Lys Asn Tyr Ala Val
50                  55                  60

Thr Ala Ile Ser Glu Asn Ala Phe Arg Leu Ser Asp Leu Thr Ala Ile
65                  70                  75                  80

Thr Ile Pro Asn Ser Val Thr Val Ile Glu Glu Gly Ala Phe Gly Tyr
                85                  90                  95

Cys Thr Asp Leu Thr Ser Val Thr Ile Pro Asn Ala Val Ala Thr Ile
            100                 105                 110

Gly Glu Asn Cys Phe Tyr Ser Cys Lys Lys Leu Arg Ser Leu Thr Ile
        115                 120                 125

Pro Asn Ser
    130

<210> SEQ ID NO 114
<211> LENGTH: 99
<212> TYPE: PRT
<213> ORGANISM: Flavobacterium psychrophilum

<400> SEQUENCE: 114

Val Thr Ser Ile Gly Asp Tyr Thr Phe Ser Asn Cys Thr Ser Leu Thr
1               5                   10                  15

Thr Val Asn Ser Tyr Ala Thr Ile Pro Leu Val Ile Asn Glu Asn Ala
            20                  25                  30

Phe His Asn Leu Asp Arg Ser Ile Cys Ala Leu Asn Val Pro Ala Gly
        35                  40                  45

Thr Glu Ala Ala Tyr Gln Ala Ala Val Trp Lys Asp Phe Ser Pro
50                  55                  60

Ile Ser Gly Ser Leu Leu Ser Asn Leu Ser Ser Phe Ala Lys Gly Asn
65                  70                  75                  80

Tyr Phe Val Glu Val Met Thr Asn Gln Gly Lys Ala Thr Lys Thr Ile
                85                  90                  95

Ile Ile Gln

<210> SEQ ID NO 115
<211> LENGTH: 151
<212> TYPE: PRT
<213> ORGANISM: Flavobacterium psychrophilum

<400> SEQUENCE: 115

Val Thr Ser Ile Gly Asp Tyr Thr Phe Ser Asn Cys Thr Ser Leu Thr
1               5                   10                  15

Thr Val Asn Ser Tyr Ala Thr Ile Pro Leu Val Ile Asn Glu Asn Ala
            20                  25                  30

Phe His Asn Leu Asp Arg Ser Ile Cys Ala Leu Asn Val Pro Ala Gly
        35                  40                  45
```

Thr Glu Ala Ala Tyr Gln Ala Ala Val Trp Lys Asp Phe Ser Pro
        50                  55                  60

Ile Ser Gly Ser Leu Leu Ser Asn His Ser Phe Ala Ile Glu Ser Asn
 65                  70                  75                  80

Leu Lys Ile Tyr Pro Asn Pro Val Ser Glu Ile Leu Asn Ile Ala Leu
                 85                  90                  95

Gln Glu Asn Leu Gln Leu Gln Lys Val Asn Phe Tyr Asn Thr Leu Gly
            100                 105                 110

Gln Leu Ile Lys Thr Thr Asn His Ser Glu Ile Asn Ile Ser Ser Phe
            115                 120                 125

Ala Lys Gly Ile Tyr Phe Val Glu Val Met Thr Asn Gln Gly Lys Ala
        130                 135                 140

Thr Lys Thr Ile Ile Val Gln
145                 150

<210> SEQ ID NO 116
<211> LENGTH: 151
<212> TYPE: PRT
<213> ORGANISM: Flavobacterium psychrophilum

<400> SEQUENCE: 116

Val Thr Ser Ile Gly Asp Tyr Thr Phe Ser Asn Cys Thr Ser Leu Thr
 1               5                  10                  15

Thr Val Asn Ser Tyr Ala Thr Ile Pro Leu Val Ile Asn Glu Asn Ala
             20                  25                  30

Phe His Asn Leu Asp Arg Ser Ile Cys Ala Leu Asn Val Pro Ala Gly
         35                  40                  45

Thr Glu Ala Ala Tyr Gln Ala Ala Val Trp Lys Asp Phe Ser Pro
     50                  55                  60

Ile Ser Gly Ser Leu Leu Ser Asn His Ser Phe Ala Ile Glu Ser Asn
 65                  70                  75                  80

Leu Lys Ile Tyr Pro Asn Pro Val Ser Glu Ile Leu Asn Ile Ala Leu
                 85                  90                  95

Gln Glu Asn Leu Gln Leu Gln Lys Val Asn Phe Tyr Asn Thr Leu Gly
            100                 105                 110

Gln Leu Ile Lys Thr Thr Asn His Ser Glu Ile Asn Ile Ser Ser Phe
            115                 120                 125

Ala Lys Gly Ile Tyr Phe Val Glu Val Met Thr Asn Gln Gly Lys Ala
        130                 135                 140

Thr Lys Thr Ile Ile Val Gln
145                 150

<210> SEQ ID NO 117
<211> LENGTH: 151
<212> TYPE: PRT
<213> ORGANISM: Flavobacterium psychrophilum

<400> SEQUENCE: 117

Val Thr Ser Ile Gly Asp Tyr Thr Phe Ser Asn Cys Thr Ser Leu Thr
 1               5                  10                  15

Thr Val Asn Ser Tyr Ala Thr Ile Pro Leu Val Ile Asn Glu Asn Ala
             20                  25                  30

Phe His Asn Leu Asp Arg Ser Ile Cys Ala Leu Asn Val Pro Ala Gly
         35                  40                  45

Thr Glu Ala Ala Tyr Gln Ala Ala Val Trp Lys Asp Phe Ser Pro
     50                  55                  60

```
Ile Ser Gly Ser Leu Leu Ser Asn His Ser Phe Ala Ile Glu Ser Asn
 65                  70                  75                  80

Leu Lys Ile Tyr Pro Asn Pro Val Ser Glu Ile Leu Asn Ile Ala Leu
                 85                  90                  95

Gln Glu Asn Leu Gln Leu Gln Lys Val Asn Phe Tyr Asn Thr Leu Gly
            100                 105                 110

Gln Leu Ile Lys Thr Thr Asn His Ser Glu Ile Asn Ile Ser Ser Phe
        115                 120                 125

Ala Lys Gly Ile Tyr Phe Val Glu Val Met Thr Asn Gln Gly Lys Ala
    130                 135                 140

Thr Lys Thr Ile Ile Val Gln
145                 150

<210> SEQ ID NO 118
<211> LENGTH: 151
<212> TYPE: PRT
<213> ORGANISM: Flavobacterium psychrophilum

<400> SEQUENCE: 118

Val Thr Ser Ile Gly Asp Tyr Thr Phe Ser Asn Cys Thr Ser Leu Thr
 1               5                  10                  15

Thr Val Asn Ser Tyr Ala Thr Ile Pro Leu Val Ile Asn Glu Asn Ala
             20                  25                  30

Phe His Asn Leu Asp Arg Ser Ile Cys Ala Leu Asn Val Pro Ala Gly
         35                  40                  45

Thr Glu Ala Ala Tyr Gln Ala Ala Val Trp Lys Asp Phe Ser Pro
     50                  55                  60

Ile Ser Gly Ser Leu Leu Ser Asn His Ser Phe Ala Ile Glu Ser Asn
 65                  70                  75                  80

Leu Lys Ile Tyr Pro Asn Pro Val Ser Glu Ile Leu Asn Ile Ala Leu
                 85                  90                  95

Gln Glu Asn Leu Gln Leu Gln Lys Val Asn Phe Tyr Asn Thr Leu Gly
            100                 105                 110

Gln Leu Ile Lys Thr Thr Asn His Ser Glu Ile Asn Ile Ser Ser Phe
        115                 120                 125

Ala Lys Gly Ile Tyr Phe Val Glu Val Met Thr Asn Gln Gly Lys Ala
    130                 135                 140

Thr Lys Thr Ile Ile Val Gln
145                 150

<210> SEQ ID NO 119
<211> LENGTH: 151
<212> TYPE: PRT
<213> ORGANISM: Flavobacterium psychrophilum

<400> SEQUENCE: 119

Val Thr His Ile Gly Gly Tyr Ala Phe Asn Asn Cys Ser Ser Leu Thr
 1               5                  10                  15

Thr Val Asn Cys Tyr Ile Thr Ile Pro Leu Val Ile Asn Val Thr Thr
             20                  25                  30

Phe Arg Lys Val Asn Lys Ser Ile Cys Ala Leu Asn Val Pro Ala Gly
         35                  40                  45

Thr Glu Ala Ala Tyr Gln Ala Ala Val Trp Lys Asp Phe Ser Pro
     50                  55                  60

Ile Ser Gly Ser Leu Leu Ser Asn His Ser Phe Ala Ile Glu Ser Ala
 65                  70                  75                  80
```

```
Leu Lys Ile Tyr Pro Asn Pro Val Ser Glu Ile Leu Asn Ile Ala Leu
                85                  90                  95
Gln Glu Asn Leu Gln Leu Glu Lys Val Asn Phe Tyr Asn Thr Leu Gly
            100                 105                 110
Gln Leu Ile Lys Thr Thr Asn His Ser Gly Ile Asn Val Ser Ser Phe
        115                 120                 125
Ala Lys Gly Asn Tyr Phe Val Glu Ile Met Thr Asn Gln Gly Lys Val
    130                 135                 140
Thr Lys Thr Ile Ile Val Gln
145                 150

<210> SEQ ID NO 120
<211> LENGTH: 151
<212> TYPE: PRT
<213> ORGANISM: Flavobacterium psychrophilum

<400> SEQUENCE: 120

Val Thr Asp Ile Gly Val Gly Ala Phe Tyr Asp Cys Thr Ser Leu Ser
1               5                   10                  15
Thr Val Asn Cys Gln Ile Thr Ile Pro Leu Val Ile Asn Val Thr Thr
            20                  25                  30
Phe Arg Lys Val Asn Lys Ser Ile Cys Ala Leu Asn Val Pro Ala Gly
        35                  40                  45
Thr Glu Ala Ala Tyr Gln Ala Ala Ala Val Trp Lys Asp Phe Asn Leu
    50                  55                  60
Ile Tyr Gly Ser Leu Leu Ser Asn His Ser Phe Ala Ile Glu Ser Asn
65                  70                  75                  80
Leu Lys Ile Tyr Pro Asn Pro Val Ser Glu Ile Leu Asn Ile Ala Leu
                85                  90                  95
Gln Glu Gly Leu Gln Leu Glu Lys Val Asn Phe Tyr Asn Thr Leu Gly
            100                 105                 110
Gln Leu Ile Lys Thr Thr Asn His Ser Glu Ile Asn Ile Ser Ser Phe
        115                 120                 125
Ala Lys Gly Asn Tyr Phe Val Glu Val Met Thr Asn Gln Gly Lys Ala
    130                 135                 140
Thr Lys Thr Ile Ile Val Gln
145                 150

<210> SEQ ID NO 121
<211> LENGTH: 151
<212> TYPE: PRT
<213> ORGANISM: Flavobacterium psychrophilum

<400> SEQUENCE: 121

Val Thr Asp Ile Gly Val Gly Ala Phe Tyr Asp Cys Thr Ser Leu Ser
1               5                   10                  15
Thr Val Asn Cys Gln Ile Thr Ile Pro Leu Val Ile Asn Val Thr Thr
            20                  25                  30
Phe Arg Lys Val Asn Lys Ser Ile Cys Ala Leu Asn Val Pro Ala Gly
        35                  40                  45
Thr Glu Ala Ala Tyr Gln Ala Ala Ala Val Trp Lys Asp Phe Ser Leu
    50                  55                  60
Ile Tyr Gly Ser Leu Leu Ser Asn His Ser Phe Ala Ile Glu Ser Asn
65                  70                  75                  80
Leu Lys Ile Tyr Pro Asn Pro Val Ser Glu Ile Leu Asn Ile Ala Leu
                85                  90                  95
```

Gln Glu Asp Leu Gln Leu Glu Lys Val Asn Phe Tyr Asn Thr Leu Gly
                100                 105                 110

Gln Leu Ile Lys Thr Thr Asn His Ser Glu Ile Asn Val Ser Ser Phe
            115                 120                 125

Thr Lys Gly Asn Tyr Phe Val Glu Ile Met Thr Asn Gln Gly Lys Val
        130                 135                 140

Thr Lys Thr Ile Ile Val Gln
145                 150

<210> SEQ ID NO 122
<211> LENGTH: 151
<212> TYPE: PRT
<213> ORGANISM: Flavobacterium psychrophilum

<400> SEQUENCE: 122

Val Thr Asp Ile Gly Val Gly Ala Phe Tyr Asp Cys Thr Ser Leu Ser
1               5                   10                  15

Thr Val Asn Cys Gln Ile Thr Ile Pro Leu Val Ile Asn Val Thr Thr
            20                  25                  30

Phe Arg Lys Val Asn Lys Ser Ile Cys Ala Leu Asn Val Pro Ala Gly
        35                  40                  45

Thr Glu Ala Ala Tyr Gln Ala Ala Val Trp Lys Asp Phe Ser Leu
    50                  55                  60

Ile Tyr Gly Ser Leu Leu Ser Asn His Ser Phe Ala Ile Glu Ser Asn
65                  70                  75                  80

Leu Lys Ile Tyr Pro Asn Pro Val Ser Glu Ile Leu Asn Ile Ala Leu
                85                  90                  95

Gln Glu Asp Leu Gln Leu Glu Lys Val Asn Phe Tyr Asn Thr Leu Gly
                100                 105                 110

Gln Leu Ile Lys Thr Thr Asn His Ser Glu Ile Asn Val Ser Ser Phe
            115                 120                 125

Thr Lys Gly Asn Tyr Phe Val Glu Ile Met Thr Asn Gln Gly Lys Val
        130                 135                 140

Thr Lys Thr Ile Ile Val Gln
145                 150

<210> SEQ ID NO 123
<211> LENGTH: 151
<212> TYPE: PRT
<213> ORGANISM: Flavobacterium psychrophilum

<400> SEQUENCE: 123

Val Thr Asp Ile Gly Val Gly Ala Phe Tyr Asp Cys Thr Ser Leu Ser
1               5                   10                  15

Thr Val Asn Cys Gln Ile Thr Ile Pro Leu Val Ile Asn Ala Thr Ala
            20                  25                  30

Phe Arg Lys Val Asn Lys Ser Ile Cys Ala Leu Asn Val Pro Ala Gly
        35                  40                  45

Thr Glu Ala Ala Tyr Gln Ala Ala Val Trp Lys Asp Phe Ser Leu
    50                  55                  60

Ile Tyr Gly Ser Leu Leu Ser Asn His Ser Phe Ala Ile Glu Ser Asn
65                  70                  75                  80

Leu Lys Ile Tyr Pro Asn Pro Val Ser Glu Ile Leu Asn Ile Ala Leu
                85                  90                  95

Gln Glu Asp Leu Gln Leu Glu Lys Val Asn Phe Tyr Asn Thr Leu Gly
                100                 105                 110

Gln Leu Ile Lys Thr Thr Asn His Ser Glu Ile Asn Val Ser Ser Phe
            115                 120                 125

Thr Lys Gly Asn Tyr Phe Val Glu Ile Met Thr Asn Gln Gly Lys Val
        130                 135                 140

Thr Lys Thr Ile Ile Val Gln
145                 150

<210> SEQ ID NO 124
<211> LENGTH: 151
<212> TYPE: PRT
<213> ORGANISM: Flavobacterium psychrophilum

<400> SEQUENCE: 124

Leu Thr Val Ile Gly Asn Gly Ala Phe Ser Glu Cys Thr Gly Leu Arg
1               5                   10                  15

Thr Val Asn Cys Gln Ile Thr Ile Pro Phe Ala Ile Asn Thr Asn Thr
            20                  25                  30

Phe Tyr Asn Leu Asn Arg Ser Ile Cys Ala Leu Asn Val Pro Pro Gly
        35                  40                  45

Thr Glu Ala Ala Tyr Lys Ala Ala Val Trp Lys Asp Phe Ser Pro
    50                  55                  60

Ile Ser Gly Gly Phe Leu Ser Ser Asn Ser Phe Ala Ile Glu Ser Asn
65                  70                  75                  80

Leu Lys Ile Tyr Pro Asn Pro Val Ser Glu Ile Leu Asn Ile Ala Leu
                85                  90                  95

Gln Glu Asp Leu Gln Leu Glu Lys Val Asn Phe Tyr Asn Thr Leu Gly
            100                 105                 110

Gln Leu Ile Lys Thr Thr Asn His Ser Glu Ile Asn Val Ser Ser Phe
            115                 120                 125

Ala Lys Gly Asn Tyr Phe Val Glu Ile Met Thr Asn Gln Gly Lys Val
        130                 135                 140

Thr Lys Thr Ile Ile Val Gln
145                 150

<210> SEQ ID NO 125
<211> LENGTH: 151
<212> TYPE: PRT
<213> ORGANISM: Flavobacterium psychrophilum

<400> SEQUENCE: 125

Leu Thr Val Ile Gly Asn Gly Ala Phe Ser Glu Cys Thr Gly Leu Arg
1               5                   10                  15

Thr Val Asn Cys Gln Ile Thr Ile Pro Phe Ala Ile Asn Thr Asn Thr
            20                  25                  30

Phe Tyr Asn Leu Asn Arg Ser Ile Cys Ala Leu Asn Val Pro Pro Gly
        35                  40                  45

Thr Glu Ala Ala Tyr Lys Ala Ala Val Trp Lys Asp Phe Ser Pro
    50                  55                  60

Ile Ser Gly Gly Phe Leu Ser Ser Asn Ser Phe Ala Ile Glu Ser Asn
65                  70                  75                  80

Leu Lys Ile Tyr Pro Asn Pro Ala Ser Glu Ile Leu Asn Ile Ala Leu
                85                  90                  95

Gln Glu Gly Leu Gln Leu Glu Lys Val Asn Phe Tyr Asn Thr Leu Gly
            100                 105                 110

Gln Leu Ile Lys Thr Thr Asn His Ser Glu Ile Asn Val Ser Ser Phe
            115                 120                 125

Ala Lys Gly Asn Tyr Phe Val Glu Val Met Thr Asn Gln Gly Lys Val
    130                 135                 140

Thr Lys Ser Val Ile Ile Gln
145                 150

<210> SEQ ID NO 126
<211> LENGTH: 151
<212> TYPE: PRT
<213> ORGANISM: Flavobacterium psychrophilum

<400> SEQUENCE: 126

Leu Thr Val Ile Gly Asn Gly Ala Phe Ser Glu Cys Thr Gly Leu Arg
1               5                   10                  15

Thr Val Asn Cys Gln Ile Thr Ile Pro Phe Ala Ile Asn Thr Asn Thr
                20                  25                  30

Phe Tyr Asn Leu Asn Arg Ser Ile Cys Ala Leu Asn Val Pro Pro Gly
            35                  40                  45

Thr Glu Ala Ala Tyr Lys Ala Ala Val Trp Lys Asp Phe Ser Pro
    50                  55                  60

Ile Ser Gly Gly Phe Leu Ser Ser Asn Ser Phe Ala Ile Glu Ser Asn
65              70                  75                  80

Leu Lys Ile Tyr Pro Asn Pro Val Ser Glu Ile Leu Asn Ile Ala Leu
                85                  90                  95

Gln Glu Gly Leu Gln Leu Glu Lys Val Asn Phe Tyr Asn Thr Leu Gly
            100                 105                 110

Gln Leu Ile Lys Thr Thr Asn His Ser Glu Ile Asn Val Ser Ser Phe
        115                 120                 125

Ala Lys Gly Asn Tyr Phe Val Glu Val Met Thr Asn Gln Gly Lys Val
    130                 135                 140

Thr Lys Ser Val Ile Ile Gln
145                 150

<210> SEQ ID NO 127
<211> LENGTH: 151
<212> TYPE: PRT
<213> ORGANISM: Flavobacterium psychrophilum

<400> SEQUENCE: 127

Leu Thr Val Ile Gly Asn Gly Ala Phe Ser Glu Cys Thr Gly Leu Arg
1               5                   10                  15

Thr Val Asn Cys Gln Ile Thr Ile Pro Phe Ala Ile Asn Thr Asn Thr
                20                  25                  30

Phe Tyr Asn Leu Asn Arg Ser Ile Cys Ala Leu Asn Val Pro Pro Gly
            35                  40                  45

Thr Glu Ala Ala Tyr Lys Ala Ala Val Trp Lys Asp Phe Ser Pro
    50                  55                  60

Ile Ser Gly Gly Phe Leu Ser Ser Asn Ser Phe Ala Ile Glu Ser Asn
65              70                  75                  80

Leu Lys Ile Tyr Pro Asn Pro Val Ser Glu Ile Leu Asn Ile Ala Leu
                85                  90                  95

Gln Glu Gly Leu Gln Leu Glu Lys Val Asn Phe Tyr Asn Thr Leu Gly
            100                 105                 110

Gln Leu Ile Lys Thr Thr Asn His Ser Glu Ile Asn Val Ser Ser Phe
        115                 120                 125

Ala Lys Gly Asn Tyr Phe Val Glu Val Met Thr Asn Gln Gly Lys Ala
    130                 135                 140

```
Thr Lys Ser Val Ile Ile Gln
145                 150
```

<210> SEQ ID NO 128
<211> LENGTH: 105
<212> TYPE: PRT
<213> ORGANISM: Flavobacterium psychrophilum

<400> SEQUENCE: 128

```
Leu Thr Val Ile Gly Asn Gly Ala Phe Ser Glu Cys Thr Gly Leu Arg
1               5                   10                  15

Thr Val Asn Cys Gln Ile Thr Ile Pro Phe Ala Ile Asn Thr Asn Thr
                20                  25                  30

Phe Tyr Asn Leu Asn Arg Ser Ile Cys Ala Leu Asn Val Pro Pro Gly
            35                  40                  45

Thr Glu Ala Ala Tyr Lys Ala Ala Val Trp Lys Asp Phe Ser Pro
        50                  55                  60

Ile Ser Gly Gly Phe Leu Ser Ser Asn Ser Phe Ala Ile Asn Val Ser
65                  70                  75                  80

Ser Phe Ala Lys Gly Asn Tyr Phe Val Glu Ile Met Thr Asn Gln Gly
                85                  90                  95

Lys Ala Thr Lys Ser Val Ile Ile Gln
            100                 105
```

<210> SEQ ID NO 129
<211> LENGTH: 151
<212> TYPE: PRT
<213> ORGANISM: Flavobacterium psychrophilum

<400> SEQUENCE: 129

```
Leu Thr Val Ile Gly Asn Gly Ala Phe Ser Glu Cys Thr Gly Leu Arg
1               5                   10                  15

Thr Val Asn Cys Gln Ile Thr Ile Pro Phe Ala Ile Asn Thr Asn Thr
                20                  25                  30

Phe Tyr Asn Leu Asn Arg Ser Ile Cys Ala Leu Asn Val Pro Pro Gly
            35                  40                  45

Thr Glu Ala Ala Tyr Lys Ala Ala Val Trp Lys Asp Phe Ser Pro
        50                  55                  60

Ile Ser Gly Gly Phe Leu Ser Ser Asn Ser Phe Ala Ile Glu Ser Asn
65                  70                  75                  80

Leu Lys Ile Tyr Pro Asn Pro Val Ser Glu Ile Leu Asn Ile Ala Leu
                85                  90                  95

Gln Glu Gly Leu Gln Leu Glu Lys Val Asn Phe Tyr Asn Thr Leu Gly
            100                 105                 110

Gln Leu Ile Lys Thr Thr Asn His Ser Glu Ile Asn Val Ser Ser Phe
        115                 120                 125

Ala Lys Gly Asn Tyr Phe Val Glu Val Met Thr Asn Gln Gly Lys Ala
    130                 135                 140

Thr Lys Ser Val Ile Ile Gln
145                 150
```

<210> SEQ ID NO 130
<211> LENGTH: 11
<212> TYPE: PRT
<213> ORGANISM: Artificial Sequence
<220> FEATURE:
<223> OTHER INFORMATION: Synthetic peptide

<400> SEQUENCE: 130

Asn Thr Leu Cys Lys Thr Ile Leu Ile Gln Cys
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic peptide

<400> SEQUENCE: 131

Asn Thr Leu Cys Lys Ser Ile Leu Ile Gln Cys
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic peptide

<400> SEQUENCE: 132

Asn Thr Leu Cys Lys Glu Leu Ile Gln Cys
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Synthetic peptide

<400> SEQUENCE: 133

Asn Thr Leu Cys Glu Asp Cys Leu Ile Gln Cys
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Synthetic peptide

<400> SEQUENCE: 134

Asn Thr Leu Cys Lys Thr Ile Leu Ile Gln Cys
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic peptide

<400> SEQUENCE: 135

Asn Thr Leu Cys Lys Ser Ile Leu Ile Gln Cys
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic peptide

<400> SEQUENCE: 136

```
Asn Thr Leu Cys Lys Glu Leu Ile Asn Cys
1               5                   10
```

<210> SEQ ID NO 137
<211> LENGTH: 11
<212> TYPE: PRT
<213> ORGANISM: Artificial Sequence
<220> FEATURE:
<223> OTHER INFORMATION: Synthetic peptide

<400> SEQUENCE: 137

```
Asn Thr Leu Cys Glu Asp Cys Leu Ile Gln Cys
1               5                   10
```

<210> SEQ ID NO 138
<211> LENGTH: 20
<212> TYPE: PRT
<213> ORGANISM: Dictyostelium purpureum

<400> SEQUENCE: 138

```
Thr Ser Cys Gly Pro Gln Asn Lys Arg His Glu Asp Tyr Trp Phe Met
1               5                   10                  15

Val Ile Leu Ala
            20
```

<210> SEQ ID NO 139
<211> LENGTH: 20
<212> TYPE: PRT
<213> ORGANISM: Dictyostelium purpureum

<400> SEQUENCE: 139

```
Ala Leu Ile Val Met Phe Trp Tyr Asp Glu His Arg Lys Asn Gln Pro
1               5                   10                  15

Gly Cys Ser Thr
            20
```

<210> SEQ ID NO 140
<211> LENGTH: 33
<212> TYPE: PRT
<213> ORGANISM: Solanum lycopersicum

<400> SEQUENCE: 140

```
Leu Gln Gln Leu Tyr Gln Phe Gln Val Arg Gly Gly Glu Asn Asp Tyr
1               5                   10                  15

Gln Gly Asn Glu Phe Glu Pro Pro Ser Asn Val Gln Pro Ile Asn Ile
            20                  25                  30

Pro
```

<210> SEQ ID NO 141
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 141
gtttactttc taatcattca aataaacgtt tca                           33

TARGET RECOGNITION MOTIFS AND USES THEREOF

CROSS-REFERENCE TO RELATED APPLICATIONS

This application claims the benefit of U.S. Provisional Application No. 62/877,358, filed Jul. 23, 2019. The entire contents of the above-identified application are hereby fully incorporated herein by reference.

STATEMENT REGARDING FEDERALLY SPONSORED RESEARCH

This invention was made with government support under grant numbers MH110049 and HL141201 awarded by the National Institutes of Health. The government has certain rights in the invention.

REFERENCE TO AN ELECTRONIC SEQUENCE LISTING

The contents of the electronic sequence listing ("BROD-4740US_ST25.txt"; Size is 144,641 bytes and it was created on Aug. 6, 2020) is herein incorporated by reference in its entirety.

TECHNICAL FIELD

The subject matter disclosed herein is generally directed to novel programmable targeting sequences and applications thereof. The targeting sequences can be engineered for binding to proteins, polypeptides, and other macromolecules.

BACKGROUND

The harnessing of biological diversity is providing advances in human health, agriculture and industry. Available methods offer limited variability and do not offer the diversity of structure and function found in nature. There is a need to expand the repertoire of tools and techniques for targeting and modifying biological systems and components.

Citation or identification of any document in this application is not an admission that such document is available as prior art to the present invention.

SUMMARY

In one aspect, the present disclosure provides an engineered protein or polypeptide comprising one or more leucine rich repeats (LRRs) and a trafficking domain.

In some embodiments, the engineered protein or polypeptide comprises one or more LRR_5 motifs. In some embodiments, the engineered protein or polypeptide comprises [$X_1$-Proline/glycine-$X_2$-threonine/serine-$X_3$-phenylalanine-$X_4$]z, wherein: $X_1$ is 4 to 6 amino acids in length and comprises non-charged polar amino acids and aliphatic hydrophobic amino acids; $X_2$ is 2 to 4 amino acids in length and comprises a charged or non-charged polar amino acid and/or an aliphatic hydrophobic amino acid; $X_3$ is 1 to 6 amino acids in length and comprises polar and/or non-polar amino acids; $X_4$ is 1 to 5 amino acids and comprises at least one polar amino acid; and z is any integer from 1 to 10. In some embodiments, the engineered protein or polypeptide comprises [$X_1$-Proline/glycine-$X_2$-alanine/asparagine-$X_3$-phenylalanine-$X_4$]z, wherein: $X_1$ is 4 to 6 amino acids in length and comprises non-charged polar amino acids and aliphatic hydrophobic amino acids; $X_2$ is 2 to 4 amino acids in length and comprises a charged or non-charged polar amino acid and/or an aliphatic hydrophobic amino acid; $X_3$ is 1 to 6 amino acids in length and comprises polar and/or non-polar amino acids; $X_4$ is 1 to 5 amino acids and comprises at least one polar amino acid; and z is any integer from 1 to 10.

In some embodiments, $X_1$ comprises (leucine-$X_{1a}$-isoleucine), wherein $X_{1a}$ comprises threonine, serine, and/or valine; $X_2$ comprises asparagine, serine, and/or valine; wherein $X_3$ comprises isoleucine; and wherein $X_4$ comprises cysteine. In some embodiments, the aliphatic hydrophobic amino acids of $X_1$ comprise leucine, isoleucine, and/or valine. In some embodiments, the non-charged polar amino acids of $X_3$ comprise serine and/or threonine. In some embodiments, the polar amino acid of $X_2$ comprises a charged and/or a non-charged amino acid. In some embodiments, $X_2$ comprises an asparagine and/or a serine. In some embodiments, $X_2$ comprises an aspartate and/or an arginine. In some embodiments, the polar amino acids of $X_3$ comprise charged and/or non-charged polar amino acids. In some embodiments, the non-polar amino acids of $X_3$ comprise aliphatic and/or aromatic hydrophobic amino acids. In some embodiments, $X_3$ comprises an alanine. In some embodiments, $X_3$ comprises a threonine. In some embodiments, $X_3$ comprises a cysteine. In some embodiments, the aliphatic hydrophobic amino acids of $X_3$ comprise alanine, valine, glycine, and/or isoleucine. In some embodiments, the non-charged polar amino acids of $X_3$ comprise tyrosine, serine, asparagine, and/or threonine. In some embodiments, the charged polar amino acids of $X_3$ comprise aspartate and/or glutamate. In some embodiments, $X_4$ comprises a charged or a non-charged polar amino acid. In some embodiments, the charged polar amino acid of $X_4$ comprises lysine or arginine. In some embodiments, the non-charged polar amino acid of $X_4$ comprises serine, tyrosine, asparagine and/or cysteine. In some embodiments, $X_1$ comprises leucine, serine, threonine, valine, and/or isoleucine; $X_2$ comprises asparagine, serine, and/or valine; $X_3$ comprises isoleucine, glycine, serine, threonine, and/or alanine; and $X_4$ comprises cysteine, serine, isoleucine, and/or glycine.

In some embodiments, the engineered protein or polypeptide comprises one or more LRR sequences of any one of SEQ ID NOs: 49-87. In some embodiments, the trafficking domain comprises a Type IX secretion system (T9SS) substrate. In some embodiments, the trafficking domain comprises a secretion signal peptide. In some embodiments, the protein or polypeptide further comprises an amino acid sequence capable of directing clearance from a cell or organism. In some embodiments, the trafficking domain is capable of binding to an Fc receptor, binding to a dendritic cell, and/or directing antigen processing. In some embodiments, the protein or polypeptide binds to a pathogen. In some embodiments, the protein or polypeptide binds to a virus. In some embodiments, the protein or polypeptide binds to a toxin. In some embodiments, the protein or polypeptide blocks an activity of the pathogen, virus or toxin.

In another aspect, the present disclosure provides a protein array comprising the engineered protein or polypeptide herein. In some embodiments, the array comprises two or more engineered polypeptides, each of the two or more polypeptides differing from another of the two or more polypeptides by at least one amino acid. In some embodiments, at least two proteins of the array are linked by a cleavable linker. In some embodiments, the linker is cleavable in vitro or in vivo.

In another aspect, the present disclosure provides polynucleotide encoding the engineered protein or polypeptide described herein. In some embodiments, the sequence of the polynucleotide is optimized for expression in a host cell. In some embodiments, the host cell is a prokaryotic cell. In some embodiments, the host cell is a eukaryotic cell. In some embodiments, the eukaryotic cell is a human cell, a mammalian cell, a plant cell, or a yeast cell. In some embodiments, the polynucleotide comprises a regulatory element. In some embodiments, the regulatory element is inducible.

In another aspect, the present disclosure provides a vector comprising a polynucleotide herein. In some embodiments, the vector comprises a viral vector, a bacteriophage vector, or a plasmid vector. In another aspect, the present disclosure provides a delivery system comprising the protein or polypeptide herein, a polynucleotide herein, and/or a vector herein.

In another aspect, the present disclosure provides a method of engineering a protein or polynucleotide of claim 1 to bind to a target of interest, which comprises one or more of: duplicating an LRR, mutating an LRR, substituting an LRR, shuffling an LRR, linking an LRR from a different source; and detecting whether the protein or polypeptide binds to the target. In some embodiments, the protein or polypeptide is associated with a detectable moiety. In some embodiments, the protein or polypeptide and the detectable moiety are covalently linked. In some embodiments, the target comprises a macromolecule. In some embodiments, the macromolecule comprises a protein or polypeptide. In some embodiments, the macromolecule comprises a toxin. In some embodiments, the macromolecule comprises a virus component.

In another aspect, the present disclosure provides method of engineering a protein or polypeptide to bind to a target of interest, which comprises inserting or modifying an LRR according to an LRR motif in the protein or polypeptide; and detecting whether the engineered protein or polypeptide binds to the target substrate. In some embodiments, the engineered protein or polypeptide and the target are contacted in vivo, ex vivo, or in vitro.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 3A-C. Proteins. (FIG. 3A) depicts a 16S rRNA tree of organisms having similar loci encoding multiple proteins comprising an N-terminal signal peptide, leucine rich repeat (LRR)-like domains of pfam13306, and a Type IX secretion system (T9SS) sorting C-terminal domain. (FIG. 3B) depicts the structure of a related protein (BACOVA_01565 from *Bacteroides ovatus*) containing LRR-like domains (PDB: 4FDW). (FIG. 3C) depicts a hypervariable locus in *Flavobacterium psychrophilum* encoding multiple homologs (paralogs) of proteins each comprising an N-terminal signal peptide, leucine rich repeat (LRR)-like domains of pfam13306, and a Type IX secretion system (T9SS) sorting C-terminal domain. (LRR-like domain identifiers: FP0180; FP0179; FP0178; FP0177; FP0176; FP0175; FP0174; FP0173; FP0172; FP0171; FP0170; FP0169; FP0168; FP0167; FP0166; FP0165.

FIGS. 7A-7C compares sequences of intact leucine-rich repeat proteins across 12 strains of *Flavobacterium psychrophilum*. (FIG. 7A) Sequence conservation of 111 intact leucine-rich repeat proteins (top; yellow/green bars), with three example proteins (bottom). (FIG. 7B) Histogram of the number of repeat units within individual proteins. (FIG. 7C) Web logo of the nucleotide (top) and amino acid (bottom) repeat motif for all n=628 repeat units with high-quality genome sequencing (excluding repeats with ambiguous nucleotides).

(FIG. 8A) A comparison of different nucleic acid binding modules according to their modularity. Zinc Fingers, TALEs, and CRISPRs use repeats, while TALEs and CRISPRs have hypervariable regions within their repeats that precisely determine the DNA binding specificity. (FIG. 8B) A schematic of different types of repeats and their diversification. (FIG. 8C) Basic mechanisms of diversification in prokaryotic genomes.

FIGS. 9A-9F: Computational pipeline design for repeat protein analysis. (FIG. 9A) Schematic of protein-scale repeat pipeline. (FIG. 9B) Schematic of genome-scale repeat pipeline. The hypervariation score is based on computing an adjusted, non-redundant distance matrix between the hypervariable regions, and similarly for the constant regions. The score is the ratio of the sum of the adjusted distance matrices. (FIG. 9C) Histogram of non-zero repeat rearrangement scores for hits from the protein-scale repeat pipeline, with an indicator for the score of the highest scoring TALE cluster. (FIG. 9D) Distribution of cluster sizes from the genome-scale repeat pipeline. (FIG. 9E) Distribution of the hypervariation divergence score of all hits, with an indicator for score of the highest scoring TALE cluster. (FIG. 9F) Scatter plot of all within cluster percent identities and corresponding hypervariation divergence score.

(FIG. 10A) Nucleotide-resolution annotation of the LRR protein loci from ten strains of *Flavobacterium psychrophilum*. (FIG. 10B) Domain architecture and sequence identity of a prototypical LRR protein (JIP02/86 #8). (FIG. 10C) Amino acid sequence logo of individual repeat units (n=628) within intact LRR proteins. (FIG. 10D) Histogram of the number of repeat units within intact LRR proteins. (FIG. 10E) Structural model (trRosetta) of a prototypical LRR protein, highlighting the hypervariable positions (red) within the repeat units. The model was constructed from the first LRR protein in strain JIP02/86 (WP_011962357.1). (FIG. 10F) Size distribution of intact LRR proteins (red; n=111) and protein fragments (blue; n=206). (FIG. 10G) DNA microhomologies at high-confidence fragment-fragment junctions.

(FIG. 11A) Repeat architectures of four representative *D. purpureum* LRR proteins. (FIG. 11B) Sequence logo of the LRR motifs. (FIG. 11C) Structural model of a representative LRR protein, with hypervariable residues shown as sticks. (FIG. 11D) Distribution of all pairs of hypervariable residues within a single LRR unit.

(FIG. 12A) Splicing isoforms for the *Solanum lycopersicum* transcription factor LOC101240705 (Solyc02 g091030). A majority of isoforms differ only in the displayed region containing a tandem array of amino acid repeats. (FIG. 12B) Top: sequence logo of the 12 amino acid repeats without deletions. Bottom: Psipred secondary structure prediction of a representative repeat.

FIGS. 13A-13F: An array of serine proteases containing a hypervariable insert within the protease domain. (FIG. 13A) Nucleotide-resolution annotation of the protease locus from eight representative *Streptosporangiaceae* strains. (FIG. 13B) Domain architecture and sequence identity of a prototypical protease (*M. glauca* #14). (FIG. 13C) Sequence logo of the catalytic serine and neighboring residues from n=223 proteases. (FIG. 13D) Histogram of hypervariable insert lengths. (FIG. 13E) Amino acid sequences of the inserts within the proteases from a representative locus (*Herbidospora cretacea* NBRC 15474). (FIG. 13F) Structural models (trRosetta) of representative proteases, constructed (left to right) from WP_061297158.1, WP_061297163.1, and WP_068929153.1.

(FIG. 14A) Nucleotide-resolution annotation of 7 representative loci from *Photorhabdus* species. (FIG. 14B) Domain architecture and sequence identity of a prototypical L protein (*P. thracensis* #2). (FIG. 14C) Amino acid sequences of the hypervariable inserts within the fifteen L proteins shown in (FIG. 14A). (FIG. 14D-FIG. 14E) Yeast two-hybrid assay for *P. thracensis* L-S protein interactions (HIS3 reporter). The L protein #2 from *P. thracensis* (WP_046976484.1) was used as the fixed scaffold for all L proteins in the assay. (FIG. 14F) Comparison with the ids gene cluster from *Proteus mirabilis*, which confers self-identity and social recognition. The genes idsB, idsC, and idsF are shared between the *Photorhabdus* and *Proteus mirabilis* loci.

(FIG. 16A) Computational approach for high-resolution mapping of ORF fragments. (FIG. 16B) Histogram of fragment ends (n=206) as a function of position in DNA (green: non-coding; magenta: leucine-rich repeat motif region). Multiple repeat units were concatenated into a single unit for visualization purposes.

Figure 1:
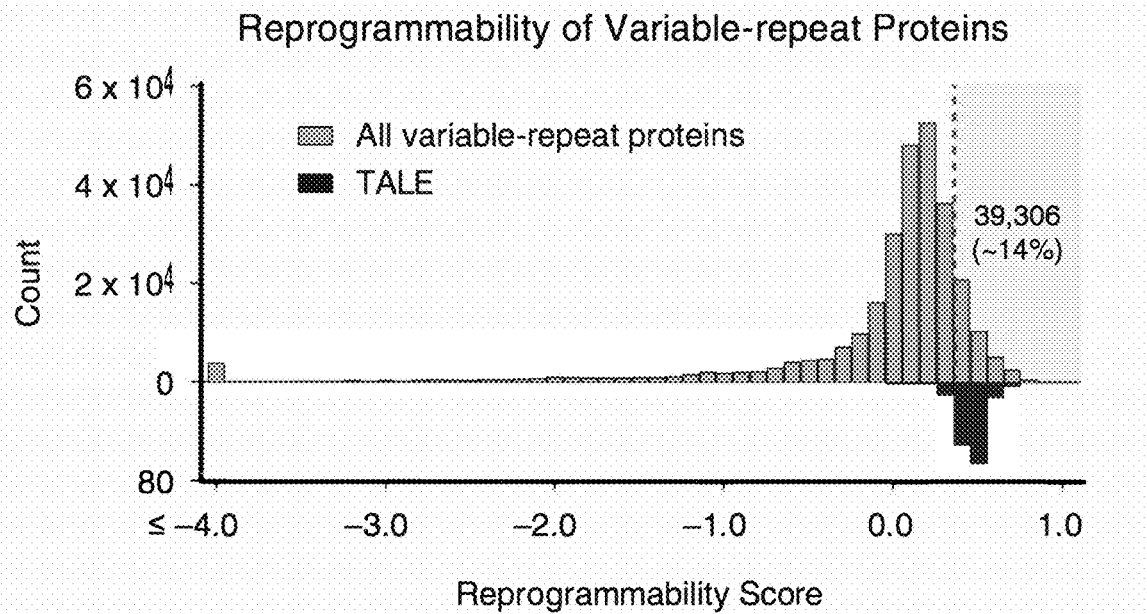
FIG. 1 is a chart showing reprogrammability as a function of repetition. 106,000,000 unique proteins of the UniProt database were analyzed, revealing 283,489 unique proteins with repetitive domains. Proteins were scored for reprogrammability based on i) repeats having common hypervariable regions, ii) evolutionary conservation of protein family, and iii) recombination of repeat domains.
Figure 2:
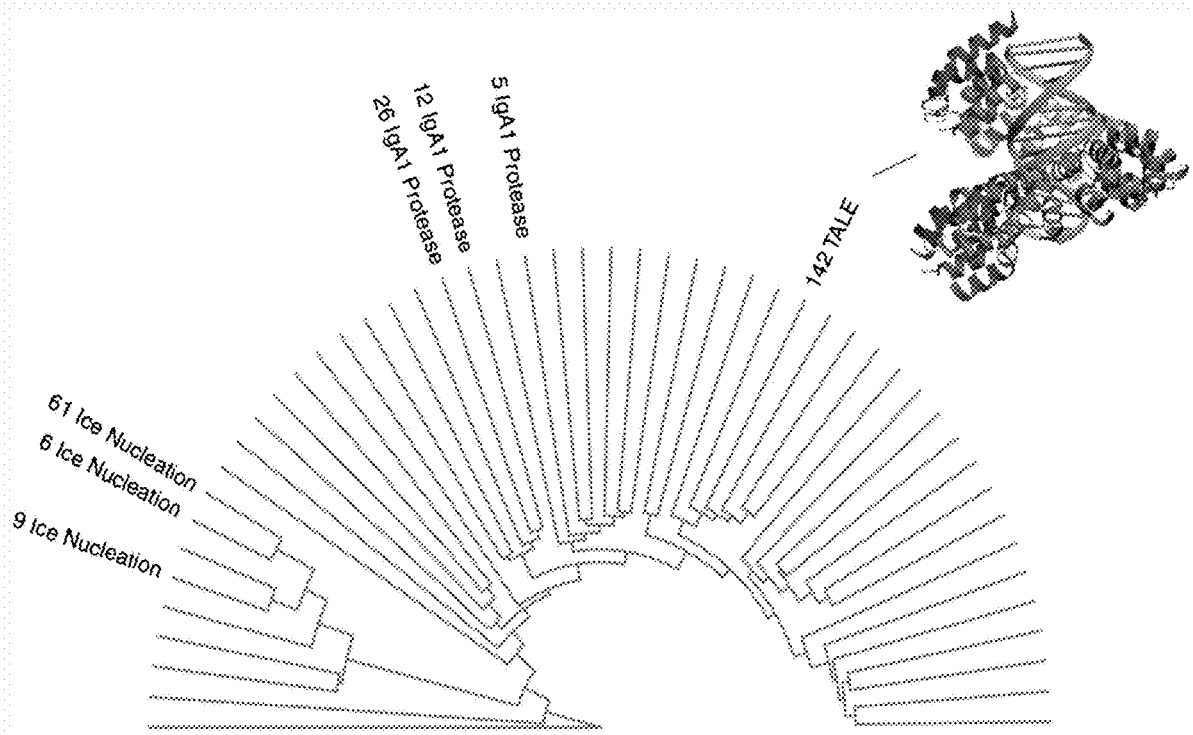
FIG. 2 exemplifies clustering of candidate proteins comprising repetitive domains.
Figure 4:
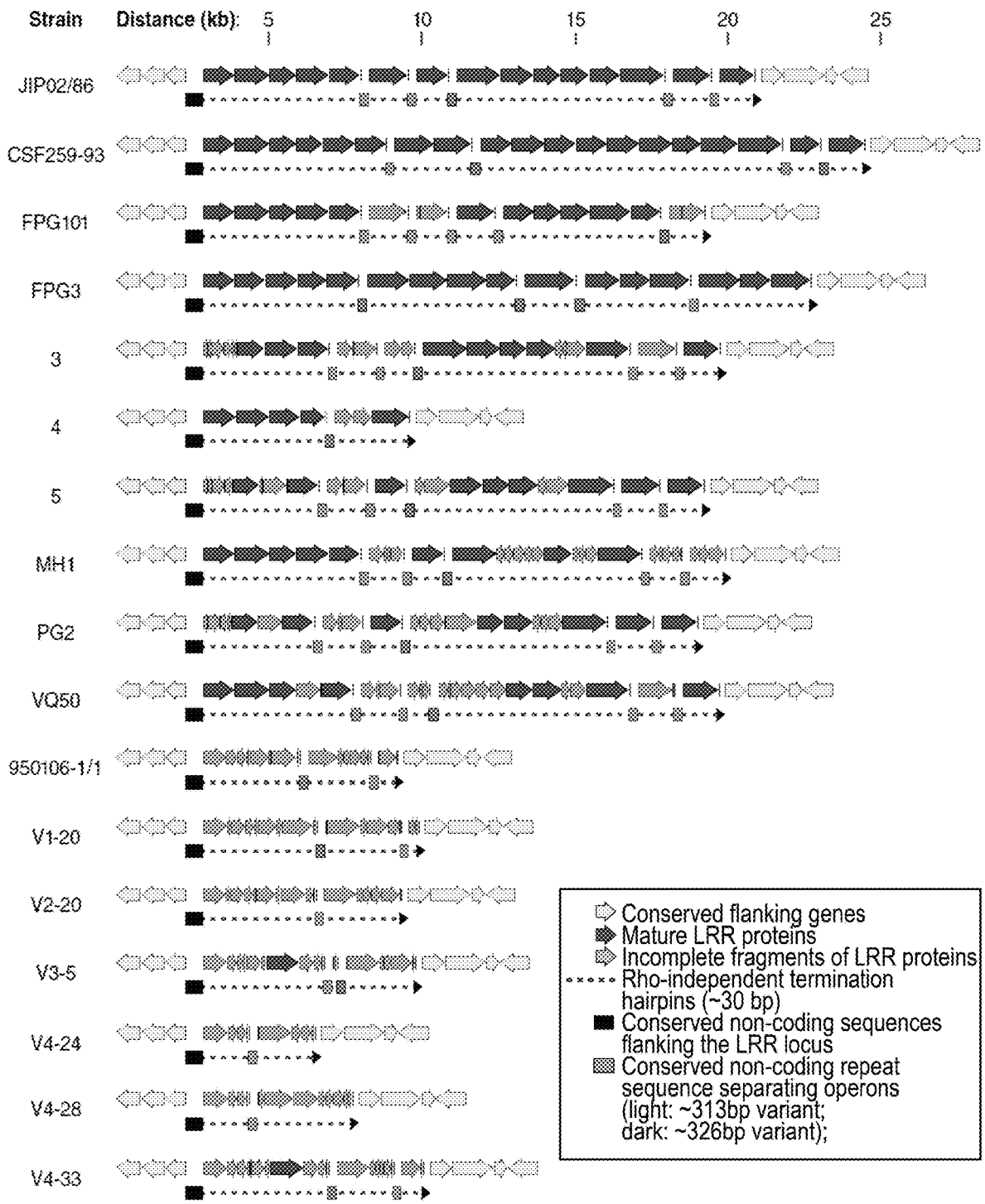
FIG. 4 depicts locus organization of the leucine-rice repeat (LRR) locus in genomes of 17 *F. psychrophilum* strains. The phylogenetic relationship of 10 strains by 16S rRNA is shown in FIG. 3A. The bottom six strains are phage-resistant clones of 950106-1/1 after several days of phage challenge.
Figure 5A:
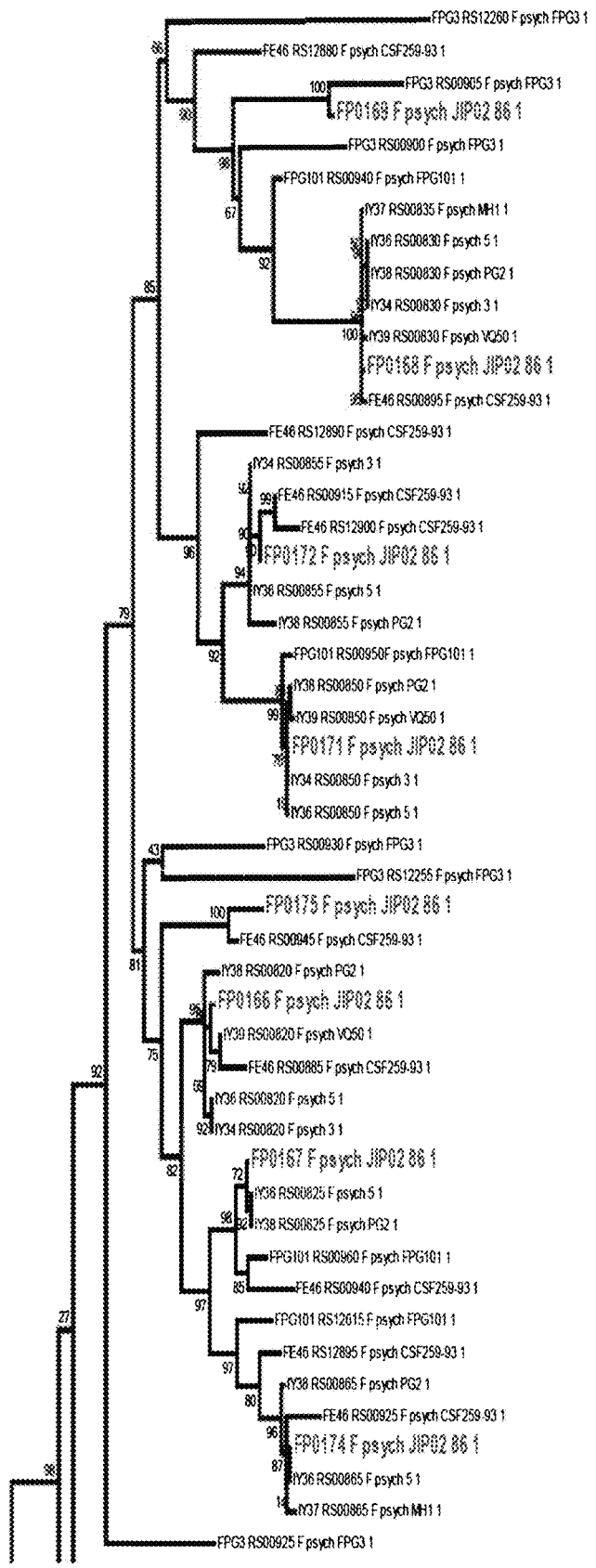
FIG. 5A shows relationships among proteins comprising diverse LRR-like domains arranged phylogenetically by 16S rRNA. The tree indicates diversification by tandem duplication and shuffling. The box encloses a clade of closely related *Flavobacterium psychrophilum* sequences, including WP_011962357.1.
Figure 5A:
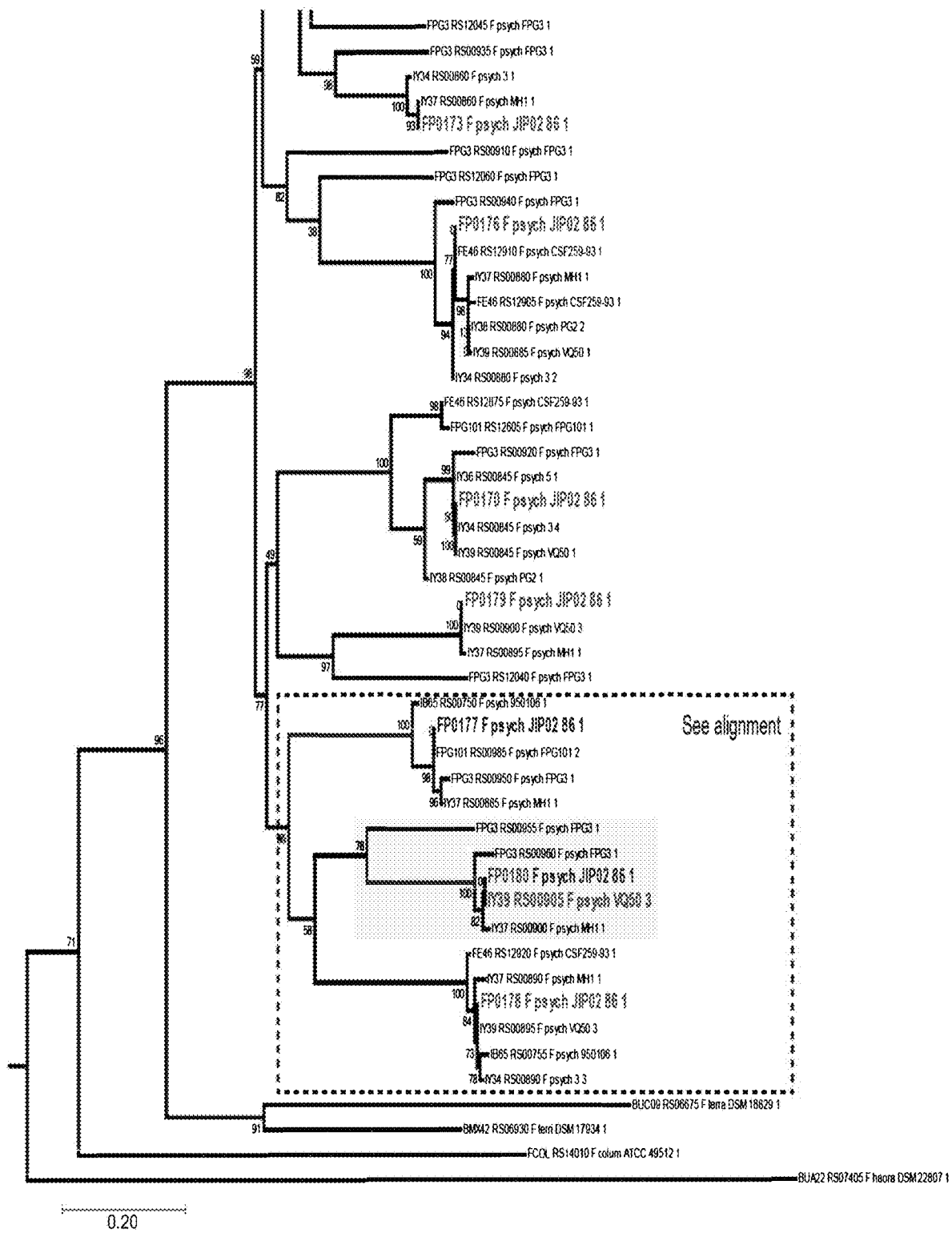
Figure 5B:
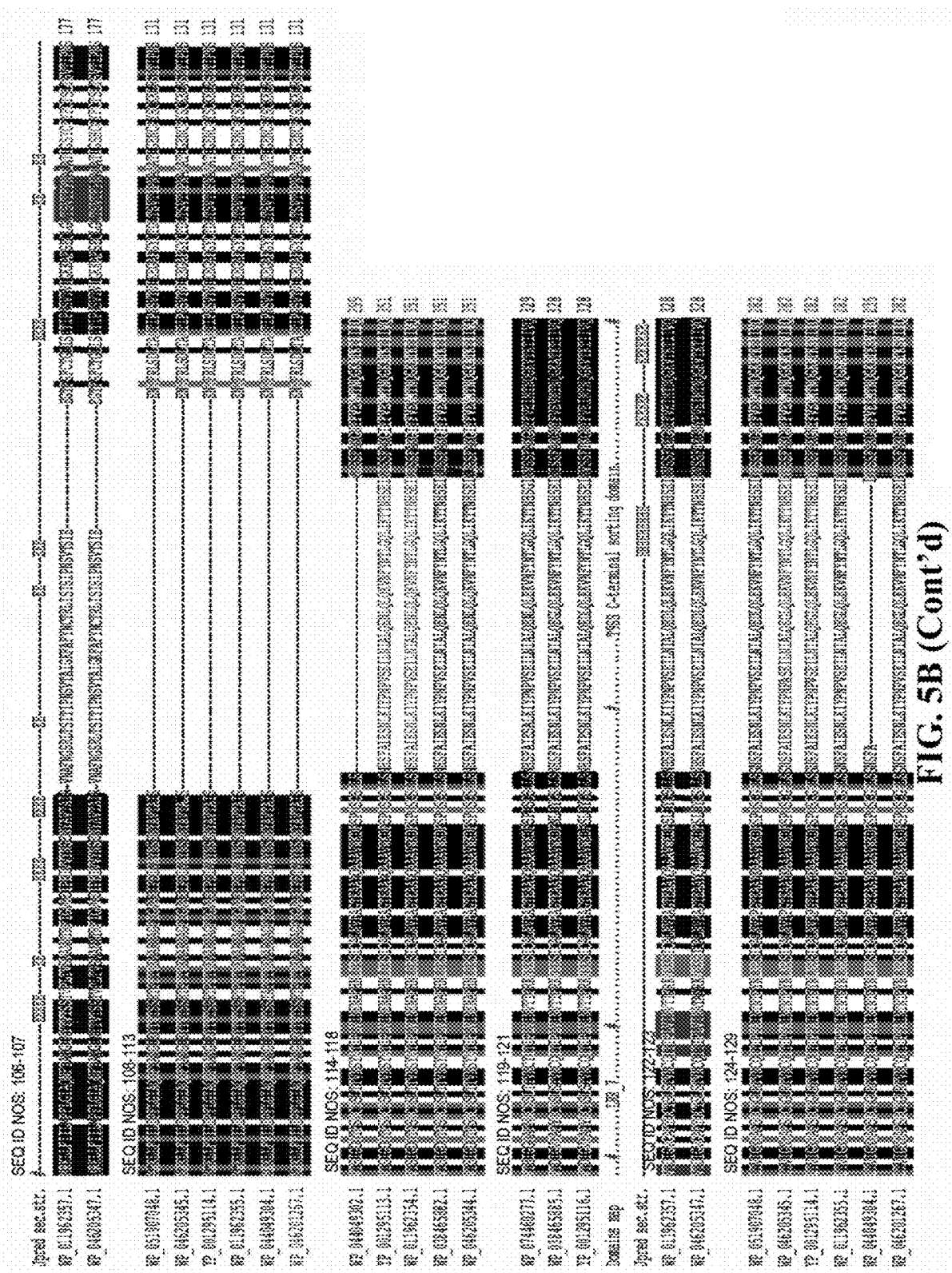
(FIG. 5B) shows a sequence alignment of the 16 proteins enclosed in the box of FIG. 5A, indicating domains and secondary structure prediction. Variation in the sequences indicates by mutation as well as duplication and loss of LRR repeats.
Figure 6:
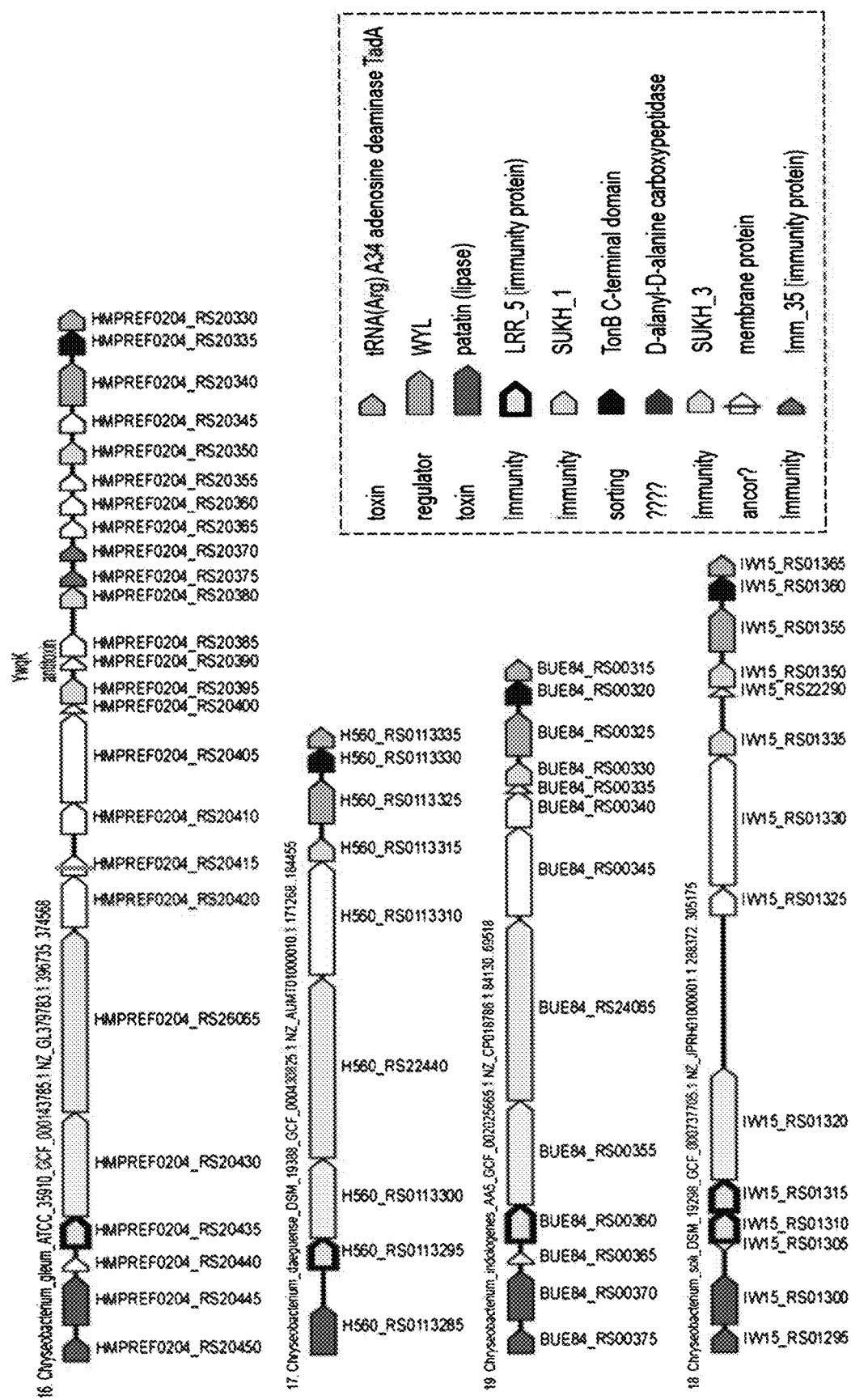
FIG. 6 shows examples of pfam13306 (LRR_5) domain containing proteins is other organisms at loci also encoding toxins.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

In an aspect, the present disclosure provides novel engineered LRR-containing proteins and polypeptides. In some embodiments, the LRR regions are engineered (e.g., designed or selected) to bind to one or more targets of interest. In certain embodiments, the LRR-containing proteins and polypeptides comprise domains engineered to direct the LRR-containing protein to a desired location, such as but not limited to an intercellular location, or a cell or tissue of an organism. For example, the engineered protein or polypeptide may comprise one or more LRRs and a trafficking domain. In certain embodiments, engineering of target recognition regions comprising LRRs is guided by target characteristics. In some instances, targets are large and distributed. In some instances, targets are small and localized. In some instances, binding to targets is influenced by the environment, for example, location of a target in a particular extracellular environment can influence engineering of a target recognition region compatible with the extracellular environment. In an example, a macromolecule in blood can advantageously be targeted by a target recognition region comprising LRRs compatible with that environment. The engineered protein or polypeptide may comprise an amino acid sequence capable of directing clearance from a cell or organism.

Accordingly, in embodiments of the invention, target recognition regions can comprise one or more LRR motifs, such as 1, 2, 3, 4, 5, 6, 7, 8, 9, 10, 11, 12, 13, 14, 15, 16, 17, 18, 19, or 20 or more LRR motifs. In embodiments of the invention, LRR motifs can be short or long, for example, 10, 11, 12, 13, 14, 15, 16, 17, 18, 19, 20, 21, 22, 23, 24, 25, 26, 27, 28, 29, 30 or more amino acids. In certain embodiments, variation within a LRR motif encompasses only a subset of amino acid positions in the motif while other amino acids of the motif are comparatively constant. In certain embodiments, such motifs are advantageously employed in the engineering of large target recognition regions comprising multiple LRR motifs. In theory and without limitation, relatively invariant amino acids govern the overall structure of the recognition region, whereas the variable amino acids determine target binding. In certain embodiments, variations can be made within a LRR at any of the amino acids of the LRR motif. In certain embodiments, a LRR includes relatively invariant amino acids that flank variable amino acids. For example, a LRR may include a series of adjacent hypervariable amino acids flanked by invariant amino acids. In theory and without being bound, relatively invariant amino acids govern the structure of the LRR whereas the hypervariable amino acids determine target binding. In certain embodiments, such motifs advantageously may be employed in the engineering of small target recognition regions. In certain embodiments, multiple LRR-containing proteins or polypeptides are used in combination, such as 2, 3, 4, 5, 6, 7, 8, 9, 10, or more which are distinct from one another in sequence and/or binding characteristics.

In some embodiments, the invention provides engineered proteins and polypeptides which comprise target recognition regions comprising LRR motifs disclosed herein. According to the invention, engineering of target recognition regions involves one or more of varying the number of LRRs (e.g., increasing or decreasing the number of LRRs), varying the sequence of LRRs (e.g., introducing mutations, insertions and/or deletions), varying the order of LRRs (e.g., shuffling), varying the spacing between LRRs (e.g., inserting or deleting amino acids between LRRs), and incorporating LRRs of target-binding domains from other sources.

In one aspect, the invention provides a non-naturally occurring or engineered composition, or one or more polynucleotides encoding components of said composition, or vector or delivery systems comprising one or more polynucleotides encoding components of said composition for use in recognizing or targeting a target molecule or a target molecule in a target cell. In some embodiments, the composition comprises an engineered protein or polypeptide comprising one or more target recognition regions comprising one or more engineered leucine rich repeats (LRRs). In preferred embodiments, a LRR may include a series of adjacent hypervariable amino acids flanked by invariant amino acids. In some embodiments, the LRR is derived from a prokaryotic organism. In some embodiments, the LRR may be derived from a bacteria defense-mechanism related protein. The bacteria protein may be toxins, including a variety of insecticidal toxins, as well as adhesins, proteases, and lipases, or any orthologs thereof.

In one aspect, the invention provides a non-naturally occurring or engineered composition, or one or more polynucleotides encoding components of said composition, or vector or delivery systems comprising one or more polynucleotides encoding components of said composition for use in modifying a target molecule or a target molecule in a target cell. In some embodiments, the composition comprises an engineered protein or polypeptide comprising one or more hypervariable amino acid residues. In some embodiments, the composition comprises an engineered protein or polypeptide comprising one or more engineered LRR. In some embodiments, the LRR is derived from a prokaryotic organism. In some embodiments, the LRR may be derived from a bacteria defense-mechanism related protein. The bacteria protein may be toxins, including a variety of insecticidal toxins, as well as adhesins, proteases, and lipases, or any orthologs thereof.

In some embodiments, libraries of LRR-containing proteins are prepared, each protein comprising one or more LRR(s), wherein the one or more LRR(s) have undergone one or more of varying the number of LRR(s), varying the sequence of LRR(s), varying the order of LRR(s), varying the spacing between LRR(s), and incorporating LRR(s) from other sources. The libraries are then screened to identify candidates having desired binding characteristics for a target of interest, including but not limited to target affinity and/or target specificity. The libraries can comprise LRR proteins expressed from a biological system or artificially synthesized.

In one aspect, the invention provides an engineered protein or polypeptide capable of recognizing a target comprising one or more LRR. In some embodiments, the LRR is derived from a prokaryotic organism. In some embodiments, the LRR is derived from a bacteria defense-mechanism related protein. In one aspect, the invention provides a non-naturally occurring or engineered composition, or one or more polynucleotides encoding components of said composition, or vector or delivery systems comprising one or more polynucleotides encoding components of said composition for use in recognizing or targeting a target molecule or a target molecule in a target cell. In some embodiments, the composition comprises an engineered protein or polypeptide comprising one or more target recognition regions comprising one or more engineered target recognition sequences (LRRs). In preferred embodiments, a LRR may include a series of adjacent hypervariable amino acids flanked by invariant amino acids. In some embodiments, the LRR is derived from a prokaryotic organism. In some embodiments, the LRR may be derived from a bacteria defense-mechanism related protein.

In one aspect, the invention provides a non-naturally occurring or engineered composition, or one or more polynucleotides encoding components of said composition, or vector or delivery systems comprising one or more polynucleotides encoding components of said composition for use in modifying a target molecule or a target molecule in a target cell. In some embodiments, the composition comprises an engineered protein or polypeptide comprising one or more hypervariable amino acid residues. In some embodiments, the composition comprises an engineered protein or polypeptide comprising one or more engineered LRRs. In some embodiments, the LRR is derived from a prokaryotic organism. In some embodiments, the LRR may be derived from a bacteria defense-mechanism related protein. The bacteria protein may be toxins, including a variety of insecticidal toxins, as well as adhesins, proteases, and lipases, or any orthologs thereof.

In certain embodiments, modulations of binding efficiency can be exploited by modifying the engineered protein. In some embodiments, modulations of binding efficiency can be exploited by modifying the LRR. In some embodiments, modification of binding efficiency can be achieved by introducing mutations to the hypervariable regions of the engineered protein.

In certain embodiments, the engineered protein is engineered to cleave a target, for example by linage to a domain comprising nuclease or protease activity. In some embodiments, the target is a protein. In some embodiments, the target is a polypeptide. In some embodiments, binding between the engineered protein and the target is directed by the LRR. In certain embodiments, modulations of cleavage efficiency can be exploited by modifying the engineered protein. In some embodiments, modulations of cleavage efficiency can be exploited by modifying one or more LRRs.

The methods according to the invention as described herein comprehend inducing one or more engineered proteins in a host cell, organism, or environment as herein discussed comprising delivering an LRR protein or nucleic acid encoding such. In some embodiments, the host cell or organism is a eukaryotic cell. In some embodiments, the host cell is a prokaryotic cell. The cell or organism may be a mammalian cell or organism. The mammalian cell or organism many be a non-human primate, bovine, porcine, rodent, mouse, or poultry cell or organism. In certain embodiments, the cell or organism is a non-mammalian eukaryotic cell or organism such as fish or shrimp. In certain embodiments, the cell may also be a plant cell. The plant cell may be of a crop plant such as cassava, corn, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

For minimization of toxicity, it is important to control the concentration of the engineered protein delivered to the host cell. Optimal concentrations of the engineered protein can be determined by testing different concentrations in a cellular or non-human eukaryote animal model.

In some embodiments, the engineered protein or polypeptide may be modified by altering the sequence of one or more LRR. In some embodiments, the LRR is duplicated. In some embodiments, the LRR is mutated. In some embodiments, one or more amino acid residues in the LRR are substituted. In some embodiments, one or more amino acid residues in the LRR are substituted with one or more amino acid residues from a heterologous LRR derived from a different source. In some embodiments, one or more amino acid residues in the LRR are substituted with one or more amino acid residues from a LRR derived from the same species or related species. In some embodiments, the engineered protein or polypeptide comprises one or more LRR generated by shuffling of one or more LRR. In some embodiments, the engineered protein or polypeptide comprises one or more LRR generated by linking a LRR to one or more LRR from a different source. In some embodiments, one or more LRR is modified by introducing a mutation to a non-hypervariable region. In a preferred embodiment, one or more LRR is modified by introducing a mutation to a hypervariable region. In some embodiments, one or more LRR is modified by introducing a mutation to a non-hypervariable or conserved region, wherein the engineered protein or polypeptide comprises two or more LRR sequences.

Leucine Rich Repeat (Lrr)

The leucine-rich repeat (LRR) is a protein structural motif composed of repeating amino acid stretches (e.g., 20-30 amino acid stretches) often rich in leucine residues. In some embodiments, a LRR comprises an N-terminal part comprising a conserved 11-residue sequence, often rich in leucines at defined positions (e.g. LxxLxLxxNxL (SEQ ID NO:1)), where x is any amino acid and the leucine and asparagine residues can be substituted with other hydrophobic residues. In another embodiment, LRRs can comprise either the 11-residue sequence LxxLxLxxNxL (SEQ ID NO: 1) or the 12-residue sequence LxxLxLxxCxxL (SEQ ID NO:22), where x is any amino acid; L is Leu, Ile, Val, or Phe; N is Asn, Thr, Ser, or Cys; and C is Cys, Ser, or Asn. Examples of LRRs include those described in Kobe B. et al., *The leucine-rich repeat as a protein recognition motif*, Curr. Opin. Struct. Biol. Vol 11:725-732; Ng et al., *Human leucine-rich repeat proteins: a genome-wide bioinformatic categorization and functional analysis in innate immunity*, Proc. Natl. Acad. Sci. U.S.A., Mar. 15, 2011, Vol. 108, Suppl 1, pp. 4631-4638 (observed that almost half of 375 human LRR-proteins do not contain non-LRR domains from which functional insights potentially can be gleaned, therefore attempted categorization of certain LRR-containing proteins into classes, for example on the basis of non-LRR domains that they contain, and distributed LRR-only proteins among non-LRR-containing proteins).

The diversity of LRRs is substantially broader, including, for example, sequences and motifs that fold into a range of defined structures and sequences and motifs that may not contain any leucine residues. In certain embodiments, LRR-containing proteins or polypeptides of the invention comprise one or more LRR_5 motifs. LRR_5 motif may comprise the sequence of STQTLKLIETHLKTIPSLAFSSLPNISRIYLSIDATLQR-LEPHSFYNLSKMTHIEIRNTRSLTY IDP-DALTELPLLKFLGIFNTGLRIFPDLTKIYSTDIF (SEQ ID NO:88).

The LRR-containing engineered protein may comprise a conserved N-terminal secretion peptide and C-terminal type 9 secretion signal, which may provide an anchor to the cell surface via a conjugated lipoprotein.

In certain embodiments, LRR-containing protein or polypeptides comprise $[X_1\text{-phenylalanine-}X_2\text{-}X_3\text{-glycine/proline-}X_4\text{-threonine/serine-}X_5]_z$ wherein: $X_1$ is 1-4 amino acids in length and comprises alanine or a non-charged polar amino acid; $X_2$ is 1 to 5 amino acids comprising at least one polar amino acid; $X_3$ comprises 4 to 6 amino acids comprising one or more non-charged polar amino acids and aliphatic hydrophobic amino acids; $X_4$ is 2 to 4 amino acids comprising a charged or non-charged polar amino acid and/or an aliphatic hydrophobic amino acid; $X_5$ is 3 to 6 amino acids comprising a charged or non-charged polar amino acid, an aliphatic hydrophobic amino acid, and/or an aromatic hydrophobic amino acid; and z is any integer from 1 to 10.

In certain embodiments, LRR-containing proteins or polypeptides comprise $[X_1\text{-phenylalanine-}X_2\text{-}X_3\text{-glycine/proline-}X_4\text{-alanine/asparagine-}X_5]_z$ wherein: $X_1$ is 1 to 4 amino acids in length and comprises alanine or a non-charged polar amino acid; $X_2$ is 1 to 5 amino acids comprising at least one polar amino acid; $X_3$ comprises 4 to 6 amino acids comprising one or more non-charged polar amino acids and aliphatic hydrophobic amino acids; $X_4$ is 2 to 4 amino acids comprising a polar amino acid and/or an aliphatic hydrophobic amino acid; $X_5$ is about 3 to 6 amino acids comprising a polar amino acid, an aliphatic hydrophobic amino acid, and/or an aromatic hydrophobic amino acid; and z is any integer from 1 to 10. In such embodiments, $X_1$ can comprise alanine, can comprise threonine, or can comprise cysteine. In such embodiments, $X_2$ can comprise a charged or a non-charged polar amino acid, which can be lysine, arginine, serine, tyrosine, asparagine or cysteine. In such embodiments, the aliphatic hydrophobic amino acid of $X_3$ comprises leucine, isoleucine, or valine. In such embodiments, the non-charged polar amino acid of $X_3$ comprises serine or threonine. In such embodiments, the polar amino acid of $X_4$ comprises a charged and/or a non-charged amino acid. In certain embodiments, $X_4$ comprises asparagine, serine, aspartate, or arginine. In such embodiments, the aliphatic hydrophobic amino acid of $X_5$ can comprise alanine, valine, glycine, and/or isoleucine. In such embodiments, the polar amino acid of $X_5$ can comprise a charged or a non-charged amino acid, which can be tyrosine, serine, asparagine, threonine, aspartate and/or glutamate.

In some embodiments, the engineered protein or polypeptide comprises $[X_1\text{-Proline/glycine-}X_2\text{-threonine/serine-}X_3\text{-phenylalanine-}X_4]_z$ wherein: $X_1$ is 4 to 6 amino acids in length and comprises non-charged polar amino acids and aliphatic hydrophobic amino acids; $X_2$ is 2 to 4 amino acids in length and comprises a charged or non-charged polar amino acid and/or an aliphatic hydrophobic amino acid; $X_3$ is 1 to 6 amino acids in length and comprises polar and/or non-polar amino acids; $X_4$ is 1 to 5 amino acids and comprises at least one polar amino acid; and z is any integer from 1 to 10. In some embodiments, the engineered protein or polypeptide comprises $[X_1\text{-Proline/glycine-}X_2\text{-alanine/asparagine-}X_3\text{-phenylalanine-}X_4]_z$ wherein: $X_1$ is 4 to 6 amino acids in length and comprises non-charged polar amino acids and aliphatic hydrophobic amino acids; $X_2$ is 2 to 4 amino acids in length and comprises a charged or non-charged polar amino acid and/or an aliphatic hydrophobic amino acid; $X_3$ is 1 to 6 amino acids in length and comprises polar and/or non-polar amino acids; $X_4$ is 1 to 5 amino acids and comprises at least one polar amino acid; and z is any integer from 1 to 10. In some embodiments, $X_1$ comprises (leucine-$X_{1a}$-isoleucine), wherein $X_{1a}$ comprises threonine, serine, and/or valine; wherein $X_2$ comprises asparagine, serine, and/or valine; wherein $X_3$ comprises isoleucine; and wherein $X_4$ comprises cysteine. In some embodiments, the aliphatic hydrophobic amino acids of $X_1$ comprise leucine, isoleucine, and/or valine. In some embodiments, the non-charged polar amino acids of $X_3$ comprise serine and/or threonine. In some embodiments, the polar amino acid of $X_2$ comprises a charged and/or a non-charged amino acid. In some embodiments, $X_2$ comprises an asparagine and/or a serine. In some embodiments, $X_2$ comprises an aspartate and/or an arginine. In some embodiments, the polar amino acids of $X_3$ comprise charged and/or non-charged polar amino acids. In some embodiments, the non-polar amino acids of $X_3$ comprise aliphatic and/or aromatic hydrophobic amino acids. In some embodiments, $X_3$ comprises an alanine. In some embodiments, $X_3$ comprises a threonine. In some embodiments, $X_3$ comprises a cysteine. In some embodiments, the aliphatic hydrophobic amino acids of $X_3$ comprise alanine, valine, glycine, and/or isoleucine. In some embodiments, the non-charged polar amino acids of $X_3$ comprise tyrosine, serine, asparagine, and/or threonine. In some embodiments, the charged polar amino acids of $X_3$ comprise aspartate and/or glutamate. In some embodiments, $X_4$ comprises a charged or a non-charged polar amino acid. In some embodiments, the charged polar amino acid of $X_4$ comprises lysine or arginine. In some embodiments, the non-charged polar amino acid of $X_4$ comprises serine, tyrosine, asparagine and/or cysteine. In some embodiments, $X_1$ comprises leucine, serine, threonine, valine, and/or isoleucine, wherein $X_2$ comprises asparagine, serine, and/or valine; wherein $X_3$ comprises isoleucine, glycine, serine, threonine, and/or alanine; and wherein $X_4$ comprises cysteine, serine, isoleucine, and/or glycine. In some embodiments, the engineered protein or polypeptide comprises one or more LRR sequences of any one of SEQ ID NOs:49-87.

LRRs can also be identified by secondary structure with motifs that diverge substantially from the classic repeat motif. For example, the repeats commonly fold together to form a leucine-rice repeat domain having a solenoid structure. Typically, each repeat unit has a beta strand-turn-alpha helix structure, the region between the helices and sheets tightly packed with hydrophobic residues, often leucine. The curved structure of the LRR domain forms a large binding surface which makes the LRR domain an effective protein-binding motif, and LRRs are frequently involved in protein-protein interactions.

LRR-containing proteins may comprise one or more LRR repeats, e.g., at least 1, at least 2, at least 3, at least 4, at least 5, at least 6, at least 7, at least 8, at least 9, at least 10, at least 15, at least 20, at least 30, at least 40, or at least 50 LRR repeats. An example of an LRR protein is the one with a structure described as ribonuclease inhibitor (RI) (Kobe and Deisenhofer, 1995). The LRRs in this protein are relatively long, typically 27-29 amino acids in length, and all LRRs have three to four turns of α-helix on their convex surfaces opposite the β sheet. RI contains 16 LRRs that do not form a complete circle, but form a horseshoe structure. In certain examples, in the innate immune system, a family of cytoplasmic sensors known as "Nod-like receptors" (NLRs) contain nine or fewer contiguous RI-like LRRs at their C-terminal ends, which are thought to be involved in target recognition. Based on the RI structure, the LRRs are predicted to form banana-shaped structures with a β sheet on their concave surfaces and α-helices on their convex surfaces. TLR extracellular domains (TLR-ECDs) typically contain 19-25 LRRs that, like RI, form horseshoe structures. In contrast to RI, the LRRs of TLRs are shorter, approximately 24 residues in length, which limits the extent of multi-turn α-helices on their convex sides. TLR-ECDs frequently comprise LRRs that are longer than the consensus 24 residues. The extra-residues may produce loops that protrude from the TLR-ECD horseshoe, usually on the convex side of the LRR. Examples of such LRRs can be found in TLRs 7, 8, and 9.

LRR motifs may be comprised in various functionally unrelated proteins. LRR-containing domains are evolutionarily conserved in many proteins associated with innate immunity. In plants, nucleotide-binding site-LRR proteins function to recognize pathogen products of a virulence genes. In certain instances, LRRs promote formation of protein complexes, such as receptor-coreceptor complexes. For example, toll-like receptors (TLRs) and NOD-like receptors (NLRs) bind to diverse bacterial, fungal, parasite, and viral-derived components. A comparative analysis of LRR-encoding genes has shown that the LRR superfamily has expanded greatly in mammals as compared to other less complex eukaryotes. For example, many LRR-encoding genes are expressed in the nervous system and exhibit strikingly specific expression patterns. Such LRR proteins are often involved in axon guidance and dendrite arborization.

According to the invention, the target of a protein or polypeptide or other macromolecule comprising a LRR of the invention can be without limitation, a macromolecule such as a protein or polypeptide or a nucleic acid which can be naturally occurring or synthetic.

The present disclosure provides a method of engineering an LRR-containing protein or polypeptide to bind to a target of interest, and a method to improve binding to a target of interest. The methods comprise inserting one or more LRR of the invention or modifying one or more LRRs of a LRR-containing binding region and detecting whether the engineered protein or polypeptide binds to the target, or has improved binding to the target. Improved binding can comprise, without limitation, changes in binding affinity and/or changes in binding specificity. In certain embodiments, binding of an engineered protein or polypeptide is assessed by detecting whether the protein or polypeptide modifies the target. For example, the protein can comprise, without limitation, a protease, a ligase, a kinase, a phosphorylase, or other catalytic domain or activity. The invention provides a method of engineering a protein or polypeptide to bind to a target of interest, which comprises inserting one or more of the aforementioned LRRs and detecting whether the engineered protein or polypeptide binds to the target, or has improved binding to the target.

According to the invention, LRR-containing proteins and polypeptides of the invention can be engineered and optionally expressed or delivered to bind to targets in vivo, ex vivo, or in vitro. The LRR-containing proteins and polypeptides can be engineered to target biological targets as well as industrial targets and in any suitable location. Biological target locations can be, without limitation, intracellular, extracellular, humoral, or lymphatic.

The present disclosure includes an LRR-containing protein or polypeptide which comprises one or more nuclear localization signal (NLS). In an embodiment, the LRR-containing protein is engineered to be translocated to the nucleus of a eukaryotic cell when introduced or expressed therein. In an embodiment, the LRR-containing protein comprises a domain that is functional in the nucleus. In an embodiment, the LRR-containing protein binds and chaperones to the nucleus and agent that is functional in the nucleus.

LRR-proteins can be expressed, delivered, or otherwise provided by any system suitable to their application. In certain embodiments, LRR proteins are delivered individually. In other embodiments, LRR proteins are delivered in combinations. In an embodiment, the combination comprises two or more LRR proteins, each designed to interact with a distinct target. In another embodiment, the combination comprises two or more LRR proteins engineered to interact with a target and variants of a target. A non-limiting example involves a combination of LRR proteins or an array of protein encoding nucleic acids, each LRR protein containing one or more LRRs, the LRRs among the LRR proteins varying in a subset of amino acids. When expressed from nucleic acids, the LRR protein combination can be expressed from individual genes, or be from multiple LRR proteins expressed from an operon, or from multiple LRR proteins expressed as a polyprotein, optionally cleavable, or a combination of the aforementioned expression constructs. The combination of LRR proteins can comprise multiple LRR proteins engineered to bind to a target and variants of the target. In certain embodiments, variants of a target comprise target mutants that would otherwise escape binding by the LRR protein and can comprise unpredictable escape mutants which or mutants previously or frequently observed to arise.

Trafficking Domain

In embodiments of the invention, LRR-containing proteins and peptides comprise elements capable of directing transport or location, referred to herein as trafficking domains. A trafficking domain may comprise one or more components for the trafficking function. Trafficking includes, without limitation, a) secretion, b) nuclear localization, c) nuclear export, d) transport to an organelle, e) lysosomal transport, f) injection (such as from a pathogen into a target cell, g) binding to a cell surface receptor, h) binding to a soluble receptor, i) binding to a soluble target, and j) binding to an immobilized target.

In some examples, the trafficking domain comprises a substrate of a secretion system (e.g., Type IX secretion system). In some examples, the trafficking domain comprises a secretion signal peptide.

A trafficking domain may comprise one or more amino acid sequence capable of binding to another molecule (e.g., a receptor, antigen, antibody) or a cell. For example, the trafficking domain may comprise one or more amino acid sequence capable of binding to an Fc receptor, binding to a dendritic cell, and/or directing antigen processing.

A trafficking domain may be a component of a specific binding pair (SBP). SBPs include without limitation, antigen-antibody binding, ligand-receptor binding, and more generally protein-protein interactions such as avidin-biotin. In such embodiments, the trafficking domain can be used to target a protein or polypeptide to a cellular receptor or cell type. In one non-limiting example, a protein or polypeptide of the invention can be targeted to an immune cell for processing. In another non-limiting example, a protein or polypeptide of the invention can be targeted for elimination from serum of a subject, for example by normal physiological processes or by filtration. In certain embodiments, the targeting is inducible, for example by providing a protein or polypeptide of the invention and separately providing at or for a selected time an agent that binds to or forms a complex with the protein or polypeptide of the invention and directs the complex to a ligand, receptor, or cell type.

Secretion Systems

In some embodiments, the trafficking domain comprise one or more substrates of a secretion system. Without limitation, secretion systems are central to translocation of proteins to or across cell membranes, transport into and out of cells, and to cell-cell interactions. For reviews of bacterial-host cell interactions which can be pathogenic, commensal or mutualistic, see e.g., Tseng et al., *Protein secretion systems in bacterial-host associations, and their description in the Gene Ontology*, BMC Microbiology 2009, 9(Suppl 1):S2 doi:10.1186/1471-2180-9-S1-S2. The secretion (Sec) pathway and Tat translocation pathway are well studied and universal to eubacteria, archaea and eukaryotes. See, Papanikou et al., *Bacterial protein secretion through the translocase nanomachine*. Nat Rev Microbiol. 2007, 5 (11): 839-851. 10.1038/nrmicro1771; Muller M: *Twin-arginine-specific protein export in Escherichia coli*. Research in Microbiology. 2005, 156 (2): 131-136; Albers et al., *Protein secretion in the Archaea: multiple paths towards a unique cell surface*. Nat Rev Microbiol. 2006, 4 (7): 537-547. 10.1038/nrmicrol440.

In some embodiments, the invention includes an LRR-containing protein or polypeptide which comprises a secretion signal peptide. In an embodiment, the secretion signal peptide provides export from a bacterial cell. In an embodiment, the secretion signal peptide provides export from a eukaryotic cell. In an embodiment, the secretion signal peptide provides export from a mammalian cell. In an embodiment, LRR-containing proteins of the invention can be collected and purified from culture media.

In certain embodiments, the invention involves an engineered protein or polypeptide comprising one or more LRRs and a trafficking domain, a variety of which are described herein, capable of directing and/or localizing the protein or polypeptide in use and/or in production. In certain embodiments, the trafficking domain comprises a substrate of a secretion system. In certain embodiments, the trafficking domain comprises an N-terminal secretion signal peptide. In certain embodiments, the trafficking domain comprises a substrate of a Type II, Type III, Type IV, Type V, Type VI, Type VII, Type VIII, or Type IX secretion system. The invention includes an LRR-containing protein or polypeptide which comprises a substrate for a secretion system including but not limited to a Type II, Type II, Type IV, Type V, Type VI, Type VII, Type VIII, or Type IX secretion system. The secretion system substrate provides export from a cell which comprises the secretion system. By way of example, a substrate of a Type II secretion system, also known in *E. coli* as the Sec dependent protein secretion, is the classic N-terminal signal sequence.

The machinery of the Sec pathway recognizes a signal peptide, usually at the N-terminal on proteins destined for secretion, and facilitates translocation of the protein by a secretory mechanism comprising secYEG to the cellular membrane of proteins destined for the inner membrane, outer membrane, periplasm, or secretion out of the bacterial cell. The mechanism translocates proteins in an unfolded state, using ATP hydrolysis and a proton gradient for energy. The secretion pathway may be referred to as the Sec-dependent system or Type II secretion system (T2SS). In eukaryotes, a homologous system exists by which proteins are translocated to the endoplasmic reticulum.

The machinery of the twin-arginine translocation (Tat) secretion pathway recognizes an N-terminal signal peptide motif rich in basic amino acid residues (consensus motif S/T-R-R-X-F-L-K (SEQ ID NO:23) where X is often a polar amino acid) and translocates the proteins in a folded state using a proton gradient as an energy source. The Tat translocase consists of the components TatA, TatB, and TatC, and in some instances TatA and TatC. Palmer et al., *The twin-arginine translocation* (*Tat*) *protein export pathway*. Nat Rev Microbiol. 2012; 10:483-496. doi: 10.1038/nrmicro2814.

The type III secretion system (T3SS) is found in Gram-negative bacteria that target both plant and animal hosts. In some cases, effector proteins are secreted out of the bacterial cell. In others, the system injects effector proteins across the bacterial and target cell membranes into the cytosol of target cells. Grant et al., *Subterfuge and manipulation: type III effector proteins of phytopathogenic bacteria*. Annu Rev Microbiol. 2006, 60: 425-449. 10.1146/annurev.micro.60.080805.142251.

The type IV secretion system (T4SS) is unusual in its ability to transport nucleic acids in addition to proteins. Christie et al., Structural and dynamic properties of bacterial type IV secretion systems. Mol Membr Biol. 2005, 22 (1-2): 51-61. 10.1080/09687860500063316. The T4SS usually consists of 12 components and functions in transport of proteins, protein-protein complexes; and protein-DNA complexes.

Other non-limiting secretion systems include, without limitation, type V secretion system (T5SS), type VI secretion system (T6SS), *Photorhabdus* virulence cassette pathway (PVC), and PrsW transmembrane peptidase. In certain embodiments, a trafficking domain comprises a substrate of a secretion system, not limited to the aforementioned systems.

Mycobacteria possess secretion systems referred to as Type VII Secretion Systems (T7SS). Bitter et al. 2009, Systematic genetic nomenclature for type VII secretion systems. PLoS Pathog 5: e1000507. Virulent *Mycobacterium tuberculosis* (Mtb) possesses several regions of genetic virulence that are lacking in avirulent *M. bovis* BCG. One of these regions of difference, RD1, is present in all virulent strains and lacking in all avirulent strains tested. Deletion of this 9.5 kb region from Mtb yields attenuation of virulence, and this mutant can be complemented with the cloned region. This system is called the early secreted antigen 6 kilodaltons (ESAT-6) secretion system 1 (ESX1) or secretion in mycobacteria (Snm), and it delivers virulence factors into host macrophages during infection. Four proteins have been shown to be secreted via this system: ESAT-6, CFP-10, Rv3483c (MM1553 in *M. marinum*) and Rv3881c (Mb3881c in *M. marinum*). Xu et al. 2007, A unique *Mycobacterium* ESX-1 protein co-secretes with CFP-10/ESAT-6 and is necessary for inhibiting phagosome maturation. Mol. Microbiol. 66: 787-800. Es loci are characterized by the secretion of small (~100 aas) proteins with a conserved Trp-X-Gly (WXG) motif which contributes to the formation of a helix-turn-helix structure in the center of the protein, and the presence of a gene that encode a TM protein of the FtsK/SpoIIIE ATPase family. Gröschel et al. 2016, ESX secretion systems: mycobacterial evolution to counter host immunity. Nat. Rev. Microbiol. 14: 677-691.

Various strains of bacteria are able to produce a unique class of functional amyloids termed curli, which are critical for biofilm formation, host cell adhesion, and colonization of inert surfaces. Curli are secreted via the type VIII bacterial secretion system (T8SS), and share biochemical and structural characteristics with amyloid fibers that have been implicated in deleterious disease in humans. Cao et al., 2014, Structure of the nonameric bacterial amyloid secretion channel, Proc Natl Acad Sci USA 2014 Dec. 1; 111(50): E5439-44. Epub 2014 Dec. 1.

Another secretion system is the type IX secretion system (T9SS found in some species of the Bacteroidetes phylum. T9SS plays two roles, either a means of movement (called gliding motility) for non-pathogens or a weapon for pathogens. In *Porphyromonas gingivalis* and some other periodontopathogens, T9SS translocates proteins, especially virulence factors, across the outer membrane (OM). Proteins destined for secretion bear a conserved C-terminal domain (CTD) that directs the cargo to the OM translocon. At least 18 proteins are involved, with some engaged in the post-translational modification of T9SS cargo proteins. Upon translocation across the OM, the CTD is removed by a protease with sortase-like activity, and an anionic LPS is attached to the newly formed C-terminus. As a result, a cargo protein can be secreted into the extracellular milieu or covalently attached to the bacterial surface. Tannerella forsythia and *Prevotella intermedia* (also oral pathogenic bacteria) use the T9SS secretion pathway to secrete their effector proteins. Accordingly, in certain embodiments, a trafficking domain comprises a substrate of T9SS. The T9SS and secretion substrates have been reviewed in detail, for example by Lasica et al., 2017, The Type IX Secretion System (T9SS): Highlights and Recent Insights into Its Structure and Function, *Front. Cell. Infect. Microbiol.,* 7:215. doi: 10.3389/fcimb.2017.00215 and references cited therein.

Vesicle Transport and Targeting in Eukaryotic Cells

The eukaryotic secretory pathway involves sorting and targeting components and mechanisms, e.g., transport from golgi to plasma membrane, retention in the endoplasmic reticulum, and transport from golgi to lysosome. The default pathway for ER/golgi proteins is encapsulation in vesicles storing secretory proteins followed by membrane fusion of vesicles, which may be regulated, resulting in secretion of vesicle contents. Regulated secretion, e.g., neurotransmitter release or insulin release from pancreatic cells, involves a signal to trigger secretory granule fusion with the cell membrane. Proteins can have labels or be modified to enable transport to other locations. For example, KDEL receptors direct retrieval and retention of certain proteins comprising KDEL (SEQ ID NO: 89) sequences in the ER. Proteins destined for the lysosome are conjugated to mannose-6-P (M6P) and bind M6P receptor in the trans golgi network (TGN), which directs transport to the lysosome via clathrin-coated vesicles.

Specific Binding Pairs

In certain embodiments, LRR-containing proteins comprise trafficking domains suitable for location to a particular cell type or receptor, or for elimination from an organism. In an embodiment, the trafficking domain is a first member of a specific binding pair (SBP), the second member of which is then used to bind to the first member of the SBP, for example to collect or partition the first SPB with linked LRRs and any component adhered to the LRRs. Specific binding pairs include any pair of molecules, either naturally derived or synthetically produced in which one of the pair has an area which binds to the other molecule. Non-limiting examples of SPBs include antibody-antigen pairs, antibody-Fc receptor pairs, hormone-hormone receptor, receptor-ligand, enzyme-substrate, and IgG-protein A, and avidin-biotin. Accordingly, in an embodiment, an LRR-containing protein comprising a trafficking domain is administered to a subject where it binds to a preselected target, followed by removal of the LRR protein with the target molecule.

Bacteria Secretion Systems and Toxins

Prokaryotic protein toxins are distributed across all major bacterial lineages and are involved in multiple levels of cell-associated functions. Many of these proteins appear to vary their toxin domains through recombination, for example, by replacing an existing toxin domain by a distinct one encoded by standalone cassettes, while retaining the rest of the protein's architecture intact. These systems often are linked chromosomally to immunity proteins that helps in protecting cells against their own toxin. Prokaryotic protein toxins contain terminal domains involved in secretion, cell surface anchoring, and/or motility, domains that bear toxin activity, and single to multiple central domains. The central domains can be characterized by variable repeats that can form extended fibrous or filamentous structures, usually involved in recognition, adhesion or presentation to target cells. For example, several pathogenic bacteria, both gram positive and gram negative, express virulence factors with LRR regions. An example is the *L. monocytogenes* protein InlA, which binds to human E-cadherin and promotes adhesion to and invasion of cells in the intestinal epithelium.

A typical prokaryotic toxin may contain one or more secretion domain(s) at either N-terminus or C-terminus, one or more central repeat domains followed by one or more C-terminal toxin domain, which may or may not be followed by more repeat domains. These prokaryotic toxins exhibit high level of polymorphism, characterized by high diversity of the C-terminal toxin domain and the central repeat domain. The C-terminal toxin domain of prokaryotic toxins may include protein domains with peptidase activity, transglutaminase activity, nuclease activity, deaminase activity, nucleotide modification activity (including kinase activity, phosphatase activity, glycosyltransferase activity, and ribosyltransferase activity), lipid modification activity, carbohydrate modification activity, and transcription regulation activity. The C-terminal domain may also include protein domains that form membrane-spanning structures.

Prokaryotic polymorphic toxins are associated with and recognized by several distinct secretion systems, at least including type II secretion system (T2SS), type V secretion system (T5SS), type VI secretion system (T6SS), type VII secretion system (T7SS), type-IX secretion system (T9SS), *Photorhabdus* virulence cassettes (PVC) system, and PrsW-dependent MuF phage-capsid-like systems. A toxin may be associated with multiple secretion systems and are either directedly injected into target cells or be anchored on the surface of the producing bacteria cell and delivered upon contact with the target cell.

Prokaryotic polymorphic toxins are often associated with poly-immunity proteins that protect the cells against their own toxins. In certain systems, the toxin and antitoxin interact physically.

The immune systems are typically capable of neutralizing several distinct types of toxin domains. The immunity proteins or domains may belong to immunity protein SUKH, SuFu, or LRR superfamilies, Imm-NTF2 and Imm-NTF2-2 (NTF2 fold domain), Imm-MyosinCBD (related to the cargo-binding domain of the type VI myosins of animals), Imm-LRR (leucine-rich repeats), Imm-Ank (Ankyrin repeats), or Imm-HEAT (HEAT repeats), which display domains that are widely used in protein-protein interactions across several cellular systems. The SUKH and SuFu superfamily proteins are reported as immunity proteins for toxin domains that are deaminases, DOC-like protein AMP/UMPylating enzymes, TIM-barrel aldo-keto reductase, α/β hydrolases, or peptidases, nuclease domains of the HNH/EndoVII fold, the ParB domain, Ntox7 nuclease domain, peptidase, glycerophosphodiester phosphodiesterase domain. The immunity proteins may work across toxins which utilize unrelated biochemical mechanisms and target distinct types of macromolecules (RNA, DNA, proteins, lipids and carbohydrates) by being able to bind diverse target proteins by means of sequence variability in their respective versatile binding interfaces (Zhang et al., Nucleic Acids Res 2011, 39(11): 4532-4552). These immunity genes or immunity domains may be organized in tandem in polyimmunity loci, which may comprise tandem repeats encoding homogeneous paralogs of immunity domains or repeats of a wide range of structurally unrelated heterogeneous immunity domains (Iyer et al., Nucleic Acids Res 2011, 39(22): 9473-9497; Zhang et al., Biology Direct 2012, 7:18). Because the polyimmunity loci have been identified adjacent to genes encoding recombinases such as Xer C/D recombinases, it has been proposed that accumulation of new immunity genes may be accomplished through recombination (Zhang et al., Biology Direct 2012, 7:18).

Protein Arrays, Polynucleotides, and Vectors

The present disclosure further provides compositions related to the engineered proteins or polypeptides. In an aspect, the present disclosure provides a protein array comprising one or more of the engineered proteins or polypeptides. In some examples, the protein array comprises two or more engineered polypeptides, each of the two or more polypeptides differing from another of the two or more polypeptides by at least one amino acid. In some embodiments, at least two proteins of the array are linked by a cleavable linker. In some embodiments, the linker is cleavable in vitro or in vivo.

In another aspect, the present disclosure provides a polynucleotide comprising one or more coding sequences for the engineered protein or polypeptide. In some embodiments, the sequence of the polynucleotide is optimized for expression in a host cell. The host cell may be a prokaryotic cell. The host cell may be a eukaryotic cell. For example, the eukaryotic cell may be a human cell, a mammalian cell, a plant cell, or a yeast cell. In an embodiment, the sequence of the polynucleotide is optimized for expression in a host cell. Non-limiting examples include codon optimization, codon pair optimization, optimization of GC content, including CpG dinucleotides.

The polynucleotide comprises a regulatory element. The Regulatory sequences may regulate the replication and/or transcription of the sequences on the plasmids in the host cells and/or the target cells. The regulatory sequences may include transcription control sequences, translation control sequences, origins of replication. In some examples, the plasmids comprise a replication origin sequence, plasmid replication genes, plasmid stability genes. The regulatory sequence may comprise transcription control sequences, e.g., sequences which control the initiation, elongation and termination of transcription. Examples of transcription control sequences include those control transcription initiation, such as promoter, enhancer, operator and repressor sequences. In some cases, regulatory element may be a transcription terminator or a sequence encoding thereof.

The regulatory element may be inducible. In some cases, the inducible regulatory element is an inducible promoter. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Examples of inducible promoters include promoters that respond to heavy metals, to thermal shocks, to hormones, and promoters that respond to chemical agents, such as glucose, lactose, galactose or antibiotic (e.g., tetracycline or doxycycline). Examples of inducible promoters also include drug-inducible promoters, for example tetracycline/doxycycline inducible promoters, tamoxifen-inducible promoters, as well as promoters that depend on a recombination event in order to be active, for example, the cre-mediated recombination of loxP sites. Examples of inducible promoters further include physically-inducible promoters, e.g., in particular a temperature-inducible promoter or a light-inducible promoter.

In another aspect, the present disclosure includes a vector. The vector may comprise one or more polynucleotides, e.g., polynucleotides with encoding the engineered proteins or polypeptides. The vector may be a viral vector, a bacteriophage vector, or a plasmid vector.

The vectors may comprise one or more regulatory elements (or sequences encoding thereof), such as transcription control sequences, e.g., sequences which control the initiation, elongation and termination of transcription. Particularly important transcription control sequences are those which control transcription initiation, such as promoter, enhancer, operator and repressor sequences. In some cases, the regulatory element may be a transcription terminator or a sequence encoding thereof. A transcription terminator may comprise a section of nucleic acid sequence that marks the end of a gene or operon in genomic DNA during transcription. This sequence may mediate transcriptional termination by providing signals in the newly synthesized transcript RNA that trigger processes which release the transcript RNA from the transcriptional complex. A regulatory element may be an antisense sequence. In certain cases, a regulatory element may be a sense sequence.

Exemplary Applications of Lrr Proteins in Plants and Fungi
Plants and Resistance Genes Plant genomes encode large numbers of highly variable resistance (R) genes to defend against multiple pathogens. Most plant R genes encode proteins with nucleotide binding and leucine-rich repeat (NB-LRR) domains that interact with pathogen avirulence (Avr) gene products (effector proteins) to induce defense responses, such as effector-triggered immunity (ETI). In certain instances, LRR proteins promote formation of protein complexes, such as receptor-coreceptor complexes. Multiple studies indicate that the LRR domains play a pivotal role in defining pathogen recognition specificity, although other regions of the proteins may also function in pathogen recognition. Depending on N-terminal domain present, most plant NB-LRRs can be classified as Toll/interleukin-1 receptor (TTR)-NB-LRRs (TNLs) or coiled-coil (CC)-NB-LRRs (CNLs).

Examples of LRR-containing proteins in nature further include toll-like receptors (TLRs) and NOD-like receptors (NLRs), which bind to diverse bacterial, fungal, parasite, and viral-derived components. Toll-like receptors (TLRs) comprise a family of evolutionarily conserved proteins that recognize microbial components and directly activate immune cells. The first member of the family, Toll, was identified as essential for pattern formation in *Drosophila*, then shown to be critical in an antifungal response of flies. TLRs are type I integral membrane glycoproteins characterized by the extracellular domains containing varying numbers of leucine-rich-repeat (LRR) motifs and a cytoplasmic signaling domain.

NOD-like receptors (NLRs), involved in detection of pathogens, one mechanism is direct interaction of NLR with a pathogen derived component, another mechanism is pathogen component-host component interaction (binding or host-component modification) recognized by NLR. Reviewed in Kourelis 2018.

A comparative analysis of LRR-encoding genes has shown that the LRR superfamily has expanded greatly in mammals as compared to other less complex eukaryotes. For example, many LRR-encoding genes are expressed in the nervous system and exhibit strikingly specific expression patterns. Several of such LRR proteins are involved in axon guidance and dendrite arborization.

Pathogens, Toxins, Viruses

In certain embodiments, engineered LLR-containing proteins and peptides of the invention are used to monitor and/or protect organisms against pathogens. In some embodiments, the protein or polypeptide binds to a pathogen. In some embodiments, the protein or polypeptide binds to a virus. In some embodiments, the protein or polypeptide binds to a toxin. In some embodiments, the protein or polypeptide blocks an activity of the pathogen, virus or toxin. The pathogen, virus or toxin herein include those capable of infecting plants, animals, bacteria, fungi, and any other types of organism.

Methods for administering or treating with LRR-containing agents include, without limitation, direct application, expression in the organism to be treated, and expression in and optionally secretion from an accessory organism. For example, for administering or treating a plant, such organisms include without limitation, bacterial hosts that colonize plants.

To treat a plant, an LRR-containing agent can be applied directly to the plant, such as to the leaf, root, or fruit of the plant as a spray, in a surface coating, dipping solution, hydroponics, or injection into soil in the vicinity of the root system. An appropriate agent may be expressed in or from an organism applied to the plant.

Biofilms

Biofilms comprise aggregates of microorganisms which adhere on a surface and are frequently embedded in an extracellular polymeric matrix produced by the microorganisms. The matrix may comprise extracellular DNA, proteins, and polysaccharides, and is protective of the microorganisms contained within. Biofilms form in a variety of locations such as on or in the human body where they may be implicated in chronic infections, including but not limited to teeth, gums, ears, prostate, lungs, and heart. More generally, biofilms occur in nature in moist or wet environments such as slime on river rocks, marshes, and the like. Biofilms also occur in medical devices and equipment, including but not limited to contact lenses and catheters, and are a major source of hospital infections. Biofilms are more difficult to reduce or eliminate than are individual bacteria due to the formation of the protective matrix as well as adaptations that the bacteria undergo either individually or collectively in the biofilm matrix, and/or in response to hot interactions.

Plant Associated Microorganisms
Plant Associated Bacteria

All plants have microbes living on their surfaces (epiphytes) or inside them (endophytes), which can be beneficial or detrimental. Developing populations of bacteria as they infect and colonize plants may be evident as biofilms, aggregates, and viscous matter for example plugging plant vessels. Bacterial population development and infection often involves chemical communications among the bacteria, with other organisms, and/or with the host, such as by quorum sensing.

The plant innate immune system contains a limited nucleotide-binding-site and leucine-rich-repeat (NBS-LRR; NLR) repertoire that functions to recognize all potential pathogens. Yoder et al., Host plant resistance to parasitic weeds; recent progress and bottlenecks, *Curr Opin Plant Biol.* 2010 August; 13(4):478-84. doi: 10.1016/j.pbi.2010.04.011. Epub 2010 Jun. 2, describes mechanisms of response of crop plants to parasitic witchweeds and broom rapes, which invade the roots of crop plants connecting to the vascular system to obtain nutrients and water. The resistance gene encodes a nucleotide-binding-site and leucine-rich-repeat (NBS-LRR) resistance protein of a type that is abundant and widely distributed in plants, whose functions include monitoring pathogenic proteins and interacting with other host proteins in defense against invasive pathogenic effectors.

One example of direct interaction between a NB-LRR protein and pathogen effector is Pi-ta, an R gene from rice that specifies resistance to strains of the rice blast fungus

*Magnaporthe grisea*, which expresses the effector AVR-Pita. Experiments detected interaction of a portion of AVR-Pita with the LRR-like domain of Pi-ta. Jia et al., Direct interaction of resistance gene and avirulence gene products confers rice blast resistance. EMBO J. 2000; 19:4004-4014. Another example is the L resistance locus of flax which encodes L protein that interacts directly with the corresponding AvrL variants from the flax rust fungus *Melampsora lini*. Dodds P N, et al. *Direct protein interaction underlies gene-for-gene specificity and coevolution of the flax resistance genes and flax rust avirulence genes*. Proc Natl Acad Sci USA. 2006; 103:8888-8893.

Many R genes indirectly recognize effectors. According to the "guard hypothesis," certain R genes guard host proteins by detecting modifications made by pathogen effectors and activating defensive signal transduction pathways. *Arabidopsis* RIN4 (RPM1− interacting protein 4) is a protein targeted by multiple effectors. RPM1 and RPS2 sense RIPK− dependent phosphorylation and cleavage of RIN4 by AvrRpm1 or AvrRpt2 effectors of the bacterial pathogen *Pseudomonas syringae*. Also, BSL1, which encodes putative plant phosphatase, is an R protein against the oomycete pathogen *Phytophthora infestans*. An NB-LRR-type R2 protein guards BSL1.

Similarly, LRR-containing proteins and polypeptides of the invention can be engineered to comprise functional domains such as nucleotide binding sites or signal transduction components which are active upon pathogen binding.

In certain embodiments, engineered LLR-containing proteins and peptides of the invention are used to bind and inactivate pathogens, toxins, or viruses. The proteins and peptides may further function to remove the pathogen, toxin or virus.

*Listeria monocytogenes* possesses a large number of leucine-rich repeat (LRR)-containing proteins, including among a large family of internalin proteins, two internalins InlA and InlB, which respectively target the host cell adhesion molecule E-cadherin and the hepatocyte growth factor receptor Met. While internalins display several other less conserved regions that confer certain functions, receptor recognition depends primarily on the LRR. See Bonazzi et al., *Listeria monocytogenes* internalin and E-cadherin: from structure to pathogenesis, Cellular Microbiology 2009; 11(5):693-702. doi.org/10.1111/j.1462-5822.2009.01293.x.

T. Zhang et al. constructed deletion mutants of the LRR-containing molecule LMOh7858_0369 in the H7858 strain, which resulted in significant reduction in organ colonization, bacteremia and invasion of the brain and reduction of several proinflammatory cytokines and chemokines compared with the parental wild-type strain. See Zhang, T. et al., LMOh7858_0369, a gene encoding a putative leucine-rich repeat-containing protein, is required for virulence of *Listeria monocytogenes*. FEMS Microbial. Lett. 2016 May; 363(9), doi: 10.1093/femsle/fnw060. Epub 2016 Mar. 13.

In an embodiment of the invention, an LRR-containing protein is engineered to bind to an internalin protein, for example to an LRR of a *Listeria monocytogenes* internalin protein or other virulence factor and block host cell interaction. The engineered LRR-containing protein can further comprise a functional domain to promote killing or clearance of the bacteria.

LRR domains are abundant in extracellular matrix and its components and are involved in host cell immune response signaling as well as pathogen adherence and invasion. In mammals, leucine-rich repeat proteins are a second class of proteins abundant in the extracellular matrix, where they function in cell growth, adhesion, migration, and bind with other extracellular matrix components including collagens. LRR-containing proteins such as NOD-like receptors and Toll-like receptors also serve as important pathogen-detection molecules, recognizing key pathogen-associated molecular patterns (PAMPs). It has been proposed that LRR proteins are major targets of molecular mimicry between host and pathogen species, which may include mimics that are not directly involved in virulence but might still play a role in persistence of commensal bacteria inside the host, or have other effects such as the extensively studied role of peptide mimicry in generation of autoimmune disease (Albert L J, Inman R D. Molecular mimicry and autoimmunity. N Engl J Med 1999; 341:2068-74; dx.doi.org/10.1056/NEJM199912303412707). For example, Doxey and McConkey, Prediction of molecular mimicry candidates in human pathogenic bacteria, Virulence 2013; 4(6): 453-466, doi: 10.4161/viru.25180, identifies similarity between a human LRR protein and an LRR protein from *Streptococcus pyogenes* as well as *Listeria* internalin virulence factors, and proposes mimicry of host LRR domains by pathogenic bacteria species or vice versa via lateral transfer or parallel evolution. The LRR-containing protein or polypeptide of this invention may be designed to mimic antitoxins or ligands of the virulence factors by engineering repeat domains and selection of functional domains to remove pathogens or virus. In some embodiments, the LRR-containing protein or polypeptide of this invention may be used to identify pathogenic species from non-pathogenic species.

Toll-like receptors (TLRs) play an important role in the innate immune system. TLRs typically contain extracellular LRRs, transmembrane domain(s) and intracellular receptor domains. The role of LRR domains have been identified in TLR3 and TLR4 mediated signaling pathways, and is considered to be involved in the innate immune response to LPS challenge and production of proinflammatory cytokines and chemokines (Carpenter and O'Neill, Recent insights into the structure of Toll-like receptors and post-translational modifications of their associated signaling proteins. The Biochemical journal. 2009; 422:1-10; Carpenter et al., Toll-like receptor 3 (TLR3) signaling requires TLR4 Interactor with leucine-rich Repeats (TRIL) The Journal of biological chemistry. 2011; 286:38795-38804). Wochal et al., Wochal P, Rathinam V A K, Dunne A, et al. TRIL is involved in cytokine production in the brain following *Escherichia coli* infection. Journal of immunology (Baltimore, Md: 1950). 2014; 193(4):1911-1919. doi:10.4049/jimmunol.1302392, reports that TLR4 interactor with LRR function as a modulator of the innate immune response following *E. coli* infection in glial cells and enhances neuronal cytokine responses to the infection. Raby et al., Targeting the TLR co-receptor CD14 with TLR2-derived peptides modulates immune responses to pathogens. *Sci. Transt. Med.* 2013; 5*185)" 185ra64. doi: 10.1126/scitranslmed.3005544, reports that LRRs in TLR2 are involved in interaction with CD14 and enhancing proinflammatory responses to bacterial pathogens. LRRs are also identified in TLR and the *Anopheles gambiae* proteins APL1 and LRIM1 in insects. Zhu et al., Leureptin: a soluble, extracellular leucine-rich repeat protein from Manduca sexta that binds lipopolysaccharide. Insect Biochem Mol Biol 2010; 40(10): 713-722. doi: 10.1016/j.ibmb.2010.07.002, describes the identification and characterization of leureptin with 13 leucine-rich repeats, which functions in insect immune response by binding bacterial LPS and associating with hemocytes after bacterial infection. Accordingly, the LRR-containing or polypeptide of the present invention can be designed to contain binding domains that bind pathogens and functional domains for removal and inactivation of pathogen toxins or virus.

NLRP1B is a receptor that upon activation recruits multiple copies of procaspase-1, which promotes cytokine processing and a proinflammatory form of cell death termed pyroptosis. NLRP1B detects anthrax lethal toxin, which disrupts immune cell signaling and migration and induces macrophage lysis. NLRP1B is also activated when cells are deprived of glucose or treated with metabolic inhibitors. It has been suggested that the LRR domain of NLRP1B is involved in ligand recognition and auto-inhibition of NLRP1B (Neiman-Zenevich et al., Distinct Regions of NLRP1B are Required to Respond to Anthrax Lethal Toxin and Metabolic Inhibition. Blanke S R, ed. *Infection and Immunity*. 2014; 82(9):3697-3703. doi:10.1128/IAI.02167-14). The LRR containing proteins and polypeptides of present invention can be designed accordingly with functional domains for detection and removal of pathogens or regulation of NLRP1B activity.

In certain embodiments, the LRRs may be computationally designed for predictable protein structure and high thermal stability, as described in Parmeggiani et al., A general computational approach for repeat protein design. *J. Mol. Biol* 2015; 427(2): 563-575. The LRR repeats may be designed based on desired structure to allow for adjustment of geometrical features including length, curvature, and helical twist, and assembled into structures with predefined geometrical shapes and/or optimized interface control, as described in Ramisch et al., Computational design of a leucine-rich repeat protein with a predefined geometry. *Proc. Natl. Acad. Sci. U.S.A.* 2014; 111(50): 17875-17880.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A.; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4$^{th}$ Ed.—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| | Set | Sub-set | |
|---|---|---|---|
| Hydro-phobic | F W Y H K M I L V A G C (SEQ ID NO: 24) | Aromatic Aliphatic | F W Y H I L V |
| Polar | W Y H K R E D C S T N Q (SEQ ID NO: 25) | Charged Positively charged Negatively charged | H K R E D H K R E D |
| Small | V C A G S P T N D (SEQ ID NO: 26) | Tiny | A G S |

Other Exemplary Applications in Plants and Fungi

The present invention may also be applied to treat bacterial, fungal and parasitic pathogens. Most research efforts have focused on developing new antibiotics, which once developed, would nevertheless be subject to the same problems of drug resistance. The invention provides novel alternatives which overcome those difficulties. Furthermore, unlike existing antibiotics, treatments provided by the present can be made pathogen specific, inducing bacterial cell death of a target pathogen while avoiding beneficial bacteria.

A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendants of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as Agrobacterium or Rhizobium which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus,* or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis,* a.k.a. *Pichia* kudriavzevii and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guide RNA may more often be a rate-limiting component in genome engineering of polyploid cells than in haploid cells, and thus the methods using the targeting system described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2 plasmids, yeast integrative plasmids, yeast replicative plasmids, shuttle vectors, and episomal plasmids.

In one aspect, the present invention provides a method of gene targeting and/or editing in host cells. The engineered protein or polypeptide of the targeting system may be associated with one or more functional domains with regulatory activities, such as nucleotide recognition and/or manipulation activities. Accordingly, the targeting system can be used for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. The targeting system can be used with regard to plants in Site-Directed Integration (SDI) or Gene Editing (GE) or any Near Reverse Breeding (NRB) or Reverse Breeding (RB) techniques. Aspects of utilizing the herein described targeting systems and engineered proteins or polypeptides may be analogous to the use of the CRISPR-Cas (e.g. CRISPR-Cas9) system in plants, and mention is made of the University of Arizona website "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR-Cas system," Plant Methods 2013, 9:39 (doi:10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi: 10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and, the enzymes herein having reduced off-target effects and systems employing such enzymes can be used in plant applications, including those mentioned herein.

The targeting system of the invention may be used in the detection of plant viruses. Gambino et al. (Phytopathology. 2006 November; 96(11):1223-9. doi: 10.1094/PHYTO-96-1223) relied on amplification and multiplex PCR for simultaneous detection of nine grapevine viruses. The targeting systems and proteins of the instant invention may similarly be used to detect multiple targets in a host related to plant virus infection and virus-host interaction mechanism.

Murray et al. (Proc Biol Sci. 2013 Jun. 26; 280(1765): 20130965. doi: 10.1098/rspb.2013.0965; published 2013 Aug. 22) analyzed 12 plant RNA viruses to investigate evolutionary rates and found evidence of episodic selection possibly due to shifts between different host genotypes or species. The targeting systems and proteins of the instant invention may be used to target or immunize against such viruses in a host. For example, the systems of the invention can be used to target and cleave viron proteins, or block viral RNA expression hence replication. Moreover, the systems of the invention can be multiplexed with multiple LRR so as to hit multiple targets or multiple isolate of the same virus.

The targeting system of the invention may be used in detecting and providing resistance against plant pathogens. For example, Proteobacteria in *Xanthomonas* genus infect plants by secretion of transcription effector like proteins through type III secretion pathway to impact expression of plant genes (Wichmann et al., The noncanonical type III secretion system of *Xanthomonas translucens* pv. *graminis* is essential for forage grass infection. Mol Plant Pathol. 2013 August; 14(6):576-88). The targeting system and proteins of the present invention may be used to target and/or cleave or inactivate bacteria proteins delivered to plant host cells by such pathogen, either transiently or transgenic by introduction of the targeting system or nucleic acid molecules encoding thereof to the plant genome.

Organisms such as yeast and microalgae are widely used for synthetic biology. Stovicek et al. (Metab. Eng. Comm., 2015; 2:13 describes genome editing of industrial yeast, for example, *Saccharomyces cerevisiae*, to efficiently produce robust strains for industrial production.

Kurthe t al, J Virol. 2012 June; 86(11):6002-9. doi: 10.1128/JVI.00436-12. Epub 2012 Mar. 21) developed an RNA virus-based vector for the introduction of desired traits into grapevine without heritable modifications to the genome. The vector provided the ability to regulate expression of endogenous genes by virus-induced gene silencing. The targeting systems and proteins of the instant invention similarly can be used to silence genes and proteins without heritable modification to the genome.

In some embodiments, the plant may be a legume plant. Peanut allergies and allergies to legumes generally are a real and serious health concern. The targeting system of the present invention can be used to identify, bind to, inactivate or modify allergenic proteins of such legumes. Without limitation as to such genes and proteins, Nicolaou et al. identifies allergenic proteins in peanuts, soybeans, lentils, peas, lupin, green beans, and mung beans. See, Nicolaou et al., Current Opinion in Allergy and Clinical Immunology 2011; 11(3):222).

In plants, pathogens are often host-specific. For example, *Fusarium oxysporum* f. sp. *lycopersici* causes tomato wilt but attacks only tomato, and *F. oxysporum* f *dianthi Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, the hypervariability of the targeting system of the present invention may be used to develop and confer broad resistance to plants. The natural sources of resistance genes include native or foreign Varieties, Heirloom Varieties, Wild Plant Relatives, and Induced Mutations, e.g., treating plant material with mutagenic agents. Using the present invention, plant breeders are provided with a new tool to transiently or stably (where the targeting system or nucleic acid molecules encoding thereof is introduced to plant genome) confer pathogen resistance. Accordingly, one skilled in the art can analyze the genome and proteome of sources of resistance genes, and in Varieties having desired characteristics or traits employ the present invention to target, modify, activate or inactivate target molecules, with more precision than previous mutagenic agents and hence accelerate and improve plant breeding programs.

Aside from the plants otherwise discussed herein and above, engineered plants modified by the effector protein and suitable guide, and progeny thereof, as provided. These may include disease or drought resistant crops, such as wheat, barley, rice, soybean or corn; plants modified to remove or reduce the ability to self-pollinate (but which can instead, optionally, hybridize instead); and allergenic foods such as peanuts and nuts where the immunogenic proteins have been disabled, destroyed or disrupted by targeting via a effector protein and suitable guide.

Stable Integration of System Components in the Genome of Plants and Plant Cells

In particular embodiments, it is envisaged that the polynucleotides encoding the components of the targeting system are introduced for stable integration into the genome of a plant cell. In these embodiments, the design of the transformation vector or the expression system can be adjusted depending on for when, where and under what conditions the engineered protein or polypeptide is expressed.

In particular embodiments, it is envisaged to introduce the components of the targeting system stably into the genomic DNA of a plant cell. Additionally or alternatively, it is envisaged to introduce the components of the targeting system for stable integration into the DNA of a plant organelle such as, but not limited to a plastid, mitochondrion or a chloroplast.

The expression system for stable integration into the genome of a plant cell may contain one or more of the following elements: a promoter element that can be used to express the components of the targeting system in a plant cell; a 5' untranslated region to enhance expression; an intron element to further enhance expression in certain cells, such as monocot cells; a multiple-cloning site to provide convenient restriction sites for inserting the nucleic acid sequences and other desired elements; and a 3' untranslated region to provide for efficient termination of the expressed transcript.

The elements of the expression system may be on one or more expression constructs which are either circular such as a plasmid or transformation vector, or non-circular such as linear double stranded DNA.

DNA construct(s) containing and/or encoding the components of the targeting system, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue, and regenerating plant cells or plants therefrom.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993)).

In particular embodiments, the DNA constructs containing components of the targeting system may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g. Fraley et al., (1985), Rogers et al., (1987) and U.S. Pat. No. 5,563,055).

Plant Promoters

In order to ensure appropriate expression in a plant cell, the components of the targeting system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the targeting system components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome), such as a Light Inducible Transcriptional Effector (LITE) that direct changes in transcriptional activity in a sequence-specific manner. The components of a light inducible system may include a engineered protein or polypeptide of the targeting system, an enzyme or functional domain associated thereby, a light-responsive cytochrome heterodimer (e.g. from *Arabidopsis thaliana*), and a transcriptional activation/repression domain.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

Translocation to and/or Expression in Specific Plant Organelles

The expression system may comprise elements for translocation to and/or expression in a specific plant organelle.

Chloroplast Targeting

In particular embodiments, it is envisaged that the targeting system is used to specifically modify chloroplast genes or to ensure expression in the chloroplast. For this purpose, use is made of chloroplast transformation methods or compartmentalization of the targeting system components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in International Patent Publication No. WO 2010061186.

Alternatively, it is envisaged to localize one or more of the targeting system components to the plant chloroplast. This is achieved by incorporating in the expression construct a sequence encoding a chloroplast transit peptide (CTP) or plastid transit peptide, operably linked to the 5' region of the sequence encoding the engineered targeting protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180).

Introduction of Polynucleotides Encoding the Engineered Protein in Algal Cells

Transgenic algae (or other plants such as rape) may be particularly useful in the production of vegetable oils or biofuels such as alcohols (especially methanol and ethanol) or other products. These may be engineered to express or overexpress high levels of oil or alcohols for use in the oil or biofuel industries.

Introduction of Polynucleotides Encoding Targeting System Components in Yeast Cells In particular embodiments, the invention relates to the use of the targeting system for genome editing of yeast cells. Methods for transforming yeast cells which can be used to introduce polynucleotides encoding the targeting system components are well known to the artisan and are reviewed by Kawai et al., 2010, Bioeng Bugs. 2010 November-December; 1(6): 395-403). Non-limiting examples include transformation of yeast cells by lithium acetate treatment (which may further include carrier DNA and PEG treatment), bombardment or by electroporation.

Transient Expression of the Targeting System Components in Plants and Plant Cell In particular embodiments, it is envisaged that nucleic acid molecules encoding the engineered targeting protein are transiently expressed in the plant cell. As the expression of the engineered protein is transient, plants regenerated from such plant cells typically contain no foreign DNA.

In particular embodiments, the targeting system components can be introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of the engineered protein is for instance a pEAQ vector, which is tailored for *Agrobacterium*-mediated transient expression (Sainsbury F. et al., Plant Biotechnol J. 2009 September; 7(7):682-93) in the protoplast. In particular embodiments, double-stranded DNA fragments encoding the engineered protein can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the engineered targeting protein is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged.

Delivery of Targeting System Components to the Plant Cell

In particular embodiments, it is of interest to deliver one or more components of the targeting system directly to the plant cell. This is of interest, inter alia, for the generation of non-transgenic plants (see below). In particular embodiments, one or more of the targeting system components is prepared outside the plant or plant cell and delivered to the cell. For instance in particular embodiments, the engineered targeting protein is prepared in vitro prior to introduction to the plant cell. The engineered targeting protein can be prepared by various methods known by one of skill in the art and include recombinant production. After expression, the engineered targeting protein is isolated, refolded if needed, purified and optionally treated to remove any purification tags, such as a His-tag. Once crude, partially purified, or more completely purified targeting protein is obtained, the protein may be introduced to the plant cell.

The individual components or pre-assembled ribonucleoprotein can be introduced into the plant cell via electroporation, by bombardment with coated particles, by chemical transfection or by some other means of transport across a cell membrane.

In particular embodiments, the targeting system components are introduced into the plant cells using nanoparticles. The components, either as protein or nucleic acid or in a combination thereof, can be uploaded onto or packaged in nanoparticles and applied to the plants (such as for instance described in International Patent Publication No. WO 2008042156 and US Patent Publication No. 20130185823). In particular, embodiments of the invention comprise nanoparticles uploaded with or packed with DNA molecule(s) encoding the C2c1 protein, DNA molecules encoding the guide RNA and/or isolated guide RNA as described in WO2015089419.

Further means of introducing one or more components of the targeting system to the plant cell is by using cell penetrating peptides (CPP). Accordingly, particular embodiments of the invention comprise compositions comprising a cell penetrating peptide linked to the engineered targeting protein. In particular embodiments of the present invention, the engineered protein is coupled to one or more CPPs to effectively transport them inside plant protoplasts; see also Ramakrishna (20140 Genome Res. 2014 June; 24(6):1020-7 for Cas9 in human cells). In other embodiments, the engineered protein is encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type1, penetratin, Kaposi fibroblast growth factor (FGF) signal peptide sequence, integrin p3 signal peptide sequence; polyarginine peptide Args sequence, Guanine rich-molecular transporters, sweet arrow peptide, etc.

In particular embodiments, the invention encompasses the use of the targeting system as described herein for detection and/or modification of macromolecule substrates of interest, including protein, polypeptide, DNA or RNA molecules including one or more plant expressible gene(s) or gene products. In further particular embodiments, the invention encompasses methods and tools using the targeting system as described herein modification, cleavage, activation or de-activation of one or more plant gene products such as proteins, or for partial or complete deletion of one or more plant expressed gene(s). In other further particular embodiments, the invention encompasses methods and tools using the targeting system as described herein to ensure modification of one or more plant-expressed genes by mutation, substitution, insertion of one of more nucleotides. In other particular embodiments, the invention encompasses the use of the targeting system as described herein to ensure modification of expression of one or more plant-expressed genes by specific modification of one or more of the regulatory elements directing expression of said genes.

In particular embodiments, the invention encompasses methods which involve the introduction of exogenous genes and/or the targeting of endogenous genes and their regulatory elements, such as listed below.

1. Genes that confer resistance to pests or diseases:

Plant disease resistance genes. A plant can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* may be RSP2 gene for resistance to *Pseudomonas syringae*). A plant gene that is upregulated or down regulated during pathogen infection can be engineered for pathogen resistance. See, e.g., Thomazella et al., bioRxiv 064824; doi: doi.org/10.1101/064824 Epub. Jul. 23, 2016 (tomato plants with deletions in the SlDMR6-1 which is normally upregulated during pathogen infection).

Genes conferring resistance to a pest, such as soybean cyst nematode. See e.g., International Patent Publication Nos. WO 96/30517 and WO 93/19181.

*Bacillus thuringiensis* proteins see, e.g., Geiser et al., Gene 48:109 (1986).

Lectins, see, for example, Van Damme et al., Plant Molec. Biol. 24:25 (1994).

Vitamin-binding protein, such as avidin, see PCT application US93/06487, teaching the use of avidin and avidin homologues as larvicides against insect pests.

Enzyme inhibitors such as protease or proteinase inhibitors or amylase inhibitors. See, e.g., Abe et al., J. Biol. Chem. 262:16793 (1987), Huub et al., Plant Molec. Biol. 21:985 (1993)), Sumitani et al., Biosci. Biotech. Biochem. 57:1243 (1993) and U.S. Pat. No. 5,494,813.

Insect-specific hormones or pheromones such as ecdysteroid or juvenile hormone, a variant thereof, a mimetic based thereon, or an antagonist or agonist thereof. See, for example Hammock et al., Nature 344:458 (1990).

Insect-specific peptides or neuropeptides which, upon expression, disrupts the physiology of the affected pest. For example Regan, J. Biol. Chem. 269:9 (1994) and Pratt et al., Biochem. Biophys. Res. Comm. 163:1243 (1989). See also U.S. Pat. No. 5,266,317.

Insect-specific venom produced in nature by a snake, a wasp, or any other organism. For example, see Pang et al., Gene 116: 165 (1992).

Enzymes responsible for a hyperaccumulation of a monoterpene, a sesquiterpene, a steroid, hydroxamic acid, a phenylpropanoid derivative or another nonprotein molecule with insecticidal activity.

Enzymes involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO93/02197, Kramer et al., Insect Biochem. Molec. Biol. 23:691 (1993) and Kawalleck et al., Plant Molec. Biol. 21:673 (1993).

Molecules that stimulate signal transduction. For example, see Botella et al., Plant Molec. Biol. 24:757 (1994), and Griess et al., Plant Physiol. 104:1467 (1994).

Viral-invasive proteins or a complex toxin derived therefrom. See Beachy et al., Ann. rev. Phytopathol. 28:451 (1990).

Developmental-arrestive proteins produced in nature by a pathogen or a parasite. See Lamb et al., Bio/Technology 10:1436 (1992) and Toubart et al., Plant J. 2:367 (1992).

A developmental-arrestive protein produced in nature by a plant. For example, Logemann et al., Bio/Technology 10:305 (1992).

In plants, pathogens are often host-specific. For example, some *Fusarium* species will cause tomato wilt but attacks only tomato, and other *Fusarium* species attack only wheat. Plants have existing and induced defenses to resist most pathogens. Mutations and recombination events across plant generations lead to genetic variability that gives rise to susceptibility, especially as pathogens reproduce with more frequency than plants. In plants, there can be non-host resistance, e.g., the host and pathogen are incompatible or there can be partial resistance against all races of a pathogen, typically controlled by many genes and/or also complete resistance to some races of a pathogen but not to other races. Such resistance is typically controlled by a few genes. Accordingly, one can analyze the genome of sources of resistance genes, and in plants having desired characteristics or traits, use the method and components of the targeting system to induce the rise of resistance genes. The present systems can do so with more precision than previous mutagenic agents and hence accelerate and improve plant breeding programs.

2. Genes involved in plant diseases, such as those listed in International Patent Publication No. WO 2013046247:

Rice diseases: *Magnaporthe grisea, Cochliobolus miyabeanus, Rhizoctonia solani, Gibberella fujikuroi*; Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici*-repentis; Barley diseases: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani*; Maize diseases: *Ustilago maydis, Cochliobolus heterostrophus, Gloeocercospora sorghi, Puccinia polysora, Cercospora zeae-maydis, Rhizoctonia solani;*

Citrus diseases: *Diaporthe citri, Elsinoe fawcettii, Penicillium digitatum, P. italicum, Phytophthora parasitica, Phytophthora citrophthora*; Apple diseases: *Monilinia mali, Valsa ceratosperma, Podosphaera leucotricha, Alternaria alternata* apple pathotype, *Venturia inaequalis, Colletotrichum acutatum, Phytophtora cactorum;*

Pear diseases: *Venturia nashicola, V. pirina, Alternaria alternata* Japanese pear pathotype, *Gymnosporangium haraeanum, Phytophthora cactorum;*

Peach diseases: *Monilinia fructicola, Cladosporium carpophilum, Phomopsis* sp.;

Grape diseases: *Elsinoe ampelina, Glomerella cingulata, Uncinula necator, Phakopsora ampelopsidis, Guignardia bidwellii, Plasmopara viticola;*

Persimmon diseases: *Gloeosporium kaki, Cercospora kaki, Mycosphaerella nawae;*
Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;
Tomato diseases: *Alternaria solani, Cladosporium fulvum, Phytophthora infestans; Pseudomonas syringae* pv. Tomato; *Phytophthora capsici; Xanthomonas;*
Eggplant diseases: *Phomopsis vexans, Erysiphe cichoracearum;*
Brassicaceous vegetable diseases: *Alternaria japonica, Cercosporella brassicae, Plasmodiophora brassicae, Peronospora parasitica;*
Welsh onion diseases: *Puccinia allii, Peronospora destructor;*
Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora cassilcola, Sclerotinia sclerotiorum;*
Kidney bean diseases: *Colletotrichum lindemuthianum;*
Peanut diseases: *Cercospora personata, Cercospora arachidicola, Sclerotium rolfsii;*
Pea diseases pea: *Erysiphe pisi;*
Potato diseases: *Alternaria solani, Phytophthora infestans, Phytophthora erythroseptica, Spongospora subterranea,* f. sp. *Subterranea;*
Strawberry diseases: *Sphaerotheca humuli, Glomerella cingulata;*
Tea diseases: *Exobasidium reticulatum, Elsinoe leucospila, Pestalotiopsis* sp., *Colletotrichum theae-sinensis;*
Tobacco diseases: *Alternaria longipes, Erysiphe cichoracearum, Colletotrichum tabacum, Peronospora tabacina, Phytophthora nicotianae;*
Rapeseed diseases: *Sclerotinia sclerotiorum, Rhizoctonia solani;*
Cotton diseases: *Rhizoctonia solani;*
Beet diseases: *Cercospora beticola, Thanatephorus cucumeris, Thanatephorus cucumeris, Aphanomyces cochlioides;*
Rose diseases: *Diplocarpon rosae, Sphaerotheca pannosa, Peronospora sparsa;*
Diseases of *Chrysanthemum* and asteraceae: *Bremia lactuca, Septoria chrysanthemi-indici, Puccinia horiana;*
Diseases of various plants: *Pythium aphanidermatum, Pythium debaryanum, Pythium graminicola, Pythium irregulare, Pythium ultimum, Botrytis cinerea, Sclerotinia sclerotiorum;*
Radish diseases: *Alternaria brassicicola;*
Zoysia diseases: *Sclerotinia homoeocarpa, Rhizoctonia solani;*
Banana diseases: *Mycosphaerella fijiensis, Mycosphaerella musicola;*
Sunflower diseases: Plasmopara *halstedii;*
Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., or the like;
Virus diseases of various plants mediated by *Polymyxa* spp., *Olpidium* spp., or the like.
3. Examples of genes that confer resistance to herbicides:
Resistance to herbicides that inhibit the growing point or meristem, such as an imidazolinone or a sulfonylurea, for example, by Lee et al., EMBO J. 7:1241 (1988), and Miki et al., Theor. Appl. Genet. 80:449 (1990), respectively.

Glyphosate tolerance (resistance conferred by, e.g., mutant 5-enolpyruvylshikimate-3-phosphate synthase (EPSPs) genes, aroA genes and glyphosate acetyl transferase (GAT) genes, respectively), or resistance to other phosphono compounds such as by glufosinate (phosphinothricin acetyl transferase (PAT) genes from *Streptomyces* species, including *Streptomyces hygroscopicus* and *Streptomyces viridochromogenes*), and to pyridinoxy or phenoxy propionic acids and cyclohexanones by ACCase inhibitor-encoding genes. See, for example, U.S. Pat. Nos. 4,940,835 and 6,248,876, 4,769,061, EP No. 0 333 033 and U.S. Pat. No. 4,975,374. See also EP No. 0242246, DeGreef et al., Bio/Technology 7:61 (1989), Marshall et al., Theor. Appl. Genet. 83:435 (1992), International Patent Publication Nos. WO 2005012515 to Castle et. al. and WO 2005107437.

Resistance to herbicides that inhibit photosynthesis, such as a triazine (psbA and gs+ genes) or a benzonitrile (nitrilase gene), and glutathione S-transferase in Przibila et al., Plant Cell 3:169 (1991), U.S. Pat. No. 4,810,648, and Hayes et al., Biochem. J. 285: 173 (1992).

Genes encoding Enzymes detoxifying the herbicide or a mutant glutamine synthase enzyme that is resistant to inhibition, e.g. n U.S. patent application Ser. No. 11/760,602. Or a detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Hydroxyphenylpyruvatedioxygenases (HPPD) inhibitors, i.e. naturally occurring HPPD resistant enzymes, or genes encoding a mutated or chimeric HPPD enzyme as described in International Patent Publication Nos. WO 96/38567, WO 99/24585, and WO 99/24586, WO 2009/144079, WO 2002/046387, or U.S. Pat. No. 6,768,044.

4. Examples of genes involved in Abiotic stress tolerance:
Transgene capable of reducing the expression and/or the activity of poly(ADP-ribose) polymerase (PARP) gene in the plant cells or plants as described in WO 00/04173 or, WO/2006/045633.

Transgenes capable of reducing the expression and/or the activity of the PARG encoding genes of the plants or plants cells, as described e.g. in WO 2004/090140.

Transgenes coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Genes that improve drought resistance. For example, WO 2013122472 discloses that the absence or reduced level of functional Ubiquitin Protein Ligase protein (UPL) protein, more specifically, UPL3, leads to a decreased need for water or improved resistance to drought of said plant. Other examples of transgenic plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/083911 describes a plant having an increased tolerance to drought stress due to a reduced activity of an ABC transporter which is expressed in guard cells. Another example is the work by Kasuga and co-authors (1999), who describe that overexpression of cDNA encoding DREB1 A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291).

In further particular embodiments, crop plants can be improved by influencing specific plant traits. For example, by developing pesticide-resistant plants, improving disease resistance in plants, improving plant insect and nematode resistance, improving plant resistance against parasitic weeds, improving plant drought tolerance, improving plant nutritional value, improving plant stress tolerance, avoiding self-pollination, plant forage digestibility biomass, grain yield, etc. A few specific non-limiting examples are provided hereinbelow.

Use of the Targeting System to Affect Fruit-Ripening

Ripening is a normal phase in the maturation process of fruits and vegetables. Only a few days after it starts it renders a fruit or vegetable inedible. This process brings significant losses to both farmers and consumers. In particular embodiments, the methods of the present invention are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil bacterium. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

Thus in particular embodiments, the methods comprise the use of the targeting system to ensure one or more modifications of the gene products of a plant cell such as described above, and regenerating a plant therefrom. In particular embodiments, the plant is a tomato plant.

Increasing Storage Life of Plants

In particular embodiments, the methods of the present invention are used to modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

The Use of the Targeting System to Ensure a Value Added Trait

In particular embodiments the targeting system is used to produce nutritionally improved agricultural crops. In particular embodiments, the methods provided herein are adapted to generate "functional foods", i.e. a modified food or food ingredient that may provide a health benefit beyond the traditional nutrients it contains and/or "nutraceutical", i.e. substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Examples of nutritionally improved crops include (Newell-McGloughlin, Plant Physiology, July 2008, Vol. 147, pp. 939-953):

modified protein quality, content and/or amino acid composition, such as have been described for Bahiagrass (Luciani et al. 2005, Florida Genetics Conference Poster), Canola (Roesler et al., 1997, Plant Physiol 113 75-81), Maize (Cromwell et al, 1967, 1969 J Anim Sci 26 1325-1331, O'Quin et al. 2000 J Anim Sci 78 2144-2149, Yang et al. 2002, Transgenic Res 11 11-20, Young et al. 2004, Plant J 38 910-922), Potato (Yu J and Ao, 1997 Acta Bot Sin 39 329-334; Chakraborty et al. 2000, Proc Natl Acad Sci USA 97 3724-3729; Li et al. 2001) Chin Sci Bull 46 482-484, Rice (Katsube et al. 1999, Plant Physiol 120 1063-1074), Soybean (Dinkins et al. 2001, Rapp 2002, In Vitro Cell Dev Biol Plant 37 742-747), Sweet Potato (Egnin and Prakash 1997, In Vitro Cell Dev Biol 33 52A).

essential amino acid content, such as has been described for Canola (Falco et al. 1995, Bio/Technology 13 577-582), Lupin (White et al. 2001, J Sci Food Agric 81 147-154), Maize (Lai and Messing, 2002, Agbios 2008 G M crop database (Mar. 11, 2008)), Potato (Zeh et al. 2001, Plant Physiol 127 792-802), Sorghum (Zhao et al. 2003, Kluwer Academic Publishers, Dordrecht, The Netherlands, pp 413-416), Soybean (Falco et al. 1995 Bio/Technology 13 577-582; Galili et al. 2002 Crit Rev Plant Sci 21 167-204).

Oils and Fatty acids such as for Canola (Dehesh et al. (1996) Plant J 9 167-172 [PubMed]; Del Vecchio (1996) INFORM International News on Fats, Oils and Related Materials 7 230-243; Roesler et al. (1997) Plant Physiol 113 75-81 [PMC free article] [PubMed]; Froman and Ursin (2002, 2003) Abstracts of Papers of the American Chemical Society 223 U35; James et al. (2003) Am J Clin Nutr 77 1140-1145 [PubMed]; Agbios (2008, above); cotton (Chapman et al. (2001). J Am Oil Chem Soc 78 941-947; Liu et al. (2002) J Am Coll Nutr 21 205S-211S [PubMed]; O'Neill (2007) Australian Life Scientist. http #www.biotechnews-.com.au/index.php/id;866694817;fp;4;fpid;2 (Jun. 17, 2008), Linseed (Abbadi et al., 2004, Plant Cell 16: 2734-2748), Maize (Young et al., 2004, Plant J 38 910-922), oil palm (Jalani et al. 1997, J Am Oil Chem Soc 74 1451-1455; Parveez, 2003, AgBiotechNet 113 1-8), Rice (Anai et al., 2003, Plant Cell Rep 21 988-992), Soybean (Reddy and Thomas, 1996, Nat Biotechnol 14 639-642; Kinney and Kwolton, 1998, Blackie Academic and Professional, London, pp 193-213), Sunflower (Arcadia, Biosciences 2008).

Carbohydrates, such as Fructans described for Chicory (Smeekens (1997) Trends Plant Sci 2 286-287, Sprenger et al. (1997) FEBS Lett 400 355-358, Sevenier et al. (1998) Nat Biotechnol 16 843-846), Maize (Caimi et al. (1996) Plant Physiol 110 355-363), Potato (Hellwege et al., 1997 Plant J 12 1057-1065), Sugar Beet (Smeekens et al. 1997, above), Inulin, such as described for Potato (Hellewege et al. 2000, Proc Natl Acad Sci USA 97 8699-8704), Starch, such as described for Rice (Schwall et al. (2000) Nat Biotechnol 18 551-554, Chiang et al. (2005) Mol Breed 15 125-143), Vitamins and carotenoids, such as described for Canola (Shintani and DellaPenna (1998) Science 282 2098-2100), Maize (Rocheford et al. (2002). J Am Coll Nutr 21 191S-198S, Cahoon et al. (2003) Nat Biotechnol 21 1082-1087, Chen et al. (2003) Proc Natl Acad Sci USA 100 3525-3530), Mustardseed (Shewmaker et al. (1999) Plant J 20 401-412, Potato (Ducreux et al., 2005, J Exp Bot 56 81-89), Rice (Ye et al. (2000) Science 287 303-305, Strawberry (Agius et al. (2003), Nat Biotechnol 21 177-181), Tomato (Rosati et al. (2000) Plant J 24 413-419, Fraser et al. (2001) J Sci Food Agric 81 822-827, Mehta et al. (2002) Nat Biotechnol 20 613-618, Diaz de la Garza et al. (2004) Proc Natl Acad Sci USA 101 13720-13725, Enfissi et al. (2005) Plant Biotechnol J 3 17-27, DellaPenna (2007) Proc Natl Acad Sci USA 104 3675-3676.

Functional secondary metabolites, such as described for Apple (stilbenes, Szankowski et al. (2003) Plant Cell Rep 22: 141-149), Alfalfa (resveratrol, Hipskind and Paiva (2000) Mol Plant Microbe Interact 13 551-562), Kiwi (resveratrol, Kobayashi et al. (2000) Plant Cell Rep 19 904-910), Maize and Soybean (flavonoids, Yu et al. (2000) Plant Physiol 124 781-794), Potato (anthocyanin and alkaloid glycoside, Lukaszewicz et al. (2004) J Agric Food Chem 52 1526-1533), Rice (flavonoids & resveratrol, Stark-Lorenzen et al. (1997) Plant Cell Rep 16 668-673, Shin et al. (2006) Plant Biotechnol J 4 303-315), Tomato (+resveratrol, chlorogenic acid, flavonoids, stilbene; Rosati et al. (2000) above, Muir et al. (2001) Nature 19 470-474, Niggeweg et al. (2004) Nat Biotechnol 22 746-754, Giovinazzo et al. (2005) Plant Biotechnol J 3 57-69), wheat (caffeic and ferulic acids, resveratrol; United Press International (2002)); and Mineral availabilities such as described for Alfalfa (phytase, Austin-Phillips et al. (1999) www.molecularfarming.com/nonmedical.html), Lettuce (iron, Goto et al. (2000) Theor Appl Genet 100 658-664), Rice (iron, Lucca et al. (2002) J Am Coll Nutr 21 184S-190S), Maize, Soybean and wheat (phytase, Drakakaki et al. (2005) Plant Mol Biol 59 869-880, Denbow et al. (1998) Poult Sci 77 878-881, Brinch-Pedersen et al. (2000) Mol Breed 6 195-206).

In particular embodiments, the value-added trait is related to the envisaged health benefits of the compounds present in the plant. For instance, in particular embodiments, the value-added crop is obtained by applying the methods of the invention to ensure the modification of or induce/increase the synthesis of one or more of the following compounds:

Carotenoids, such as α-Carotene present in carrots which Neutralizes free radicals that may cause damage to cells or β-Carotene present in various fruits and vegetables which neutralizes free radicals Lutein present in green vegetables which contributes to maintenance of healthy vision Lycopene present in tomato and tomato products, which is believed to reduce the risk of prostate cancer Zeaxanthin, present in citrus and maize, which contributes to maintenance of healthy vision Dietary fiber such as insoluble fiber present in wheat bran which may reduce the risk of breast and/or colon cancer and β-Glucan present in oat, soluble fiber present in *Psyllium* and whole cereal grains which may reduce the risk of cardiovascular disease (CVD)

Fatty acids, such as ω-3 fatty acids which may reduce the risk of CVD and improve mental and visual functions, Conjugated linoleic acid, which may improve body composition, may decrease risk of certain cancers and GLA which may reduce inflammation risk of cancer and CVD, may improve body composition Flavonoids such as Hydroxycinnamates, present in wheat which have Antioxidant-like activities, may reduce risk of degenerative diseases, flavanols, catechins and tannins present in fruits and vegetables which neutralize free radicals and may reduce risk of cancer Glucosinolates, indoles, isothiocyanates, such as Sulforaphane, present in Cruciferous vegetables (broccoli, kale), horseradish, which neutralize free radicals, may reduce risk of cancer Phenolics, such as stilbenes present in grape which May reduce risk of degenerative diseases, heart disease, and cancer, may have longevity effect and caffeic acid and ferulic acid present in vegetables and citrus which have Antioxidant-like activities, may reduce risk of degenerative diseases, heart disease, and eye disease, and epicatechin present in cacao which has Antioxidant-like activities, may reduce risk of degenerative diseases and heart disease Plant stanols/sterols present in maize, soy, wheat and wooden oils which May reduce risk of coronary heart disease by lowering blood cholesterol levels Fructans, inulins, fructo-oligosaccharides present in Jerusalem artichoke, shallot, onion powder which may improve gastrointestinal health Saponins present in soybean, which may lower LDL cholesterol Soybean protein present in soybean which may reduce risk of heart disease Phytoestrogens such as isoflavones present in soybean which May reduce menopause symptoms, such as hot flashes, may reduce osteoporosis and CVD and lignans present in flax, rye and vegetables, which May protect against heart disease and some cancers, may lower LDL cholesterol, total cholesterol.

Sulfides and thiols such as diallyl sulphide present in onion, garlic, olive, leek and scallion and Allyl methyl trisulfide, dithiolthiones present in cruciferous vegetables which may lower LDL cholesterol, helps to maintain healthy immune system.

Tannins, such as proanthocyanidins, present in cranberry, cocoa, which may improve urinary tract health, may reduce risk of CVD and high blood pressure.

In addition, the methods of the present invention also envisage modifying protein/starch functionality, shelf life, taste/aesthetics, fiber quality, and allergen, antinutrient, and toxin reduction traits.

Accordingly, the invention encompasses methods for producing plants with nutritional added value, said methods comprising introducing into a plant cell a gene encoding an enzyme involved in the production of a component of added nutritional value using the targeting system as described herein and regenerating a plant from said plant cell, said plant characterized in an increase expression of said component of added nutritional value. In particular embodiments, the targeting system is used to modify the endogenous synthesis of these compounds indirectly, e.g. by modifying one or more transcription factors that controls the metabolism of this compound. Methods for introducing a gene of interest into a plant cell and/or modifying an endogenous gene using the targeting system are described herein above.

Screening Methods for Endogenous Genes of Interest

The methods provided herein further allow the identification of genes of value encoding enzymes involved in the production of a component of added nutritional value or generally genes affecting agronomic traits of interest, across species, phyla, and plant kingdom. By selectively targeting e.g. enzymes of metabolic pathways in plants using the targeting system as described herein, the genes responsible for certain nutritional aspects of a plant can be identified. Similarly, by selectively targeting enzymes which may affect a desirable agronomic trait, the relevant genes can be identified. Accordingly, the present invention encompasses screening methods for genes encoding enzymes involved in the production of compounds with a particular nutritional value and/or agronomic traits.

Use of the Targeting System in Biofuel Production

The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation.

In particular embodiments, the methods using the targeting system as described herein are used to alter the properties of the cell wall in order to facilitate access by key hydrolyzing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in International Patent Publication WO 2008/064289 A2.

Modifying Yeast for Biofuel Production

In particular embodiments, the engineered targeting protein provided herein is used for bioethanol production by recombinant micro-organisms. For instance, the engineered protein can be used to engineer micro-organisms, such as yeast, to generate biofuel or biopolymers from fermentable sugars and optionally to be able to degrade plant-derived lignocellulose derived from agricultural waste as a source of fermentable sugars.

Accordingly, in more particular embodiments, the methods described herein are used to modify a micro-organism as follows:

to introduce at least one engineered protein or nucleic acid encoding thereof that modify the gene product or alter expression of at least one endogenous nucleic acid encoding a plant cell wall degrading enzyme, such that said micro-organism is capable of expressing said nucleic acid and of producing and secreting said plant cell wall degrading enzyme;

to modify at least one nucleic acid encoding for an enzyme in a metabolic pathway in said host cell, wherein said pathway produces a metabolite other than acetaldehyde from pyruvate or ethanol from acetaldehyde, and wherein said modification results in a reduced production of said metabolite, or to introduce at least one nucleic acid encoding for an inhibitor of said enzyme.

The Use of the Targeting System in the Generation of Micro-Organisms Capable of Organic Acid Production The methods provided herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase.

In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

The Use of the Targeting System in the Generation of Improved Xylose or Cellobiose Utilizing Yeasts Strains In particular embodiments, the targeting system may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S. J., et al. (2011) Proc. Natl. Acad. Sci. USA 108(2):504-9 and Galazka, J. M., et al. (2010) Science 330(6000):84-6.

Improved Plants and Yeast Cells

The present invention also provides plants and yeast cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or over-express high levels of oil or alcohols for use in the oil or biofuel industries.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods for genome editing using the targeting system as described herein can be used to confer desired traits on essentially any plant, algae, fungus, yeast, etc. A wide variety of plants, algae, fungus, yeast, etc. and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc. of any foreign gene, including those encoding the targeting system components, so as to avoid the presence of foreign DNA in the genome of the plant. This can be of interest as the regulatory requirements for non-transgenic plants are less rigorous.

The targeting systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the generation of "improved plants, algae, fungi, yeast, etc." in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of a gene product is ensured and no foreign genes are introduced or maintained in the plant, algae, fungi, yeast, etc. genome, the resulting genetically modified crops contain no foreign genes and can thus basically be considered non-transgenic.

Screening, Selection and Production of LRR Proteins

LRR proteins can be screened and selected, and/or produced by biological-based methods. For example, LRR proteins can be produced by bacteria, fungi, or other organism, from which they can be secreted, extracted, and/or purified for use. LRR proteins can be screened or selected by, for example phage display, or evolved by phage-assisted continuous evolution (PACE). Packer et al., 2017, Phage-assisted continuous evolution of proteases with altered substrate specificity, Nature Communications 8:956 DOI: 10.1038/s41467-017-01055-9.

LRR proteins can be produced synthetically, for screening and selection, as well as for production. Chemical methods enable total synthesis of protein molecules. See, e.g., Gates, Z P et al., 2018, Xenoprotein engineering via synthetic libraries, Proc. Natl. Acad. Sci. U.S.A. 115(23), E5298-E5306. doi: 10.1073/pnas.1722633115. Epub 2018 May 21. Synthetic proteins can be engineered that comprise or consist of canonical, amino acids, non-canonical amino acids, and combinations. Non-canonical amino acids include, without limitation, selenocysteine, pyrrolysine, and right-handed D-amino acids. In certain applications, the synthesis methods can be combined with screens to identify proteins of interest, for example in one-bead one-compound protein libraries. In an embodiment, LRR-containing proteins are synthesized which comprise LRR motifs and candidates identified by screening for target binding and/or other activity. In an embodiment, candidate LRR proteins are modified, for example by amino acid substitutions, insertions, or deletions, and screened for activity.

In certain uses, it may be desirable to engineer LRR proteins that are resistant to degradatory processes such as proteolysis. In certain embodiments, LRR proteins comprise or consist of amino acid analogs. In certain embodiments, LRR proteins comprise or consist of D-amino acids.

An L-peptide has three analogs that can be synthesized from L and D amino acids. One is the D-enantiomer or inverso-peptide with the same sequence, but composed of D-amino acids, which has a mirror conformation. Another is the retro-peptide, consisting of the same sequence of L amino acids but in reverse order. A third is the retro-inverso or D-retro-enantiomer peptide, consisting of D-amino acids in the reversed sequence from the L-peptide. The L-peptide and the D-retro-inverso-peptide share a similar arrangement of side-chains, although their carboxyl and amino groups point in opposing directions, and likely have similar binding affinity with a target.

Mirror-image display and selection methods are useful to develop analogs composed of D-amino acids that bind to L-amino acid targets. First, the D-enantiomer of the L-amino acid-containing target of interest is chemically synthesized. A library of L-amino acid peptides is then screened or selected, for example by phage display, which may comprise one or more rounds of mutation and selection. Once a candidate L-amino acid peptide is selected that binds to the D-amino acid analog of the target, the D-enantiomer of the candidate L-amino acid peptide is synthesized, which binds to the L-amino acid target.

The term "associated with" is used here in relation to the association of the functional domain to engineered targeting protein or polypeptide. It is used in respect of how one molecule 'associates' with respect to another, for example between an engineered protein and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the engineered protein or polypeptide is associated with a functional domain by binding thereto. In other embodiments, the engineered protein or polypeptide is associated with a functional domain because the two are fused together, optionally via an intermediate linker.

Any of the herein described improved functionalities may be made to any engineered protein or polypeptide of the present invention. It will be appreciated that any of the functionalities described herein may be engineered into the engineered proteins or polypeptides from other orthologs, including chimeric functional protein domains comprising fragments from multiple orthologs.

In one aspect, the invention provides for methods of recognizing a target substrate. In some embodiments, the target substrate is a macromolecule. In some embodiments, the target substrate is a protein, polypeptide, nucleic acid molecule, or a sugar molecule. In some embodiments, the target substrate is in a host cell, which may be in vivo, ex vivo or in vitro. The host cell may be a prokaryotic cell, a eukaryotic cell, a plant cell, a fungal cell, an animal cell, an insect cell, a non-human mammalian cell, or a human cell.

In another aspect, the invention provides for methods of modifying a target substrate. In some embodiments, the target substrate is a macromolecule. In some embodiments, the target substrate is a protein, polypeptide, nucleic acid molecule, or a sugar molecule. In some embodiments, the target substrate is in a host cell, which may be in vivo, ex vivo or in vitro. The host cell may be a prokaryotic cell, a eukaryotic cell, a plant cell, a fungal cell, an animal cell, a non-human mammalian cell, or a human cell.

In one aspect, the invention provides a method of modifying a target cell in vivo, ex vivo or in vitro. The target cell may be a prokaryotic cell, a eukaryotic cell, a plant cell, a fungal cell, an animal cell, a non-human mammalian cell, or a human cell. In some embodiments, modification may be conducted in a manner alters the cell such that once modified the progeny or cell line of the modified cell retains the altered phenotype. The modified cells and progeny may be part of a multi-cellular organism such as a plant or animal with ex vivo or in vivo application of system to desired cell types. The invention may be a therapeutic method of treatment. The therapeutic method of treatment may comprise gene or genome editing, gene therapy, or protein based therapy. In some embodiments, the method comprises sampling a cell or population of cells from a human or non-human animal, and modifying the cell or cells. Culturing may occur at any stage ex vivo. The cell or cells may be re-introduced into the non-human animal or plant. In some embodiments, the re-introduced cells are stem cells. These sampling, culturing and re-introduction options apply across the aspects of the present invention.

In some embodiments, the method comprises allowing an engineered protein or polypeptide comprising a LRR to bind to the target. In some embodiments, the method comprises allowing an engineered protein or polypeptide comprising a LRR to cleave the target. In some embodiments, the method comprises allowing an engineered protein or polypeptide comprising a LRR to modify the target.

In one aspect, the invention provides a method of modifying expression of a substrate molecule in a eukaryotic cell. The substrate molecule may be a protein, polypeptide, nucleic acid, polysaccharide, lipid, or any other substrate molecule. In some embodiments, the method comprises allowing an engineered protein or polypeptide comprising a LRR to bind to the target such that said binding results in increased or decreased expression of said target. In some embodiments, the method comprises allowing an engineered protein or polypeptide comprising a LRR to cleave or modify the target such that said binding results in increased or decreased expression of said target.

The terms "non-naturally occurring" or "engineered" are used interchangeably and indicate the involvement of the hand of man. The terms, when referring to proteins, nucleic acid molecules or polypeptides mean that the protein, nucleic acid molecule, or the polypeptide is at least substantially free from at least one other component with which they are naturally associated in nature and as found in nature. Furthermore, the terms "non-naturally occurring" and "engineered" may be used interchangeably and so can therefore be used alone or in combination and one or other may replace mention of both together. In particular, "engineered" is preferred in place of "non-naturally occurring" or "non-naturally occurring and/or engineered."

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Homology modelling: Corresponding residues in the engineered protein and/or LRR can be identified by the methods of Zhang et al., 2012 (Nature; 490(7421): 556-60) and Chen et al., 2015 (PLoS Comput Biol; 11(5): e1004248)—a computational protein-protein interaction (PPI) method to predict interactions mediated by domain-motif interfaces. PrePPI (Predicting PPI), a structure based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbors by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbor in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

Vectors

In certain aspects the invention involves vectors. As used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

Regulatory Elements

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein. With regards to regulatory sequences, mention is made of U.S. patent application Ser. No. 10/491,026, the contents of which are incorporated by reference herein in their entirety. With regards to promoters, mention is made of International Patent Publication No. WO 2011/028929 and U.S. application Ser. No. 12/511,940, the contents of which are incorporated by reference herein in their entirety.

Vectors can be designed for expression of the engineered protein or polypeptide (e.g., nucleic acid transcripts, proteins, or enzymes) in prokaryotic or eukaryotic cells. For example, nucleic acid molecules encoding the engineered protein or polypeptides, including DNA and RNA molecules, can be introduced and/or expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or nonfusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 1id (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerevisiae* include pYepSec1 (Baldari, et al., 1987. *EMBO J.* 6: 229-234), pMFa (Kuijan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Luckow and Summers, 1989. *Virology* 170: 31-39).

In some embodiments, a vector is capable of driving expression of one or more sequences in mammalian cells using a mammalian expression vector. Examples of mammalian expression vectors include pCDM8 (Seed, 1987. *Nature* 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid molecule encoding the engineered protein or polypeptide of the present invention preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

Targeting Systems

In general, "targeting system" or "substrate targeting system" as used in the present application refers collectively to engineered proteins or polypeptides, nucleic acid molecules encoding engineered proteins or polypeptides thereof, functional domains or functional proteins associated with the engineered proteins or polypeptides with or without fusion, with or without a linker moiety, and any other component of the targeting system.

In some embodiments, one or more elements of a targeting system is derived from a particular organism comprising an endogenous LRR. In some embodiments, one or more elements of a targeting system are derived from a prokaryotic organism. In some embodiments, one or more elements of a targeting system is derived from a bacteria defense mechanism related protein.

In general, a targeting system is characterized by elements that promote the formation of a target recognition a target sequence, structure, or formation. In some embodiments, target may comprise a protein or polypeptide, a protein or polypeptide structure, a protein or polypeptide sequence, and any protein or polypeptide homologs or modifications, including protein phosphorylation, glycosylation, nitrosylation, methylation, acetylation, lipidation, myristoylation, palmitoylation, prenylation and any other modification thereof.

In some embodiments, target may comprise nucleic acid molecules, sugar molecules, or other macromolecules. In some embodiments, a target is located in the nucleus or cytoplasm of a cell. In some embodiments, the target may be within an organelle of a eukaryotic cell, for example, mitochondrion or chloroplast. In some embodiments, the target may be located on the surface of a cell. In some embodiments, the target may be located across a cell membrane structure. In some embodiments, the target may be located in intercellular space of a tissue or an organism. In some embodiments, the target may be located in a specific cell type, tissue, organ, or structure of an organism, such as muscle, neuron, bone, skin, blood, liver, pancreas, lymphocytes.

In some embodiments, an engineered protein or polypeptide may form a component of an inducible targeting system. The inducible nature of the system would allow for spatiotemporal control of gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc.), or light inducible systems (Phytochrome, LOV domains, or cryptochrome).

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a targeting system is delivered to a cell.

In some embodiments, the nucleic acid molecule encoding the engineered protein is codon optimized. In some embodiments, an enzyme coding sequence encoding the engineered protein is codon optimized for expression in particular cells. In some embodiments, the host cell is a prokaryotic cell. In some embodiments, the host cell is a eukaryotic cell. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In some embodiments, nucleic acid molecule encoding the engineered protein is fused to one or more nuclear localization sequences (NLSs) or nuclear export signals (NESs), such as about or more than about 1, 2, 3, 4, 5, 6, 7, 8, 9, 10, or more NLSs or NESs. In some embodiments, the engineered protein comprises about or more than about 1, 2, 3, 4, 5, 6, 7, 8, 9, 10, or more NLSs or NESs at or near the amino-terminus, about or more than about 1, 2, 3, 4, 5, 6, 7, 8, 9, 10, or more NLSs or NESs at or near the carboxy-terminus, or a combination of these (e.g. zero or at least one or more NLS or NES at the amino-terminus and zero or at one or more NLS or NES at the carboxy terminus). When more than one NLS or NES is present, each may be selected independently of the others, such that a single NLS or NES may be present in more than one copy and/or in combination with one or more other NLSs or NESs present in one or more copies. In some embodiments, an NLS or NES is considered near the N- or C-terminus when the nearest amino acid of the NLS or NES is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV(SEQ ID NO:27); the NLS from nucleoplasmin (e.g. the nucleoplasmin bipartite NLS with the sequence KRPAATKKAGQAKKKK) (SEQ ID NO:28); the c-myc NLS having the amino acid sequence PAAKRVKLD (SEQ ID NO:29) or RQRRNELKRSP (SEQ ID NO:30); the hRNPA1 M9 NLS having the sequence NQSSNFGPMKGGNFGGRSSGPYGGGGQYFAK-PRNQGGY(SEQ ID NO:31); the sequence RMRIZFKNKGKDTAELRRRRVEVSVELRKAKKD- EQILKRRNV (SEQ ID NO:32) of the IBB domain from importin-alpha; the sequences VSRKRPRP (SEQ ID NO:33) and PPKKARED (SEQ ID NO:34) of the myoma T protein; the sequence PQPKKKPL (SEQ ID NO:35) of human p53; the sequence SALIKKKKKMAP (SEQ ID NO:36) of mouse c-abl IV; the sequences DRLRR (SEQ ID NO:37) and PKQKKRK (SEQ ID NO:38) of the influenza virus NS1; the sequence RKLKKKIKKL (SEQ ID NO:39) of the Hepatitis virus delta antigen; the sequence REKKKFLKRR (SEQ ID NO:40) of the mouse Mx1 protein; the sequence KRKGDEVDGVDEVAKKKSKK (SEQ ID NO:41) of the human poly(ADP-ribose) polymerase; and the sequence RKCLQAGMNLEARKTKK (SEQ ID NO:42) of the steroid hormone receptors (human) glucocorticoid. Non-limiting examples of NESs include an NES sequence LYPERLRRILT (SEQ ID NO:43) (CTGTACCCT-GAGCGGCTGCGGCGGATCCTGACC) (SEQ ID NO:44). In general, the one or more NLSs or NESs are of sufficient strength to drive accumulation of the engineered protein in a detectable amount in respectively the nucleus or the cytoplasm of a eukaryotic cell. In general, strength of nuclear localization/export activity may derive from the number of NLSs/NESs in the engineered protein, the particular NLS(s) or NES(s) used, or a combination of these factors.

In certain embodiments, a detectable marker may be fused to the engineered protein, such that location within a cell may be visualized, such as in combination with a means for detecting the location of the nucleus (e.g. a stain specific for the nucleus such as DAPI) or cytoplasm. In certain embodiments, other localization tags may be fused to the engineered protein, such as without limitation for localizing the engineered protein to particular sites in a cell, such as organelles, such mitochondria, plastids, chloroplast, vesicles, golgi, (nuclear or cellular) membranes, ribosomes, nucleolus, ER, cytoskeleton, vacuoles, centrosome, nucleosome, granules, centrioles, etc.

In certain aspects the invention involves vectors, e.g. for delivering or introducing in a cell nucleic acid molecule encoding the engineered protein. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked.

Aspects of the invention relate to screening and identification of novel effector proteins associated with the function(s) of the engineered protein. In some embodiments, the effector protein is a substrate of the engineered protein. In some embodiments, the effector protein is associated with in a regulatory pathway in which the engineered protein is involved. In particular embodiments, the regulatory pathway is a kinase cascade. In some embodiments, the engineered protein is a protease. In particular embodiments, the engineered protein is an IgA1 protease. In a further embodiment, the effector protein is functional in prokaryotic or eukaryotic cells for in vitro, in vivo or ex vivo applications. An aspect of the invention encompasses computational methods and algorithms to predict novel effector proteins associated with the engineered protein.

The protein or polypeptide acids-targeting systems, the vector systems, the vectors and the compositions described herein may be used in various protein or peptide-targeting applications, altering or modifying a genetic element such as a protein or polypeptide, trafficking and visualization of target protein, detecting and tracing of target protein or polypeptide, isolation of target protein, etc.

Inducible Systems

In one embodiment, fusion complexes comprising the engineered protein capable of binding and/or cleaving or modifying a target are designed to be inducible, for instance light inducible or chemically inducible. Such inducibility allows for activation of the engineered protein and/or the effector component at a desired moment in time.

Light inducibility is for instance achieved by designing a fusion complex wherein CRY2 PHR/CIBN pairing is used for fusion. This system is particularly useful for light induction of protein interactions in living cells (Konermann S, et al. Nature. 2013; 500:472-476).

Chemical inducibility is for instance provided for by designing a fusion complex wherein FKBP/FRB (FK506 binding protein/FKBP rapamycin binding) pairing is used for fusion. Using this system rapamycin is required for binding of proteins (Zetsche et al. Nat Biotechnol. 2015; 33(2):139-42 describes the use of this system for Cas9).

Further, when introduced in the cell as DNA, the engineered protein of the invention can be modulated by inducible promoters, such as tetracycline or doxycycline controlled transcriptional activation (Tet-On and Tet-Off expression system), hormone inducible gene expression system such as for instance an ecdysone inducible gene expression system and an arabinose-inducible gene expression system. When delivered as RNA, expression of the engineered protein can be modulated via a riboswitch, which can sense a small molecule like tetracycline (as described in Goldfless et al. Nucleic Acids Res. 2012; 40(9):e64). A riboswitch (also known as an aptozyme) is a regulatory segment of a messenger RNA molecule that binds a small molecule. This typically results in a change in production of the proteins encoded by the mRNA. This may be through cleavage of, or binding to, the riboswitch. In particular, reduction of riboswitch activity is envisaged. This may be useful in assaying riboswitch function in vivo or in vitro, but also as a means of controlling therapies based on riboswitch activity, in vivo or in vitro.

Aspects of the invention also encompass methods and uses of the compositions and systems described herein in genome or proteome engineering, e.g. for altering or manipulating the (protein) expression of or one or more gene products, in prokaryotic or eukaryotic cells, in vitro, in vivo or ex vivo. In an aspect, the invention provides methods and compositions for modulating, e.g., reducing, expression of a target protein in cells. In the subject methods, the invention provides a system with the engineered protein that interferes with expression, stability, and modification of a target protein.

In certain embodiments, an effective amount of the engineered protein is used to cleave a target protein or polypeptide, or interfere with target expression. In an advantageous embodiment, the engineered protein binds to the target specifically.

In certain embodiments, the engineered protein according to the invention as described herein is associated with or fused to a destabilization domain (DD). In some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT.

In some embodiments, one or two DDs may be fused to the N-terminal end of the engineered protein with one or two DDs fused to the C-terminal of the engineered protein of the present invention. In some embodiments, the at least two DDs are associated with the engineered protein and the DDs are the same DD, i.e. the DDs are homologous. Thus, both (or two or more) of the DDs could be ER50 DDs. Alternatively, both (or two or more) of the DDs could be DHFR50 DDs. In some embodiments, at least two DDs are associated with the engineered protein and the DDs are different DDs, i.e. the DDs are heterologous. Thus, one of the DDS could be ER50 while one or more of the DDs or any other DDs could be DHFR50. Having two or more DDs which are heterologous may be advantageous as it would provide a greater level of degradation control. A tandem fusion of more than one DD at the N or C-term may enhance degradation. It is envisaged that high levels of degradation would occur in the absence of either stabilizing ligand, intermediate levels of degradation would occur in the absence of one stabilizing ligand and the presence of the other (or another) stabilizing ligand, while low levels of degradation would occur in the presence of both (or two of more) of the stabilizing ligands. Control may also be imparted by having an N-terminal ER50 DD and a C-terminal DHFR50 DD.

In some embodiments, the fusion of the engineered protein with the DD comprises a linker between the DD and engineered protein. In some embodiments, the linker is a GlySer linker. In some embodiments, the fusion of the engineered protein with the DD further comprises at least one Nuclear Export Signal (NES). In some embodiments, the fusion of the engineered protein with the DD comprises two or more NESs. In some embodiments, the fusion of the engineered protein with the DD comprises at least one Nuclear Localization Signal (NLS). This may be in addition to an NES. HA or Flag tags are also within the ambit of the invention as linkers. Applicants use NLS and/or NES as linker and also use Glycine Serine linkers as short as GS up to (GGGGS)$_3$ (SEQ ID NO:47).

Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, A temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with the engineered protein confers to protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to the engineered protein of this invention and its stability can be regulated or perturbed using a ligand. Another DD can be a 12-kDa (107-amino-acid) tag based on a mutated FKBP protein, stabilized by Shield-1 ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282: 24866-24872; and Rodriguez, Chem Biol. Mar. 23, 2012; 19(3): 391-398-all of which are incorporated herein by reference and may be employed in the practice of the invention in selected a DD to associate with a engineered protein in the practice of this invention.

In an aspect the invention provides a method for modifying gene expression comprising the administration to a host or expression in a host in vivo of one or more of the compositions comprising the engineered protein as herein-discussed.

In an aspect the invention provides a herein-discussed method comprising the delivery of the composition or nucleic acid molecule(s) coding therefor, wherein said nucleic acid molecule(s) are operatively linked to regulatory sequence(s) and expressed in vivo. In an aspect the invention provides a herein-discussed method wherein the expression in vivo is via a lentivirus, an adenovirus, or an AAV.

In an aspect the invention provides a cell or a population of cells as herein-discussed comprising the engineered protein, wherein the cell is, optionally, a human cell or a mouse cell.

In an aspect the invention provides a nucleic acid molecule(s) encoding the engineered protein as herein-discussed. In an aspect the invention provides a vector comprising: a nucleic acid molecule encoding the engineered protein or polypeptide as herein discussed. In an aspect a vector can further comprise regulatory element(s) operable in a eukaryotic cell operably linked to the nucleic acid molecule encoding the engineered protein or polypeptide and/or the optional nuclear localization sequence(s).

In one aspect, the invention provides a kit comprising one or more of the components described hereinabove. In some embodiments, the kit comprises a vector system as described above and instructions for using the kit.

Administration and Delivery

Through this disclosure and the knowledge in the art, the engineered protein, or components thereof or nucleic acid molecules encoding the engineered protein thereof or nucleic acid molecules encoding or providing components thereof may be delivered by a delivery system herein described both generally and in detail.

Administration to a host or a host cell may be performed via viral vectors known to the skilled person or described herein for delivery to a host (e.g. lentiviral vector, adenoviral vector, AAV vector). Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., the engineered proteins, enzymes, modified or mutant forms thereof, fusion proteins thereof, etc.).

Advantageous vectors include lentiviruses and adeno-associated viruses, and types of such vectors can also be selected for targeting particular types of cells.

Use of different selection markers may be advantageous for eliciting an improved effect.

The engineered protein or nucleic acid molecules encoding the engineered protein can be delivered using any suitable vector, e.g., plasmid or viral vectors, such as adeno-associated virus (AAV), lentivirus, adenovirus or other viral vector types, or combinations thereof. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^9$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg Na to about 10 μg per 70 kg individual. Plasmids of the invention generally comprise (i) a promoter; (ii) a sequence encoding an engineered protein comprising a hypervariable domain, operably linked to said promoter; (iii) a selectable marker; (iv) an origin of replication; and (v) a transcription terminator downstream of and operably linked to (ii). In some embodiments, the engineered protein comprises a LRR.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments, the nucleic acid molecules encoding the engineered protein of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

mRNA delivery methods are especially promising for liver delivery currently. Much clinical work on RNA delivery has focused on RNAi or antisense, but these systems can be adapted for delivery of RNA for implementing the present invention. References below to RNAi etc. should be read accordingly.

Means of delivery of nucleic acid molecules also preferred include delivery of nucleic acid molecules via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the RNA-targeting system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E (α-tocopherol) may be conjugated with the engineered protein or polypeptide comprising target recognition regions and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain.

In terms of local delivery to the brain, this can be achieved in various ways. For instance, material can be delivered intrastriatally e.g., by injection. Injection can be performed stereotactically via a craniotomy.

Adeno-Associated Virus (AAV)

Engineered protein or polypeptide comprising one or more target recognition region can be delivered using adeno-associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome/transcriptome modification, the expression of engineered protein or polypeptide can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons: Low toxicity (this may be due to the purification method not requiring ultracentrifugation of cell particles that can activate the immune response) and Low probability of causing insertional mutagenesis because it doesn't integrate into the host genome.

AAV has a packaging limit of 4.5 or 4.75 Kb. This means that engineered protein comprising hypervariable regions of this invention as well as any fused or linked functional domain, a promoter and transcription terminator have to all fit into the same viral vector. Therefore embodiments of the invention include utilizing homologs of the engineered protein or functional domain that are shorter.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

In one embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the targeting system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used and/or adapted to the sequence specific targeting system of the present invention. A minimum of $2.5 \times 10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm$^2$ tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

Particle Delivery Systems and/or Formulations

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (m). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF MS), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of targeting system of this invention, e.g. the engineered protein or polypeptide, nucleic acid molecules encoding the engineered protein or polypeptide, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

Engineered protein or polypeptide comprising a hypervariable domain, nucleic acid molecules encoding the engineered protein or polypeptide, or other components of the protein or polypeptide targeting system may be delivered using particles or lipid envelopes; for instance, as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84).

In one embodiment, particles based on self-assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACS Nano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80;

Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used and/or adapted to the engineered protein and the protein or polypeptide targeting system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32): 12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US Patent Publication NO. 20110293703 relates to lipidoid compounds are also particularly useful in the administration of polynucleotides, which may be applied to deliver the targeting system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed Applicants to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the targeting system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the targeting system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated. LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding the engineered protein of the present invention to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilinoleyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011).

Preparation of LNPs and encapsulation of components of the protein targeting system may be used and/or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(o-methoxy-poly(ethylene glycol)2000) carbamoyl]-1,2-dimyristyloxylpropyl-3-amine (PEG-C-DOMG) may be provided by Tekmira Pharmaceuticals (Vancouver, Canada) or synthesized. Cholesterol may be purchased from Sigma (St Louis, MO). Components of the protein targeting system may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a nucleic targeting system or components thereof.

Preparation of large LNPs may be used and/or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at a RNA to total lipid ratio of approximately 1:10 (wt:wt), followed by incubation for 30 minutes at 37° C. to form loaded LNPs. The mixture may be subsequently dialyzed overnight in PBS and filtered with a 0.45 m syringe filter.

Spherical Nucleic Acid (SNA™) constructs and other particles (particularly gold particles) are also contemplated as a means to delivery nucleic acid molecules encoding the engineered protein to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J.

Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with nucleic acid molecules may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes.

In terms of this invention, it is preferred to have one or more components of the protein or polypeptide targeting system delivered using particles or lipid envelopes. Other delivery systems or vectors may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, particles of the invention have a greatest dimension of 100 nm or less. In other preferred embodiments, nanoparticles of the invention have a greatest dimension ranging between 35 nm and 60 nm.

Particles encompassed in the present invention may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can be envisioned that such methods and materials of herein-cited documents, e.g., conjugated lipomers can be used in the context of the targeting system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the engineered protein or the protein targeting system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport nucleic acids, proteins and other macromolecules and can deliver macromolecules to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide.

El-Andaloussi et al. (Nature Protocols 7, 2112-2126 (2012)) discloses how exosomes derived from cultured cells can be harnessed for delivery of nucleic acids in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of this invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. The exosomes may be co-cultured with monocytes and lymphocytes isolated from the peripheral blood of healthy donors. Therefore, it may be contemplated that exosomes containing the targeting system of the present invention may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis.

In another embodiment, the targeting system or components thereof may be administered in liposomes, such as a stable nucleic-acid-lipid particle (SNALP) (see, e.g., Morrissey et al., Nature Biotechnology, Vol. 23, No. 8, August 2005) whereby nucleic acid molecules encoding the engineered protein or polypeptide may be encapsulated. Daily intravenous injections of about 1, 3 or 5 mg/kg/day of a specific targeting system targeted in a SNALP are contemplated. The daily treatment may be over about three days and then weekly for about five weeks. In another embodiment, a specific targeting system encapsulated SNALP may be administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(ω-methoxypoly (ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780).

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total of targeting system per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177).

The lipid, lipid particle, or lipid bilayer or lipid entity of the invention can be prepared by methods well known in the art. See Wang et al., ACS Synthetic Biology, 1, 403-07 (2012); Wang et al., PNAS, 113(11) 2868-2873 (2016); Manoharan, et al., International Patent Publication No. WO 2008/042973; Zugates et al., U.S. Pat. No. 8,071,082; Xu et al., International Patent Publication No. WO 2014/186366 A1 (US20160082126). Xu et provides a way to make a nanocomplex for the delivery of saporin wherein the nanocomplex comprising saporin and a lipid-like compound, and wherein the nanocomplex has a particle size of 50 nm to 1000 nm; the saporin binds to the lipid-like compound via non-covalent interaction or covalent bonding; and the lipid-like compound has a hydrophilic moiety, a hydrophobic moiety, and a linker joining the hydrophilic moiety and the hydrophobic moiety, the hydrophilic moiety being optionally charged and the hydrophobic moiety having 8 to 24 carbon atoms. Xu et al., International Patent Publication No. WO 2014/186348 (US20160129120) provides examples of nanocomplexes of modified peptides or proteins comprising a cationic delivery agent and an anionic pharmaceutical agent, wherein the nanocomplex has a particle size of 50 to 1000 nm, the cationic delivery agent binds to the anionic pharmaceutical agent, and the anionic pharmaceutical agent is a modified peptide or protein formed of a peptide and a protein and an added chemical moiety that contains an anionic group. The added chemical moiety is linked to the peptide or protein via an amide group, an ester group, an ether group, a thioether group, a disulfide group, a hydrazone group, a sulfenate ester group, an amidine group, a urea group, a carbamate group, an imidoester group, or a carbonate group. More particularly these documents provide examples of lipid or lipid-like compounds that can be used to make the particle delivery system of the present invention, including compounds of the formula $B_1$-$K_1$-A-$K_2$-$B_2$, in which A, the hydrophilic moiety, is

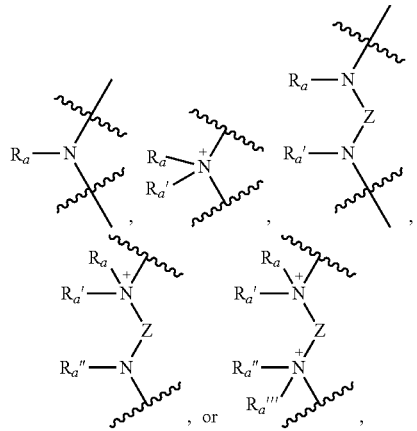

each of $R_a$, $R_{a'}$, $R_{a''}$, and $R_{a'''}$, independently, being a $C_1$-$C_{20}$ monovalent aliphatic radical, a $C_{12-20}$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical; each of $B_1$, the hydrophobic moiety, and $B_2$, also the hydrophobic moiety, independently, is a $C_{12-20}$ aliphatic radical or a $C_{12-20}$ heteroaliphatic radical; and each of $K_1$, the linker, and $K_2$, also the linker, independently, is O, S, Si, $C_1$-$C_6$ alkylene

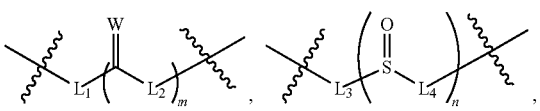

-continued

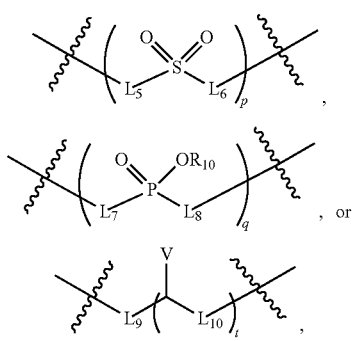

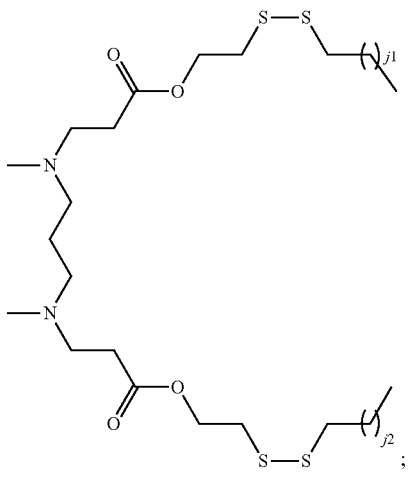

1-O16B, j1, j2 = 10; and
1-O18B, j1, j2 = 12 in which each of m, n, p, q, and t, independently, is 1-6; W is O, S, or $NR_C$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical and specific compounds.

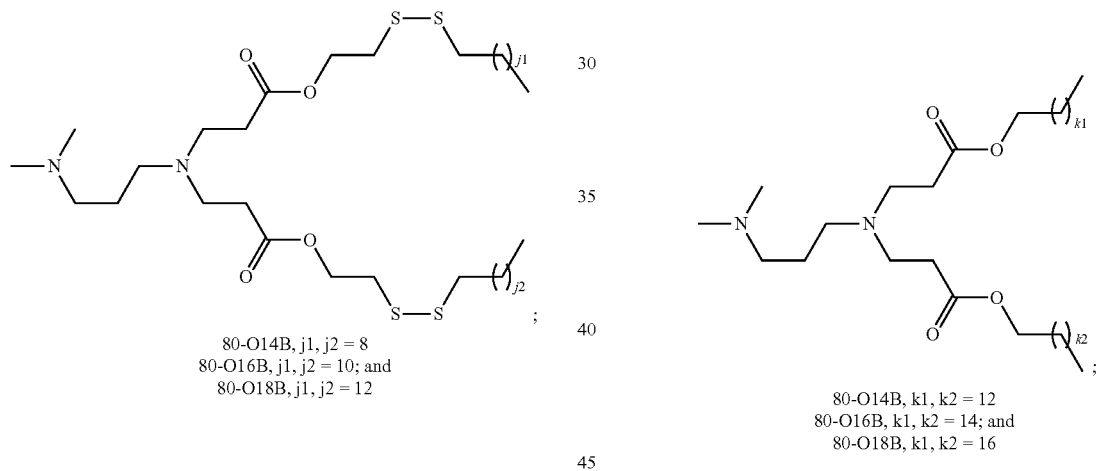

80-O14B, j1, j2 = 8
80-O16B, j1, j2 = 10; and
80-O18B, j1, j2 = 12

80-O14B, k1, k2 = 12
80-O16B, k1, k2 = 14; and
80-O18B, k1, k2 = 16

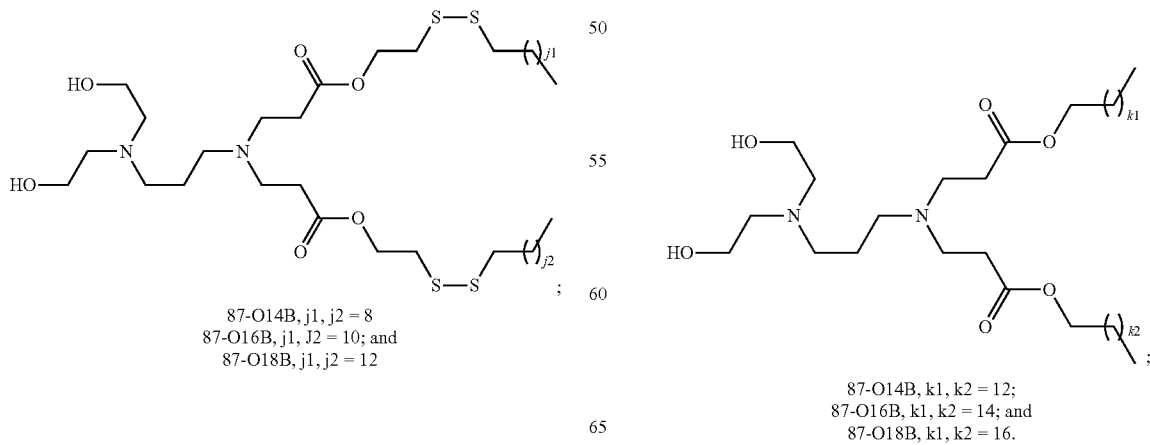

87-O14B, j1, j2 = 8
87-O16B, j1, J2 = 10; and
87-O18B, j1, j2 = 12

87-O14B, k1, k2 = 12;
87-O16B, k1, k2 = 14; and
87-O18B, k1, k2 = 16.

-continued

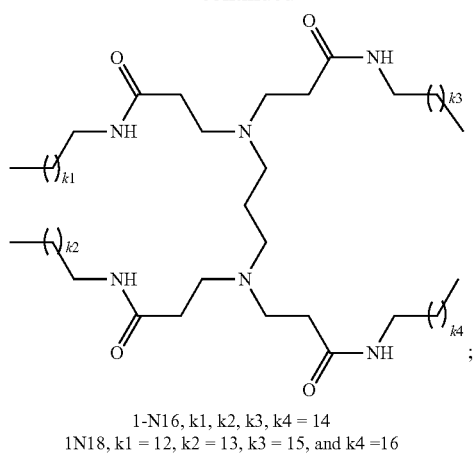

1-N16, k1, k2, k3, k4 = 14
1N18, k1 = 12, k2 = 13, k3 = 15, and k4 = 16

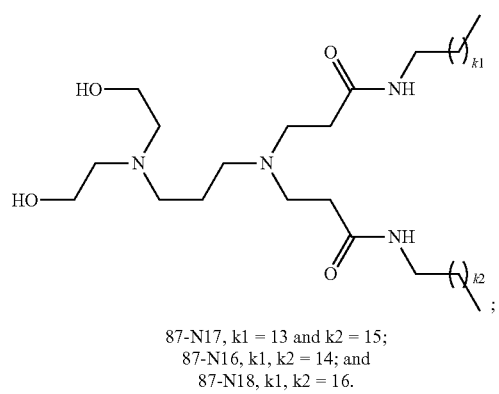

87-N17, k1 = 13 and k2 = 15;
87-N16, k1, k2 = 14; and
87-N18, k1, k2 = 16.

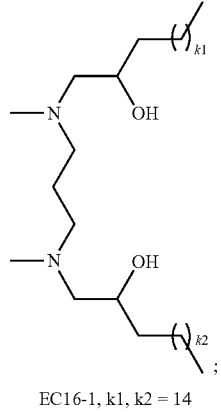

EC16-1, k1, k2 = 14

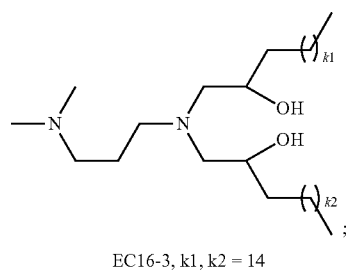

EC16-3, k1, k2 = 14

-continued

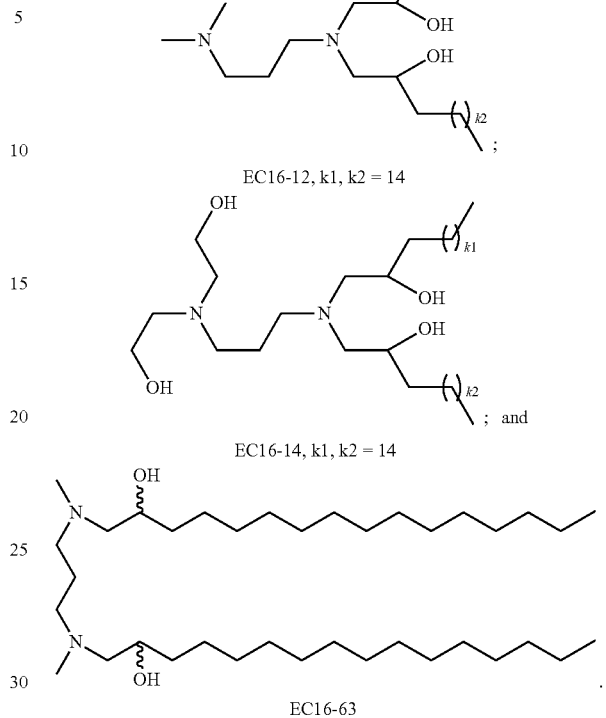

EC16-12, k1, k2 = 14

EC16-14, k1, k2 = 14; and

EC16-63

Additional examples of cationic lipid that can be used to make the particle delivery system of the invention can be found in U.S. Patent Publication No. US20150140070, wherein the cationic lipid has the formula

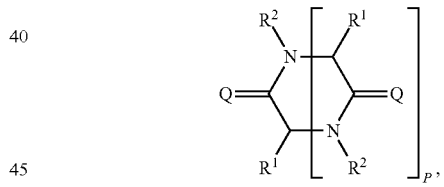

wherein p is an integer between 1 and 9, inclusive; each instance of Q is independently O, S, or $NR^Q$; $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii); each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{A1}$, $-N(R^{A1})_2$, $-SR^{A1}$, or a group of formula:

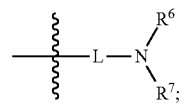

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii); each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups, together with the nitrogen atom to which they are attached, are joined to form an optionally substituted heterocyclic or optionally substituted heteroaryl ring; each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); Formulae (i), (ii), and (iii) are:

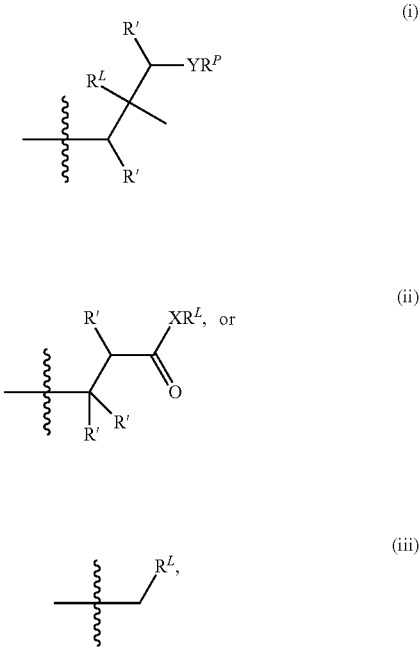

each instance of R' is independently hydrogen or optionally substituted alkyl; X is O, S, or $NR^X$; $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; Y is O, S, or $NR^Y$; R is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; $R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer; provided that at least one instance of $R^Q$, $R^2$, $R^6$, or $R^7$ is a group of the formula (i), (ii), or (iii); in Liu et al., (US 20160200779, US 20150118216, US 20150071903, and US 20150071903), which provide examples of cationic lipids to include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif), and Eufectins (JBL, San Luis Obispo, Calif). Exemplary cationic liposomes can be made from N-[1-(2,3-dioleoyloxy)-propyl]-N,N,N-trimethylammonium chloride (DOTMA), N-[1-(2,3-dioleoyloxy)-propyl]-N,N,N-trimethylammonium methylsulfate (DOTAP), 3.beta.-[N—(N',N'-dimethylaminoethane)carbamoyl]cholesterol (DC-Chol), 2,3,-dioleyloxy-N-[2(sperminecarboxamido)ethyl]-N,N-dimethyl-1-propanamin-ium trifluoroacetate (DOSPA), 1,2-dimyristyloxypropyl-3-dimethyl-hydroxyethyl ammonium bromide; and dimethyldioctadecylammonium bromide (DDAB); in WO2013/093648 which provides cationic lipids of formula

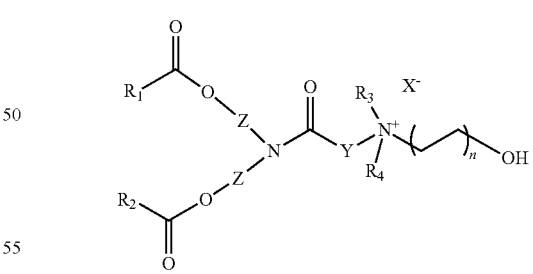

in which Z=an alkyl linker, $C_2$-$C_4$ alkyl, Y=an alkyl linker, $C_1$-$C_6$ alkyl, $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{200}$alkenyl. $C_{12}$-$C_{18}$alkenyl, $C_{13}$-$C_{17}$alkenyl, $C_{17}$alkenyl; R3 and R4 are each independently hydrogen, $C_1$-$C_6$ alkyl, or —$CH_2CH_2OH$, $C_1$-$C_6$ alkyl, $C_1$-$C_3$alkyl; n is 1-6; and X is a counterion, including any nitrogen counterion, as that term is readily understood in the art, and specific cationic lipids including

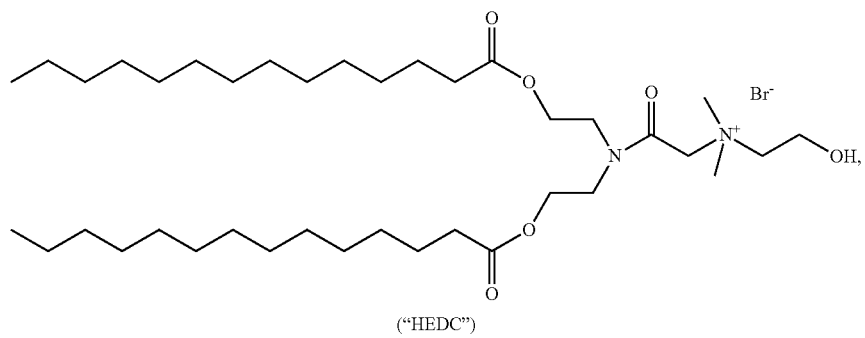

("HEDC")

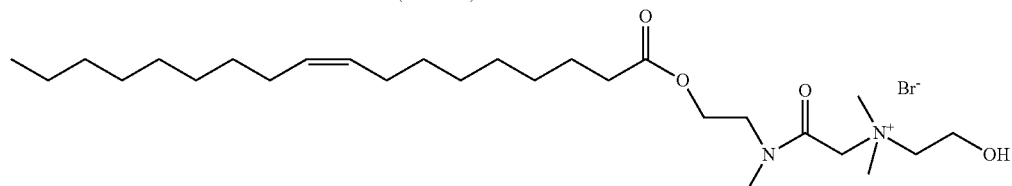

("HEDODC")

and

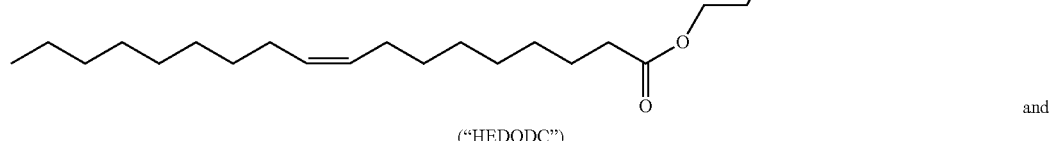

("HE-Et-DODC")

WO2013/093648 also provides examples of other cationic charged lipids at physiological pH including N,N-dioleyl-N,N-dimethylammonium chloride (DODAC), N,N-distearyl-N,N-dimethylammonium bromide (DDAB); N-(1,2-dimyristyloxyprop-3-yl)-N,N-dimethyl-N-hydroxyethylammonium bromide (DMRIE) and dioctadecylamidoglycyl carboxyspermidine (DOGS); in US 20160257951, which provides cationic lipids with a general formula

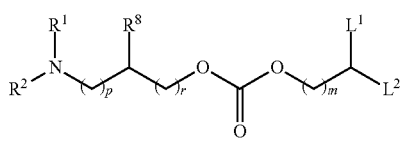

or a pharmacologically acceptable salt thereof, wherein $R^1$ and $R^2$ are each independently a hydrogen atom, a $C_1$-$C_6$ alkyl group optionally substituted with one or more substituents selected from substituent group a, a $C_2$-$C_6$ alkenyl group optionally substituted with one or more substituents selected from substituent group a, a $C_2$-$C_6$ alkynyl group optionally substituted with one or more substituents selected from substituent group a, or a $C_3$-$C_7$ cycloalkyl group optionally substituted with one or more substituents selected from substituent group a, or $R^1$ and $R^2$ form a 3- to 10-membered heterocyclic ring together with the nitrogen atom bonded thereto, wherein the heterocyclic ring is optionally substituted with one or more substituents selected from substituent group a and optionally contains one or more atoms selected from a nitrogen atom, an oxygen atom, and a sulfur atom, in addition to the nitrogen atom bonded to $R^1$ and $R^2$, as atoms constituting the heterocyclic ring; $R_8$ is a hydrogen atom or a $C_1$-$C_6$ alkyl group optionally substituted with one or more substituents selected from substituent group α; or $R^1$ and $R^8$ together are the group —$(CH_2)_q$—; substituent group α consists of a halogen atom, an oxo group, a hydroxy group, a sulfanyl group, an amino group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_6$ alkylamino group, and a $C_1$-$C_7$ alkanoyl group; $L^1$ is a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, or a ($C_1$-$C_{10}$ alkyl)-$(Q)_k$-($C_1$-$C_{10}$ alkyl) group optionally substituted with one or more substituents selected from substituent group β1; $L^2$ is, independently of $L^1$, a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a C$_3$-C$_{24}$ alkynyl group optionally substituted with one or more substituents selected from substituent group β31, a (C$_1$-C$_{10}$ alkyl)-(Q)$_k$-(C$_1$-C$_{10}$ alkyl) group optionally substituted with having one or more substituents selected from substituent group β1, a (C$_{10}$-C$_{24}$ alkoxy)methyl group optionally substituted with one or more substituents selected from substituent group β1, a (C$_{10}$-C$_{24}$ alkenyl)oxymethyl group optionally substituted with one or more substituents selected from substituent group β1, a (C$_3$-C$_{24}$ alkynyl) oxymethyl group optionally substituted with one or more substituents selected from substituent group β1, or a (C$_1$-C$_{10}$ alkyl)-(Q)$_k$-(C$_1$-C$_{10}$ alkoxy)methyl group optionally substituted with one or more substituents selected from substituent group β1; substituent group p 1 consists of a halogen atom, an oxo group, a cyano group, a C$_1$-C$_6$ alkyl group, a C$_1$-C$_6$ halogenated alkyl group, a C$_1$-C$_6$ alkoxy group, a C$_1$-C$_6$ alkylsulfanyl group, a C$_1$-C$_7$ alkanoyl group, a C$_1$-C$_7$ alkanoyloxy group, a C$_3$-C$_7$ alkoxyalkoxy group, a (C$_1$-C$_6$ alkoxy)carbonyl group, a (C$_1$-C$_6$ alkoxy)carboxyl group, a (C$_1$-C$_6$ alkoxy)carbamoyl group, and a (C$_1$-C$_6$ alkylamino) carboxyl group; Q is a group of formula:

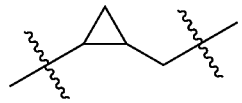 [SMILES: *CC1CC1*]

when L$^1$ and L$^2$ are each substituted with one or more substituents selected from substituent group β1 and substituent group β1 is a C$_1$-C$_6$ alkyl group, a C$_1$-C$_6$ alkoxy group, a C$_1$-C$_6$ alkylsulfanyl group, a C$_1$-C$_7$ alkanoyl group, or a C$_1$-C$_7$ alkanoyloxy group, the substituent or substituents selected from substituent group β1 in L$^1$ and the substituent or substituents selected from substituent group β1 in L$^2$ optionally bind to each other to form a cyclic structure; k is 1, 2, 3, 4, 5, 6, or 7; m is 0 or 1; p is 0, 1, or 2; q is 1, 2, 3, or 4; and r is 0, 1, 2, or 3, provided that p+r is 2 or larger, or q+r is 2 or larger, and specific cationic lipids including

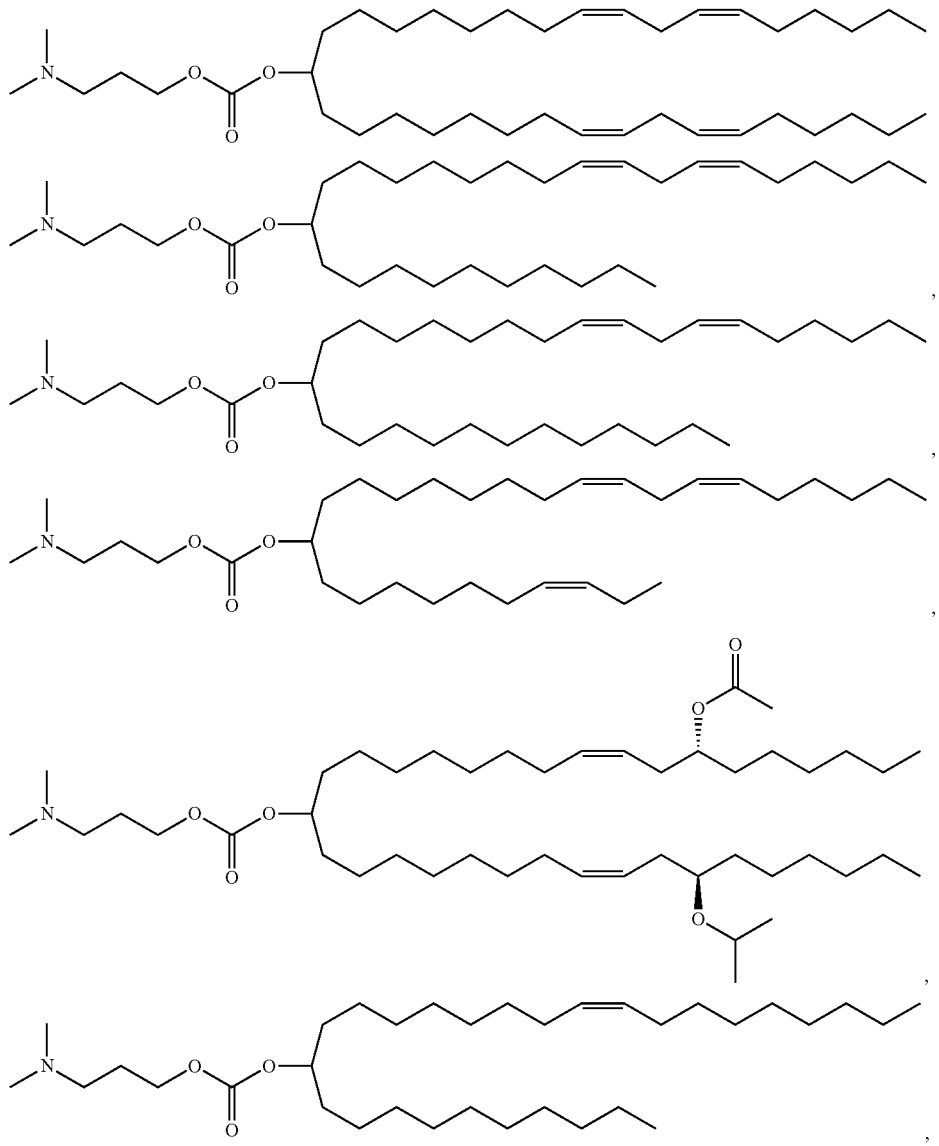

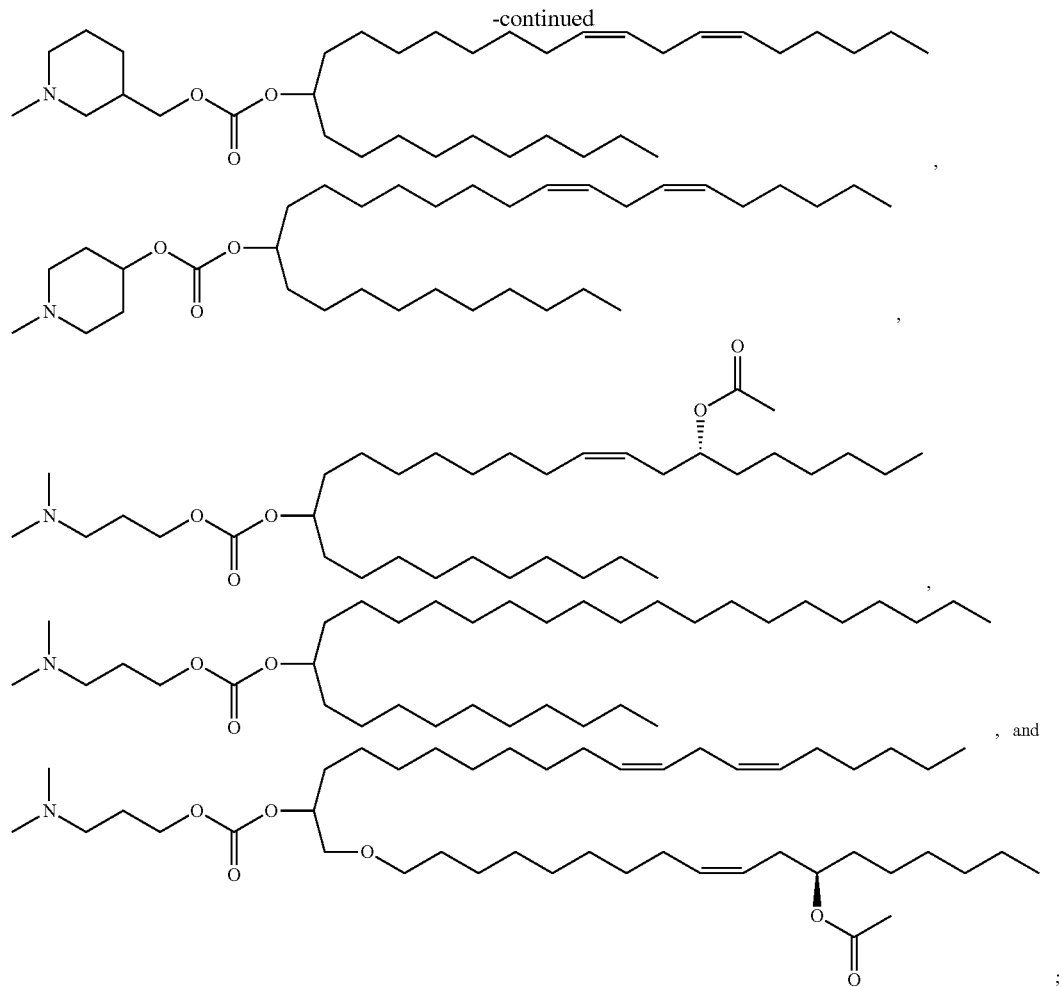

and in US Patent Publication No. 20160244761, which provides cationic lipids that include 1,2-distearyloxy-N,N-dimethyl-3-aminopropane (DSDMA), 1,2-dioleyloxy-N,N-dimethyl-β-aminopropane (DODMA), 1,2-dilinoleyloxy-N,N-dimethyl-3-aminopropane (DLinDMA), 1,2-dilinoleyloxy-N,N-dimethyl-3-aminopropane (DLenDMA), 1,2-di-.gamma.-linolenyloxy-N,N-dimethylaminopropane (.gamma.-DLenDMA), 1,2-dilinoleyloxy-keto-N,N-dimethyl-3-aminopropane (DLin-K-DMA), 1,2-dilinoleyl-4-(2-dimethylaminoethyl)-[1,3]-dioxolane (DLin-K-C$_2$-DMA) (also known as DLin-C$_2$K-DMA, XTC2, and C$_2$K), 2,2-dilinoleyl-4-(3-dimethylaminopropyl)-[1,3]-dioxolane (DLin-K-C$_3$-DMA), 2,2-dilinoleyl-4-(4-dimethylaminobutyl)-[1,3]-dioxolane (DLin-K-C$_4$-DMA), 1,2-dilinolenyloxy-4-(2-dimethylaminoethyl)-[1,3]-dioxolane (DLen-C$_2$K-DMA), 1,2-di-.gamma.-linolenyloxy-4-(2-dimethylaminoethyl)-[1,3]-dioxolane (.gamma.-DLen-C$_2$K-DMA), dilinoleylmethyl-3-dimethylaminopropionate (DLin-M-C$_2$-DMA) (also known as MC2), (6Z,9Z,28Z,31Z)-heptatriaconta-6,9,28,31-tetraen-19-yl 4-(dimethylamino) butanoate (DLin-M-C$_3$-DMA) (also known as MC3) and 3-(dilinoleylmethoxy)-N,N-dimethylpropan-1-amine (DLin-MIP-DMA) (also known as 1-B1 1).

In one embodiment, the lipid compound is preferably a bio-reducible material, e.g., a bio-reducible polymer and a bio-reducible lipid-like compound.

In embodiment, the lipid compound comprises a hydrophilic head, and a hydrophobic tail, and optionally a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged, in particular at physiological conditions such as physiological pH.

In one embodiment, the hydrophobic tail is a saturated or unsaturated, linear or branched, acyclic or cyclic, aromatic or nonaromatic hydrocarbon moiety, wherein the saturated or unsaturated, linear or branched, acyclic or cyclic, aromatic or nonaromatic hydrocarbon moiety optionally contains a disulfide bond and/or 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Other Lipids

Other cationic lipids, such as amino lipid 2,2-dilinoleyl-4-dimethylaminoethyl-[1,3]-dioxolane (DLin-KC2-DMA) may be utilized to encapsulate the targeting system of the present invention or components thereof and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver nucleic acids. Use of lipid envelopes is also preferred in the present invention.

In another embodiment, lipids may be formulated with the targeting system of the present invention or component(s) thereof or nucleic acid molecule(s) coding therefor to form lipid nanoparticles (LNPs). Lipids include, but are not limited to, DLin-KC2-DMA4, C12-200 and colipids disteroylphosphatidyl choline, cholesterol, and PEG-DMG.

The targeting system of the present invention or components thereof or nucleic acid molecule(s) coding therefor may be delivered encapsulated in PLGA Microspheres such as that further described in US Patent Publication Nos. 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumors, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US Patent Publication No. 20080267903, which discloses "Various polymers, including cationic polyamine polymers and dendrimeric polymers, are shown to possess anti-proliferative activity, and may therefore be useful for treatment of disorders characterized by undesirable cellular proliferation such as neoplasms and tumors, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumor activity may complement the activity of the agent to be delivered." The disclosures of these patent publications may be employed in conjunction with herein teachings for delivery of targeting system(s) of the present invention or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of targeting system or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112). David Liu's lab has further found +36 GFP to be an effective plasmid delivery reagent in a range of cells.

The nonviral delivery of RNA and plasmid DNA into mammalian cells are valuable both for research and therapeutic applications (Akinc et al., 2010, Nat. Biotech. 26, 561-569).

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the targeting system of the present invention. These systems of Dr. Lui and documents herein in conjunction with herein teachings can be employed in the delivery of the targeting system(s) or component(s) thereof or nucleic acid molecule(s) coding therefor.

Cell Penetrating Peptides (CPPs)

In yet another embodiment, cell penetrating peptides (CPPs) are contemplated for the delivery of the targeting system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles including nanoparticles, liposomes, chromophores, small molecules and radioactive materials. In aspects of the invention, the cargo may also comprise any component of targeting system of the present invention. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8; 614,194 and 8,044,019. CPPs can be used to deliver the targeting system or components thereof.

Implantable Devices

In another embodiment, implantable devices are also contemplated for delivery of the targeting system of the present invention or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used and/or adapted to the targeting system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

US Patent Publication 20110195123, provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non-degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide or protein or polypeptide based therapeutic agent from degradation, whether chemical in nature or due to attack from enzymes and other factors in the body of the subject.

The drug delivery system of US Patent Publication 20110195123 is optionally associated with sensing and/or activation appliances that are operated at and/or after implantation of the device, by non- and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non- and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication No. 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the targeting system of the present invention.

As another example of a specific application, neuro and muscular degenerative diseases develop due to abnormal gene expression. Local delivery of the targeting system may have therapeutic properties for interfering with such abnormal gene expression. Local delivery of anti-apoptotic, anti-inflammatory and anti-degenerative drugs including small drugs and macromolecules may also optionally be therapeutic. In such cases the Loder is applied for prolonged release at constant rate and/or through a dedicated device that is implanted separately. All of this may be used and/or adapted to the targeting system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the targeting system of the present invention.

As another example of a specific application, silencing of innate and/or adaptive immune mediators at local sites enables the prevention of organ transplant rejection. Local delivery of the targeting system and/or immunomodulating reagents with the Loder implanted into the transplanted organ and/or the implanted site renders local immune suppression by repelling immune cells such as CD8 activated against the transplanted organ. All of this may be used and/or adapted to the targeting system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, the targeting system or components thereof or nucleic acid molecules thereof or encoding or providing components may be delivered via an implantable device.

Nanoclews

The targeting system may be delivered using nanoclews, for example as described in Sun W et al, Cocoon-like self-degradable DNA nanoclew for anticancer drug delivery., J Am Chem Soc. 2014 Oct. 22; 136(42):14722-5. doi: 10.1021/ja5088024. Epub 2014 Oct. 13.

LNP

In some embodiments, delivery is by encapsulation of the engineered protein or polypeptide or nucleic acid molecules encoding thereof form in a lipid particle such as an LNP. In some embodiments, therefore, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the targeting system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding the engineered targeting protein to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilinoleyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011).

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with nucleic acid molecules may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of the engineered targeting protein is envisioned for delivery in the self-assembling nanoparticles of Schiffelers et al.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain, a biologically active material.

U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

International Patent Publication No. WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it is envisioned that such conjugated lipomers can be used in the context of the targeting system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). 7C1 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the targeting system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

In some embodiments, the LNP for delivering nucleic acid molecules or protein components of the targeting system is prepared by methods known in the art, such as those described in, for example, International Patent Publication Nos. WO 2005/105152 (PCT/EP2005/004920), WO 2006/069782 (PCT/EP2005/014074), WO 2007/121947 (PCT/EP2007/003496), and WO 2015/082080 (PCT/EP2014/003274), which are herein incorporated by reference. LNPs aimed specifically at the enhanced and improved delivery of siRNA into mammalian cells are described in, for example, Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014), which are herein incorporated by reference and may be applied to the present technology.

In some embodiments, the LNP includes any LNP disclosed in International Patent Publication Nos. WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

In some embodiments, the LNP includes at least one lipid having Formula I:

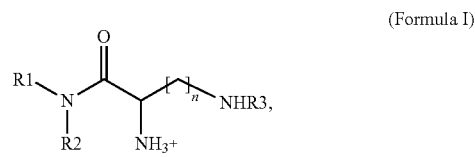

(Formula I)

wherein R1 and R2 are each and independently selected from the group comprising alkyl, n is any integer between 1 and 4, and R3 is an acyl selected from the group comprising lysyl, ornithyl, 2,4-diaminobutyryl, histidyl and an acyl moiety according to Formula II:

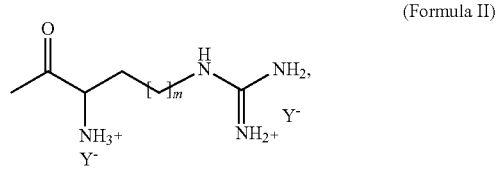

(Formula II)

wherein m is any integer from 1 to 3 and Y⁻ is a pharmaceutically acceptable anion. In some embodiments, a lipid according to Formula I includes at least two asymmetric C atoms. In some embodiments, enantiomers of Formula I include, but are not limited to, R-R; S-S; R—S and S-R enantiomer.

In some embodiments, R1 is lauryl and R2 is myristyl. In another embodiment, R1 is palmityl and R2 is oleyl. In some embodiments, m is 1 or 2. In some embodiments, Y⁻ is selected from halogenides, acetate or trifluoroacetate.

In some embodiments, the LNP comprises one or more lipids select from:
β-arginyl-2,3-diamino propionic acid-N-palmityl-N-oleyl-amide trihydrochloride (Formula III):

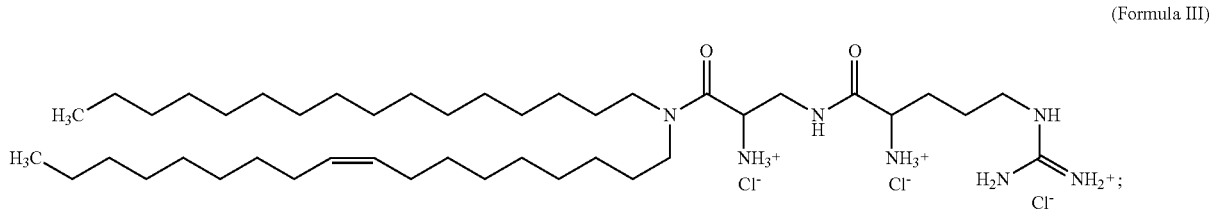 [SMILES: CCCCCCCC/C=C\CCCCCCCCN(CCCCCCCCCCCCCCCC)C(=O)C(N)CNC(=O)C(N)CCCNC(=N)N ; [Cl-] ; [Cl-] ; [Cl-]]

(Formula III)

β-arginyl-2,3-diamino propionic acid-N-lauryl-N-myristyl-amide trihydrochloride (Formula IV):

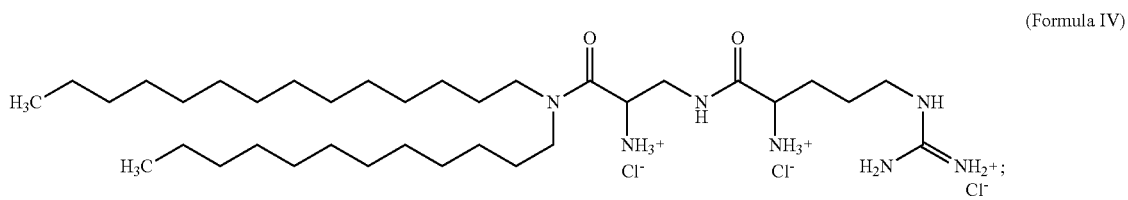 [SMILES: CCCCCCCCCCCCCCN(CCCCCCCCCCCC)C(=O)C(N)CNC(=O)C(N)CCCNC(=N)N ; [Cl-] ; [Cl-] ; [Cl-]]

(Formula IV)

and
ε-arginyl-lysine-N-lauryl-N-myristyl-amide trihydrochloride (Formula V):

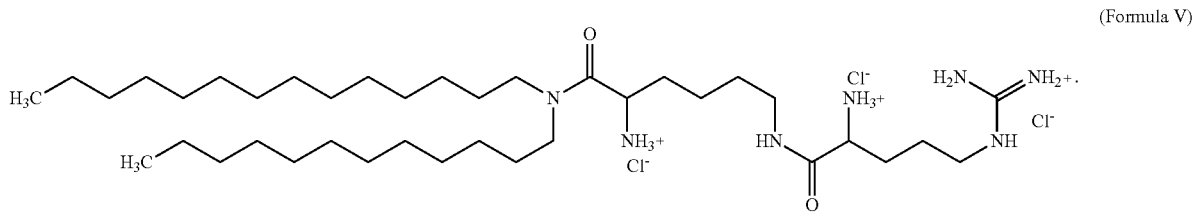 [SMILES: CCCCCCCCCCCCCCN(CCCCCCCCCCCC)C(=O)C(N)CCCCNC(=O)C(N)CCCNC(=N)N ; [Cl-] ; [Cl-] ; [Cl-]]

(Formula V)

In some embodiments, the LNP also includes a constituent. By way of example, but not by way of limitation, in some embodiments, the constituent is selected from peptides, proteins, oligonucleotides, polynucleotides, nucleic acids, or a combination thereof. In some embodiments, the constituent is an antibody, e.g., a monoclonal antibody. In some embodiments, the constituent is a nucleic acid selected from, e.g., ribozymes, aptamers, spiegelmers, DNA, RNA, PNA, LNA, or a combination thereof.

In some embodiments, the constituent of the LNP comprises the engineered protein or polypeptide of the targeting system. In some embodiments, the constituent of the LNP comprises a DNA or an mRNA encoding the engineered protein or polypeptide of the targeting system.

In some embodiments, the LNP also includes at least one helper lipid. In some embodiments, the helper lipid is selected from phospholipids and steroids. In some embodiments, the phospholipids are di- and/or monoester of the phosphoric acid. In some embodiments, the phospholipids are phosphoglycerides and/or sphingolipids. In some embodiments, the steroids are naturally occurring and/or synthetic compounds based on the partially hydrogenated cyclopenta[a]phenanthrene. In some embodiments, the steroids contain 21 to 30 C atoms. In some embodiments, the steroid is cholesterol. In some embodiments, the helper lipid is selected from 1,2-diphytanoyl-sn-glycero-3-phosphoethanolamine (DPhyPE), ceramide, and 1,2-dioleyl-sn-glycero-3-phosphoethanolamine (DOPE).

In some embodiments, the at least one helper lipid comprises a moiety selected from the group comprising a PEG moiety, a HEG moiety, a polyhydroxyethyl starch (poly-HES) moiety and a polypropylene moiety. In some embodiments, the moiety has a molecule weight between about 500 to 10,000 Da or between about 2,000 to 5,000 Da. In some embodiments, the PEG moiety is selected from 1,2-distearoyl-sn-glycero-3 phosphoethanolamine, 1,2-dialkyl-sn-glycero-3-phosphoethanolamine, and Ceramide-PEG. In some embodiments, the PEG moiety has a molecular weight between about 500 to 10,000 Da or between about 2,000 to 5,000 Da. In some embodiments, the PEG moiety has a molecular weight of 2,000 Da.

In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

In some embodiments, the LNP includes any of 3-arginyl-2,3-diaminopropionic acid-N-palmityl-N-oleyl-amide trihydrochloride, arginyl-2,3-diaminopropionic acid-N-lauryl-N-myristyl-amide trihydrochloride or arginyl-lysine-N-lauryl-N-myristyl-amide trihydrochloride in combination with DPhyPE, wherein the content of DPhyPE is about 80 mol %, 65 mol %, 50 mol % and 35 mol % of the overall lipid content of the LNP. In some embodiments, the LNP includes arginyl-2,3-diamino propionic acid-N-pahnityl-N-oleyl-amide trihydrochloride (lipid) and 1,2-diphytanoyl-sn-glycero-3-phosphoethanolamine (helper lipid). In some embodiments, the LNP includes arginyl-2,3-diamino propionic acid-N-palmityl-N-oleyl-amide trihydrochloride (lipid), 1,2-diphytanoyl-sn-glycero-3-phosphoethanolamine (first helper lipid), and 1,2-disteroyl-sn-glycero-3-phosphoethanolamine-PEG2000 (second helper lipid).

In some embodiments, the second helper lipid is between about 0.05 mol % to 4.9 mol % or between about 1 mol % to 3 mol % of the total lipid content. In some embodiments, the LNP includes lipids at between about 45 mol % to 50 mol % of the total lipid content, a first helper lipid between about 45 mol % to 50 mol % of the total lipid content, under the proviso that there is a PEGylated second helper lipid between about 0.1 mol % to 5 mol %, between about 1 mol % to 4 mol %, or at about 2 mol % of the total lipid content, wherein the sum of the content of the lipids, the first helper lipid, and of the second helper lipid is 100 mol % of the total lipid content and wherein the sum of the first helper lipid and the second helper lipid is 50 mol % of the total lipid content. In some embodiments, the LNP comprises: (a) 50 mol % of arginyl-2,3-diamino propionic acid-N-palmityl-N-oleyl-amide trihydrochloride, 48 mol % of 1,2-diphytanoyl-sn-glycero-3-phosphoethanolamine; and 2 mol % 1,2-distearoyl-sn-glycero-3-phosphoethanolamine-PEG2000; or (b) 50 mol % of arginyl-2,3-diamino propionic acid-N-palmityl-N-oleyl-amide trihyrdrochloride, 49 mol % 1,2-diphytanoyl-sn-glycero-3-phosphoethanolamine; and 1 mol % N(Carbonyl-methoxypolyethylenglycol-2000)-1,2-distearoyl-sn-glycero-3-phosphoethanolamine, or a sodium salt thereof.

In some embodiments, the LNP contains a nucleic acid, wherein the charge ratio of nucleic acid backbone phosphates to cationic lipid nitrogen atoms is about 1: 1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylengycoles (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP includes at least one lipid, a first helper lipid, and a shielding compound that is removable from the lipid composition under in vivo conditions. In some embodiments, the LNP also includes a second helper lipid. In some embodiments, the first helper lipid is ceramide. In some embodiments, the second helper lipid is ceramide. In some embodiments, the ceramide comprises at least one short carbon chain substituent of from 6 to 10 carbon atoms. In some embodiments, the ceramide comprises 8 carbon atoms. In some embodiments, the shielding compound is attached to a ceramide. In some embodiments, the shielding compound is attached to a ceramide. In some embodiments, the shielding compound is covalently attached to the ceramide. In some embodiments, the shielding compound is attached to a nucleic acid in the LNP. In some embodiments, the shielding compound is covalently attached to the nucleic acid. In some embodiments, the shielding compound is attached to the nucleic acid by a linker. In some embodiments, the linker is cleaved under physiological conditions. In some embodiments, the linker is selected from ssRNA, ssDNA, dsRNA, dsDNA, peptide, S-S-linkers and pH sensitive linkers. In some embodiments, the linker moiety is attached to the 3' end of the sense strand of the nucleic acid. In some embodiments, the shielding compound comprises a pH-sensitive linker or a pH-sensitive moiety. In some embodiments, the pH-sensitive linker or pH-sensitive moiety is an anionic linker or an anionic moiety. In some embodiments, the anionic linker or anionic moiety is less anionic or neutral in an acidic environment. In some embodiments, the pH-sensitive linker or the pH-sensitive moiety is selected from the oligo (glutamic acid), oligophenolate(s) and diethylene triamine penta acetic acid.

In any of the LNP embodiments in the previous paragraph, the LNP can have an osmolality between about 50 to 600 mosmole/kg, between about 250 to 350 mosmole/kg, or between about 280 to 320 mosmole/kg, and/or wherein the LNP formed by the lipid and/or one or two helper lipids and the shielding compound have a particle size between about 20 to 200 nm, between about 30 to 100 nm, or between about 40 to 80 nm.

In some embodiments, the shielding compound provides for a longer circulation time in vivo and allows for a better biodistribution of the nucleic acid containing LNP. In some embodiments, the shielding compound prevents immediate interaction of the LNP with serum compounds or compounds of other bodily fluids or cytoplasmic membranes, e.g., cytoplasmic membranes of the endothelial lining of the vasculature, into which the LNP is administered. Additionally or alternatively, in some embodiments, the shielding compounds also prevent elements of the immune system from immediately interacting with the LNP. Additionally or alternatively, in some embodiments, the shielding compound acts as an anti-opsonizing compound. Without wishing to be bound by any mechanism or theory, in some embodiments, the shielding compound forms a cover or coat that reduces the surface area of the LNP available for interaction with its environment. Additionally or alternatively, in some embodiments, the shielding compound shields the overall charge of the LNP.

In another embodiment, the LNP includes at least one cationic lipid having Formula VI:

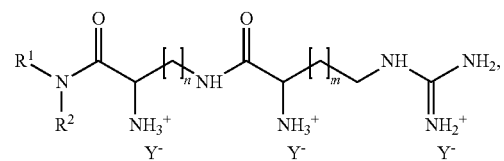

(Formula VI)

wherein n is 1, 2, 3, or 4, wherein m is 1, 2, or 3, wherein $Y^-$ is anion, wherein each of $R^1$ and $R^2$ is individually and independently selected from the group consisting of linear $C_{12}$-$C_{18}$ alkyl and linear $C_{12}$-$C_{18}$ alkenyl, a sterol compound, wherein the sterol compound is selected from the group consisting of cholesterol and stigmasterol, and a PEGylated lipid, wherein the PEGylated lipid comprises a PEG moiety, wherein the PEGylated lipid is selected from the group consisting of:

a PEGylated phosphoethanolamine of Formula VII:

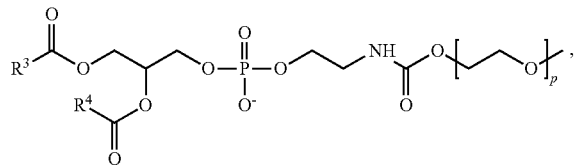

(Formula VII)

wherein $R^3$ and $R^4$ are individually and independently linear $C_{13}$-$C_{17}$ alkyl, and p is any integer between 15 to 130;

a PEGylated ceramide of Formula VIII:

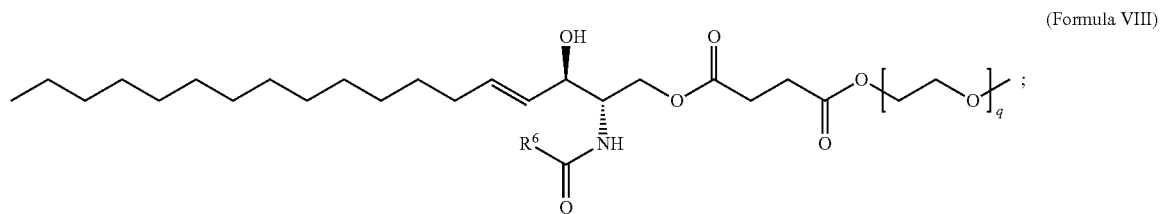

(Formula VIII)

wherein $R^5$ is linear $C_7$-$C_{15}$ alkyl, and q is any number between 15 to 130; and a PEGylated diacylglycerol of Formula IX:

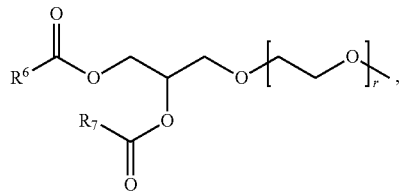

(Formula IX)

wherein each of $R^6$ and $R^7$ is individually and independently linear $C_{11}$-$C_{17}$ alkyl, and r is any integer from 15 to 130.

In some embodiments, $R^1$ and $R^2$ are different from each other. In some embodiments, $R^1$ is palmityl and $R^2$ is oleyl. In some embodiments, $R^1$ is lauryl and $R^2$ is myristyl. In some embodiments, $R^1$ and $R^2$ are the same. In some embodiments, each of $R^1$ and $R^2$ is individually and independently selected from the group consisting of $C_{12}$ alkyl, $C_{14}$ alkyl, $C_{16}$ alkyl, $C_{18}$ alkyl, $C_{12}$ alkenyl, $C_{14}$ alkenyl, $C_{16}$ alkenyl and $C_{18}$ alkenyl. In some embodiments, each of $C_{12}$ alkenyl, $C_{14}$ alkenyl, $C_{16}$ alkenyl and $C_{18}$ alkenyl comprises one or two double bonds. In some embodiments, $C_{18}$ alkenyl is $C_{18}$ alkenyl with one double bond between $C_9$ and $C_{10}$. In some embodiments, $C_{18}$ alkenyl is cis-9-octadecyl.

In some embodiments, the cationic lipid is a compound of Formula X:

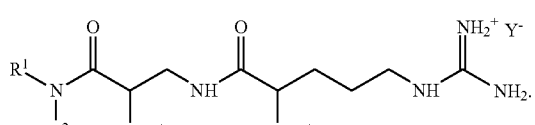

(Formula X)

In some embodiments, $Y^-$ is selected from halogenides, acetate and trifluoroacetate. In some embodiments, the cationic lipid is β-arginyl-2,3-diamino propionic acid-N-palmityl-N-oleyl-amide trihydrochloride of Formula III:

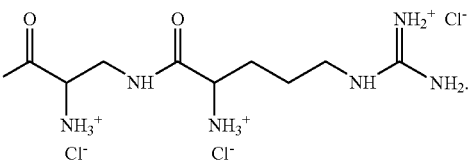

(Formula III)

In some embodiments, the cationic lipid is β-arginyl-2,3-diamino propionic acid-N-lauryl-N-myristyl-amide trihydrochloride of Formula IV:

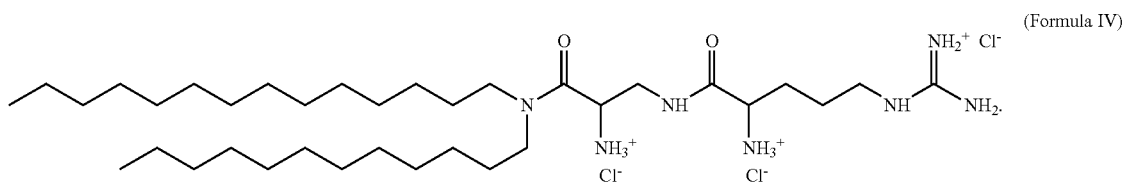

(Formula IV)

In some embodiments, the cationic lipid is ε-arginyl-lysine-N-lauryl-N-myristyl-amide trihydrochloride of Formula V:

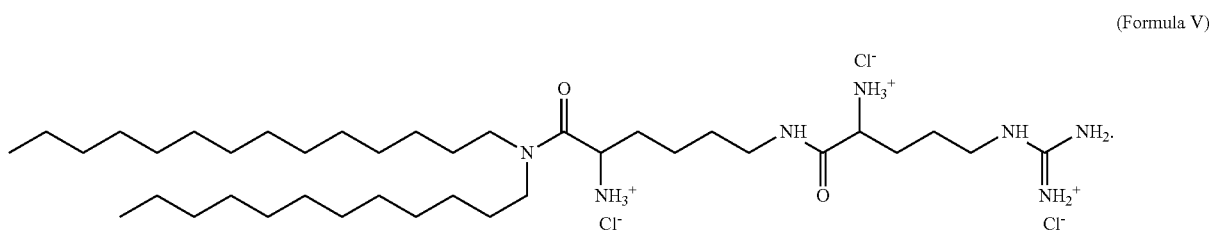 [SMILES: [Cl-] ; CCCCCCCCCCCCCCN(CCCCCCCCCCCC)C(=O)C([NH3+])CCCCNC(=O)C([NH3+])CCCNC(N)=[NH2+] ; [Cl-] ; [Cl-]]

(Formula V)

In some embodiments, the sterol compound is cholesterol. In some embodiments, the sterol compound is stigmasterin.

In some embodiments, the PEG moiety of the PEGylated lipid has a molecular weight from about 800 to 5,000 Da. In some embodiments, the molecular weight of the PEG moiety of the PEGylated lipid is about 800 Da. In some embodiments, the molecular weight of the PEG moiety of the PEGylated lipid is about 2,000 Da. In some embodiments, the molecular weight of the PEG moiety of the PEGylated lipid is about 5,000 Da. In some embodiments, the PEGylated lipid is a PEGylated phosphoethanolamine of Formula VII, wherein each of $R^3$ and $R^4$ is individually and independently linear $C_{13}$-$C_{17}$ alkyl, and p is any integer from 18, 19 or 20, or from 44, 45 or 46 or from 113, 114 or 115. In some embodiments, $R^3$ and $R^4$ are the same. In some embodiments, $R^3$ and $R^4$ are different. In some embodiments, each of $R^3$ and $R^4$ is individually and independently selected from the group consisting of $C_{13}$ alkyl, $C_{15}$ alkyl and $C_{17}$ alkyl. In some embodiments, the PEGylated phosphoethanolamine of Formula VII is 1,2-distearoyl-sn-glycero-3-phosphoethanolamine-N-[methoxy(polyethylene glycol)-2000] (ammonium salt):

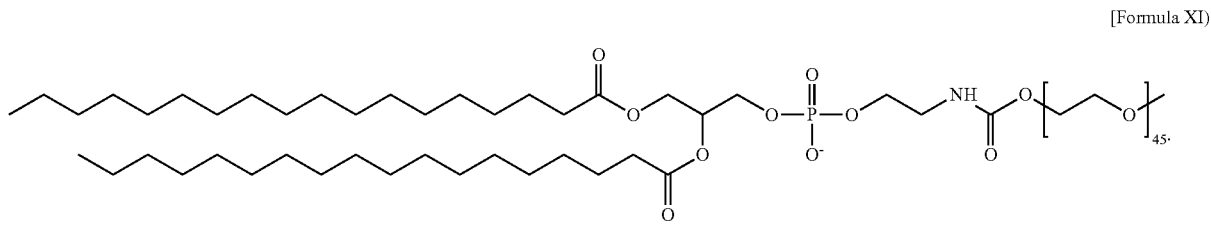

[Formula XI)

In some embodiments, the PEGylated phosphoethanolamine of Formula VII is 1,2-distearoyl-sn-glycero-3-phosphoethanolamine-N-[methoxy(polyethylene glycol)-5000](ammonium salt):

[Formula XII]

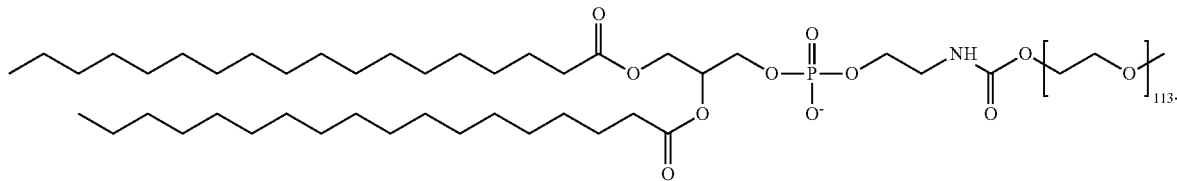

In some embodiments, the PEGylated lipid is a PEGylated ceramide of Formula VIII, wherein $R^5$ is linear $C_7$-$C_{15}$ alkyl, and q is any integer from 18, 19 or 20, or from 44, 45 or 46 or from 113, 114 or 115. In some embodiments, $R^5$ is linear $C_7$ alkyl. In some embodiments, $R^5$ is linear $C_{15}$ alkyl. In some embodiments, the PEGylated ceramide of Formula VIII is N-octanoyl-sphingosine-1-{succinyl[methoxy(polyethylene glycol)2000]}:

(Formula XIII)

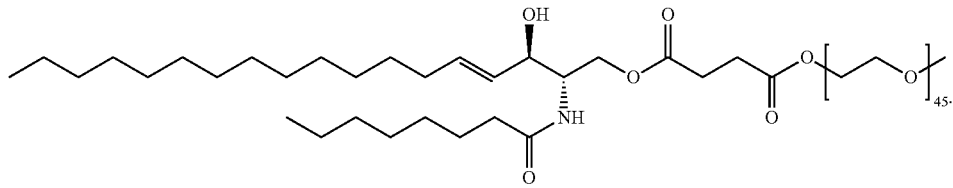

In some embodiments, the PEGylated ceramide of Formula VIII is N-palmitoyl-sphingosine-1-{succinyl[methoxy(polyethylene glycol)2000]}

(Formula XIV)

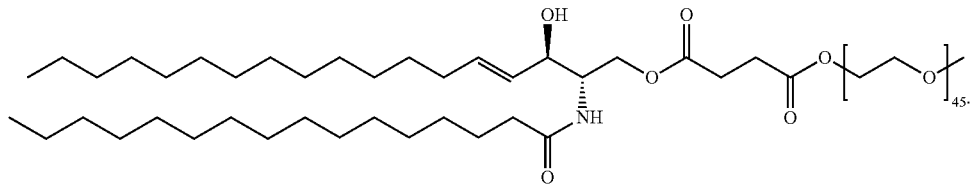

In some embodiments, the PEGylated lipid is a PEGylated diacylglycerol of Formula IX, wherein each of $R^6$ and $R^7$ is individually and independently linear $C_{11}$-$C_{17}$ alkyl, and r is any integer from 18, 19 or 20, or from 44, 45 or 46 or from 113, 114 or 115. In some embodiments, $R^6$ and $R^7$ are the same. In some embodiments, $R^6$ and $R^7$ are different. In some embodiments, each of $R^6$ and $R^7$ is individually and independently selected from the group consisting of linear $C_{17}$ alkyl, linear $C_{15}$ alkyl and linear $C_{13}$ alkyl. In some embodiments, the PEGylated diacylglycerol of Formula IX 1,2-Distearoyl-sn-glycerol [methoxy(polyethylene glycol)2000]:

(Formula XV)

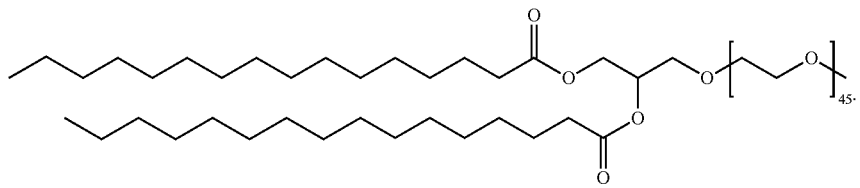

In some embodiments, the PEGylated diacylglycerol of Formula IX is 1,2-Dipalmitoyl-sn-glycerol [methoxy(polyethylene glycol)2000]:

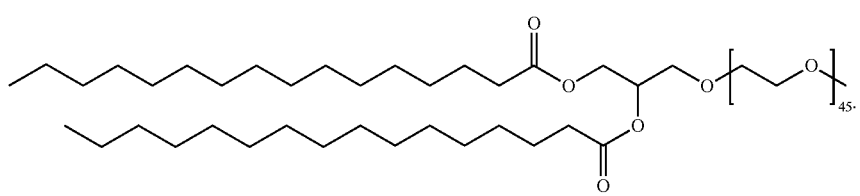

(Formula XVI)

In some embodiments, the PEGylated diacylglycerol of Formula IX is:

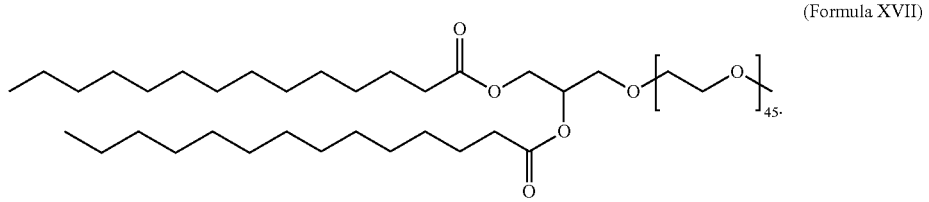

(Formula XVII)

In some embodiments, the LNP includes at least one cationic lipid selected from of Formulas III, IV, and V, at least one sterol compound selected from a cholesterol and stigmasterin, and wherein the PEGylated lipid is at least one selected from Formulas XI and XII. In some embodiments, the LNP includes at least one cationic lipid selected from Formulas III, IV, and V, at least one sterol compound selected from a cholesterol and stigmasterin, and wherein the PEGylated lipid is at least one selected from Formulas XIII and XIV. In some embodiments, the LNP includes at least one cationic lipid selected from Formulas III, IV, and V, at least one sterol compound selected from a cholesterol and stigmasterin, and wherein the PEGylated lipid is at least one selected from Formulas XV and XVI. In some embodiments, the LNP includes a cationic lipid of Formula III, a cholesterol as the sterol compound, and wherein the PEGylated lipid is Formula XI.

In any of the LNP embodiments in the previous paragraph, wherein the content of the cationic lipid composition is between about 65 mole % to 75 mole %, the content of the sterol compound is between about 24 mole % to 34 mole % and the content of the PEGylated lipid is between about 0.5 mole % to 1.5 mole %, wherein the sum of the content of the cationic lipid, of the sterol compound and of the PEGylated lipid for the lipid composition is 100 mole %. In some embodiments, the cationic lipid is about 70 mole %, the content of the sterol compound is about 29 mole % and the content of the PEGylated lipid is about 1 mole %. In some embodiments, the LNP is 70 mole % of Formula III, 29 mole % of cholesterol, and 1 mole % of Formula XI.

Aerosol Delivery

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector.

Hybrid Viral Capsid Delivery Systems

In one aspect, the invention provides a particle delivery system comprising a hybrid virus capsid protein or hybrid viral outer protein, wherein the hybrid virus capsid or outer protein comprises a virus capsid or outer protein attached to at least a portion of a non-capsid protein or peptide. The genetic material of a virus is stored within a viral structure called the capsid. The capsid of certain viruses are enclosed in a membrane called the viral envelope. The viral envelope is made up of a lipid bilayer embedded with viral proteins including viral glycoproteins. As used herein, an "envelope protein" or "outer protein" means a protein exposed at the surface of a viral particle that is not a capsid protein. For example envelope or outer proteins typically comprise proteins embedded in the envelope of the virus. Non-limiting examples of outer or envelope proteins include, without limit, gp41 and gp120 of HIV, hemagglutinin, neuraminidase and M2 proteins of influenza virus.

In one example embodiment of the delivery system, the non-capsid protein or peptide has a molecular weight of up to a megadalton, or has a molecular weight in the range of 110 to 160 kDa, 160 to 200 kDa, 200 to 250 kDa, 250 to 300 kDa, 300 to 400 kDa, or 400 to 500 kDa, the non-capsid protein or peptide comprises an engineered protein or polypeptide of the targeting system.

The present application provides a vector for delivering an effector protein and at least one targeting system comprising an engineered protein or polypeptide or nucleic acid molecule encoding thereof to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4 Kb. In an embodiment, the virus is an adeno-associated virus (AAV) or an adenovirus.

In an embodiment of the delivery system, the virus is lentivirus or murine leukemia virus (MuLV).

In an embodiment of the delivery system, the virus is an Adenoviridae or a Parvoviridae or a retrovirus or a Rhabdoviridae or an enveloped virus having a glycoprotein protein (G protein).

In an embodiment of the delivery system, the virus is VSV or rabies virus.

In an embodiment of the delivery system, the capsid or outer protein comprises a capsid protein having VP1, VP2 or VP3.

In an embodiment of the delivery system, the capsid protein is VP3, and the non-capsid protein is inserted into or attached to VP3 loop 3 or loop 6.

In an embodiment of the delivery system, the virus is delivered to the interior of a cell.

In an embodiment of the delivery system, the capsid or outer protein and the non-capsid protein can dissociate after delivery into a cell.

In an embodiment of the delivery system, the capsid or outer protein is attached to the protein by a linker.

In an embodiment of the delivery system, the linker comprises amino acids.

In an embodiment of the delivery system, the linker is a chemical linker.

In an embodiment of the delivery system, the linker is cleavable.

In an embodiment of the delivery system, the linker is biodegradable.

In an embodiment of the delivery system, the linker comprises (GGGGS)$_{1-3}$ (SEQ ID NO:45-47), ENLYFQG (SEQ ID NO:48), or a disulfide.

In an embodiment, the delivery system comprises a protease or nucleic acid molecule(s) encoding a protease that is expressed, said protease being capable of cleaving the linker, whereby there can be cleavage of the linker. In an embodiment of the invention, a protease is delivered with a particle component of the system, for example packaged, mixed with, or enclosed by lipid and/or capsid. Entry of the particle into a cell is thereby accompanied or followed by cleavage and dissociation of payload from particle. In certain embodiments, an expressible nucleic acid encoding a protease is delivered, whereby at entry or following entry of the particle into a cell, there is protease expression, linker cleavage, and dissociation of payload from capsid. In certain embodiments, dissociation of payload occurs with viral replication. In certain embodiments, dissociation of payload occurs in the absence of productive virus replication.

In an embodiment of the delivery system, each terminus of a engineered targeting protein is attached to the capsid or outer protein by a linker.

In an embodiment of the delivery system, the non-capsid protein is attached to the exterior portion of the capsid or outer protein.

In an embodiment of the delivery system, the non-capsid protein is attached to the interior portion of the capsid or outer protein.

In an embodiment of the delivery system, the capsid or outer protein and the non-capsid protein are a fusion protein.

In an embodiment of the delivery system, the non-capsid protein is encapsulated by the capsid or outer protein.

In an embodiment of the delivery system, the non-capsid protein is attached to a component of the capsid protein or a component of the outer protein prior to formation of the capsid or the outer protein.

In an embodiment of the delivery system, the protein is attached to the capsid or outer protein after formation of the capsid or outer protein.

In an embodiment, the delivery system comprises a targeting moiety, such as active targeting of a lipid entity of the invention, e.g., lipid particle or nanoparticle or liposome or lipid bilayer of the invention comprising a targeting moiety for active targeting.

With regard to targeting moieties, mention is made of Deshpande et al, "Current trends in the use of liposomes for tumor targeting," Nanomedicine (Lond). 8(9), doi:10.2217/nnm.13.118 (2013), and the documents it cites, all of which are incorporated herein by reference. Mention is also made of International Patent Publication Nos. WO 2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203: 1-15 (2015), and the documents it cites, all of which are incorporated herein by reference.

An actively targeting lipid particle or nanoparticle or liposome or lipid bilayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell sce receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also as to active targeting, with regard to targeting cell surface receptors such as cancer cell surface receptors, targeting ligands on liposomes can provide attachment of liposomes to cells, e.g., vascular cells, via a noninternalizing epitope; and, this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bilayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirus or AAV. Tf is a monomeric serum glycoprotein of approximately 80 KDa involved in the transport of iron throughout the body. Tf binds to the TfR and translocates into cells via receptor-mediated endocytosis. The expression of TfR can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR, is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody (or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bilayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG (SEQ ID NO: 92) such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention, e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. α- and β-integrins or integrins are a group of transmembrane glycoprotein receptors that mediate attachment between a cell and its surrounding tissues or extracellular matrix. Integrins contain two distinct chains (heterodimers) called α- and β-subunits. The tumor tissue-specific expression of integrin receptors can be been utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydrophobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of a particular environment or microenvironment such as an endocytic vacuole or the acidotic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly (methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes. The invention also comprehends redox-triggered delivery: The difference in redox potential between normal and inflamed or tumor tissues, and between the intra- and extra-cellular environments has been exploited for delivery; e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfide-to-thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl)phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. an MMP2-cleavable octapeptide (Gly-Pro-Leu-Gly-Ile-Ala-Gly-Gln) (SEQ ID NO: 93) can be incorporated into a linker, and can have antibody targeting, e.g., antibody 2C5. The invention also comprehends light- or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorated hydrocarbon can be triggered to release with ultrasound, e.g., low-frequency ultrasound (LFUS). Magnetic delivery: A lipid entity of the invention can be magnetized by incorporation of magnetites, such as $Fe_3O_4$ or $\gamma$-$Fe_2O_3$, e.g., those that are less than 10 nm in size. Targeted delivery can be then by exposure to a magnetic field.

Also as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA, cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

Also as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding. Other CPPs that have been used for the modification of liposomes include the following: the minimal protein transduction domain of Antennapedia, a *Drosophila* homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, mastoparan, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprehends a lipid entity of the invention modified with CPP(s), for intracellular delivery that may proceed via energy dependent macropinocytosis followed by endosomal escape. The invention further comprehends organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the invention includes the delivery system comprising an actively targeting lipid particle or nanoparticle or liposome or lipid bilayer delivery system; or comprising a lipid particle or nanoparticle or liposome or lipid bilayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

It should be understood that as to each possible targeting or active targeting moiety herein-discussed, there is an aspect of the invention wherein the delivery system comprises such a targeting or active targeting moiety. Likewise, the following table provides exemplary targeting moieties that can be used in the practice of the invention an as to each an aspect of the invention provides a delivery system that comprises such a targeting moiety.

| Targeting Moiety | Target Molecule | Target Cell or Tissue |
|---|---|---|
| folate | folate receptor | cancer cells |
| transferrin | transferrin receptor | cancer cells |
| Antibody CC52 | rat CC531 | rat colon adenocarcinoma CC531 |
| anti- HER2 antibody | HER2 | HER2 -overexpressing tumors |
| anti-GD2 | GD2 | neuroblastoma, melanoma |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) | $\alpha v \beta 3$ | glioblastoma cells, human umbilical vein endothelial cells, tumor angiogenesis |
| ASSHN peptide | | endothelial progenitor cells; anti-cancer |
| PR _b peptide | $\alpha_5 \beta_1$ integrin | cancer cells |
| AG86 peptide | $\alpha_6 \beta_4$ integrin | cancer cells |
| KCCYSL (P6. 1 peptide) | HER-2 receptor | cancer cells |
| affinity peptide LN (YEVGHRC) | Aminopeptidase N (APN/CD13) | APN-positive tumor |
| synthetic somatostatin analogue | Somatostatin receptor 2 (SSTR2) | breast cancer |
| anti-CD20 monoclonal antibody | B-lymphocytes | B cell lymphoma |

Thus, in an embodiment of the delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an aspect of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6(4):1062-73; doi: 10.1021/mp800215d (2009); Sonoke et al, "Galactose-modified cationic liposomes as a liver-targeting delivery system for small interfering RNA," Biol Pharm Bull. 34(8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13(14): 2026-2035

(2013); Molavi et al, "Anti-CD30 antibody conjugated liposomal doxorubicin with significantly improved therapeutic efficacy against anaplastic large cell lymphoma," Biomaterials 34(34):8718-25 (2013), each of which and the documents cited therein are hereby incorporated herein by reference).

Moreover, in view of the teachings herein the skilled artisan can readily select and apply a desired targeting moiety in the practice of the invention as to a lipid entity of the invention. The invention comprehends an embodiment wherein the delivery system comprises a lipid entity having a targeting moiety.

Functional Alteration and Screening

In one aspect, the present invention provides a composition comprising a library of engineered protein or polypeptide each comprising one or more LRR. The LRR may be derived from same or different organisms. The LRR may be generated by duplication, introductions of mutations, substitution of one or more amino acid residues, or shuffling of one or more LRR. In some embodiments, the LRR sequences of a library recognize different targets. In some embodiments, the LRR sequences of a library recognize same or similar targets. In some embodiments, the LRR sequences of a library recognize targets that share more than 10%, 20%, 30%, 40%, 50%, 60%, 70%, 80%, 90%, or 95% amino acid or nucleotide sequence identity with each other. In some embodiments, the LRR sequences of a library recognize targets that share structural similarities. In some embodiments, the LRR sequences of a library recognize targets that are involved in one or more cellular or biological functions, such as a metabolic pathway or a catalytic cascade. In some embodiments, the LRR is duplicated. In some embodiments, the LRR is mutated. In some embodiments, one or more amino acid residues in the LRR are substituted. In some embodiments, one or more amino acid residues in the LRR are substituted with one or more amino acid residues from a heterologous LRR derived from a different source. In some embodiments, one or more amino acid residues in the LRR are substituted with one or more amino acid residues from a LRR derived from the same species or related species. In some embodiments, the engineered protein or polypeptide comprises one or more LRR generated by shuffling of one or more LRR. In some embodiments, the engineered protein or polypeptide comprises one or more LRR generated by linking a LRR to one or more LRR from a different source. In some embodiments, one or more LRR is modified by introducing a mutation to a non-hypervariable region. In a preferred embodiment, one or more LRR is modified by introducing a mutation to a hypervariable region. In some embodiments, one or more LRR is modified by introducing a mutation to a non-hypervariable or conserved region, wherein the engineered protein or polypeptide comprises two or more LRR sequences.

In one aspect, the present invention provides for a method of functional evaluation and screening of genes and gene products. The use of the targeting system of the present invention to precisely deliver functional domains to specific targets, to modify the expression level of genes and gene products can be applied to a single cell or population of cells or with a library applied to the entire proteome in a pool of cells ex vivo or in vivo comprising the administration or expression of a library comprising a plurality of LRRs and wherein the screening further comprises use of engineered targeting protein or polypeptide, wherein the engineered protein or polypeptide is associated with a functional domain. In an aspect the invention provides a method for screening a genome, transcriptome, or proteome comprising the administration to a host or expression in a host in vivo of a library comprising a plurality of LRR and wherein the screening further comprises use of engineered targeting protein or polypeptide, wherein the engineered protein or polypeptide is associated with a functional domain. In some embodiments, the functional domain may be a transcription activation domain, a transcription repressor domain, a recombinase domain, a transposase domain, a histone remodeler, a demethylase, a methyltransferase, a cryptochrome, or a light inducible/controllable domain or a chemically inducible/controllable domain. In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. In some embodiments, the functional domain may be comprise protease activity, myristoyltransferase activity, acyltransferase activity, farnesyltransferase activity, geranylgeranyltransferase activity, acetyltransferase activity, glycinamide ribonucleotide (GAR) transformylase activity, glutamylase activity, deglutamylase activity, carboxylase activity, glycosyltransferases activity, hydroxylases activity, nucleotidyl transferase activity, kinase activity, phosphotransferase activity, phosphatase activity, or other catalytic activities. Fusion protein may comprise any additional protein sequence, and optionally a linker sequence between any two domains. Examples of protein domains that may be fused to an engineered protein or polypeptide include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). An engineered protein may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a deaminase, such as a cytidine deaminase.

In an aspect, the invention provides a method as herein discussed, wherein the screening comprises affecting and detecting gene activation, gene inhibition, or cleavage in the locus.

In an aspect, the invention provides efficient on-target activity and minimizes off target activity. In an aspect, the invention provides efficient on-target modification, including cleavage, by the engineered targeting protein or polypeptide optionally associated with a functional domain and minimizes off-target modification or cleavage by the functional domain. Accordingly, in an aspect, the invention provides target-specific regulation of protein or gene expression.

In an aspect, the invention provides a method as herein discussed, wherein the host is a eukaryotic cell. In an aspect the invention provides a method as herein discussed, wherein the host is a mammalian cell. In an aspect the invention provides a method as herein discussed, wherein the host is a non-human eukaryote. In an aspect the invention provides a method as herein discussed, wherein the non-human eukaryote is a non-human mammal. In an aspect the invention provides a method as herein discussed, wherein the non-human mammal is a mouse. An aspect the invention provides a method as herein discussed comprising the delivery of the targeting system or component(s) thereof or nucleic acid molecule(s) coding therefor, wherein said nucleic acid molecule(s) are operatively linked to regulatory sequence(s) and expressed in vivo. In an aspect the invention provides a method as herein discussed wherein the expressing in vivo is via a lentivirus, an adenovirus, or an AAV. In an aspect the invention provides a method as herein discussed wherein the delivery is via a particle, a nanoparticle, a lipid or a cell penetrating peptide (CPP).

The targeting system and the engineered protein or polypeptide described herein can be used to perform screening for substrates such as proteins in conjunction with a cellular phenotype—for instance, for determining critical minimal features and discrete vulnerabilities of functional elements required for gene expression, drug resistance, and reversal of disease. In some embodiments, the targeting system and the engineered protein or polypeptide may be used to screen for specific domains involved in functions such as drug resistance or reversal of disease by targeting sequences or structures in given protein domains. In some embodiments, a library of engineered proteins or polypeptides, or a library of nucleic acids molecules encoding a plurality of engineered proteins, or a library of vectors comprising nucleic acid molecules encoding a plurality of engineered proteins or polypeptides may be introduced into a population of cells. The library may be introduced, such that each cell receives a single engineered protein or a single vector comprising an engineered protein or coding nucleic acid molecule thereof. In the case where the library is introduced by transduction of a viral vector, as described herein, a low multiplicity of infection (MOI) is used. The engineered protein or polypeptide may include any orthologs or modifications, or may be associated with a heterologous functional domain. Any phenotype determined to be associated with modification or cleavage of the target may be confirmed by detecting cellular level(s) of the target. The library of targeting system(s) can be used in eukaryotic cells, including but not limited to mammalian and plant cells. The population of cells may be prokaryotic cells. The population of eukaryotic cells may be a population of embryonic stem (ES) cells, neuronal cells, epithelial cells, immune cells, endocrine cells, muscle cells, erythrocytes, lymphocytes, plant cells, or yeast cells.

In one aspect, the present invention provides for a method of screening for functional elements associated with a change in a phenotype. The library may be introduced into a population of cells that are adapted to contain a protein comprising a functional domain. The cells may be sorted into at least two groups based on the phenotype. The phenotype may be expression of a gene, cell growth, or cell viability. The change in phenotype may be a change in expression of a gene of interest. The target substrate of interest may be detected or modified. The cells may be sorted into a high expression group and a low expression group. The population of cells may include a reporter construct that is used to determine the phenotype. The reporter construct may include a detectable marker. Cells may be sorted by use of the detectable marker.

In another aspect, the present invention provides for a method of screening for loci associated with resistance to a chemical compound. The chemical compound may be a drug or pesticide. The library may be introduced into a population of cells, wherein each cell of the population contains no more than one engineered protein or polypeptide or no more than one LRR. The population of cells are treated with the chemical compound; and the representation of the engineered protein or polypeptide is determined after treatment with the chemical compound at a later time point as compared to an early time point, whereby target substrates associated with resistance to the chemical compound may be determined by enrichment of the engineered protein or polypeptide.

Therapeutic Applications

As will be apparent, it is envisaged that the present system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the modified cell retains the altered phenotype. The modified cells and progeny may be part of a multi-cellular organism such as a plant or animal with ex vivo or in vivo application of targeting system to desired cell types. The invention may be a therapeutic method of treatment. The therapeutic method of treatment may comprise gene or genome editing, or gene therapy.

Patient-Specific Screening Methods

The targeting system of the present invention that targets protein, polypeptide, nucleic acid, polysaccharides, or other macromolecules can be used to detect and screen patients or patient samples for the presence of such macromolecules. For example, a targeting system that targets trinucleotide repeats (associated with a class of disorders such as Huntington's disease) can be used to screen patients or patent samples for the presence of such repeats. The repeats can be the target targeting system, and if there is binding thereto by the targeting system, that binding can be detected, to thereby indicate that such a repeat is present. The patient can then be administered suitable compound(s) to address the condition; or, can be administered a targeting system to bind to and modification or reduction of the macromolecule that causes the condition and alleviate the condition.

Anti-Inflammatory and Auto-Immune Disease Treatment

In certain embodiments, the targeting system or the engineered protein or polypeptide is used in an anti-inflammatory treatment. In certain embodiments, the engineered protein or polypeptide is used in treatment for acute or sub-acute inflammation. In some embodiments, the engineered protein or polypeptide is used in treatment for glomerulonephritis. In particular embodiments, the engineered protein or polypeptide is used in treatment for IgA nephropathy (IgAN) or Berger's disease. In some embodiments, the engineered protein or polypeptide is used in treatment for glomerular inflammation, mesangial hypercellularity, and expansion of mesangial matrix. In some embodiments, the engineered protein or polypeptide is used in treatment for progressive chronic kidney disease related to IgAN.

In certain embodiments, the engineered protein or polypeptide is used in treatment of sinusitis, asthma, bronchitis, or autoimmune disorders chronic obstructive pulmonary disease. In some embodiments, the engineered protein or polypeptide is used in treatment of chronic rhinosinusitis caused by allergies, bacterial and fungal infection, or anatomical abnormalities. In particular embodiments, the engineered protein or polypeptide is used to treat chronic rhinosinusitis with or without nasal polyps. In particular embodiments, the engineered protein or polypeptide is administered during sinus surgery.

In certain embodiments, the engineered protein of the targeting system provides methods of treatment for celiac disease. Celiac disease (CD) is an autoimmune condition affecting the small intestine, triggered by the ingestion of gluten, the protein fraction of wheat, barley, and rye. Strong linkage has been shown between CD and HLA-DQ2 and HLA-DQ8 haplotypes. More than 95% of those with CD express HLA-DQ2 while the remainder expresses HLA-DQ8. However, about 30-40% of the general population expresses HLA-DQ2, so while these HLA genes are necessary, they are not sufficient for developing CD and clearly non HLA genes are also involved. To date, at least 39 non-HLA genes have been identified through genome-wide association studies as strongly associated with CD, as reviewed in Kumar and Wijmenga, From genome-wide association studies to disease mechanisms: celiac disease as a model for autoimmune diseases. Semin Immunopathol. 2012 July; 34(4):567-80. The hallmark of CD is an immune-mediated enteropathy that involves both the innate and adaptive immune system. Initially gut paracellular permeability is increased in CD in part due to peptide-induced CXCR3 activated upregulation of zonulin, an intestinal peptide involved in epithelial tight junction control. Paracellular passage of gliadin peptides follows. α-gliadin has been shown to induce apoptosis of enterocytes, upregulate MHC class I molecules, activate MAP kinase pathway, and upregulate expression of CD83, a maturation marker of dendritic cells. This peptide, and others, enhances IL15 production leading to an expansion of intraepithelial lymphocytes (IELs) and triggering the innate immune system. IL15 plays a key role in enhanced cytolytic activity of IELs via induction of NK receptors on the IEL and also contributes to promoting the CD4+ T cell adaptive response. response leading to production of the pro-inflammatory cytokine interferon-γ (IFN-γ) [7]. Tissue transglutaminase (TTG), now known to be the autoantigen in CD, plays a key role in this process. By means of deamidation, TTG converts glutamine to glutamic acid at key sites within the gliadin peptide. This increases the negative charge on the peptide molecule and enhances binding of the peptide within the peptide binding groove of the HLA-DQ2 molecule on the surface of the antigen-presenting cells. See Denham and Hill, Celiac Disease and Autoimmunity: Review and Controversies. Curr. Allergy. Asthma Rep. 2013 13(4): 347-353. Among other approaches, use of oral proteases to help degrade toxic gliadin peptides before reaching the mucosa has been proposed as an advanced therapy. Accordingly, the targeting system of the present invention may be used to provide treatment or ameliorate symptoms of celiac disease. In some embodiments, the targeting system comprises an engineered protein or polypeptide, preferably associated with a functional domain, that blocks deamination of gluten peptides by tTG and/or interrupts HLA-DQ2/8 and gluten peptide binding. In some embodiments, the targeting system comprises an engineered protein or polypeptide, preferably associated with a functional domain, that targets and modifies anti-gluten antibodies and thereby silences gluten-reactive T cells.

In certain embodiments, the engineered protein or polypeptide is used in treatment of ischemic strokes. Ischemic strokes occur as a result of an obstruction within a blood vessel supplying blood to the brain. Proteases, including serine protease tissue plasminogen activator (tPA) have been studied and applied in treatment of ischemic strokes as demonstrated in Lapchak and Boitano, Effect of the Pleiotropic Drug CNB-001 on Tissue Plasminogen Activator (tPA) Protease Activity in vitro: Support for Combination Therapy to Treat Acute Ischemic Stroke. J. Neurol. Neurophysiol., 5(4): 214 (2014); Wang et al., Activated Protein C Analog Protects from Ischemic Stroke and Extends the Therapeutic Window of Tissue-type Plasminogen Activator in Aged Female Mice and Hypertensive Rats. Stroke 44(12): 3529-36 (2013). In particular embodiments, the engineered protein or peptide is used in treatment of acute ischemic strokes, brain trauma, spinal cord injury, amyotrophic lateral sclerosis and multiple sclerosis.

In certain embodiments, the engineered protein or polypeptide is used in treatment for wound healing and debridement. In certain embodiments, the engineered protein or polypeptide is involved in development and removal of perivascular fibrin cuffs and removal of dead tissues following inflammation. In certain embodiments, the engineered protein or polypeptide is used for removal of necrotic tissue from chronic wounds and burns. In certain embodiments, the engineered protein or polypeptide is used for treatment and removal of necrotic tissue in chronic limb wounds in patients with diabetes. In certain embodiments, the engineered protein or polypeptide is administered in the form of an ointment. In particular embodiments, the engineered protein or polypeptide is administered with continuous streaming and washing as described in Yaakobi et al., Wound Debridement by Continuous Streaming of Proteolytic Enzyme Solutions: Effects on Experimental Chronic Wound Model in Porcin. Wounds. 19(7): 192-200 (2007).

In certain embodiments, the engineered protein or polypeptide is used in treatment for bacterial infection. In certain embodiments, the engineered protein or polypeptide is used to prevent formation of biofilm and adherence of biofilm to subject tissues. In certain embodiments, the engineered protein or polypeptide is used to disrupt biofilm. In certain embodiments, the engineered protein or polypeptide is used in treatment for bacterial infection in conjunction with an anti-microbial agent. In certain embodiments, the engineered protein or polypeptide is used in treatment for bacterial infection in conjunction with antibiotics. In particular embodiments, the engineered protein or polypeptide is used in treatment for bacterial infection around implanted orthopedic devices. In certain embodiments, the engineered protein or polypeptide is used in treatment for sepsis.

In certain embodiments, the engineered protein or polypeptide is used in treatment for pancreatic insufficiency. In certain embodiments, the engineered protein or polypeptide is used in pancreatic enzyme replacement therapies. In some embodiments, the engineered protein or polypeptide is used in treatment for nutrient malabsorption related to pancreatic insufficiency. In some embodiments, the engineered protein or polypeptide is used to treat or ameliorate symptoms caused by cystic fibrosis or cancer.

In certain embodiments, the engineered protein or polypeptide is used for treatment of muscular contraction disorders. In some embodiments, the engineered protein or polypeptide is used for the treatment of dystonia, strabismus or blepharospasm. In particular embodiments, the engineered protein or polypeptide is used for treatment of glabellar lines, muscle spasticity, overactive bladder, alopecia areata, or prostatic hyperplasia.

In certain embodiments, the engineered protein or polypeptide is used to treat or ameliorate cancer symptoms. In certain embodiments, the engineered protein or polypeptide is used in disruption of fibrin associated to cancer cells. In some embodiments, the engineered protein or polypeptide is administered along with chemotherapy treatment. In some embodiments, the engineered protein or polypeptide is used to limit waste build up during chemotherapy treatment. In certain embodiments, the engineered protein or polypeptide is used to prevent scarring and diminishing fibrosis. In some embodiments, the engineered protein or polypeptide is used along with radiation therapy treatment.

Proteopathy Treatment

In an aspect, the present invention provides treatments for disease and symptoms caused by protein conformational disorders, or proteopathies. Proteopathy refers to a class of diseases related to structural abnormality of certain proteins and disruption of the function of cells, tissues and organs. In certain embodiment, the targeting system recognizes abnormally conformed proteins or protein aggregates. In certain embodiment, the targeting system, optionally comprising one or more engineered protein or polypeptide associated with a functional domain, cleaves or modifies abnormally conformed proteins or protein aggregates. In certain embodiment, the targeting system, optionally comprising one or more engineered protein or polypeptide associated with a functional domain, cleaves or modifies proteins or protein aggregates in excessive amounts that are associated with the disease or symptoms. In preferred embodiments, the functional domain is a chaperone. An example and method of chaperone based therapy for protein mis-folding related disease is discussed in Cahudhuri and Paul, Protein-misfolding diseases and Chaperone-based Therapeutic Approaches. FEBS J. 273(7): 1331-49 (2006) and is incorporated herein by reference.

The targeting system of the present invention may be used for treatment or symptom amelioration of diseases include but not limited to:

| Proteopathy | Major aggregating protein |
|---|---|
| Alzheimer's Disease | Amyloid β peptide (Aβ); Tau protein |
| Cerebral β-amyloid angiopathy | Amyloid β peptide |
| Retinal ganglion cell degeneration in glaucoma | Amyloid β peptide |
| Prion disease | Prion protein |
| Parkinson's disease, synucleinopathies | α-Synuclein |
| Tauopathies | Microtubule-associated protein tau |
| Frontotemporal lobar degeneration | TDP-43 |
| FTLD-FUS | Fused in sarcoma (FUS) protein |
| Amyotrophic lateral sclerosis (ALS) | Superoxide dismutase, TDP-43 |
| Huntington's disease, trinucleotide repeat disorders | Proteins with tandem glutamine expansions |
| Familial British Dementia | ABri |
| Familial Danish Dementia | ADan |
| Hereditary Cerebral Hemorrhage with Amyloidosis | Cystatin C |
| CADASIL | Notch 3 |
| Alexander Disease | GFAP |
| Seipinopathies | Seipin |
| Familial amyloidotic neuropathy | Transthyretin |
| Serpinopathies | Serpins |
| Light chain amyloidosis | Monoclonal immunoglobulin light chains |
| Heavy chain amyloidosis | Monoclonal immunoglobulin heavy chains |
| Amyloidosis | Amyloid A protein |
| Type II diabetes | Islet amyloid polypeptide |
| Aortic medial amyloidosis | Medin (lactadherin) |
| ApoAI amyloidosis | Apolipoprotein AI |
| ApoAII amyloidosis | Apolipoprotein AII |
| ApoAIV amyloidosis | Apolipoprotein AIV |
| Familial amyloidosis of the Finnish type (FAF) | Gelsolin |
| Lysozyme amyloidosis | Lysozyme |
| Fibrinogen amyloidosis | Fibrinogen |
| Dialysis amyloidosis | Beta-2 microglobulin |
| Inclusion body myositis/myopathy | Amyloid β peptide |
| Cataracts | Crystallins |
| Retinitis pigmentosa with rhodopsin mutations | rhodopsin |
| Medullary thyroid carcinoma | Calcitonin |
| Cardiac atrial amyloidosis | Atrial natriuretic factor |
| Pituitary prolactinoma | Prolactin |
| Hereditary lattice corneal dystrophy | Keratoepithelin |

-continued

| | |
|---|---|
| Cutaneous lichen amyloidosis | Keratins |
| Mallory bodies | Keratin intermediate filament |
| Corneal lactoferrin amyloidosis | Lactoferrin |
| Pulmonary alveolar proteinosis | Surfactant protein C (SP-C) |
| Odontogenic (Pindborg) tumor amyloid | Odontogenic ameloblast-associated protein |
| Seminal vesicle amyloid | Semenogelin |
| Apolipoprotein C2 amyloidosis | Apolipoprotein C2 (ApoC2) |
| Apolipoprotein C3 amyloidosis | Apolipoprotein C3 (ApoC3) |
| Lect2 amyloidosis | Leukocyte chemotactic factor-2 (Lect2) |
| Insulin amyloidosis | Insulin |
| Galectin-7 amyloidosis (primary localized cutaneous amyloidosis) | Galectin-7 (Gal7) |
| Corneodesmosin amyloidosis | Corneodesmosin |
| Enfuvirtide amyloidosis | Enfuvirtide |
| Cystic Fibrosis | Cystic fibrosis transmembrane conductance regulator (CFTR) protein |
| Sickle cell disease | Hemoglobin |

Methods of Engineering Proteins and Polypeptides

In one aspect, the present disclosure provides for methods of engineering a LRR of an engineered protein or polypeptide. The method includes procedures and steps that can be used separately or combined and performed in any order. The invention provides a method of engineering a LRR-containing binding domain. The method includes procedures that can be used separately or combined and performed in any order. Without limitation, in certain embodiments, the method comprises duplicating the LRR; in certain embodiments, the method comprises mutating the LRR; in certain embodiments, the method comprises substituting one LRR for another LRR; in certain embodiments, the method comprises rearranging or shuffling of two or more LRRs; and in certain embodiments, the method comprises linking a LRR of the invention with a LRR from another source.

In some embodiments, the method comprises one or more of i) modifying or altering or mutating a LRR, duplicating a LRR, substituting one or more amino acid residues in a LRR with one or more amino acid residues from a different source, substituting one or more amino acid residues in a LRR with one or more amino acid residues derived from the same species or related species, mutating a LRR, linking a LRR to one or more LRR from a different source, substituting an LRR, shuffling amino acid residues from one or more LRR, or linking an LRR from a different source, and ii) detecting whether the LRR binds to the target. In some embodiments, the LRR is modified by introducing a mutation to a hypervariable region. In some embodiments, the LRR is modified by introducing a mutation to a non-hypervariable region. In some embodiments, the methods further comprise inserting or modifying an LRR according the LRR motifs described herein, and detecting whether the engineered protein or polypeptide binds to the target substrate.

In some embodiments, the protein or polypeptide is associated with a detectable moiety. In some embodiments, the protein or polypeptide and the detectable moiety are covalently linked. In some embodiments, the target comprises a macromolecule. In some embodiments, the macromolecule comprises a protein or polypeptide. In some embodiments, the macromolecule comprises a toxin. In some embodiments, the macromolecule comprises a virus component. In some embodiments, the engineered protein or polypeptide and the target are contacted in vivo, ex vivo, or in vitro.

The present invention will be further illustrated in the following Examples which are given for illustration purposes only and are not intended to limit the invention in any way.

EXAMPLES

Example 1—LRR Domain-Containing Proteins

TABLE 1

| SEQ ID NO: | |
|---|---|
| 49 | >WP_044049302.1.<br>MRKLLFIILI PFLGIAQDFT ANRIKYTVTS STAPFTVKVA RNANFTGAAE IPETVVYNSE<br>NYAVTAIADE AFKGNYNLTS VSIGDAVTSV GESAFNNCVA LTSVTIGNSV VSIGNSAFIG<br>SSLTSLTIGN SVASIGSFAF FGCFGLTSLT IPSSVTSIAN QAFSECTGLT SVTIPNFVTS<br>IGDGAFSMCS GLISVTIPNA VTSIGDYTFS NCTSLTTVNS YATIPLVINE NAFHNLDKSI<br>CALNVPAGTE AAYQAAAVWK DFSPISGSLL SNLSSFAKGN YFVEVMTNQG KATKTIIIQ |
| 50 | >YP_001295113.1.<br>MRKLLFIILI PFLGIAQDFT ANGINYTVTS STAPFTASVA SNTRFSGDAV IPETVVYNSE<br>NYAVTAIADE AFKGNYNLTS VSIGDAVTSV GESAFNNCVA LTSVTIGNSV VSIGNSAFIG<br>SSLTSLTIGN SVASIGSFAF FGCFGLTSLT IPSSVTSIAN QAFSECTGLT SVTIPNFVTS<br>IGDGAFSMCS GLISVTIPNA VTSIGDYTFS NCTSLTTVNS YATIPLVINE NAFHNLDKSI<br>CALNVPAGTE AAYQAAAVWK DFSPISGSLL SNHSFAIESN LKIYPNPVSE ILNIALQENL<br>QLQKVNFYNT LGQLIKTTNH SEINISSFAK GIYFVEVMTN QGKATKTIIV Q |
| 51 | >WP_011962354.1.<br>MRKLLFIILI PFLGIAQDFT ANGINYTVTS STAPFTASVA SNTRFSGDAV IPETVVYNSE<br>NYAVTAIADE AFKGNYNLTS VSIGDAVTSV GESAFNNCVA LTSVTIGNSV VSIGNSAFIG |

TABLE 1-continued

| SEQ ID NO: | |
|---|---|
| | SSLTSLTIGN SVASIGSFAF FGCFGLTSLT IPSSVTSIAN QAFSECTGLT SVTIPNFVTS<br>IGDGAFSMCS GLISVTIPNA VTSIGDYTFS NCTSLTTVNS YATIPLVINE NAFHNLDKSI<br>CALNVPAGTE AAYQAAAVWK DFSPISGSLL SNHSFAIESN LKIYPNPVSE ILNIALQENL<br>QLQKVNFYNT LGQLIKTTNH SEINISSFAK GIYFVEVMTN QGKATKTIIV Q |
| 52 | >WP_038465882.1.<br>MRKLLFIILM PFLGIAQDFT ENGINYTITS STAPFTASVA SNTRFSGDAV IPETVVYNSE<br>NYAVTAIADE AFKGNYNLTS VSIGDAVTSV GESAFNNCVA LTSVTIGNSV ISIGNSAFIG<br>SSLTSLTIGN SVASIGSLAF FGCFGLTSLT IPSSVTSIAN QAFSMCSGLT SVTIPNFVTS<br>IGDGAFSMCS GLISVTIPNA VTSIGDYTFM NCTSLTTVNS YATIPLVINE NAFHNLDKSI<br>CALNVPAGTE AAYQAAAVWK DFSPISGSLL SNHSFAIESN LKIYPNPVSE ILNIALQENL<br>QLQKVNFYNT LGQLIKTTNH SEINISSFAK GIYFVEVMTN QGKATKTIIV Q |
| 53 | >WP_046205344.1.<br>MRKLLFIILI PFLGIAQDFT ENGINYTITS STAPFTASVA SNTRFSGDAV IPETVVYNSE<br>NYAVTAIADE AFKGNYNLTS VSIGDAVTSV GESAFNNCVA LTSVTIGNSV VSIGNSAFIG<br>SSLTSLTIGN SVASIGSFAF FGCFGLTSLT IPSSVTSIAN QAFSMCSGLT SVTIPNFVTS<br>IGDGAFSMCS GLISVTIPNA VTSIGDYTFS NCTSLTTVNS YATIPLVINE NAFHNLDKSI<br>CALNVPAGTE AAYQAAAVWK DFSPISGSLL SNHSFAIESN LKIYPNPVSE ILNIALQENL<br>QLQKVNFYNT LGQLIKTTNH SEINISSFAK GIYFVEVMTN QGKATKTIIV Q |
| 54 | >WP_074460277.1.<br>MRKLLFVILM PFLGIAQNFT ANGINYTVTS SVAPFTVSVS DNTRFSGVAV IPETVAYNSE<br>NYAVTAITAS AFKSCSGLTS VTIGNFITSI ERDAFRDSTN LTTVTIGNSV NSIERFAFNN<br>CSRLTSITIP DSVTAIRNSA FASCTGLTSV TFPNSVSFID AFAFSRCTNL TSVTIPNSVT<br>HIGGYAFNNC SSLTTVNCYI TTPLAINVTT FRKVNKSTCA LNVPAGTEAA YQAAAVWKDF<br>SPISGSLLSN HSFAIESALK IYPNPVSEIL NIALQEDLQL EKVNFYNTLG QLIKTTNHSG<br>INVSSFAKGN YFVEIMTNQG KVTKTIIVQ |
| 55 | >WP_038465885.1.<br>MRKLLFVILM PFLGIAQNFT ANGINYTVTS SVAPFTVSVS DNTRFSGVAV IPETVAYNSE<br>NYAVTAITAS AFKSCSGLTS VTIGNFITSI ERDAFRDSTN LTTVTIGNSV NSIERFAFNN<br>CSRLTSITIP DSVTAIRNSA FASCTGLTSV TFPNSVSFID AFAFSRCTNL TSVTIPNSVT<br>HIGGYAFNNC SSLTTVNCYI TTPLAINVTT FRKVNKSTCA LNVPAGTEAA YQAAAVWKDF<br>SPISGSLLSN HSFAIESALK IYPNPVSEIL NIALQEDLQL EKVNFYNTLG QLIKTTNHSG<br>INVSSFAKGN YFVEIMTNQG KVTKTIIVQ |
| 56 | >YP_001295116.1.<br>MRKLLFIILM PFLGIAQNFT ANGINYTVTS STVPLTVSVA NNTRFTGVAE IPEIVVYNSE<br>NYAVTAIRVN AFNGSRLTSI TIPNSVTAIG KFAFYNCTRL ISISIPNSVT SIEEGTFSFC<br>TGLISITIPN SVTVIGKKAF SECLGLTSVT FPNALATIGS YCFYFCTSLT SVTIPNSVTD<br>IGVGAFYDCT SLSTVNCQIT TPLVINVTTF RKVNKSTCAL NVPAGTEAAY QAAAVWKDFS<br>LIYGSLLSNH SFAIESNLKI YPNPVSEILN IALQEDLQLE KVNFYNTLGQ LIKTTNHSEI<br>NVSSFTKGNY FVEIMTNQGK VTKTIIVQ |
| 57 | >WP_011962357.1.<br>MRKLLFIILM PFLGIAQNFT ANGINYTVTS STVPLTVSVA NNTRFTGVAE IPEIVVYNSE<br>NYAVTAIRVN AFNGSRLTSI TIPNSVTAIG KFAFYNCTRL ISISIPNSVT SIEEGTFSFC<br>TGLISITIPN SVTVIGKKAF SECLGLTSVT FPNALATIGS YCFYFCTSLT SVTIPNSVTD<br>IGVGAFYDCT SLSTVNCQIT TPLVINVTTF RKVNKSTCAL NVPAGTEAAY QAAAVWKDFS<br>LIYGSLLSNH SFAIESNLKI YPNPVSEILN IALQEDLQLE KVNFYNTLGQ LIKTTNHSEI<br>NVSSFTKGNY FVEIMTNQGK VTKTIIVQ |
| 58 | >WP_046205347.1.<br>MRKLLFIILM PFLGIAQNFT ANGINYTVTS STVPLTVSVA NNTRFTGVAE IPEIVVYNSE<br>NYAVTAIRVN AFNGSRLTSI TIPNSVTAIG KFAFYNCTRL ISISIPNSVT SIEEGTFSFC<br>TGLISITIPN SVTVIGKKAF SECLGLTSVT FPNALATIGS HCFYFCTSLT SVTIPNSVTD<br>IGVGAFYDCT SLSTVNCQIT TPLVINATAF RKVNKSTCRL NVPAGTEAAY QAAAVWKDFS<br>LIYGSLLSNH SFAIESNLKI YPNPVSEILN IALQEDLQLE KVNFYNTLGQ LIKTTNHSEI<br>NVSSFTKGNY FVEIMTNQGK VTKTIIVQ |
| 59 | >WP_051907048.1.<br>MRKLLFIILI PFLGIAQDFT ANGIKYTVTS SRTPFTVKVA RNAGFTGVAE IPETVAYNSK<br>NYAVTAISEN AFRLSDLTAI TIPNSVTVIE EGAFGYCTDL TSVTIPNAVA TIGENCFYSC<br>KKLRSLTIPN SLTVIGNGAF SECTGLRTVN CQITIPFAIN TNTFYNLNRS ICALNVPPGT<br>EAAYKAAAVW KDFSPISGGF LSSNSFAIES NLKIYPNPVS EILNIALQED IQLEKVNFYN<br>TLGQLIKTTN HSEINVSSFA KGNYFVEIMT NQGKVTKTII IQ |
| 60 | >WP_046205345.1<br>MRKLLFIILI PFLGIAQDFT ANGIKYTVTS SRTPFTVKVA RNAGFTGVAE IPETVAYNSK<br>NYAVTAISEN AFRLSDLTAI TIPNSVTVIE EGAFGYCTDL TSVTIPNAVA TIGKHCFYSC<br>KKLRSLTIPN SLTVIGNGAF SECTGLRTVN CQITIPFAIN TNTFYNLNRS ICALNVPPGT<br>EAAYKAAAVW KDFSPISGGF LSSNSFAIES NLKIYPNPAS EILNIALQEG LQLEKVNFYN<br>TLGQLIKTTN HSEINVSSFA KGNYFVEVMT NQGKVTKSVI IQ |

TABLE 1-continued

| SEQ ID NO: | |
|---|---|
| 61 | >YP_001295114.1.<br>MRKLLFIILI PFLGIAQDFT ANGIKYTVTS SRTPFTVKVA RNAGFTGVAE IPETVAYNSK<br>NYAVTAISEN AFRLSDLTAI TIPNSVTVIE EGAFGYCTDL TSVTIPNAVA TIGENCFYSC<br>KKLRSLTIPN SLTVIGNGAF SECTGLRTVN CQITIPFAIN TNTFYNLNRS ICALNVPPGT<br>EAAYKAAAVW KDFSPISGGF LSSNSFAIES NLKIYPNPVS EILNIALQEG LQLEKVNFYN<br>TLGQLIKTTN HSEINVSSFA KGNYFVEIMT NQGKATKSVI IQ |
| 62 | >WP_011962355.1.<br>MRKLLFIILI PFLGIAQDFT ANGIKYTVTS SRTPFTVKVA RNAGFTGVAE IPETVAYNSK<br>NYAVTAISEN AFRLSDLTAI TIPNSVTVIE EGAFGYCTDL TSVTIPNAVA TIGENCFYSC<br>KKLRSLTIPN SLTVIGNGAF SECTGLRTVN CQITIPFAIN TNTFYNLNRS ICALNVPPGT<br>EAAYKAAAVW KDFSPISGGF LSSNSFAIES NLKIYPNPVS EILNIALQEG LQLEKVNFYN<br>TLGQLIKTTN HSEINVSSFA KGNYFVEIMT NQGKATKSVI IQ |
| 63 | >WP_044049304.1.<br>MKKLLFVILI PFLGIAQDFT ANGIKYTVTS STAPFTVKVA RNAGFTGVAE IPETVAYNSK<br>NYAVTAISEN AFRLSDLTAI TIPNSVTVIE EGAFGYCTDL TSVTIPNAVA TIGENCFYSC<br>KKLRSLTIPN SLTVIGNGAF SECTGLRTVN CQITIPFAIN TNTFYNLNRS ICALNVPPGT<br>EAAYKAAAVW KDFSPISGGF LSSNSFAINV SSFAKGNYFV EIMTNQGKAT KSVIIQ |
| 64 | >WP_046201267.1.<br>MKKLLFFILI PFLGIAQDFT ANGIKYTVTS SRTPFTVKVA RNAGFTGVAE IPETVAYNSK<br>NYAVTAISEN AFRLSDLTAI TIPNSVTVIE EGAFGYCTDL TSVTIPNAVA TIGENCFYSC<br>KKLRSLTIPN SLTVIGNGAF SECTGLRTVN CQITIPFAIN TNTFYNLNRS ICALNVPPGT<br>EAAYKAAAVW KDFSPISGGF LSSNSFAIES NLKIYPNPVS EILNIALQEG LQLEKVNFYN<br>TLGQLIKTTN HSEINVSSFA KGNYFVEIMT NQGKATKSVI IQ |
| 65 | >WP_011962344.1<br>MKKLLFLILI PFLGIAQDFT ANRINYTITS STAPFTVKVA RNANFTGAAE IPETVAYNSE<br>NYAVTAIGES AFEHCNNLTS VTIPNSATSI GRYAFVGCSG LISVTIPNSV TTIGDEAFAD<br>CSGLTSVTIP NSVTDIENSA FFSCSGLTSV TIPNSVTTIG DGSFAECSGL TSVTIPNSVT<br>TIGEGSFAGC SGLISITIPN SVTTIRRGVF SACSGLISVT IPNSVTDIEN GAFFSCSGLT<br>SVTIPNSVTA IGKDAFAGCR SLKTVNCHIT SPLVINANVF GNITQSNCAL NVPTGTQVAY<br>QAAAVWRNFS PISGGLLSNH SFAIESALKI YPNPVSEILN IALQEGLQLQ KVNFYNTLGQ<br>LIKTTNHSEI NVSSFAKGNY FVEVITNQGK ATKTIIIQ |
| 66 | >WP_034100021.1<br>MKKLLFFILI PFLGIAQDFT ANHIRYTITS SEAPFTAKVA RNPDFSGVAV IPETVAYNSK<br>NYIVTAIGES AFEHCNNLTS VTIPNSATSI GRYAFVGCSG LISVTIPNSV TTIGDEAFAD<br>CSGLTSVTIP NSVTTIGDGS FFSCSGLTSV TIPNSVTTIG KDAFADCSGL TSVTIPNSVT<br>TIGEGSFAGC SGLISITIPN SVTVIRRGIF AGCSGLISVT IPNSVTDIEN GAFFSCSGLT<br>SVTIPNSVTA IGKDAFAGCR SLKTVNCHIT SPLVINANVF GNITQSNCAL NVPTGTQVAY<br>QAAAVWRNFS PISGGLLSNH SFAIESALKI YPNPVSEILN IALQEGLQLE KVNFYNTLGQ<br>LIKTTNHSEI NVSSFAKGNY FVEVMTNQGK ATKTIIVQ |
| 67 | >WP_059223310.1<br>MKKLLFLILI PFLGIAQDFT ANRINYTITS STAPFTVKVA RNANFTGAAE IPETVAYNSE<br>NYAVTAIGED AFEYCNNLTS VTIPNSATSI GRYAFVGCSG LISVTIPNSV TTIGDEAFAD<br>CSGLTSVTIP NSVTTIGDGS FFSCSGLTSV TIPNSVTTIG KDAFADCSGL TSVTIPNSVT<br>TIGEGSFAGC SGLISITIPN SVTTIRRGVF SACSGLISVT IPNSVTDIEN GAFFSCSGLT<br>SVTIPNSVTA IGKDAFAGCR SLKTVNCHIT SPLVINANVF GNITQSNCAL NVPTGTQVAY<br>QAAAVWRNFS PISGGLLSNH SFAIESALKI YPNPVSEILN IALQEGLQLE KVNFYNTLGQ<br>LIKTTNHSEI NVSSFAKGNY FVEVMTNQGK ATKTIIVQ |
| 68 | >WP_046201259<br>MKKLLFLILI PFLGIAQDFT ANRINYTITS STAPFTVKVA RNANFTGAAE IPETVAYNSE<br>NYAVTAIGES AFEYCNNLTS VTIPNSATSI GRYAFVGCSG LISVTIPNSV TTIGDEAFAD<br>CSGLTSVTIP NSVTDIENSA FFSCSGLTSV TIPNSVTTIG DGSFAECSGL TSVTIPNSVT<br>TIGEGSFAGC SGLISITIPN SVTTIRRGVF SACSGLISVT IPNSVTDIEN GAFFSCSGLT<br>SVTIPNSVTA IGEDAFAGCR SLKTVNCHIT SPLVINANVF GNITQSNCAL NVPTGTQVAY<br>QAAAVWRNFS PISGGLLSNH SFAIESALKI YPNPVSEILN IALQEGLQLQ KVNFYNTLGQ<br>LIKTTNHSEI NVSSFAKGNY FVEVITNQGK ATKTIIIQ |
| 69 | >UPI000903956F<br>ILIPFLGIAQ DFTANRINYT ITSSTAPFTV KVARNANFTG AAEIPETVAY NSENYIVTAI<br>GESAFIHCNN LTSVTIPNSA TSIGRYAFVG CSGLISVTIP NSVTTIGDEA FADCSGLTSV<br>TIPNSVTDIE NSAFFSCSGL TSVTIPNSVT TIGDGSFAEC SGLTSVTIPN SVTTIGEGSF<br>AGCSGLISIT IPNSVTTIGE GSFAGCSGLI SVTIPNSVTD IENGAFFSCS GLTSVTIPNS<br>VTAIGKDAFA GCRSLKTVNC HITSPLVINA NVFGNITQSN CALNVPTGTQ AVYQAAAVWR<br>NFSPISGGLL SNHSFAIESA LKIYPNPVSE ILNIALQEGL QLEKVNFYNT LGQLIKTTNH<br>LETNVSSFAK GNYFVEVMTN QGKATKTIII Q |
| 70 | >WP_034101598.1<br>MKKLLFLILI PFLGIAQDFT ANRINYTVTS STAPFTVSVA RNPYFSGVAE IPETVVYNSK<br>NYAVTYIKEI AFQECNTLTS VSIPNVTTI GNSAFERCSS LISVTIPNSV TAIGKGAFFS<br>CSGLTSVTIP NSVTTIGDEA FADCSGLTSV TIPNSVTTIG DGSFAECSGL TSVTIPNSVT |

| SEQ ID NO: | |
|---|---|
| | TIGDGSFARC SGLTSVTIPN SVITINRGAF VSCSGLTSVT IPNSVTTIGE EAFAGCSSLR TVNCHITSPL VINANVFGNV TQSNCALNVP TGTQAVYQAA AVWRNFSPIS GNLLSNHSFA IESALKIYPN PVSEILNIAL QEGLQLEKVN FYNTLGQLIK TTNHSEINVS SFAKGNYFVE IITNQGKATK TIIIQ |
| 71 | >WP_034097297.1<br>MKKLLFLILI PFLGIAQDFT ANRINYTVTS STAPFTVSVA RNPNFSGVAE IPETVVYNSK NYAVTYIKEI AFQECNTLTS VSIPNSVTTI GNSAFERCSS LISVTIPNSV TAIGNGAFFS CSGLTSVTIP NSVTTIGDEA FADCSGLTSV IPNSVTTIGE DGSFAECSGL TSVTIPNSVT TIGDGSFARC SGLTSVTIPN SVITINRGAF VSCSGLTSVT IPNSVTTIGE NAFAGCSSLR TVNCHITSPL VINANVFGNV TQSNCALNVP TGTQAVYQAA AVWRNFSPIS GNLLSNHSFA IESALKIYPN PVSEILNIAL QEGLQLEKVN FYNTLGQLIK TTNHSEINVS SFAKGNYFVE IITNQGKATK TIIIQ |
| 72 | >WP_034101008.1<br>MKKLLFLILI PFLGIAQDFT ANRINYTITS STAPFTVKVA RNANFTGAAE IPETVAYNSE NYAVTAIGES AFEHCNNLTS VTIPNSATSI GRYAFVGCSG LISVTIPNSV TTIGDEAFAD CSGLTSVTIP NSVTDIENSA FFSCSGLTSV TIPNSVTTIG DGSFAECSGL TSVTIPNSVT TIGEGSFADC SGLTSVTIPN SVTTIGRGVF SACSGLISVT IPNSVTAIGG GAFFSCSGLT SVTIPNSVTA IGNDAFEKCR SLTKVNCYIT MPLIINANVF RNITQSNCAL NVPTGTQAVY QAAAVWRNFS PISGNLLSNH SFAIESTLKI YPNPVSEILN IALQEGLQLQ KVNFYNTLGQ LIKTTNHSEI NVSSFAKGNY FVEVITNQGK ATKTIIIQ |
| 73 | >WP_034101600.1<br>MKKLLFLILI PFLGIAQDFT ANRINYTITS STAPFTVKVA RNANFTGAAE IPETVAYNSE NYAVTAIGES AFEHCNNLTS VTIPNSATSI GRYAFVGCSG LISVTIPNSV TTIGDEAFAD CSGLTSVTIP NSVTDIENSA FFSCSGLTSV TIPNSVTTIG DGSFAECSGL TSVTIPNSVT TIGEGSFAGC SGLTSVTIPN SVTSIGRGAF AACSGLTSVT IPNSVTAIGG GAFFSCSDLT SVTIPNSVTA IGNYAFEKCR SLTTVNCYIT MPLVINANVF GNVTQSNCAL NVPTGTQAVY QAAAVWRNFS PISGNLLSNH SFAIESALKI YPNPVSEILN IALQEGLQLQ KVNFYNTLGQ LIKTTNHSEI NVSSFAKGNY FVEVITNQGK ATKTIIIQ |
| 74 | >WP_034097300.1<br>MKKLLFLILI PFLGIAQDFT ANRINYTITS STAPFTVKVA RNANFTGAAE IPETVAYNSE NYAVTAIGES AFEHCNNLTS VTIPNSATSI GRYAFVGCSG LISVTIPNSV TTIGDEAFAD CSGLTSVTIP NSVTDIENSA FFSCSGLTSV TIPNSVTTIG DGSFAECSGL TSVTIPNSVT TIGEGSFAGC SGLISITIPN SVTTIRRGVF SACSGLISVT IPNSVTDIEN GAFFSCSGLT SVTIPNSVTA IGKDAFAGCR SLKTVNCHIT SPLVINANVF GNITQSNCAL NVPTGTQVAY QAAAVWRNFS PISGGLLSNH SFAIESALKI YPNPVSEILN IALQEGLQLQ KVNFYNTLGQ LIKTTNHSEI NVSSFAKGNY FVEVITNQGK ATKTIIIQ |
| 75 | >A0A076NYM9-1<br>MKKLLFLILI PFLGIAQTFT ANRINYTITS STAPFTVKVA RNANFTGAAE IPETVAYNSE NYAVTAIGES AFEHCNNLTS VTIPNSVTTI GNYTFSDCPD LTSVTIPNSV TSIGDEAFSG CTGLISVTIP NSVTSIGDEA FFNCSGLTSV TIPNSVTTIG EGSFAGCSGL ISITIPNSVT TIRGGVFSAC SGLISVTIPN SVTDIENGAF FSCSGLTSVT IPNSVITINR GAFFSCSGLT SVTIPNSVTT IRENAFADCS GLTSVTIPNS VTAIGENAFA GCSSLRTVNC HITSPLVINA NVFGNVTQSN CALNVPTGTQ AVYQAAAVWR NFSPISGNLL SNHSFAIESA LKIYPNPASE ILNIALQEGL QLEKVNFYNT LGQLIKTTNH SEINVSSFAK GNYFVEVMTN QGKATKTIII Q |
| 76 | >A0A1M5V4L6-1<br>MKKLLFLILI PFLGIAQDFT ANRINYTITS STAPFTVKVA RNANFTGAAE IPETVAYNSE NYAVTAIGES AFEHCNNLTS VTIPNSATSI GRYAFVGCSG LISVTIPNSV TTIGDEAFAD CSGLTSVTIP NSVTDIENSA FFSCSGLTSV TIPNSVTTIG DEAFADCSGL TSVTIPNSVT TIGDGSFAEC SGLTSVTIPN SVTTIGDGSF ARCSGLTSVT IPNSVITINR GAFALCSGLT SVTIPNSVTT IRENAFAGCS SLRTVNCHIT SPLVINANVF GNVTQSNCAL NVPTGTQAVY QAAAVWRNFS PISGNLLSNH SFAIESALKI YPNPASEILN IALQEGLQLE KVNFYNTLGQ LIKTTNHSEI NVSSFAKGNY FVEIITNQGK ATKTIIIQ |
| 77 | >WP_038503239<br>MKKLLFVILI PFLGIAQDFT ANHIRYTITS SEAPFTAKVA RNPDFSGVAV IPEIVTYNSE NYIVTAIGES AFFSCQGLTS VNVGNFVRSI GENAFALCSN LTSITIPNNT VTSIGGTAFE RCSGLTSVTI PNSVTTIGEG SFAGCSGLIS ITIPNSVTTI RRGVFSACSG LISVTIPNSV TDIENGAFFS CSGLTSVTIP NSVTTIGDGS FARCSGLTSV TIPNSVTTIG DEAFADCSGL TSVTIPNSVT TIGDGSFAEC SGLTSVTIPN SVTTIGDEAF ADCSGLTSVT IPNSVTAIGE NAFAGCSSLR TVNCHITSPL VINANVFGNV TQSNCALNVP TGTQAVYQAA AVWRNFSPIS GSLLSNHSFA IESALKIYPN PVSEILNIAL QEGLQLEKVN FYNTLGQLIK TTNHSEINVS SFAKGNYFVE VITNQGKATK TIIIQ |

TABLE 1-continued

| SEQ ID NO: | |
|---|---|
| 78 | >WP_071958095<br>MKKLLFVILI PFLGIAQDFT ANHIRYTITS SEAPFTAKVA RNPDFSGVAV<br>IPEIVTYNSE NYIVTAIGES AFFSCQGLTS VNVGNFVRSI GENAFALCSN<br>LTSITIPNNT VTSIGGTAFE RCSGLTSVTI PNSVTTIGEG SFAGCSGLIS<br>ITIPNSVTTI RRGVFSACSG LISVTIPNSV TDIENGAFFS CSGLTSVTIP<br>NSVTTIGDGS FARCSGLTSV TIPNSVTTIG DEAFADCSGL TSVTIPNSVT<br>TIGDGSFAEC SGLTSVTIPN SVTTIGENAF ADCSGLTSVT IPNSVTAIGE<br>NAFAGCSSLR TVNCHITSPL VINANVFGNV TQSNCALNVP TGKQVAYQAA<br>AVWRNFSPIS GSLLSNHSFA IESALKIYPN PVSEILNITL QEGLQLEKVN<br>FYNTLGQLIK TTNHSEINVS SFAKGNYFVE VMTNQGKATK TIIIQ |
| 79 | >WP_046201331<br>MKKLLFVILI PFLGIAQDFT ANHIRYTITS SEAPFTAKVA RNPDFSGVAV<br>IPEIVTYNSE NYIVTAIGES AFFSCQGLTS VNVGNFVRSI GKNAFALCSN<br>LTSITIPNNT VTSIGDAAFE RCSGLTSVTI PNSVTTIGKG SFAGCSGLIS<br>ITIPNSVTTI RRGVFSACSG LISVTIPNSV TDIENGAFFS CSGLTSVTIP<br>NSVTTIGDXS FARCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFARCSGLT SVTIPNSVTS IGDYAFNSCP SLTTINCYTT TPLVINPNVF<br>GDTNQSACTL NVPAGTEAVY QATEIWQDFS PITGGFLSSN SFAIESNLKI<br>YPNPVSEILN IALQEGLQLQ KVNFYNTLGQ LIKTTNHLET NVSSFAKGNY<br>FVEVITNQGK ATKTIIIQ |
| 80 | >WP_046201260<br>MKKLLFVILI PFLGIAQDFT ANHIRYTITS SEAPFTAKVA RNPDFSGVAV<br>IPEIVTYNSE NYIVTAIGES AFFSCQGLTS VNVGNFVRSI GKNAFALCSN<br>LTSITIPNNT VTSIGDAAFE RCSGLTSVTI PNSVTTIGKG SFAGCSGLIS<br>ITIPNSVTTI RRGVFSACSG LISVTIPNSV TDIENGAFFS CSGLTSVTIP<br>NSVTTIGDES FARCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFARCSGLT SVTIPNSVTS IGDYAFNSCP SLTTINCYTT TPLVINPNVF<br>GDTNQSACTL NVPAGTEAVY QATEIWQDFS PITGGFLSSN SFAIESNLKI<br>YPNPVSEILN IALQEGLQLQ KVNFYNTLGQ LIKTTNHLET NVSSFAKGNY<br>FVEVITNQGK ATKTIIIQ |
| 81 | >WP_011962345<br>MKKLLFVILI PFLGIAQDFT ANHIRYTITS SEAPFTAKVA RNPDFSGVAV<br>IPEIVTYNSE NYIVTAIGES AFFSCQGLTS VNVGNFVRSI GENAFALCSN<br>LTSITIPNNT VTSIGDAAFG RCSGLTSVTI PNSVTTIGEG SFAGCSGLIS<br>ITIPNSVTTI RRGVFSACSG LISVTIPNSV TDIENGAFFS CSGLTSVTIP<br>NSVTTIGDGS FARCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFARCSGLT SVTIPNSVTS IGDYAFNSCP SLTTINCYTT TPLVINPNVF<br>GDTNQSACTL NVPAGTEAVY QATEIWQDFS PITGGFLSSN SFAIESNLKI<br>YPNPVSEILN IALQEGLQLQ KVNFYNTLGQ LIKTTNHLET NVSSFAKGNY<br>FVEVITNQGK ATKTIIIQ |
| 82 | >WP_038509078.1<br>MKKLLFVILI PFLGIAQDFT ANHIRYTITS SEAPFTAKVA RNPDFSGVAV<br>IPEIVTYNSE NYIVTAIGES AFFSCQGLTS VNVGNFVRSI GENAFALCSN<br>LTSITIPNNT VTSIGDAAFD RCSGLTSVTI PNSVTTIGEG SFAGCSGLIS<br>ITIPNSVTTI RRGVFSACSG LISVTIPNSV TDIENGAFFS CSGLTSVTIP<br>NSVTTIGIGS FARCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFARCSGLT SVTIPNSVTS IGDYAFNSCP SLTTINCYTT TPLVINPNVF<br>GDTNQSACTL NVPAGTEAVY QATEIWQDFS PITGGFLSSN SFAIESNLKI<br>YPNPVSEILN IALQEGLQLQ KVNFYNTLGQ LIKTTNHLET NVSSFAKGNY<br>FVEVITNQGK ATKTIIIQ |
| 83 | >WP_034101009<br>MRKLLFVILI PFLGIAQDFT ANGIRYTITS SEAPFTAKVA RNPDFSGVAV<br>IPEIVTYNSE NYIVTAIGES AFFTCQGLTS VNVGNFVRSI EKDAFALCSN<br>LTSITIPNNT VTSIGDAAFE RCSRLTSVTI PNSVTTIGKG SFTGCSGLIS<br>VTIPNSVTSI RRDAFTACSS LISVTIPNSV TTIGNGAFFS CSGLTSVTIP<br>NSVTTIGDGS FASCSGLTSV TIPNSVTTIG DGAFADCSGL TSVTIPNSVT<br>TIGDGSFAEC SGLTSVTIPN SVTTIGDEAF ADCSGLTSVT IPNSVTTIGN<br>WSFERCSGLT SVTIPNSVTS IGDYAFNLCP SLTTINCHTT TPLVINPNVF<br>GDTNQSACTL NVPAGTEAVY QATEIWQDFS PITGGFLSSN SFAIKSNLKI<br>YPNPVSEILN IALQEGLQLE KVNFYNTLGQ LIKTTNHLET NVSSFAKGNY<br>FVEVITNQGK ATKTIIIQ |
| 84 | >WP_034097302<br>MRKLLFVILI PFLGIAQDFT ANGIRYTITS SEAPFTAKVA RNPDFSGVAV<br>IPEIVTYNSE NYIVTAIGES AFFTCQGLTS VNVGNFVRSI EKDAFALCSN<br>LTSITIPNNT VTSIGDAAFE RCSRLTSVTI PNSVTTIGKG SFTGCSGLIS<br>VTIPNSVTSI RRDAFTLCSS LISVTIPNSV TTIGNGAFFS CSGLTSVTIP |

TABLE 1-continued

| SEQ ID NO: | |
|---|---|
| | NSVTTIGNGS FASCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFAGCSGLT SVTIPNSVTS IGDYAFNLCP SLTTINCHTT TPLVINPNVF<br>GDTNQSACTL NVPAGTEAVY QATEIWQDFS PITGGFLSSN SFAIKSNLKI<br>YPNPVSEILN IALQEGLQLE KVNFYNTLGQ LIKTTNHLET NVSSFAKGNY<br>FVEVITNQGK ATKTIIIQ |
| 85 | >WP_034101602<br>MRKLLFVILI PFLGIAQDFT ANGIRYTITS SEAPFTAKVA RNPDFSGVAV<br>IPEIVTYNSE NYIVTAIGES AFFTCQGLTS VNVGNFVRSI EKDAFALCSN<br>LTSITIPNNT VTSIGDAAFE RCSRLTSVTI PNSVTTIGKG SFTGCSGLIS<br>VTIPNSVTSI RRDAFTLCSS LISVTIPNSV TAIGNGAFFS CSGLTSVTIP<br>NSVTTIGNGS FASCSGLTSV TIPNSVTTIG DEAFADCSGL TSVTIPNSVT<br>TIGDGSFAEC SGLTSVTIPN SVTTIGDEAF SDCSGLTSVT IPNSVTTIGD<br>GSFEGCSGLT SVTIPNSVTS IGDYAFNLCP SLTTINCHTT TPLVINPNVF<br>GDTNQSACTL NVPAGTEAVY QATEIWQDFS PITGGFLSSN SFAIKSNLKI<br>YPNPVSEILN IALQEGLQLE KVNFYNTLGQ LIKTTNHLET NVSSFAKGNY<br>FVEVITNQGK ATKTIIIQ |
| 86 | >WP_046205338<br>MKKLLFVILI PFLGIAQDFT ANHIRYTITS SEAPFTAKVA RNPDFSGVAV<br>IPEIVTYNSE NYIVTAIGES AFFSCQGLTS VNVGNFVRSI GENAFALCSN<br>LTSITIPNNT VTSIGDAAFE RCSGLTSVTI PNSVTTIGEG SFAGCSGLIS<br>ITIPNSVTTI RRGVFSACSG LISVTIPNSV TDIENGAFFS CSGLTSVTIP<br>NSVTTIGDGS FARCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFARCSGLT SVTIPNSVTS IGDYAFNSCP SLTTINCYTT TPLVINPNVF<br>GDTNQSACTL NVPAGTEAVY QATEIWQDFS PITGGFLSSN SFAIESNLKI<br>YPNPVSEILN IALQEGLQLQ KVNFYNTLGQ LIKTTNHLET NVSSFAKGNY<br>FVEVITNQGK ATKTIIIQ |
| 87 | >WP_046205463<br>MKKLLFVILI PFLGIAQDFT ANHIRYTITS SEAPFTAKVA RNPDFSGVAV<br>IPETVAYNSX NYIVTAIGES AFFSCQGLTS VNVGNFVRSI GXNAFALCSN<br>LTSITIPNNT VTSIGDAAFX RCSGLTSVTI PNSVTTIGEG SFAGCSGLIS<br>ITIPNSVTTI RRGVFSACSG LISVTIPNSV TDIENGAFFS CSGLTSVTIP<br>NSVTTIGDXS FARCSGLTSV TIPNSVTTIG DEAFADCSGL TSVTIPNSVT<br>TIGDGSFAEC SGLTSVTIPN SVTTIGDEAF ADCSGLTSVT IPNSVTTIGD<br>GSFAXCSGLT SVTIPNSVTS IGDYAFNSCP SLTTINCYTT TPLVINPNVF<br>GDTNQSACTL NVPAGTEAVY QATEIWQDFS PITGGFLSSN SFAIESNLKI<br>YPNPVSEILN IALQEGLQLQ KVNFYNTLGQ LIKTTNHLET NVSSFAKGNY<br>FVEVITNQGK ATKTIIIQ |

Example 2—Computational Identification of Repeat-Containing Proteins and Systems Repetitive sequence elements in proteins and nucleic acids are often signatures of adaptive or reprogrammable systems in nature. Known examples of these systems, such as TALE effectors and CRISPR, have been harnessed as powerful molecular tools with a wide range of applications including genome editing. The continued expansion of genomic sequence databases raises the possibility of prospectively identifying new such systems by computational mining. By leveraging sequence repeats as an organizing principle, here Applicants developed a systematic genome mining approach to explore new types of naturally adaptive systems, five of which are discussed in greater detail. These results highlight the existence of a diverse range of intriguing systems in nature that remain to be explored and also provide a framework for future discovery efforts.

Repetitive structures abound in nature, providing a modular substrate for evolution. At the genomic level, repeated sequences are an economical way to achieve reprogrammability of a protein or system. For example, transcriptional activator-like effectors (TALEs) from the rice pathogen *Xanthomonas* bind specific sequences of DNA using repeated blocks of 33-34 amino acids that contain two variable residues that confer individual base pair specificity. By varying these two residues and combining the repeat blocks, TALEs can target a wide range of DNA sequences. Repetitive structures also underlie adaptive response systems, such as antibodies, CRISPR-Cas systems, and polyketide synthases, which are capable of creating a large diversity of compounds from different combinations of repeated basic subunits that appear in different combinations in the synthesis enzymes.

Figure 8A:
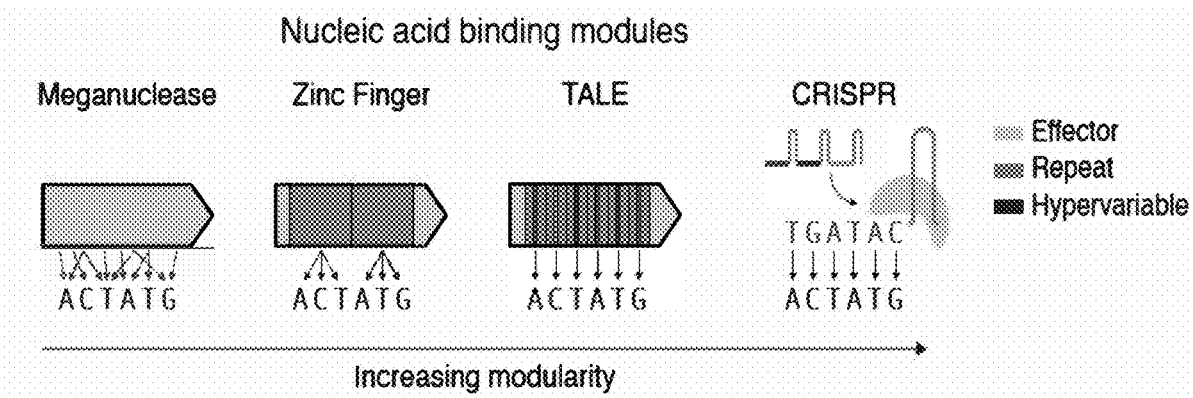
FIGS. 8A-8C: Repeat structures in proteins and systems.

As is clear even from these few examples, repetition can take different forms. Consider the case of nucleic acid targeting systems paperpile.com/c/NUakVX/07Fv, including meganucleases, TALEs, zinc fingers, and CRISPR-Cas (FIG. 8A). All of these systems share the basic feature that mutagenesis of key regions results in altered substrate specificity; however, these systems differ in their levels of modularity in determining their nucleic acid binding specificity. In contrast to meganucleases, which have multiple scattered residues that determine the binding specificity, zinc finger repeats can bind to 3-4 base pairs allowing multiple repeats to be chained together to bind longer nucleic acids in a sequence specific manner. TALEs and CRISPRs also use repeats, but additionally have a one-to-one mapping between the repeat units (protein repeat subunit and guide RNA sequence respectively) and the individual bases of the target DNA, providing more extensive modularity (FIG. 8A). For TALEs and CRISPRs, the regions in each repeat that confer binding specificity are also the most variable: for TALEs, it is the variable di-residue in each protein repeat unit, and for CRISPRs, it is the spacer RNA adjacent to each direct repeat.

Figure 8B:
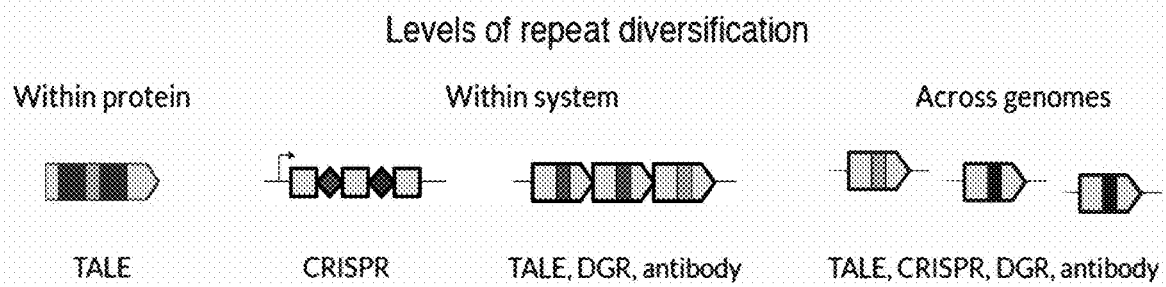

Repetition can also span across genomes (FIG. 8B). Another example of cross-system repetition is diversity-generating retroelements (DGRs). DGRs consist of a target protein with a repeated downstream template region that is mutagenized in a targeted manner by an associated retrotransposon. In eukaryotic antibody systems, an array of highly related pseudogenes recombine in different combinations in individual cells to form different kinds of antibodies or T-cell receptors capable of binding to different substrates. Modular systems often contain diversification at multiple levels. For example, CRISPR-Cas systems have diversification within each system (multiple CRISPR repeats with different spacers) and across genomes (different CRISPR arrays near identical cas genes).

Figure 8C:
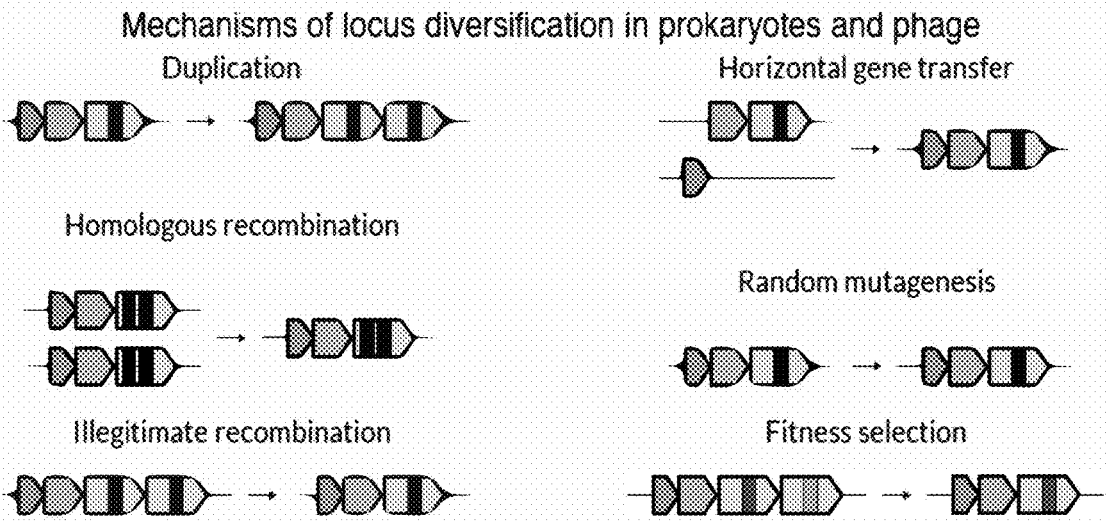

Multiple mechanisms exist for diversifying repeats at these three levels (FIG. 8C). For genes with repeat units, illegitimate recombination and homologous recombination allow rapid diversification of the gene by shuffling the order of the repeats. Gene duplication allows individual proteins to be repeated into arrays within a locus for subsequent diversification by random mutagenesis and DNA recombination. Horizontal gene transfer, homologous recombination and fitness selection additionally allow for rapid repeat diversification to occur across related genomes. Specialized mechanisms also exist for specific systems, such as Cas1-Cas2 spacer acquisition for CRISPR, or reverse transcriptase—Avd mediated homing mutagenesis for diversity generating retroelements.

From within proteins to across genomes, these examples highlight how repeat elements serve as modular templates for complex adaptive response systems, facilitating the rapid modification of key components that interact with substrates while allowing the rest of the system to stay constant. This modularity reduces the evolutionary time required to adapt to new substrate requirements in quickly changing environments.

Applicants found that a key signature for adaptive response systems was the presence of diversifying repeats. At a genomic level, this can entail multiple (e.g., neighboring) copies of a CDS or non-coding region that have at least one region of hyper variation between the copies.

The exponentially increasing number of sequenced and annotated genomes is enabling a new wave of bioinformatic mining through computational searches for genomic signatures or hallmarks, as opposed to just searching for sequence homology. This example shows a set of computational approaches to identify systems that contain evidence of repeat diversification, which may represent novel, potentially adaptive prokaryotic, eukaryotic, and viral systems. The search revealed thousands of potentially diversified clusters of systems, five of which were studied in greater detail. Together, the results demonstrate the feasibility of using repetition as a hallmark signature to seed computational searches to identify candidate novel adaptive systems and highlight the many ways molecular repetition is used throughout nature.

Results

Establishing a Computational Pipeline to Identify Repeat Signatures

Applicants searched for diversified repeats in two contexts (FIGS. 9A, 9B): within protein repeats and repeated proteins within a system. Variation occurring on the protein or within system levels occurs at a faster evolutionary time scale than variation across organisms. Applicants found that diversified repeats within these two contexts may be indicative of systems capable of responding to new selection pressures with minimal modification. Systems displaying either of these forms of diversified repeats can be mined from sequenced genomes by combining repeat motif detection algorithms with alignment scoring metrics that prioritize systems with localized hypervariation over those with random variation, which can be attributable to evolutionary drift. Localized hypervariation flanked by conserved regions can create a modular system, where small changes are embedded in the context of constant structure and function.

To computationally mine for these types of systems, Applicants first developed a pipeline for identifying systems with diversified repeats at the protein level (FIG. 9A). Applicants searched all proteins in UniRef100 for repeat motifs, filtered for repeats with hypervariable positions, and then clustered the proteins with repeats into families on the basis of their repeat features. For each family of repeat proteins, the repeats found in the family were grouped into major repeat archetypes (e.g. TALE repeat) and subtypes (e.g. TALE repeats containing hypervariable residues HD vs NI vs NN) and used a repeat rearrangement scoring metric to identify protein families that display extensive rearrangement of the protein (FIGS. 9C, 9D). Applicants identified 3865 candidate hypervariable repeat protein clusters (FIG. 9E). The representative TALE cluster scored among the highest of all candidates, suggesting that repeat protein families with both localized hypervariation and extensive rearrangement of repeats across different variants are exceptionally rare in nature. Applicants identified three candidate systems for further analysis—a tomato transcription factor, a slime mold leucine-rich repeat (LRR) protein with only two hypervariable amino acids, and a bacterial cell-surface LRR protein.

Applicants subsequently developed a pipeline for identifying systems with repeated, non-identical copies of the same protein (which were referred to as variants) in the locus (FIG. 9B). Because genes with related functions tend to spatially cluster in prokaryotic genomes, Applicants restricted this search to prokaryotic genomes and metagenomes to find diversified systems for which inference of function would more likely be possible. For each genomic contig, Applicants clustered all the proteins on that contig and retained clusters with 6 or more variants. Next, for each cluster, Applicants aligned the proteins and used a hyper-variation divergence scoring metric to identify clusters with at least one region in the protein with high sequence variation flanked by two regions of high sequence conservation (FIG. 9F). All candidate systems from the analysis were further clustered into 3040 candidate families of systems. In addition to being diversified repeat proteins, TALEs can also be found in multiple copies with regions of hyper variation (insertion and deletions of entire repeats in the middle of the protein) in the same genomic contig. Representative TALE clusters scored similarly to many other clusters, suggesting that many other systems share the within-system diversification feature that natural TALE loci possess. In the following sections, Applicants describe a number of interesting systems that came out of their initial analysis.

A Locus Containing Tandem Repeats of LRR Proteins.

Figure 10A:
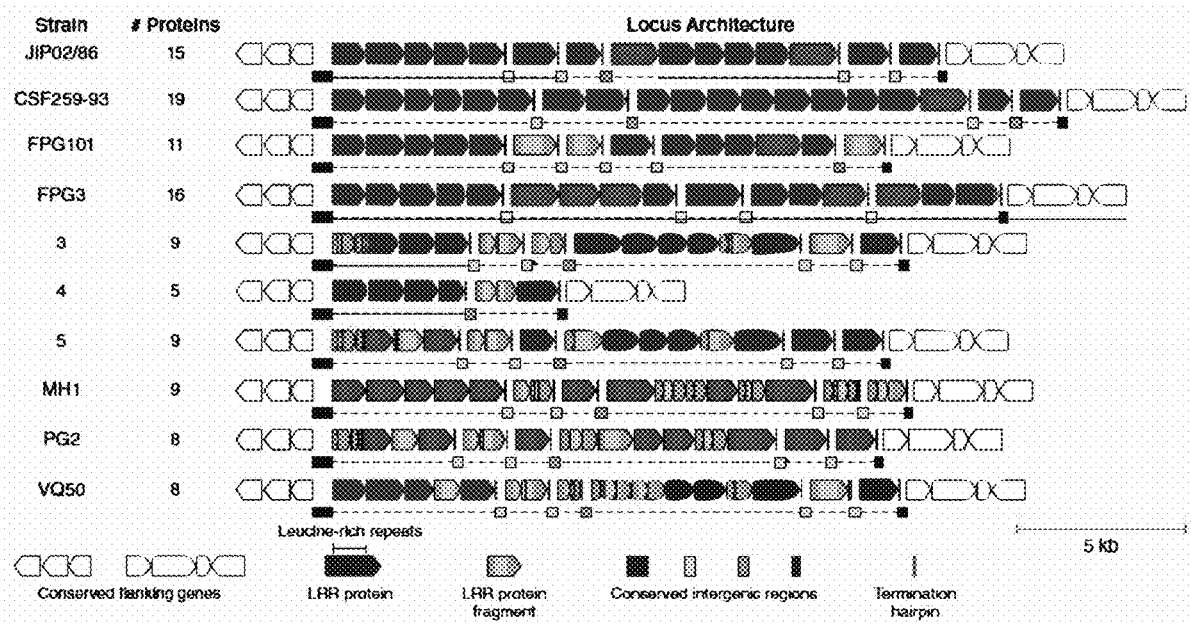
FIGS. 10A-10G: Extensive signatures of modularity and recombination in a leucine-rich repeat (LRR) protein locus from *Flavobacterium psychrophilum*.
Figure 10B:
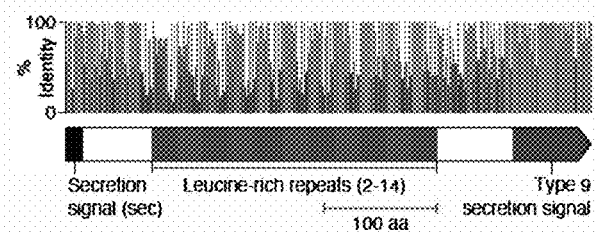
Figure 10C:
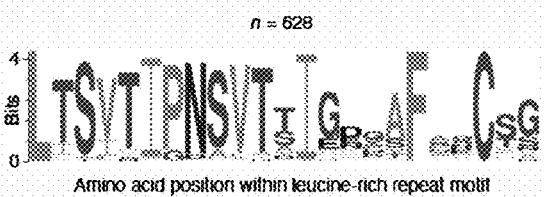
Figure 10D:
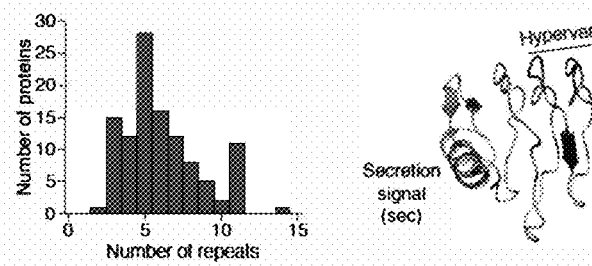
Figure 10E:
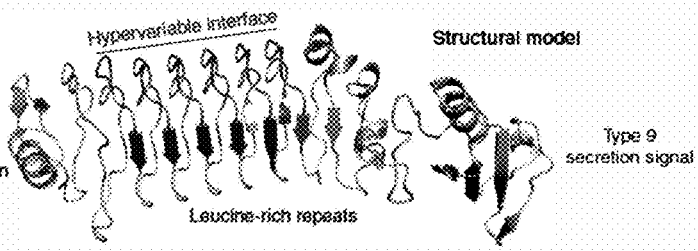

Using both pipelines, Applicants identified a genomic region in 17 isolates of *Flavobacterium psychrophilum*, a fish pathogen that causes bacterial cold water disease in rainbow trout. These regions contained up to 19 tandem repeats of a putative cell surface protein (FIG. 10A). Each protein contained 2-14 internal LRRs (FIGS. 10B-10D), a class of ~22-residue repeat motifs that contain several hypervariable positions. LRRs, which are also present in VLR antibodies in lampreys and hagfish, have been shown to mediate tight binding to diverse molecular targets. The *F. psychrophilum* LRR proteins also contained a conserved N-terminal secretion peptide and C-terminal type 9 secretion signal, which can provide an anchor to the cell surface via a conjugated lipoprotein. Structural modeling suggests these proteins adopt a fold similar to known LRR proteins, with the repeat units arranged in a solenoidal configuration and the hypervariable residues concentrated on one side, forming a putative binding interface (FIG. 10E). The proteins can play a role in bacterial adhesion and can also be utilized by bacteriophage as receptors.

Figure 10F:
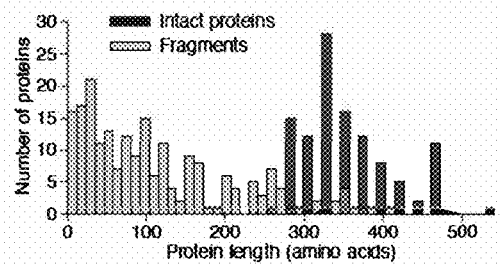
Figure 15:
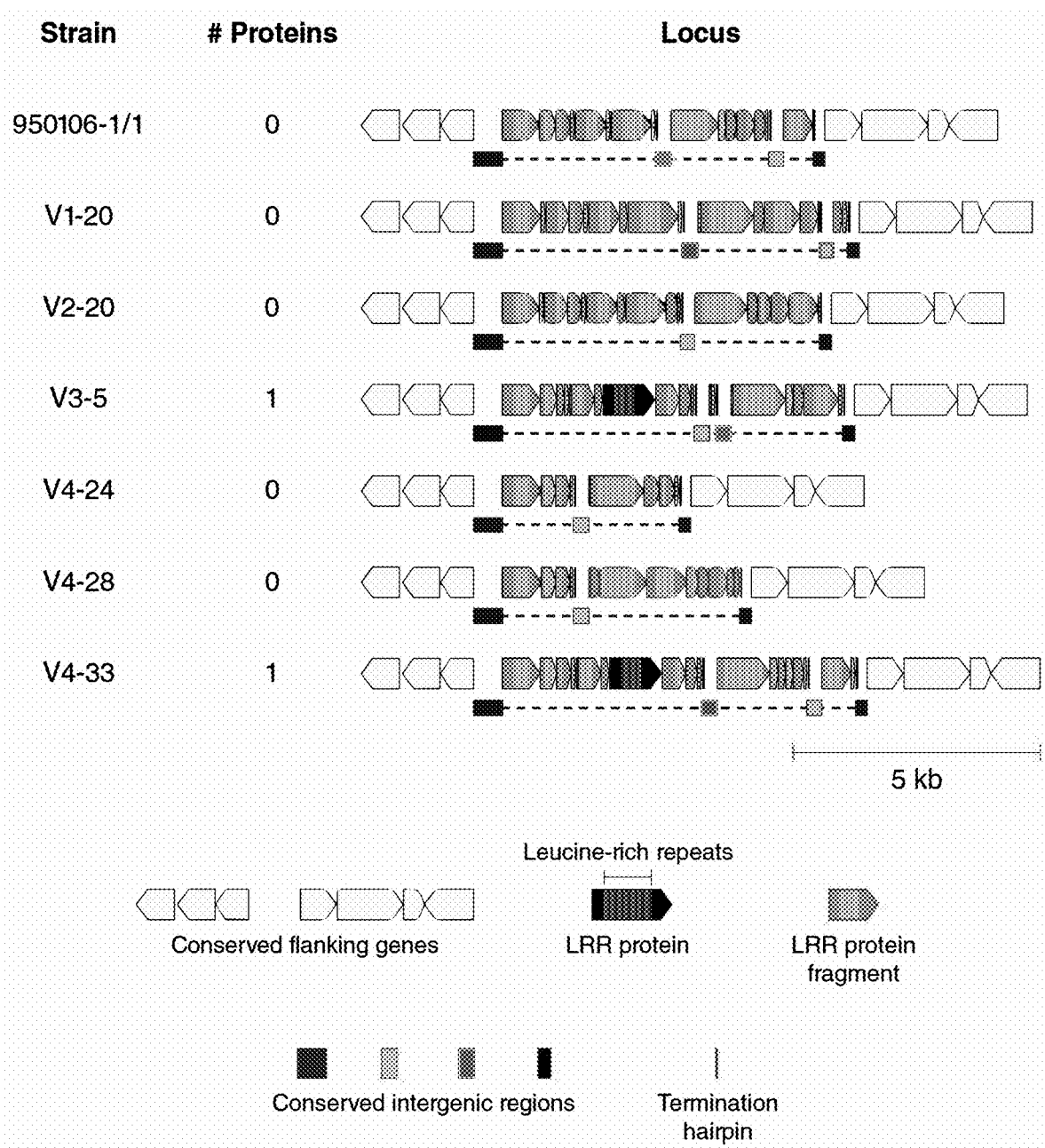
FIG. 15: Leucine-rich repeat protein loci from 6 additional strains of *Flavobacterium psychrophilum*. The final six strains are phage-resistant clones derived from 950106-1/1 after several days of phage challenge.

Applicants' examination of all the sequenced genomes of all strains of *F. psychrophilum* in Genbank revealed that each strain had significant differences in the number and lengths of LRR proteins as well as in the sequences of their repeat motifs, despite strict conservation of flanking genes (FIG. 10A and FIG. 15). Analysis of these loci at the nucleotide resolution revealed signatures of extensive recombination: The large stretches of DNA between LRR proteins, previously unannotated, in fact had broken fragments of LRR genes stuck together (FIGS. 10A, 10F). Indeed, every nucleotide was either part of an intact LRR gene, an LRR gene fragment, or one of two conserved types of putative intergenic regions (FIG. 10A).

Figure 10G:
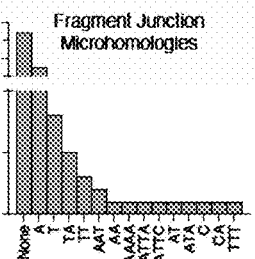
Figure 16A:
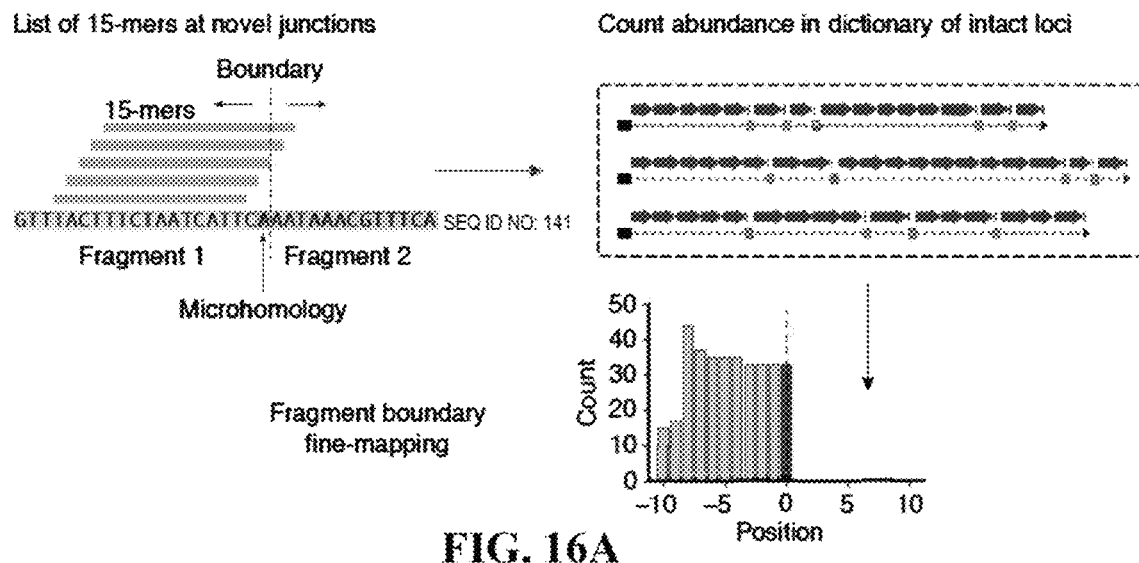
FIGS. 16A-16B: Characterization of LRR protein fragments.
Figure 16B:
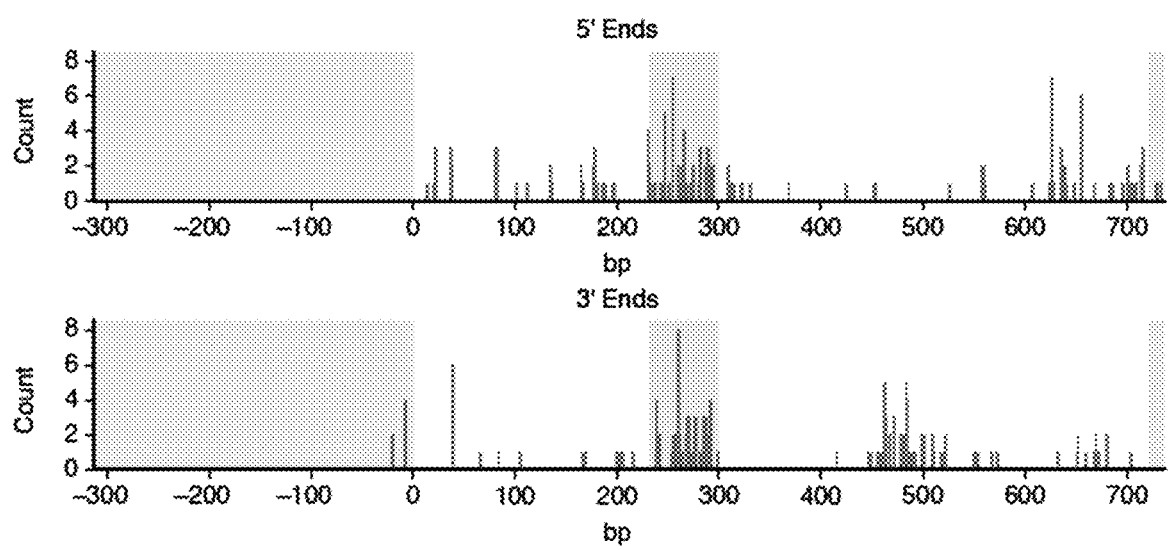

Given that these loci were marked by a complete absence of mobilome genes (e.g., transposons), Applicants sought to further characterize the recombination within the LRR loci by mapping the boundaries of each gene fragment at single-nucleotide resolution (FIG. 16A). Fragment-fragment junctions occur mostly within coding regions (FIG. 16B) and are dominated by 1-5 base pair (bp) overlapping microhomologies (FIG. 10G). The pattern of fragmentation with junction microhomologies is consistent with illegitimate recombination, such as from strand slippage during replication or targeted DNA double-strand breaks. Moreover, recombination within the LRR loci may occur on short timescales. *F. psychrophilum* clones obtained after several days of phage challenge acquired differences in the DNA sequences of their LRR loci relative to the parental strain (FIG. 15).

Leucine-Rich Repeat (LRR) Proteins from *Dictyostelium purpureum*

Figure 11A:
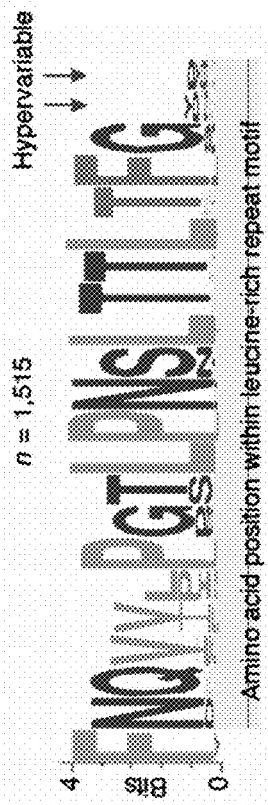
FIGS. 11A-11D: Leucine-rich repeat (LRR) proteins from Dictyostelium *purpureum*.
Figure 11B:
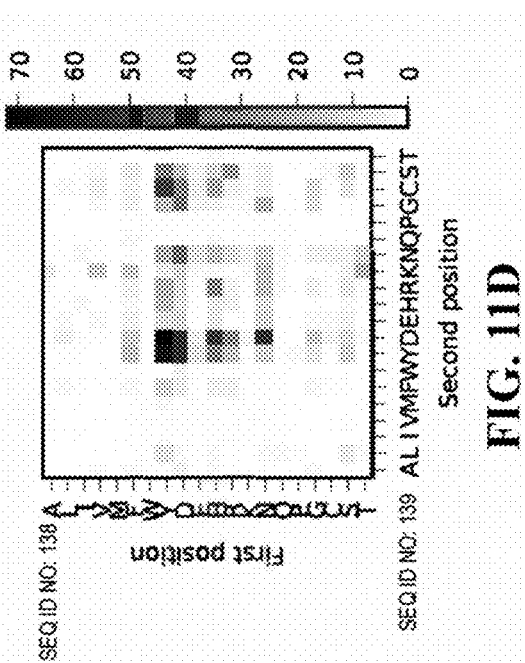
Figure 11C:
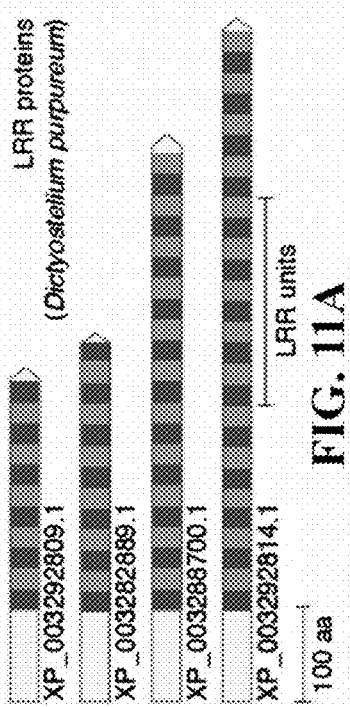
Figure 11D:
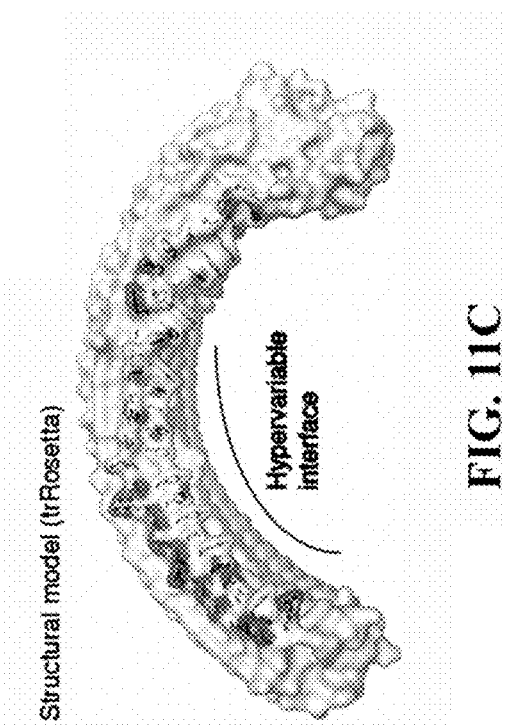

Applicants also identified over 90 LRR proteins encoded in the genome of *Dictyostelium purpureum*, a species of social amoeba named for its distinctively purple spores. These proteins vary in the number of repeat motifs they contain (FIG. 11A). The LRR motifs in *D. purpureum* were distinct from those in *F. psychrophilum* and contained two consecutive hypervariable residues within the motif, which bears resemblance to the variable di-residue found in TALEs (FIG. 11B). The amino acid composition of the first hypervariable position was dominated by tyrosine (22%), aspartic acid (19%), histidine (13%), and asparagine (11%), while the amino acid composition of the second hypervariable position is dominated by aspartic acid (22%), tyrosine (15%), cysteine (10%), and asparagine (9%). Some pairs of hypervariable residues are more likely to be present than others, such as YD, YY, DD, YC, and ND (FIG. 11D). Structural modeling indicated an extended horseshoe-like structure (FIG. 11C) with the hypervariable residues (sticks) forming an interface along a side of the horseshoe. The low frequency of the hydrophobic amino acids tryptophan, valine, leucine, isoleucine, methionine, phenylalanine, and alanine suggest the hypervariable interface was likely solvent exposed. Given their similarity to TALEs, these LRR proteins may bind specifically to nucleic acids, possibly in a manner similar to pumilio proteins paperpile.com/c/NU-akVX/He79, or other LRR proteins that bind to nucleic acids. Regardless of the substrate, however, the presence of numerous variable di-residue pairs suggest that these proteins could bind in a way that is possibly modular and reprogrammable.

Tomato Transcription Factors.

Figures 12A, 12B:
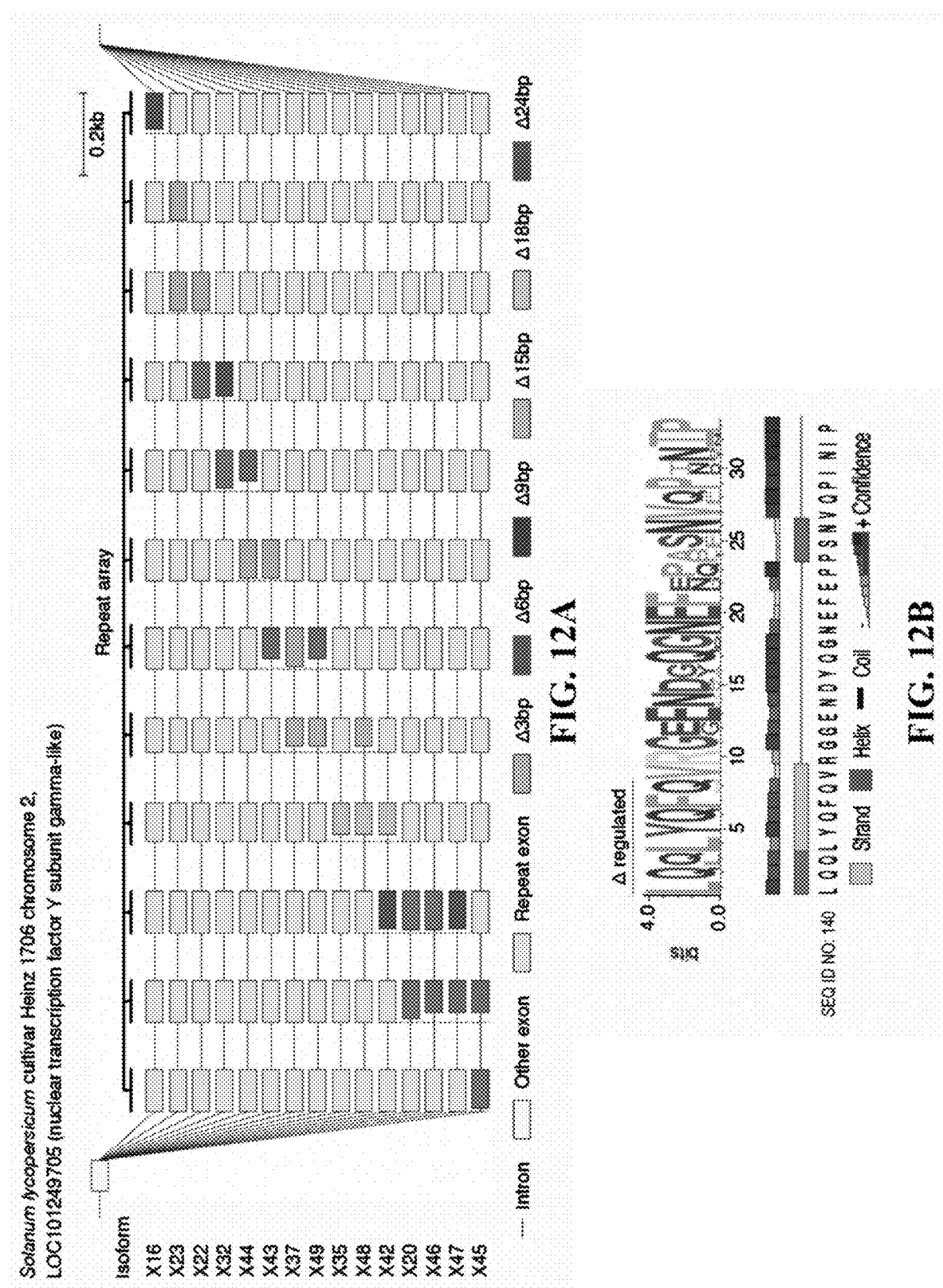
FIGS. 12A-12B.

Using the within protein repeat pipeline, Applicants identified a single nuclear transcription factor Y subunit gamma (NF-YC) gene, Solyc02 g091030, in *Solanum lycopersicum* that contains an array of 12 tandem amino acid repeats of an unknown fold (FIG. 12A). Unlike other systems described in this paper, the diversity in this protein is found at the transcriptome level and arises through splicing. At least 50 isoforms were identified for this protein, the majority of which only contain differences in the repeat array itself. Each repeat was encoded by a separate exon, and all isoform differences occurred as deletions at the 5' of each exon. Each deletion was a multiple of three nucleotides, resulting in various isoforms differing by in-frame deletions. Deletions typically occurred on a single or multiple adjacent repeats. Secondary structure prediction of the repeat unit showed that the 5' deletions in each repeat occur in the only region of high confidence secondary structure (FIG. 12B), suggesting that the deletions regulate the overall secondary and possibly tertiary structure of the repeat array. NF-Y genes are typically involved in maturation and adaptive stress response. The NF-YC subunit can dimerize with the NF-YB subunit in the cytoplasm before being imported into the nucleus where the dimer trimerizes with NF-YA, altering the ability of NF-YA to bind to promoters. Expression of Solyc02 g091030 did not vary greatly across different tissue types, suggesting it may have some role other than tissue-specific maturation. Other relatives of *Solanum lycopersicum* also possessed variants of this transcription factor, such as *Solanum pennellii*, suggesting that the mechanism for this splicing based diversification may have evolved over the time scale of speciation.

Secreted proteins containing a serine protease domain split over a hypervariable insert.

Figure 17:
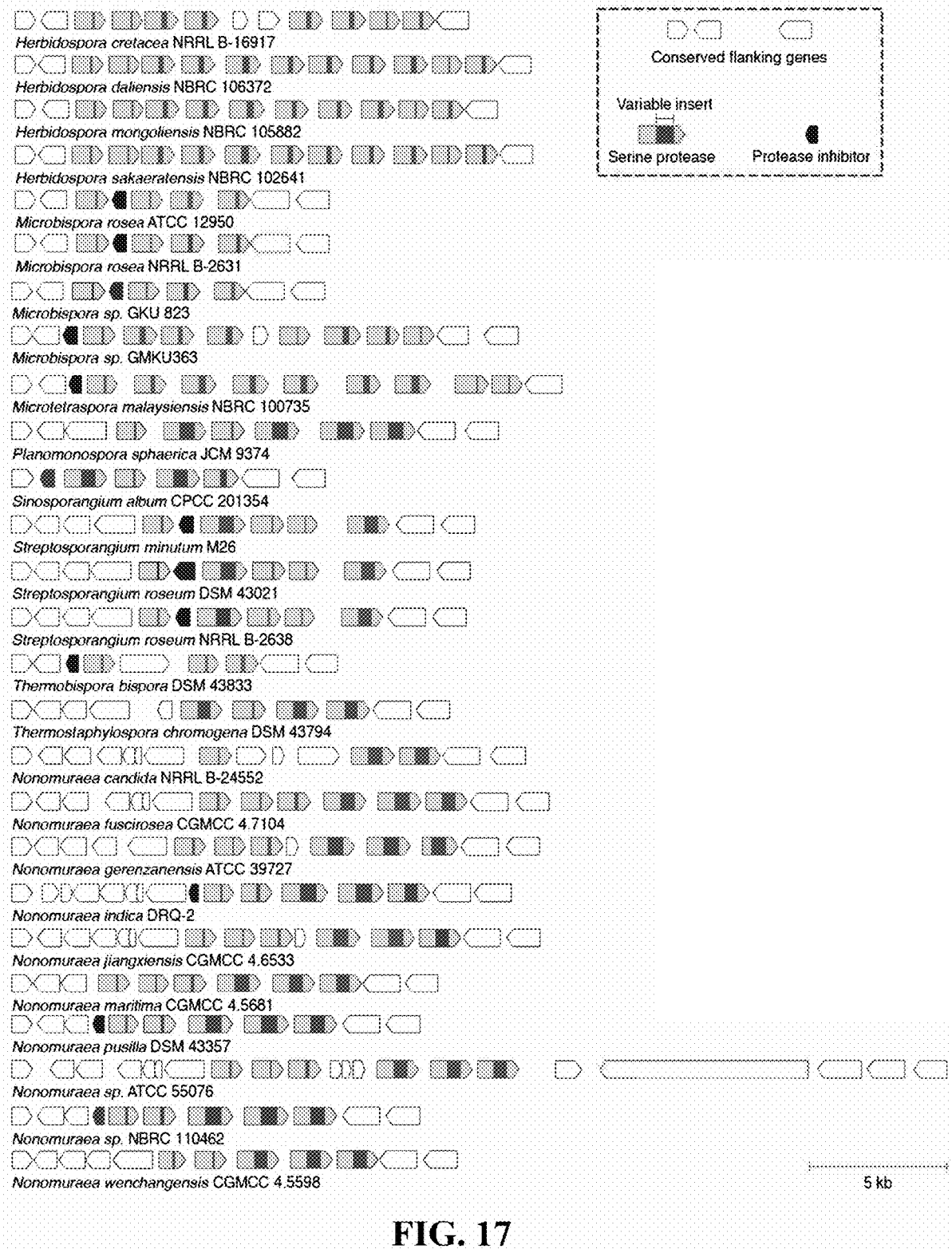
FIG. 17: Architectures of 26 additional *Streptosporangiaceae* loci containing hypervariable serine proteases.

Applicants also identified tandem repeats of up to 14 proteins, each containing a serine protease domain, present in strains within *Streptosporangiaceae*, a gram-positive family of bacteria within the *Actinobacteria phylum* that is widely distributed in soil (FIG. 13A and FIG. 17). The protease domain was relatively conserved (FIG. 13B) but was likely to be catalytically inactive, as the active site serine was often substituted with aspartate, leucine, or other residues (FIG. 13C). Of note, each protease domain contained an insertion in the middle that was highly variable across homologs, with a broad size range from less than 10 to over 200 amino acids (FIGS. 13B, 13D-13E). Structural modeling indicated that these proteins retain the core serine protease fold and accommodate the insertion as a separate domain joined by flexible linkers (FIG. 13F). These proteins also contained a predicted N-terminal secretion peptide (FIG. 13B), suggesting extracellular localization.

The proteins were predicted to be able to secrete into the extracellular environment, which suggests that they may play a role in interspecies bacterial conflict. For instance, Applicants found that the hypervariable insert can act as a toxin that was supported by a serine protease scaffold and released upon secretion. In fact, over half of the analyzed loci also encoded a protease inhibitor predicted to be intracellular (FIG. 13A), e.g., to mitigate toxicity to the host cell.

Alternating protein pairs from *Photorhabdus* implicated in self-nonself recognition.

Figure 14A:
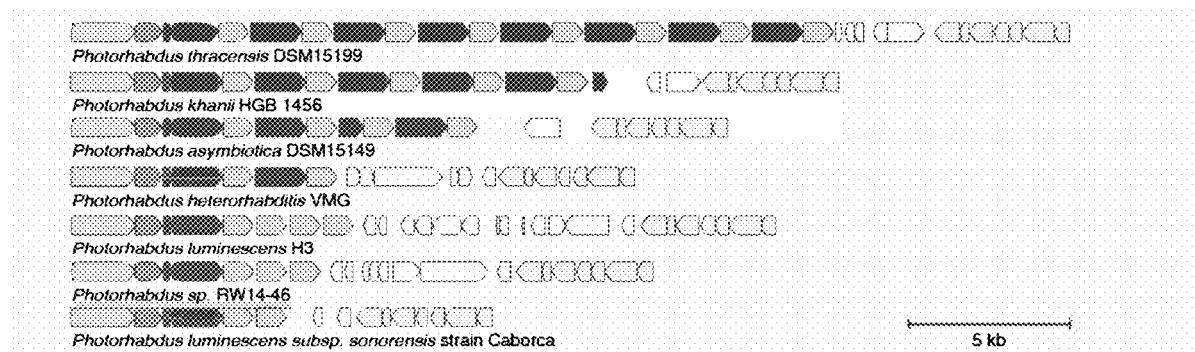
FIGS. 14A-14F: An array of alternating protein pairs from *Photorhabdus* containing localized variation.
Figures 14B, 14C:
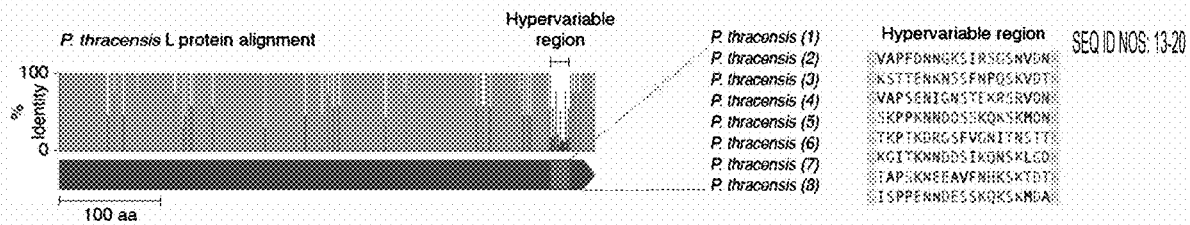
Figure 14D:
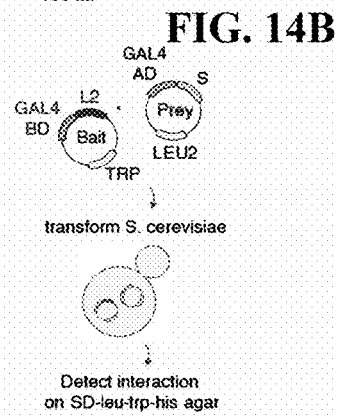
Figure 14E:
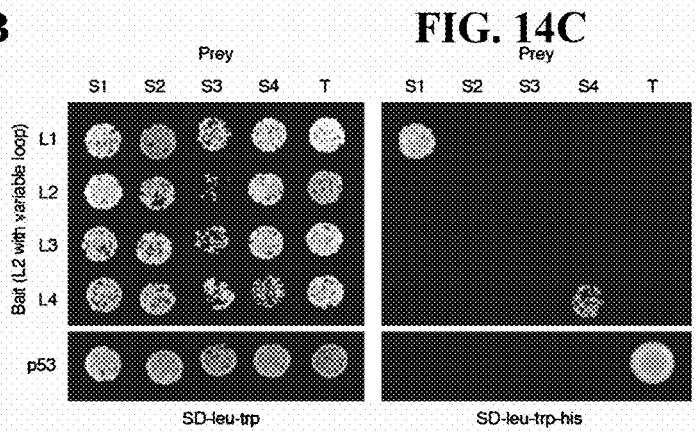

Applicants identified tandem repeats of a pair of proteins within strains of *Photorhabdus* (FIG. 14A), a genus of symbiotic, bioluminescent, gram-negative bacilli. Each pair consists of a long (L) protein (~530 amino acids) and a short (S) protein (~300 amino acids). L proteins can be intracellular, while S proteins contained a predicted secretion signal peptide at their N termini; however, neither protein has a known function or annotated domains. Eight repeats of the L-S pair (16 proteins total) were present in a single locus in *P. thracensis* DSM15199, and five repeats were present in *P. khanii* HGB 1456. Notably, the L protein had a 17-19 amino acid hypervariable region at the C terminus, whereas the other regions of the protein were nearly identical (FIGS. 14B-14C). The S proteins were also variable, but the variable positions were distributed throughout its sequence. Using a yeast two-hybrid assay, Applicants detected specific pairwise binding interactions between two sets of adjacent L and S proteins (FIGS. 14D-14E). In the assay, the non-variable regions of each L protein were kept identical, and only the hypervariable insert was changed, indicating that the hypervariable residues in L determine binding specificity.

Figure 14F:
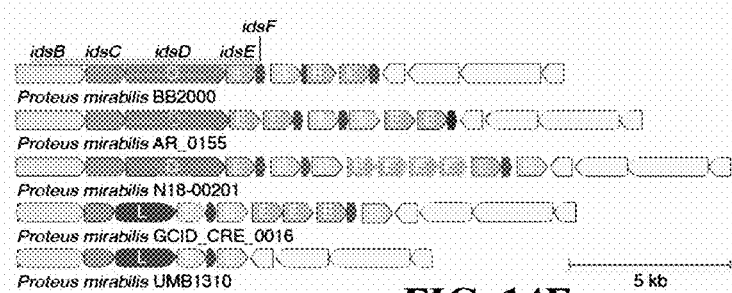

The L-S locus resembled the ids gene cluster in *Proteus mirabilis*, which conferred self-identity and social recognition between different *P. mirabilis* strains by mediating the formation of boundaries between swarming colonies paperpile.com/c/NUakVX/82aX. The ids locus had 5 genes (idsBCDEF) that were essential for social recognition (FIG. 14F), three which (idsB, idsC, and idsF) were also present in the L-S locus. However, in the L-S locus, the ORFs encoding idsD and idsE that were usually present within the idsBCDEF operon were replaced by L and S, which had no sequence homology to idsD or idsE (FIG. 14B). Like L and S, idsD and idsE also interacted in a pairwise manner, and idsD contained a variable region at its C terminus that was responsible for conferring interaction specificity with idsE. Moreover, some ids loci also encoded multiple copies of idsE, similar to the multiple S genes present in some of the *Photorhabdus* strains. Finally, in *P. mirabilis*, homologs of S were sometimes present within the ids locus, downstream of the idsBCDEF operon; likewise, homologs of idsE were sometimes present downstream of the L-S locus (FIG. 14F).

The similarities between the L-S and ids loci suggested that the *Photorhabdus* L and S proteins confer self vs. non-self recognition between different *Photorhabdus* species. The pairwise binding specificity between adjacent L and S homologs, as well as the presence of multiple S genes in a locus with only one L gene (e.g., for *Photorhabdus luminescens* H3), was also consistent with a signature of interspecies conflict or recognition. However, since neither L nor S are predicted to be membrane proteins, in contrast to idsDE, the mechanism of recognition by L-S was likely distinct from that of idsDE.

The approach presented here demonstrated the feasibility of identifying novel proteins and systems computationally using genomic hallmarks. Applicants applied this method to systematically analyze all available proteins for protein repeat elements that contain strong localized variation within a fixed scaffold, as well as all available prokaryotic genomes and metagenomes for systems that contain multiple copies of the same protein with strong localized variation. This search revealed a number of interesting candidates that Applicant examined in more depth.

Of the systems Applicants selected for deeper analysis, some, such as the serine protease and the tomato NF-YC transcription factor, may involve unusual mechanisms of diversification. Additionally, three systems were implicated in interspecies conflict, a common theme in repeat-containing proteins and systems, such as TALEs, LRR-containing proteins, and CRISPR-Cas systems. The findings here further highlighted the role of diversified repeats in adaptive responses. The candidate systems from this study were found in widely divergent organisms, ranging from bacteria to plants and amoebae, underscoring the generality of the evolutionary strategy of using modular repeats. Furthermore, these findings highlighted the importance of biodiversity in the discovery of new molecular systems.

By aggregating all available genomic sequencing data from multiple data sources, such as NCBI genomes, JGI, and NCBI WGS into a single database with a common format, Applicants were able to implement comprehensive, domain-of-life wide discovery pipelines that far exceeded the capacity of homology based searches. By querying the database for non-homology based features, such as spatially clustered proteins with hypervariation, or repeat proteins with rearrangement, Applicants discovered systems with previously undescribed mechanisms and functions.

Materials and Methods

Identifying Hypervariable Repeat Proteins

All unique proteins (at 100% sequence identity) were downloaded from UniRef100. Protein repeats were annotated with RADAR, and all proteins with 4 or more repeats were retained for further analysis. Repeat proteins were filtered for evidence of hypervariation by analyzing their dot plots. Specifically, proteins with hypervariable repeats contain dot plots with off-diagonal block identity matrices that contain a short internal segment of zeroes (signifying hypervariable positions). Repeats with hypervariable insertions and deletions can also be identified using a similar strategy in the dot plot, but as an identity matrix followed by zero band matrix and then a shifted identity matrix. To implement the off-diagonal pattern matching on the dot matrix, a 2D convolution was performed using the aforementioned filter matrices. Using the hypervariable positions determined by the convolution filter as the reference for the repeat start and end points, the positional amino acid distribution of each repeat family was calculated and used as features for multi-dimensional clustering with hDBscan, resulting in 4017 clusters. For each cluster, the repeat rearrangement score for a given family was computed as follows. Because predictions for repeat start and end sites may differ across different variants of the same repeat cluster, all repeats within the cluster were dephased using a linear optimization approach to produce consistent start and end positions for each repeat of the same archetype in the cluster. All repeats in the family were clustered into major archetypes, and with each archetype, subtypes were formed on the basis of their hypervariable resides. Each repeat in every protein of the family was assigned a label based on the repeat subtype they belong to. An estimate for the repeat transition probability matrix, P, was generated as follows. Initialize P as a zero m×m matrix, where m is the number of repeat subtypes. For each protein, if repeat subtype i is followed by repeat subtype j in that protein, set $P_{ij}=P_{ij}+1$, and Applicants normalized P by the sum of P. The repeat rearrangement score is then the variation information of P, or the joint entropy of I,J minus the mutual information of I,J. Intuitively, the higher the score, the more similar P is to a uniform distribution, indicating that repeat units are used extensively in different combinations.

Identifying Hypervariable, Repeated Proteins

All genomes from NCBI and assembled meta-genomes from JGI, NCBI WGS, and MG-RAST. Applicants predicted all ORFs larger than 80a amino acids on all curated contigs larger than 5 kb. Within each contig, all ORFs were clustered at 45% identity using MMseqs2 linclust, and all clusters of size 6 or larger were retained for further analysis. These clusters were then aligned using MAFFT, and the alignments were analyzed for localized hypervariation by searching for non-conserved regions surrounded by highly conserved regions. Systems with hypervariation divergence scores of <25 were discarded, leaving 42129 systems. Because translated ORFs appearing in CRISPRs often appear hypervariable when clustered, Applicants filtered out systems with 90% of its ORFs within 200 bp of a CRISPR containing 10 or more repeats. Removing translated CRISPRs resulted in 35701 candidate systems.

All protein systems were ranked on the basis of their hypervariation divergence score, and their loci were retrieved for further analysis. Representative proteins from each system were clustered at 30% identity and 30% coverage to group systems together into 3040 families. By investigating the patterns of hypervariation, as well as putative functions of these families, Applicants identified systems for further analysis.

Sequence Analysis of Candidate Systems

Homologs of candidate genes were identified using BLAST or PSIBLAST searches followed by manual curation of genomic loci. Percent identity was calculated as the pairwise identity between non-gap residues at each position in the multiple sequence alignment. Sequence logos were generated using WebLogo 3 without adjustment for composition. Structural models were generated using trRosetta. All models had an estimated TM-score of greater than 0.5.

Yeast Two-Hybrid Assay

The L2 protein scaffold was cloned into pBGKT7 and the 19 amino acid hypervariable regions from L1-L4 were inserted. S proteins were cloned into pGADT7 (Takara). Y2HGold *S. cerevisiae* (Takara) were co-transformed with combinations of bait/prey plasmids and colonies selected on SD-leu-trp agar. Overnight liquid cultures were grown in SD-leu-trp, normalized by optical density, diluted, plated on SD-leu-trp and SD-leu-trp-his and grown for 2-3 days at 30 C. Yeast two-hybrid controls were performed using the SV40 large T antigen (T) and pGBKT7-53 (p53) plasmids (Takara).

REFERENCES

Adamala, K. P., Martin-Alarcon, D. A. and Boyden, E. S. (2016) "Programmable RNA-binding protein composed of repeats of a single modular unit," Proceedings of the National Academy of Sciences of the United States of America, 113(19), pp. E2579-88.

Aravind, L. (2000) "Guilt by association: contextual information in genome analysis," Genome research, 10(8), pp. 1074-1077.

Boch, J. et al. (2009) "Breaking the code of DNA binding specificity of TAL-type III effectors," Science, 326(5959), pp. 1509-1512.

Boehm, T. et al. (2012) "VLR-based adaptive immunity," Annual review of immunology, 30, pp. 203-220.

Castillo, D. et al. (2015) "Bacteriophage resistance mechanisms in the fish pathogen *Flavobacterium psychrophilum*: linking genomic mutations to changes in bacterial virulence factors," Applied and environmental microbiology, 81(3), pp. 1157-1167.

Castillo, D. et al. (2016) "Comparative Genome Analysis Provides Insights into the Pathogenicity of *Flavobacterium psychrophilum*," PloS one, 11(4), p. e0152515.

Darmon, E. and Leach, D. R. F. (2014) "Bacterial Genome Instability," Microbiology and Molecular Biology Reviews, pp. 1-39. doi: 10.1128/mmbr.00035-13.

Doron, S. et al. (2018) "Systematic discovery of antiphage defense systems in the microbial pangenome," Science, 359(6379). doi: 10.1126/science.aar4120.

Duchaud, E. et al. (2007) "Complete genome sequence of the fish pathogen *Flavobacterium psychrophilum*," Nature biotechnology, 25(7), pp. 763-769.

Gaj, T., Gersbach, C. A. and Barbas, C. F., 3rd (2013) "ZFN, TALEN, and CRISPR/Cas-based methods for genome engineering," Trends in biotechnology, 31(7), pp. 397-405.

Gibbs, K. A., Urbanowski, M. L. and Greenberg, E. P. (2008) "Genetic Determinants of Self Identity and Social Recognition in Bacteria," Science, pp. 256-259. doi: 10.1126/science.1160033.

Goodfellow, M. and Quintana, E. T. (2015) "*Streptosporangiaceae*," Bergey's Manual of Systematics of Archaea and Bacteria, pp. 1-10. doi: 10.1002/9781118960608.fbm00047.

Heger, A. and Holm, L. (2000) "Rapid automatic detection and alignment of repeats in protein sequences," Proteins, 41(2), pp. 224-237.

Herrin, B. R. et al. (2008) "Structure and specificity of lamprey monoclonal antibodies," Proceedings of the National Academy of Sciences of the United States of America, 105(6), pp. 2040-2045.

Hille, F. et al. (2018) "The Biology of CRISPR-Cas: Backward and Forward," Cell, 172(6), pp. 1239-1259.

Katoh, K. et al. (2002) "MAFFT: a novel method for rapid multiple sequence alignment based on fast Fourier transform," Nucleic acids research, 30(14), pp. 3059-3066.

Khosla, C. et al. (1999) "Tolerance and specificity of polyketide synthases," Annual review of biochemistry, 68, pp. 219-253.

Kobe, B. (2001) "The leucine-rich repeat as a protein recognition motif," Current Opinion in Structural Biology, pp. 725-732. doi: 10.1016/s0959-440x(01)00266-4.

Koonin, E. V. and Wolf, Y. I. (2008) "Genomics of bacteria and archaea: the emerging dynamic view of the prokaryotic world," Nucleic acids research, 36(21), pp. 6688-6719.

Land, M. et al. (2015) "Insights from 20 years of bacterial genome sequencing," Functional & integrative genomics, 15(2), pp. 141-161.

Lasica, A. M. et al. (2017) "The Type IX Secretion System (T9SS): Highlights and Recent Insights into Its Structure and Function," Frontiers in cellular and infection microbiology, 7, p. 215.

Li, S. et al. (2016) "Genome-wide analysis of tomato NF-Y factors and their role in fruit ripening," BMC genomics, 17, p. 36.

Li, X. et al. (2019) "Viral DNA Binding to NLRC3, an Inhibitory Nucleic Acid Sensor, Unleashes STING, a Cyclic Dinucleotide Receptor that Activates Type I Interferon," Immunity, 50(3), pp. 591-599.e6.

Makarova, K. S. et al. (2020) "Evolutionary classification of CRISPR-Cas systems: a burst of class 2 and derived variants," Nature reviews. Microbiology, 18(2), pp. 67-83.

McInnes, L., Healy, J. and Astels, S. (2017) "hdbscan: Hierarchical density based clustering," The Journal of Open Source Software, p. 205. doi: 10.21105/joss.00205.

Moscou, M. J. and Bogdanove, A. J. (2009) "A simple cipher governs DNA recognition by TAL effectors," Science, 326(5959), p. 1501.

Ng, A. and Xavier, R. J. (2011) "Leucine-rich repeat (LRR) proteins: integrators of pattern recognition and signaling in immunity," Autophagy, 7(9), pp. 1082-1084.

O'Day, D. H. et al. (2006) "Isolation, characterization, and bioinformatic analysis of calmodulin-binding protein cmbB reveals a novel tandem IP22 repeat common to many *Dictyostelium* and Mimivirus proteins," Biochemical and biophysical research communications, 346(3), pp. 879-888.

Ross, B. D. et al. (2019) "Human gut bacteria contain acquired interbacterial defence systems," Nature, 575 (7781), pp. 224-228.

Roux, S. et al. (no date) "Ecology and molecular targets of hypermutation in the global microbiome." doi: 10.1101/2020.04.01.020958.

Steinegger, M. and Soding, J. (2017) "MMseqs2 enables sensitive protein sequence searching for the analysis of massive data sets," Nature biotechnology, 35(11), pp. 1026-1028.

Steinegger, M. and Soding, J. (2018) "Clustering huge protein sequence sets in linear time," Nat. Commun., 9(1), p. 2542.

Yang, J. et al. (2020) "Improved protein structure prediction using predicted interresidue orientations," Proceedings of the National Academy of Sciences of the United States of America, 117(3), pp. 1496-1503.

Yan, W. X. et al. (2019) "Functionally diverse type V CRISPR-Cas systems," Science, 363(6422), pp. 88-91.

Zhang, D. et al. (2012) "Polymorphic toxin systems: Comprehensive characterization of trafficking modes, processing, mechanisms of action, immunity and ecology using comparative genomics," Biology direct, 7, p. 18.

Zhao, H. et al. (2017) "The *Arabidopsis thaliana* Nuclear Factor Y Transcription Factors," Frontiers in Plant Science. doi: 10.3389/fpls.2016.02045.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An engineered protein or polypeptide, comprising two or more engineered, heterologous *Flavobacterium psychrophilum* leucine-rich repeats (LRRs) and a trafficking domain, wherein (a) at least one of the one or more LRRs comprises $X_1$(P/G)$X_2$(T/S)$X_3$F$X_4$, wherein:

$X_1$ is 4 to 6 amino acids in length and comprises non-charged polar amino acids and aliphatic hydrophobic amino acids, $X_2$ is 2 to 4 amino acids in length and comprises a charged or non-charged polar amino acid and/or an aliphatic hydrophobic amino acid, $X_3$ is 1 to 6 amino acids in length and comprises any amino acid, $X_4$ is 1 to 5 amino acids and comprises at least one polar amino acid, and (b) at least one of the LRRs comprises L$X_1$I(P/G)$X_2$(T/S)IFC, wherein:

$X_1$ comprises one or more of T, S, and V, and $X_2$ comprises one or more of N, S, and V; and the trafficking domain comprises a secretion signal peptide and either a secretion system substrate or a member of a specific binding pair.

2. The engineered protein or polypeptide of claim 1, wherein:

the aliphatic hydrophobic amino acids of $X_1$ is independently selected from the group consisting of leucine, isoleucine, and valine, one or more amino acids of $X_3$ are independently selected from the group consisting of serine, threonine, alanine, and cysteine, or the polar amino acid of $X_2$ is independently selected from the group consisting of asparagine, a serine, and an aspartate.

3. The engineered protein or polypeptide of claim 1, wherein one or more amino acids of $X_3$ are independently selected from the group consisting of charged and non-charged polar amino acids.

4. The engineered protein or polypeptide of claim 1, wherein one or more amino acids of $X_3$ are independently selected from the group consisting of aliphatic and aromatic hydrophobic amino acids.

5. The engineered protein or polypeptide of claim 4, wherein the aliphatic hydrophobic amino acids of $X_3$ are independently selected from the group consisting of alanine, valine, glycine, and isoleucine.

6. The engineered protein or polypeptide of claim 3, wherein the non-charged polar amino acids of $X_3$ are independently selected from the group consisting of tyrosine, serine, asparagine, and threonine, or the charged polar amino acids of $X_3$ are independently selected from the group consisting of aspartate and glutamate.

7. The engineered protein or polypeptide of claim 1, wherein the at least one polar amino acid of $X_4$ is independently selected from the group consisting of a charged and a non-charged polar amino acid.

8. The engineered protein or polypeptide of claim 7, wherein the charged polar amino acid of $X_4$ is selected from the group consisting of lysine and arginine, and the non-charged polar amino acid of $X_4$ is selected from the group consisting of serine, tyrosine, asparagine, and cysteine.

9. The engineered protein or polypeptide of claim 1, wherein at least one amino acid of $X_1$ is independently selected from the group consisting of leucine, serine, threonine, valine, and isoleucine;

wherein at least one amino acid of $X_2$ is independently selected from the group consisting of asparagine, serine, and valine;

wherein at least one amino acid of $X_3$ is independently selected from the group consisting of isoleucine, glycine, serine, threonine, and alanine; and wherein at least one amino acid of $X_4$ is independently selected from the group consisting of cysteine, serine, isoleucine, and glycine.

10. The engineered protein or polypeptide of claim 1, wherein the two or more LRRs are independently selected from the group consisting of SEQ ID NOs: 49-69 and 71-87.

11. The engineered protein or polypeptide of claim 1, wherein the trafficking domain comprises a Type IX secretion system (T9SS) substrate, further comprises an amino acid sequence capable of directing clearance from a cell or organism, the trafficking domain is capable of binding to an Fc receptor, binding to a dendritic cell, or directing antigen processing, the protein or polypeptide binds to a pathogen, the protein or polypeptide binds to a virus, the protein or polypeptide binds to a toxin, or the protein or polypeptide blocks an activity of a pathogen, virus or toxin.

12. An isolated polynucleotide encoding the engineered protein or polypeptide of claim 1.

13. A The polynucleotide of claim 12, wherein the polynucleotide is optimized for expression in an isolated host cell.

14. The polynucleotide of claim 13, wherein the isolated host cell is a prokaryotic cell.

15. The polynucleotide of claim 13, wherein the isolated host cell is a eukaryotic cell.

16. The polynucleotide of claim 15, wherein the eukaryotic cell is a human cell, a mammalian cell, a plant cell, or a yeast cell.

17. The polynucleotide of claim 12, wherein the polynucleotide comprises a regulatory element.

18. The polynucleotide of claim 17, wherein the regulatory element is inducible.

19. A vector comprising the polynucleotide of claim 12.

20. The vector of claim 19, wherein the vector is a viral vector, a bacteriophage vector, or a plasmid vector.

* * * * *